United States Patent
Bright

(10) Patent No.: US 11,446,359 B2
(45) Date of Patent: *Sep. 20, 2022

(54) SYSTEMS AND METHODS FOR CARDIAC PLEXUS NEUROMODULATION

(71) Applicant: Tulavi Therapeutics, Inc., Los Gatos, CA (US)

(72) Inventor: Corinne Bright, Los Altos Hills, CA (US)

(73) Assignee: Tulavi Therapeutics, Inc., Los Gatos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/275,120

(22) Filed: Feb. 13, 2019

(65) Prior Publication Data
US 2019/0216899 A1    Jul. 18, 2019

Related U.S. Application Data

(63) Continuation of application No. 15/848,518, filed on Dec. 20, 2017, which is a continuation of application
(Continued)

(51) Int. Cl.
| | | |
|---|---|---|
| *A01N 43/00* | (2006.01) |
| *A01N 43/46* | (2006.01) |
| *A61K 31/55* | (2006.01) |
| *A61K 38/21* | (2006.01) |
| *A61N 5/02* | (2006.01) |
| *A61B 18/14* | (2006.01) |
| *A61B 90/30* | (2016.01) |
| *A61B 17/34* | (2006.01) |
| *A61K 45/06* | (2006.01) |
| *A61B 8/12* | (2006.01) |
| *A61B 18/18* | (2006.01) |
| *A61K 31/4422* | (2006.01) |
| *A61K 31/475* | (2006.01) |
| *A61K 47/10* | (2017.01) |
| *A61K 9/06* | (2006.01) |

(Continued)

(52) U.S. Cl.
CPC ............ *A61K 38/217* (2013.01); *A61B 8/12* (2013.01); *A61B 17/3403* (2013.01); *A61B 18/1492* (2013.01); *A61B 18/1815* (2013.01); *A61B 90/30* (2016.02); *A61K 9/06* (2013.01); *A61K 9/5161* (2013.01); *A61K 31/045* (2013.01); *A61K 31/19* (2013.01); *A61K 31/337* (2013.01); *A61K 31/4422* (2013.01); *A61K 31/475* (2013.01); *A61K 31/55* (2013.01); *A61K 45/06* (2013.01); *A61K 47/10* (2013.01); *A61K 47/36* (2013.01); *A61L 27/18* (2013.01); *A61L 27/52* (2013.01); *A61L 27/56* (2013.01); *A61L 31/06* (2013.01); *A61L 31/145* (2013.01); *A61L 31/146* (2013.01); *A61N 5/022* (2013.01); *A61N 7/022* (2013.01); *A61P 9/00* (2018.01); *A61P 25/02* (2018.01); *A61P 29/02* (2018.01); *A61B 8/0808* (2013.01); *A61B 17/3401* (2013.01); *A61B 2017/3413* (2013.01); *A61B 2018/0044* (2013.01); *A61B 2018/00434* (2013.01); *A61B 2018/1861* (2013.01); *A61B 2018/1869* (2013.01); *A61L 2400/06* (2013.01); *A61N 2007/0021* (2013.01)

(58) Field of Classification Search
None
See application file for complete search history.

(56) References Cited

U.S. PATENT DOCUMENTS

| | | | |
|---|---|---|---|
| 2,339,482 A | 1/1944 | Huttkay |
| 2,339,846 A | 1/1944 | Du Bois et al. |

(Continued)

FOREIGN PATENT DOCUMENTS

| | | | |
|---|---|---|---|
| CA | 2 351 787 A1 | 12/2001 |
| CN | 1682693 A | 10/2005 |

(Continued)

OTHER PUBLICATIONS

Abbott, O. A., W. A. Hopkins, et al. (1950). "Therapeutic status of pulmonary autonomic nerve surgery." J Thorac Surg 20(4): 571-83; passim.

(Continued)

*Primary Examiner* — Layla Soroush
(74) *Attorney, Agent, or Firm* — Knobbe Martens Olson & Bear, LLP

(57) ABSTRACT

Methods, devices and systems are described for decreasing the activity of the sympathetic nervous innervation to and from the lungs and the vessels supplying the lungs to treat pulmonary medical conditions such as asthma. In one embodiment, the method may involve advancing an intravascular instrument to a target location in a blood vessel within the intercostal vasculature to ablate either or both the sympathetic afferent and efferent nerves lying within the paravertebral gutter including the visceral fibers that travel to the cardiothoracic cavity and abdominopelvic viscera and the T1 to T4/5 sympathetic chain. In another embodiment, an intravascular instrument may be advanced to the bronchial vessels to ablate either or both the sympathetic afferent and efferent nerves in and around the posterior pulmonary plexus. In one embodiment the ablative agent is a neurolytic agent delivered in a gel. This approach may be utilized to treat other cardiac and pulmonary diseases.

7 Claims, 17 Drawing Sheets

Related U.S. Application Data

No. 15/140,254, filed on Apr. 27, 2016, now Pat. No. 9,855,317.

(60) Provisional application No. 62/179,027, filed on Apr. 27, 2015.

(51) Int. Cl.

| | |
|---|---|
| A61K 47/36 | (2006.01) |
| A61K 9/51 | (2006.01) |
| A61K 31/045 | (2006.01) |
| A61K 31/19 | (2006.01) |
| A61K 31/337 | (2006.01) |
| A61N 7/02 | (2006.01) |
| A61L 27/18 | (2006.01) |
| A61L 27/52 | (2006.01) |
| A61L 27/56 | (2006.01) |
| A61L 31/06 | (2006.01) |
| A61L 31/14 | (2006.01) |
| A61P 9/00 | (2006.01) |
| A61P 29/02 | (2006.01) |
| A61P 25/02 | (2006.01) |
| A61B 18/00 | (2006.01) |
| A61B 8/08 | (2006.01) |
| A61N 7/00 | (2006.01) |

(56) References Cited

U.S. PATENT DOCUMENTS

| | | |
|---|---|---|
| 4,029,793 A | 6/1977 | Adams et al. |
| 4,582,865 A | 4/1986 | Balazs et al. |
| 4,601,169 A | 7/1986 | Hesse et al. |
| 5,279,825 A | 1/1994 | Wehling |
| 6,152,943 A | 11/2000 | Sawhney |
| 6,165,201 A | 12/2000 | Sawhney et al. |
| 6,179,862 B1 | 1/2001 | Sawhney |
| 6,379,373 B1 | 4/2002 | Sawhney et al. |
| 6,514,534 B1 | 2/2003 | Sawhney |
| 6,545,067 B1 | 4/2003 | Büchner et al. |
| 6,566,406 B1 | 5/2003 | Pathak et al. |
| 6,605,294 B2 | 8/2003 | Sawhney |
| 6,610,713 B2 | 8/2003 | Tracey |
| 6,629,969 B2 | 10/2003 | Chan et al. |
| 6,632,457 B1 | 10/2003 | Sawhney |
| 6,673,093 B1 | 1/2004 | Sawhney |
| 6,676,675 B2 | 1/2004 | Mallapragada et al. |
| 6,689,148 B2 | 2/2004 | Sawhney et al. |
| 6,703,047 B2 | 3/2004 | Sawhney et al. |
| 6,746,464 B1 | 6/2004 | Makower |
| 6,818,018 B1 | 11/2004 | Sawhney |
| 6,887,974 B2 | 5/2005 | Pathak |
| 6,932,971 B2 | 8/2005 | Bachmann et al. |
| 6,937,896 B1 | 8/2005 | Kroll |
| 7,009,034 B2 | 3/2006 | Pathak et al. |
| 7,025,990 B2 | 4/2006 | Sawhney |
| 7,057,019 B2 | 6/2006 | Pathak |
| 7,211,651 B2 | 5/2007 | Pathak |
| 7,220,270 B2 | 5/2007 | Sawhney et al. |
| 7,332,566 B2 | 2/2008 | Pathak et al. |
| 7,347,850 B2 | 3/2008 | Sawhney |
| 7,413,752 B2 | 8/2008 | Sawhney |
| 7,592,418 B2 | 9/2009 | Pathak et al. |
| 7,597,882 B2 | 10/2009 | Pathak et al. |
| 7,605,232 B2 | 10/2009 | Pathak |
| 7,648,713 B2 | 1/2010 | Sawhney |
| 7,708,979 B2 | 5/2010 | Lowman et al. |
| 7,744,913 B2 | 6/2010 | Noyes |
| 7,772,359 B2 * | 8/2010 | Pacetti ............... A61L 27/54 528/288 |
| 7,776,063 B2 | 8/2010 | Sawhney et al. |
| 7,780,980 B2 | 8/2010 | Sawhney |
| 7,790,192 B2 | 9/2010 | Sawhney et al. |
| 7,862,538 B2 | 1/2011 | Sawhney et al. |
| 7,872,068 B2 | 1/2011 | Khosravi et al. |
| 7,914,541 B2 | 3/2011 | Sawhney et al. |
| 7,928,141 B2 | 4/2011 | Li |
| 8,003,705 B2 | 8/2011 | Sawhney et al. |
| 8,044,137 B2 | 10/2011 | Khosravi et al. |
| 8,105,622 B2 | 1/2012 | Sawhney |
| 8,175,711 B2 | 5/2012 | Demarais et al. |
| 8,206,299 B2 | 6/2012 | Foley et al. |
| 8,211,017 B2 | 7/2012 | Foley et al. |
| 8,257,723 B2 | 9/2012 | Noyes |
| 8,383,161 B2 | 2/2013 | Campbell et al. |
| 8,399,443 B2 | 3/2013 | Seward |
| 8,409,606 B2 | 4/2013 | Sawhney et al. |
| 8,465,752 B2 | 6/2013 | Seward |
| 8,470,362 B2 | 6/2013 | Sawhney et al. |
| 8,480,651 B2 | 7/2013 | Abuzaina et al. |
| 8,512,749 B2 | 8/2013 | Sawhney et al. |
| 8,535,705 B2 | 9/2013 | Pathak et al. |
| 8,557,535 B2 | 10/2013 | Pathak |
| 8,563,027 B2 | 10/2013 | Jarrett et al. |
| 8,708,995 B2 | 4/2014 | Seward et al. |
| 8,741,328 B2 | 6/2014 | Suzuki et al. |
| 8,795,709 B2 | 8/2014 | Sawhney et al. |
| 8,852,230 B2 | 10/2014 | Sawhney et al. |
| 8,852,646 B2 | 10/2014 | Campbell et al. |
| 8,916,611 B2 | 12/2014 | Roy et al. |
| 8,961,501 B2 | 2/2015 | Jarrett et al. |
| 8,986,730 B2 | 3/2015 | Sawhney et al. |
| 9,011,879 B2 | 4/2015 | Seward |
| 9,023,023 B2 | 5/2015 | McKay et al. |
| 9,125,807 B2 | 9/2015 | Sawhney et al. |
| 9,131,975 B2 | 9/2015 | McKay |
| 9,186,197 B2 | 11/2015 | McKay |
| 9,199,065 B2 | 12/2015 | Seward |
| 9,205,150 B2 | 12/2015 | Jarrett et al. |
| 9,254,267 B2 | 2/2016 | Sawhney |
| 9,308,283 B2 | 4/2016 | Campbell et al. |
| 9,358,374 B2 | 6/2016 | Dacey et al. |
| 9,370,485 B2 | 6/2016 | Sawhney et al. |
| 9,386,969 B2 | 7/2016 | Sawhney et al. |
| 9,386,990 B2 | 7/2016 | Muir et al. |
| 9,463,004 B2 | 10/2016 | Campbell et al. |
| 9,498,557 B2 | 11/2016 | Pathak et al. |
| 9,669,117 B2 | 6/2017 | Campbell et al. |
| 9,687,216 B2 | 6/2017 | Sawhney et al. |
| 9,707,000 B2 | 7/2017 | Hoke et al. |
| 9,730,986 B2 | 8/2017 | Roy et al. |
| 9,775,906 B2 | 10/2017 | Sawhney et al. |
| 9,789,161 B2 | 10/2017 | Roy et al. |
| 9,855,317 B2 | 1/2018 | Bright |
| 10,420,724 B2 | 9/2019 | Jarrett et al. |
| 10,842,494 B2 | 1/2020 | Agarwal et al. |
| 10,550,187 B2 | 2/2020 | Sawhney et al. |
| 10,675,085 B2 | 6/2020 | Clark et al. |
| 10,786,462 B2 | 9/2020 | Jarrett et al. |
| 2002/0037919 A1 | 3/2002 | Hunter |
| 2003/0152637 A1 | 8/2003 | Chasin et al. |
| 2004/0096507 A1 | 5/2004 | Kwang et al. |
| 2004/0166088 A1 | 8/2004 | Shalaby |
| 2004/0186488 A1 | 9/2004 | Droese |
| 2004/0220296 A1 | 11/2004 | Lowman et al. |
| 2005/0203206 A1 | 9/2005 | Trieu |
| 2005/0228460 A1 | 10/2005 | Levin et al. |
| 2005/0261672 A1 | 11/2005 | Deem et al. |
| 2006/0177481 A1 | 8/2006 | Sawhney |
| 2006/0184185 A1 | 8/2006 | Olausson et al. |
| 2006/0280797 A1 | 12/2006 | Shoichet et al. |
| 2006/0287678 A1 | 12/2006 | Shafer |
| 2007/0016274 A1 | 1/2007 | Boveja et al. |
| 2007/0253960 A1 | 11/2007 | Roy et al. |
| 2007/0255379 A1 * | 11/2007 | Williams ............... A61N 1/05 607/120 |
| 2008/0114092 A1 | 5/2008 | Sawhney |
| 2008/0147137 A1 | 6/2008 | Cohen et al. |
| 2009/0047349 A1 | 2/2009 | Bennett et al. |
| 2010/0119451 A1 | 5/2010 | Sawhney |
| 2010/0168625 A1 | 7/2010 | Swain et al. |
| 2010/0255060 A1 | 10/2010 | Kajii et al. |
| 2011/0104061 A1 | 5/2011 | Seward |

(56) References Cited

U.S. PATENT DOCUMENTS

| | | |
|---|---|---|
| 2012/0039862 A1 | 2/2012 | Borodic |
| 2012/0049689 A1 | 3/2012 | Bennett et al. |
| 2013/0035682 A1 | 2/2013 | Weil |
| 2013/0071462 A1 | 3/2013 | Jarrett et al. |
| 2013/0204068 A1 | 8/2013 | Gnanashanmugam et al. |
| 2013/0225664 A1 | 8/2013 | Horsager et al. |
| 2013/0274674 A1 | 10/2013 | Fischell et al. |
| 2013/0287698 A1 | 10/2013 | Seward |
| 2013/0296646 A1 | 11/2013 | Barbut et al. |
| 2013/0304174 A1 | 11/2013 | Langhals et al. |
| 2014/0052168 A1 | 2/2014 | Sawhney |
| 2014/0094932 A1 | 4/2014 | Deister et al. |
| 2014/0221975 A1 | 8/2014 | Gnanashanmugam et al. |
| 2014/0271717 A1 | 9/2014 | Goshayeshgar et al. |
| 2014/0276590 A1 | 9/2014 | Hiller et al. |
| 2014/0341836 A1 | 11/2014 | Sawhney et al. |
| 2014/0350327 A1 | 11/2014 | Poon et al. |
| 2014/0363382 A1 | 12/2014 | Campbell et al. |
| 2014/0363498 A1 | 12/2014 | Sawhney et al. |
| 2015/0065945 A1 | 3/2015 | Zarins et al. |
| 2015/0132409 A1 | 5/2015 | Stein et al. |
| 2015/0305799 A1 | 10/2015 | Trieu |
| 2015/0374887 A1 | 12/2015 | Romero-Ortega et al. |
| 2016/0045602 A1 | 2/2016 | Jarrett et al. |
| 2016/0106587 A1 | 4/2016 | Jarrett et al. |
| 2016/0166504 A1 | 6/2016 | Jarrett et al. |
| 2016/0296623 A1 | 10/2016 | Sawhney et al. |
| 2016/0331738 A1 | 11/2016 | Jarrett et al. |
| 2016/0367235 A1 | 12/2016 | Campbell et al. |
| 2017/0020729 A1 | 1/2017 | Jarrett et al. |
| 2017/0143409 A1 | 5/2017 | Clark et al. |
| 2017/0266324 A1 | 9/2017 | Campbell et al. |
| 2018/0147260 A1 | 5/2018 | Bright |
| 2018/0185390 A1 | 7/2018 | Eviston et al. |
| 2019/0038646 A1 | 2/2019 | Bright et al. |
| 2020/0085809 A1 | 3/2020 | Bright et al. |
| 2020/0206365 A1 | 7/2020 | Campbell et al. |
| 2020/0206366 A1 | 7/2020 | Campbell et al. |
| 2020/0206367 A1 | 7/2020 | Campbell et al. |
| 2020/0207860 A1 | 7/2020 | Sawhney et al. |
| 2021/0046221 A1 | 2/2021 | Deister |
| 2021/0187160 A1 | 6/2021 | Bright et al. |

FOREIGN PATENT DOCUMENTS

| | | |
|---|---|---|
| CN | 102125516 A | 7/2011 |
| CN | 103385850 A | 11/2013 |
| CN | 103750919 A | 4/2014 |
| CN | 103816111 A | 5/2014 |
| CN | 104069485 A | 10/2014 |
| CN | 104288091 A | 1/2015 |
| CN | 104399131 A | 3/2015 |
| CN | 109395165 A | 3/2019 |
| JP | 2000-139976 | 5/2000 |
| JP | 5453776 B2 | 3/2014 |
| RU | 2582226 C1 | 4/2016 |
| WO | WO 2001/089526 | 11/2001 |
| WO | WO 2004/002449 | 1/2004 |
| WO | WO 2009/146030 | 12/2009 |
| WO | WO 2011/085166 | 7/2011 |
| WO | WO 2012/075337 A2 | 6/2012 |
| WO | WO 2013/165714 | 11/2013 |
| WO | WO 2014/130419 | 8/2014 |
| WO | WO 2016/019000 | 4/2016 |
| WO | WO 2016/144166 | 9/2016 |
| WO | WO 2016/176333 | 11/2016 |
| WO | WO 2017/139487 | 8/2017 |
| WO | WO 2018/005848 | 1/2018 |
| WO | WO 2018/125822 A2 | 7/2018 |
| WO | WO 2019/027272 | 2/2019 |
| WO | WO 2019/178564 | 9/2019 |
| WO | WO 2020/010123 | 1/2020 |
| WO | WO 2020/010164 | 1/2020 |

OTHER PUBLICATIONS

Abdi, Salahadin, et al. "A new and easy technique to block the stellate ganglion." Pain Physician 7.3 (2004): 327-332.

Adar, R., A. Kurchin, et al. (1977). "Palmar hyperhidrosis and its surgical treatment: a report of 100 cases." Ann Surg 186(1): 34-41.

Albers, James, et al. "Interventions for preventing neuropathy caused by cisplatin and related compounds." Cochrane Database Syst Rev 1.1 (2007).

Antila, H., and O. Kirvelä. "Neurolytic thoracic paravertebral block in cancer pain." Acta anaesthesiologica scandinavica 42.5 (1998): 581-585.

Antolak SJ, et al. "Therapeutic Pudendal Nerve Blocks Using Corticosteriods Cure Pelvic Pain after Failure of Sacral Neuromodulation" Pain Medicine 2009, vol. 10, No. 1, pp. 185-189.

B Braun Plexus Anaesthesia product guide (2014) in 10 pages.

Baumgartner, F. J. (2008). "Surgical approaches and techniques in the management of severe hyperhidrosis." Thorac Surg Clin 18(2): 167-81.

Baumgartner, Fritz J., et al. "Thoracoscopic sympathicotomy for disabling palmar hyperhidrosis: a prospective randomized comparison between two levels." The Annals of thoracic surgery 92.6 (2011): 2015-2019.

BD PuraMatrix Peptide Hydrogel Brochure (2004) in 4 pages.

Blades, B., E. J. Beattie, Jr., et al. (1950). "The surgical treatment of intractable asthma." J Thorac Surg 20(4): 584-91; passim.

Boezaart, AndréP. Atlas of peripheral nerve blocks and anatomy for orthopaedic anesthesia. Elsevier Health Sciences, p. 218, 2008.

Bolderman et al., International Journal of Cardiology, 2011, 149, p. 341-346 (Year: 2011).

Cai, "Injectable glycosaminoglycan hydrogels for controlled release of human basic fibroblast growth factor" Biomaterials 26 (2005) 6054-6067 (Year: 2005).

Carli, Mirjana, et al. "Tph2 gene deletion enhances amphetamine-induced hypermotility: effect of 5-HT restoration and role of striatal noradrenaline release." Journal of neurochemistry 135.4 (2015): 674-685.

Carr, D. and H. Chandler (1948). "Dorsal sympathetic ganglionectomy for intractable asthma." J Thorac Surg 17(1): 1-12.

Chaibundit, Chiraphon, et al. "Effect of ethanol on the gelation of aqueous solutions of Pluronic F127." Journal of colloid and interface science 351.1 (2010): 190-196.

Chaibundit, Chiraphon, et al. "Effect of Ethanol on the Micellization and Gelation of Pluronic P123." Langmuir 24.21 (2008): 12260-12266.

Chang, Jason Y., Kevin D. Phelan, and Janet A. Chavis. "Neurotoxicity of 25-OH-cholesterol on sympathetic neurons." Brain research bulletin 45.6 (1998): 615-622.

Cheema, S., J. Richardson, and P. McGurgan. "Factors affecting the spread of bupivacaine in the adult thoracic paravertebral space." Anaesthesia 58.7 (2003): 684-687.

Cressman, Erik NK, and David A. Jahangir. "Dual mode single agent thermochemical ablation by simultaneous release of heat energy and acid: hydrolysis of electrophiles." International Journal of Hyperthermia 29.1 (2013): 71-78.

Cunningham, D. J. (1913). Cunningham's Textbook of Anatomy, William Wood (648-734).

Da Rocha, R. P., A. Vengjer, et al. (2002). "Size of the collateral intercostal artery in adults: anatomical considerations in relation to thoracocentesis and thoracoscopy." Surg Radiol Anat 24(1): 23-6.

Denby, Christine, et al. "Temporary sympathectomy in chronic refractory angina: a randomised, double-blind, placebo-controlled trial." British journal of pain 9.3 (2015): 142-148.

Dimitrov-Szokodi, D., G. Balogh, et al. (1957). "Lung denervation in the therapy of intractable bronchial asthma." J Thorac Surg 33(2): 166-84.

Downing, S. Evans, and John C. Lee. "Nervous control of the pulmonary circulation." Annual Review of Physiology 42.1 (1980): 199-210.

Drott, C. and G. Claes (1996). "Hyperhidrosis treated by thoracoscopic sympathicotomy." Cardiovasc Surg 4(6): 788-90; discussion 790-1.

Dumont, Pascal. "Side effects and complications of surgery for hyperhidrosis." Thoracic surgery clinics 18.2 (2008): 193-207.

(56) References Cited

OTHER PUBLICATIONS

Dun, N. J., and A. G. Karczmar. "Evidence for a presynaptic inhibitory action of 5-hydroxytryptamine in a mammalian sympathetic ganglion." Journal of Pharmacology and Experimental Therapeutics 217.3 (1981): 714-718.
Evicore. Clinical Guidelines. Aug. 11, 2017. [Retrieved Sep. 3, 2019] Retrieved from online URL: https://www.evicore.corn/-/media/files/evicore/clinical-guidelines/solut1on /m sk-advance/archive/cmm-207—oain-eoidural-adhesiolvsiseffOB1117 102118.pdf.
Feinberg, Samuel M. "Progress in Asthma: Literature for 1934 and 1935." Journal of Allergy 7.3 (1936): 268-294.
Finucane 2017, "complications of regional anesthesia" published by Springer, 2017 p. 213.
Fredman, B., E. Zohar, et al. (2000). "Video-assisted transthoracic sympathectomy in the treatment of primary hyperhidrosis: friend or foe?" Surg Laparosc Endosc Percutan Tech 10(4): 226-9.
Freeman, N. E., R. H. Smithwick, et al. (1934). "Adrenal Secretion in Man." Am. J. Physiol. 107(3): 529.
http://www.fziomed.com/core-science/ web page last updated Aug. 19, 2016 in 2 pages.
Garcia-Morales, Luis et al., "Intraoperative Surgical Sealant Application during Cardia Defect Repair", Texas Heart Institute Journal, vol. 41, No. 4, Aug. 1, 2014, pp. 440-442.
Gay, L. N. and W. M. Reinhoff (1934). "Further Observations on the Treatment of Intractable Bronchial Asthma by Bilateral Resection of the Pulmonary Plexus." J. Allergy 13(6): 626-631.
Gloor et al., J Clin Invest., 1983, 71(5), p. 1457-1466 (Year: 1983).
Gossot, D., H. Kabiri, et al. (2001). "Early complications of thoracic endoscopic sympathectomy: a prospective study of 940 procedures." Ann Thorac Surg 71 (4): 1116-9.
Gossot, D., L. Toledo, et al. (1997). "Thoracoscopic sympathectomy for upper limb hyperhidrosis: looking for the right operation." Ann Thorac Surg 64(4): 975-8.
Haam, Seokjin, et al. "An anatomical study of the relationship between the sympathetic trunk and intercostal veins of the third and fourth intercostal spaces during thoracoscopy." Clinical Anatomy 23.6 (2010): 702-706.
Hayakawa, Kazuhiro, et al. "Nerve growth factor prevention of aged-rat sympathetic neuron injury by cisplatin, vincristine and taxol-in vitro explant study." Neuroscience letters 274.2 (1999): 103-106.
Hsu, C. P., C. Y. Chen, et al. (1998). "Resympathectomy for palmar and axillary hyperhidrosis." Br J Surg 85(11): 1504-5.
Huang, B., et al. "[Therapeutic feasibility of percutaneous puncture and chemical neurolysis of thoracic sympathetic nerve block in palmar hyperhidrosis under the guidance of computed tomograph]." Zhonghua yi xue za zhi 91.38 (2011): 2710-2713.
Ilfeld, et al. "Ultrasound-guided Percutaneous Peripheral Nerve Stimulation for Analgesia Following Total Knee Arthroplsaty: a Prospective Feasibility Study" Journal of Orthopaedic Surgery and Research 2017, vol. 12, No. 4, pp. 1-9.
Imrich, Richard, et al. "Functional effects of cardiac sympathetic denervation in neurogenic orthostatic hypotension." Parkinsonism & related disorders 15.2 (2009): 122-127.
Ireland, S. J., and C. C. Jordan. "Pharmacological characterization of 5-hydroxytryptamine-induced hyperpolarization of the rat superior cervical ganglion." British journal of pharmacology 92.2 (1987): 417-427.
Ischemia. Wikipedia. Dec. 24, 2017. [Retrieved Sep. 3, 2019] Retrieved from online URL:https://en.wikipedia.org/w/index.php?title=lschemia&oldid=816854406.
Karmakar, M. K., T. Gin, and AM-H. Ho. "Ipsilateral thoracolumbar anaesthesia and paravertebral spread after low thoracic paravertebral injection." British journal of anaesthesia 87.2 (2001): 312-316.
Kaur, Gurjinder, et al. "Estrogen regulation of neurotrophin expression in sympathetic neurons and vascular targets." Brain research 1139 (2007): 6-14.
Kimura, Tomohiko, Toshitake Shimamura, and Susumu Satoh. "Effects of pirenzepine and hexamethonium on adrenal catecholamine release in responses to endogenous and exogenous acetylcholine in anesthetized dogs." Journal of cardiovascular pharmacology 20.6 (1992): 870-874.
Klodell, Charles T., et al. "Oximetry-derived perfusion index for intraoperative identification of successful thoracic sympathectomy." The Annals of thoracic surgery 80.2 (2005): 467-470.
Koyama et al., Circ. J., 2002, 66, p. 645-648 (Year: 2002).
Krediet, Annelot C., et al. "Different Approaches to Ultrasound-guided Thoracic Paravertebral BlockAn Illustrated Review." The Journal of the American Society of Anesthesiologists 123.2 (2015): 459-474.
Lee, Ju Young, et al. "In vivo efficacy of paclitaxel-loaded injectable in situ-forming gel against subcutaneous tumor growth." International journal of pharmaceutics 392.1 (2010): 51-56.
Lee, Sang Beom, et al. "Morphometric Study of the Upper Thoracic Sympathetic Ganglia." Journal of Korean Neurosurgical Society 50.1 (2011): 30-35.
Levin, G. L. (1935). "The Treatment of Bronchial Asthma by Dorsal Sympathectomy: Direct and Indirect." Ann Surg 102(2): 161-70.
Li, et al. "Controlled Release of Protein from Biodegradable Mutio-Senstitive Injectable Poly (ether-urethane) Hydrogel" ACS Appl. Mater. Interfaces 2014, vol. 6, No. 5, pp. 3640-3647.
Lin K L et al. "DuraSeal as a Ligature in the Anastomosis of rat Sciatic Nerve Gap Injury", Journal of Surgical Research, Academic Press Inc. San Diego CA US, vol. 161, No. 1, Jun. 1, 2010, pp. 101-110.
Lin, Zhiqiang, et al. "Novel thermo-sensitive hydrogel system with paclitaxel nanocrystals: High drug-loading sustained drug release and extended local retention guaranteeing better efficacy and lower toxicity." Journal of Controlled Release 174 (2014): 161-170.
Liu, et al., 2009, European J of Cariothoracic Surgery, 35, 398-402.
Macaya, D., and M. Spector. "Injectable hydrogel materials for spinal cord regeneration: a review." Biomedical materials 7.1 (2012): 012001.
Mahajan, Mohit, P. Utreja, and S. K. Jain. "Paclitaxel Loaded Nanoliposomes in Thermosensitive Hydrogel: A Dual Approach for Sustained and Localized Delivery." Anti-cancer agents in medicinal chemistry (2015).
Malik, Tariq. "Ultrasound-Guided Paravertebral Neurolytic Block: A Report of Two Cases." Pain Practice 14.4 (2014): 346-349.
Marinescu, Mark A., et al. "Coronary microvascular dysfunction, microvascular angina, and treatment strategies." JACC: Cardiovascular Imaging 8.2 (2015): 210-220.
Matchett, Gerald. "Intercostal Nerve Block and Neurolysis for Intractable Cancer Pain." Journal of Pain & Palliative Care Pharmacotherapy (2016): 1-4.
Mehdizadeh, Mohammadreza, and Jian Yang. "Design strategies and applications of tissue bioadhesives." Macromolecular bioscience 13.3 (2013): 271-288.
Microstimulation. Wikipedia. Jun. 30, 2016. [Retrieved Sep. 3, 2019) Retrieved from online URL:https://en.wikipedia.org/w/index.php?title=Microstimulation&oldid=727594711.
Moawad, H. M. M., and H. Jain. "Development of nano-macroporous soda-lime phosphofluorosilicate bioactive glass and glass-ceramics." Journal of Materials Science: Materials in Medicine 20.7 (2009): 1409-1418.
Murray, Gary L., and Joseph Colombo. "Ranolazine preserves and improves left ventricular ejection fraction and autonomic measures when added to guideline-driven therapy in chronic heart failure." Heart International 9.2 (2014): 66-73.
Naja, M. Z., et al. "Varying anatomical injection points within the thoracic paravertebral space: effect on spread of solution and nerve blockade." Anaesthesia 59.5 (2004): 459-463.
Ng, Ivan, and Tseng-Tsai Yeo. "Palmar hyperhidrosis: intraoperative monitoring with laser Doppler blood flow as a guide for success after endoscopic thoracic sympathectomy." Neurosurgery 52.1 (2003): 127-131.
Nunn, J. F., and G. Slavin. "Posterior intercostal nerve block for pain relief after cholecystectomy anatomical basis and efficacy." British journal of anaesthesia 52.3 (1980): 253-260.
Oblasti primeneniya protivospacchnogo gelya Mezogel [online] 20 10-11-27 retrieved on Aug. 2, 2016 from URL: http://www.mesogel.ru/prod/mesogel4.htm>.

(56) References Cited

OTHER PUBLICATIONS

Ostermann Pa et al. "The ligament system of the spleen and its significance for surgical interventions" Langenbecks Arch Chir 1987;371 (3):207-16, abstract.
Pai, et al., "Spleen Anatomy" (Medscape, 2014, p. 1-6). (Year: 2014).
Pandin, Pierre, Samia Rettab, and Alphonse Lubansu. "Ultrasound Guidance Is Helpful for Paravertebral Block Performance and Catheter Placement in Patients with Laminectomy after Thoracotomy or Lumbotomy: A Case Series Imaging Study." (2013).
Paredi, P. and P. J. Barnes (2009). "The airway vasculature: recent advances and clinical implications." Thorax 64(5): 444-50.
Parlato, Matthew, et al. "Adaptable poly (ethylene glycol) microspheres capable of mixed-mode degradation." Acta biomaterialia 9.12 (2013): 9270-9280.
Phillips, E. W. and W. J. M. Scott (1929). "The Surgical Treatment of Bronchial Asthma." Arch Surg. 19(6): 1425-1456.
Pierce, Nathan E. et al, "Hydrogel sutureless facial nerve repair: Pilot Clinical Investigation: Sutureless Facial Nerve Repair", The Laryngoscope, Jun. 2015. vol. 125, No. 6, First Published, Dec. 4, 2014, pp. 1456-1459.
Ponce Gonzalez, M. A., G. J. Serda , et al. (2005). "Long-term pulmonary function after thoracic sympathectomy." The Journal of Thoracic and Cardiovascular Surgery 129(6): 1379-1382.
Richardson and Lonnqvist, (1998) "Thoracic Paravertebral Block" British Journal of Anaesthesia 81: 230-238.
Rienhoff WF Jr, G. L. (1938). "Treatment of Intractable Bronchial Asthma by Bilateral Resection of the Posterior Pulmonary Plexus. ." Arch Surg. 37(3): 456-469.
Riquet, M. (2007). "Bronchial arteries and lymphatics of the lung." Thorac Surg Clin 17(4): 619-38, viii.
Robinson, Eric A., et al. "Estimating sympathetic tone by recording subcutaneous nerve activity in ambulatory dogs." Journal of cardiovascular electrophysiology 26.1 (2015): 70-78.
Rongen, Gerard A., et al. "Presynaptic inhibition of norepinephrine release from sympathetic nerve endings by endogenous adenosine." Hypertension 27.4 (1996): 933-938.
Rosas-Ballina, et al., "Cholingergic control of inflammation" *J. Intern Med.* Jun. 2009; 265(6): 663-679.
Shvaichak E. Zavisimost vyazkosti vodnogo rastvora gialuronovoi kisloty ot ee mikrostruktury. Chast 1. Rossysky zhurnal biomekhaniki, tom 7, No. 3: 87-98, 2003.
Singh, Narendra K., and Doo Sung Lee. "In situ gelling pH-and temperature-sensitive biodegradable block copolymer hydrogels fordrug delivery." Journal of Controlled Release 193 (2014): 214-227.
Takatori, Mayumi, Yoshihiro Kuroda, and Munetaka Hirose. "Local anesthetics suppress nerve growth factor-mediated neurite outgrowth by inhibition of tyrosine kinase activity of TrkA." Anesthesia & Analgesia 102.2 (2006): 462-467.
Vallieres, E. (2007). "The costovertebral angle." Thorac Surg Clin 17(4): 503-10.
Van der Velden, Vincent HJ, and Anthon R. Hulsmann. "Autonomic innervation of human airways: structure, function, and pathophysiology in asthma." Neuroimmunomodulation 6.3 (1999): 145-159.
Van Maanen, et al., "The cholinergic anti-inflammatory pathway: towards innovative treatment of rheumatoid arthritis" (Nature Reviews, Rheumatology, 5, Apr. 2009, 229-232) (Year: 2009).
Vanaclocha, V., N. Saiz-Sapena, et al. (2000). "Uniportal endoscopic superior thoracic sympathectomy." Neurosurgery 46(4): 924-8.
Vida, Gergely, et al., "α7-Cholinergic Receptor Mediates Vagal Induction of Splenic Norepinephrine", *J Immunol* 2011; 186:4340-4346; Prepublished online Feb. 21, 2011.

Vida, Gergely, et al., "β2-Adrenoreceptors of regulatory lymphocytes are essential for vagal neuromodulcation of the innate immune system", The FASEB Journal, vol. 25, Dec. 2011, pp. 4476-4485.
Wallace D G et al., "A tissue sealant based on reactive multifunctional polyenthylene glycol", Journal of BioMedical Materials Research, Wiley, New York, NY US. vol. 58, No. 5, Apr. 25, 2015 pp. 545-555.
Wang, Peizong, et al. "Antinociceptive effect of intrathecal amiloride on neuropathic pain in rats." Neuroscience letters 604 (2015): 24-29.
Weksler et al., 2008, Thorac Surg Clin, 18, 183-191.
Westerlund, Taina, Ville Vuorinen, and Matias Roytta. "The perineurium modifies the effects of phenol and glycerol in rat sciatic nerve." Acta neuropathologica 108.4 (2004): 319-331.
Wilensky, H. M. (1940). "Peri-Sympathetic Injection Treatment of Asthma." Can Med Assoc J 43(1): 59-62.
Xu, Xian, et al. "Hyaluronic acid-based hydrogels: from a natural polysaccharide to complex networks." Soft matter 8.12 (2012): 3280-3294.
Yahagi, Naoki, Tsuyoshi Akiyama, and Toji Yamazaki. "Effects of ω-conotoxin GVIA on cardiac sympathetic nerve function." Journal of the autonomic nervous system 68.1 (1998): 43-48.
Yamazaki, Toji, Tsuyoshi Akiyama, and Toru Kawada. "Effects of ouabain on in situ cardiac sympathetic nerve endings." Neurochemistry international 35.6 (1999): 439-445.
Yohn, Samantha E., et al. "Not all antidepressants are created equal: differential effects of monoamine uptake inhibitors on effort-related choice behavior." Neuropsychopharmacology (2015).
Zarse, Markus, et al. "Selective increase of cardiac neuronal sympathetic tone: a catheter-based access to modulate left ventricular contractility." Journal of the American College of Cardiology 46.7 (2005): 1354-1359.
Zhang, Hongling, and Javier Cuevas. "Sigma Receptors Inhibit High-Voltage-Activated Calcium Channels in Rat Sympathetic and Parasympathetic Neurons." Journal of neurophysiology 87.6 (2002): 2867-2879.
Zhao, Ying-Zheng, et al. "Using NGF heparin-poloxamer thermosensitive hydrogels to enhance the nerve regeneration for spinal cord injury." Acta biomaterialia 29 (2016): 71-80.
U.S. Appl. No. 15/140,254 (U.S. Pat. No. 9,855,317) filed Apr. 27, 2016 (Jan. 2, 2018), Systems and Methods for Sympathetic Cardiopulmonary Neuromodulation.
U.S. Appl. No. 15/848,518, filed Dec. 20, 2017, Systems and Methods for Sympathetic Cardiopulmonary Neuromodulation.
U.S. Appl. No. 16/313,856, filed Dec. 27, 2018, Treatment of Sepsis and Related Inflammatory Conditions by Local Neuromodulation of the Autonomic Nervous System.
U.S. Appl. No. 16/076,308, filed Aug. 7, 2018, Methods, Agents, and Devices for Local Neuromodulation of Autonomic Nerves.
U.S. Appl. No. 16/981,199, filed Sep. 15, 2020, Systems and Methods for Gel-Based Neuromodulation.
U.S. Appl. No. 17/257,266, filed Dec. 30, 2020, Systems and Methods for Visceral Neuromodulation.
U.S. Appl. No. 17/138,703, filed Dec. 30, 2020, Methods and Devices for In Situ Formed Nerve Cap.
U.S. Appl. No. 17/148,427, filed Jan. 13, 2021, Methods and Devices for In Situ Formed Nerve Cap with Rapid Release.
U.S. Appl. No. 16/076,308, Aug. 7, 2018, Methods, Agents, and Devices for Local Neuromodulation of Autonomic Nerves.
Kopecek, "Peptide-directed self assembly of hydrogels" Acta Biomater. Mar. 2009; 5(3): 805-816 (Year: 2009).
Sudoh, "Tricyclic antidepressants as long-acting local anesthetics" Pain 103 (2003) 49-55 (Year: 2003).

\* cited by examiner

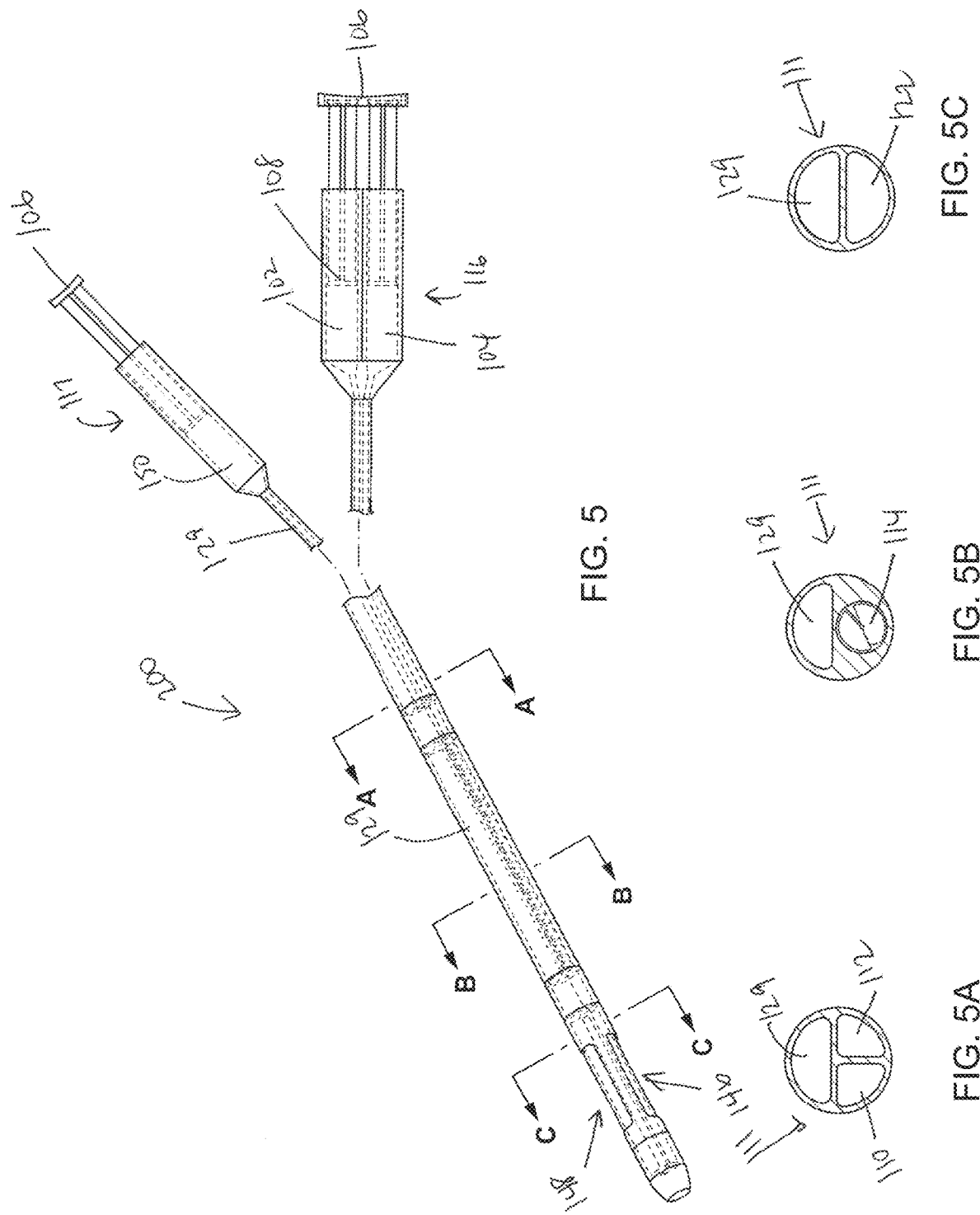

SYSTEMS AND METHODS FOR CARDIAC PLEXUS NEUROMODULATION

INCORPORATION BY REFERENCE TO ANY PRIORITY APPLICATIONS

This application claims the benefit under 35 U.S.C. § 120 as a continuation application of U.S. patent application Ser. No. 15/848,518 filed on Dec. 20, 2017, which is a continuation application of U.S. patent application Ser. No. 15/140,254 filed on Apr. 27, 2016, which in turn claims the benefit under 35 U.S.C. § 119(e) as a nonprovisional application of U.S. Prov. App. No. 62/179,027 filed on Apr. 27, 2015. Each of the foregoing applications are hereby incorporated by reference in their entireties. Furthermore, any and all applications for which a foreign or domestic priority claim is identified in the Application Data Sheet as filed with the present application are hereby incorporated by reference under 37 CFR 1.57.

BACKGROUND

Field of the Invention

The invention relates in some aspects to systems and methods for sympathetic neuromodulation, including cardiopulmonary sympathetic neuromodulation.

Description of the Related Art

Asthma is a common chronic airway disorder characterized by episodic reversible airflow obstruction, or asthma attacks, that are characterized by breathlessness, coughing, wheezing, and chest tightness. Airflow is obstructed by contraction of the smooth muscle surrounding the airway that is thought to be a result of airway hyperreactivity. Inflammation and increased mucous secretions are also thought to play a role in exacerbating the asthma attack. Exposures such as exercise, infection, allergens, chemicals, or airborne irritants may trigger an asthma attack. At this time, it is not clear how to prevent the development of asthma and there is no known cure. Pharmacologic methods to control the disease and prevent exacerbations are well-established and as a result symptomatic treatment has improved over the past 20 years.

Asthma prevalence is now at its highest level at over 8% of the population in United States. In 2010, an estimated 25.7 million people had asthma: 18.7 million adults aged 18 and over and 7 million children aged 0-17 years. As a result of the increasing prevalence of the disease, asthma has been a focus for public health action. The prevalence of asthma attacks among persons with asthma, although declining, remains above 50% and there are an estimated 46.7 million lost school, work and activity days per year. Asthma visits to the emergency department and hospitalizations were stable from 2001 to 2009 but death rates are declining from 2001 to 2009. There are approximately 2 million ED visits, 500,000 hospitalizations, and 10 million outpatient visits for asthma. Each day, this translates to approximately 40,000 unscheduled physician office visits, 5,000 emergency room visits, and 1,000 hospitalizations due to asthma. Predictors of death due to asthma include three or more ED visits in the past year, as asthma hospitalization or ED visit in the past month, overuse of short-acting beta agonists. There are approximately 4,000 deaths per year attributable to asthma and deaths occur at a rate of 3.3% per year. The care for asthma patients costs over $18 billion of healthcare resources each year. As a result of the better medications available to patients, they are living longer but with a higher overall cost to the healthcare system since there is no cure for the disease.

Asthma is classified as intermittent, mild persistent, moderate persistent, and severe persistent. Severe or treatment-resistant asthma is increasingly recognized as a major unmet clinical need. Asthma may also be classified as atopic (extrinsic) if symptoms are triggered by allergens (smoke, air pollution, pollen) or non-atopic. Asthma may also be classified exercise-induced, occupational or nocturnal. Poorly controlled severe asthma, called severe persistent asthma, constitutes about 5 to 10 percent of asthma patients in United States, or approximately 1 to 2 million patients. A new procedure has been developed for the treatment of these severe persistent asthmatic patients, called Alair bronchial thermoplasty. This is a bronchoscopic procedure in which a minimally-invasive radiofrequency catheter is delivered through a bronchoscope into the patients airways to directly ablate the smooth muscle lining the bronchi with the goal of reducing the contractions of these muscles. The procedure typically requires a total of three separate procedures separated by two to three weeks for up to one hour each under moderate sedation. The FDA approved the therapy in 2010 based on significant improvements in patients' quality of life after the procedure. Boston Scientific reported sales of $15-20 MM in 2010 and expected $40-50 MM in sales in 2013.

As a result a new treatment for asthma, as well as other diseases, is needed with the potential of cure. Ideally the treatment would be minimally invasive and require minimal, if any, hospital stay. The procedure would, in some cases, avoid direct disruption to bronchial tissue and should not necessitate inserting a bronchoscope directly into the hyper-reactive airways in some embodiments. Ideally, the treatment could be performed in one or two outpatient or office visits under a local anesthetic. This is desirable for both pediatric and adult patients. The treatment can reduce or eliminate the need for chronic pharmaceutical therapy. Finally, the treatment may preferably be long lasting or permanent. The treatment can result in a significant cost reduction to the healthcare system by reducing medication consumption as well as outpatient, emergency department visits and hospitalizations each year.

SUMMARY

Disclosed herein are systems and methods for neuromodulating sympathetic nerves of a patient, according to some embodiments of the invention. Some embodiments involve a method that includes inserting a catheter percutaneously into a first blood vessel; advancing the catheter into a second blood vessel; penetrating a wall of the second blood vessel with a portion of the catheter, thereby accessing the paravertebral gutter; and neuromodulating sympathetic nerves within the paravertebral gutter.

In some embodiments, the second blood vessel could be, for example, an azygous vein, a hemiazygous vein, an accessory hemiazygous vein, a superior intercostal vein, an intercostal vein other than the superior intercostal vein, a costocervical trunk, and a subclavian artery.

Neuromodulation can include delivery of electromagnetic energy, such as RF, microwave, and/or ultrasound energy to a desired anatomic location, such as a portion of the paravertebral gutter, for example. In some embodiments, neuromodulation can include delivering a gel, such as a hydrogel to the paravertebral gutter. The hydrogel could include, for example, an in situ polymerizing hydrogel, or an injectable hydrogel slurry. The neuromodulation could reduce the signs, symptoms, or otherwise prevent or treat various conditions, including but not limited to asthma, hypertension, congestive heart failure, coronary artery disease, arrhythmias including atrial fibrillation, ventricular tachycardia, and ventricular fibrillation, angina pectoris, and pulmonary hypertension.

The sympathetic nerves to be treated can be present at one, two, or more spinal levels, or adjacent ribs (e.g., in the thoracic region). In some embodiments, the nerves reside proximate the C7 or T1 to T4 to T5 spinal levels, or various other levels as disclosed herein.

The neuromodulation could be unilateral or bilateral, e.g., on the left side, right side, or both, and can be stepwise or within the same operative procedure.

Also disclosed herein is a method of modulating sympathetic nerves of a patient, that includes accessing a paravertebral gutter of the patient; and neuromodulating sympathetic nerves within the paravertebral gutter, wherein neuromodulating comprises flowing a gel comprising a therapeutic agent into the paravertebral gutter. The therapeutic agent could include a neurolytic agent, such as, for example, a non-depolarizing agent. The neurolytic agent could prevents or blocks the release of norepinephrine, and/or be coadministered with a blocking agent. Some examples of neurolytic agents that can be used include, for example, nifedipine, lamotrigine, minoxidil, reserpine, tetrabenazine, amiodarone, dextromethorphan, valproic acid, mecamylamine, phenoxybenzmine, alfuzosin, haloperidol, desipramine, bretylium tosylate, doxepin, bupropion, taxol, and oxaliplatin. The agent could be combined by an anesthetic, or include ethanol. A gel could have any desired porosity, such as less than about 50 μm, 20 μm, 10 μm, 5 μm, or even less. The gel could include a biodegradable or bioerodable polymer, or an injectable hydrogel. The gel could include any number of the following characteristics: in situ forming, PEG-NHS, PEG-ester, a PEG hydrogel, shear-thinning, or hyaluronic acid. In some embodiments, the gel has a volume that occupies at least about 50% of the volume of the paravertebral gutter at the levels in which it is delivered to, or covers substantially the entire paravertebral gutter at the levels in which it is delivered to. In some embodiments, the gel has a volume of between about 2 cc and about 30 cc, such as between about 10 cc and about 20 cc. The gel can be delivered unilaterally or bilaterally, such as in a rostral or caudal direction, or both. The gel can be flowed at one level (e.g., via one injection site), and flow to a plurality such as 2, 3, 4, 5, 6, 7, or more levels.

In some embodiments disclosed herein is a method of selectively modulating sympathetic nerves of a patient, that includes accessing the paravertebral gutter of the patient; and protecting a first group of nerves or neurons within the paravertebral gutter from neurolysis, wherein protecting comprises flowing a first hydrogel into the paravertebral gutter in a first direction; and neuromodulating a first group of nerves or neurons within the paravertebral gutter, wherein neuromodulating comprises flowing a second hydrogel into the paravertebral gutter. The first hydrogel can include, for example a neuroprotectant. In some cases, the first hydrogel is released proximate the first rib toward the inferior cervical ganglion or the region of the stellate ganglion comprising the inferior cervical ganglion. The second hydrogel can include a neurolytic agent, and be delivered to the thoracic sympathetic ganglia and associated nerves or the thoracic paravertebral gutter.

Also disclosed herein in some embodiments is a system configured for sympathetic neuromodulation. The system can include a catheter configured for being positioned percutaneously within a blood vessel directly proximate the paravertebral gutter and for delivering a therapeutic agent to the target nerve or target neurons within the paravertebral gutter; and a first hydrogel comprising a neurolytic agent. The system can also include a second hydrogel. The second hydrogel can include, for example, a blank or neuroprotective hydrogel. The catheter can include, for example, at least one energy delivery effector, such as an RF electrode, microwave antenna, ultrasonic transducer, and the like.

Also disclosed herein in some embodiments is a hydrogel for use in sympathetic neuromodulation by delivery to the paravertebral gutter of a patient, or other anatomical locations as disclosed herein. The hydrogel can include, for example, a neurolytic active agent; and a biodegradable polymer. The hydrogel can have a porosity of less than about 50 μm in some embodiments. The gel could include a biodegradable or bioerodable polymer, or an injectable hydrogel. The gel could include any number of the following characteristics: in situ forming, PEG-NHS, PEG-ester, a PEG hydrogel, shear-thinning, or hyaluronic acid.

BRIEF DESCRIPTION OF THE DRAWINGS

FIGS. 5-5C are views of a schematic illustration of a delivery catheter system including one or more therapeutic agent housings (e.g., syringes) removably connected to a catheter configured to deliver a plurality of therapeutic agents into different anatomical locations.

DETAILED DESCRIPTION

Figure 1:
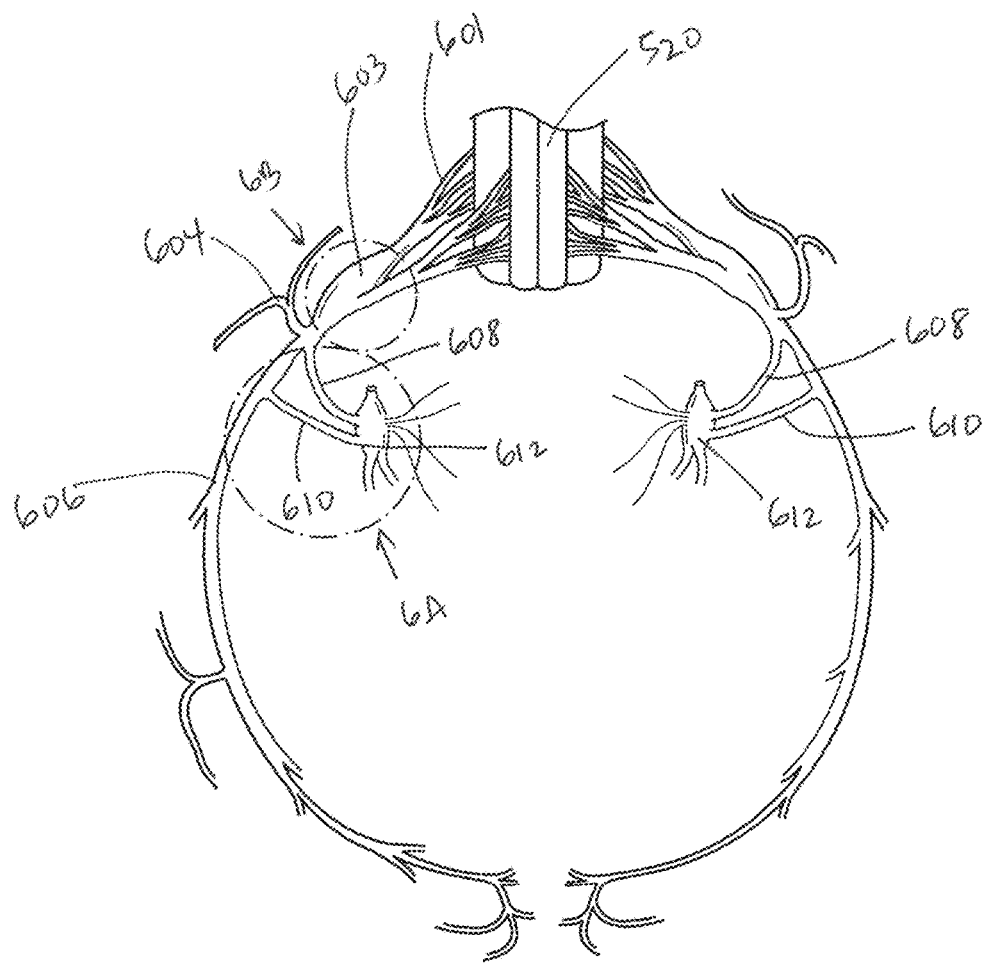
FIG. 1 illustrates neural anatomy at a single thoracic level.

Most clinicians agree that a primary cause of asthma attacks is the increased resistance of air movement through the respiratory tree due to an acute reduction in the lumen of the bronchial/bronchioles and associated finer air passages. Bronchial/bronchiole narrowing may be caused by bronchospasm of the intrinsic (and possibly hypertrophied) bronchial muscles as well as mucosal swelling. In addition, the attack may be attributed to the reduction in airway caliber as a result of edema in smaller bronchioles, bronchorrhea, and excessive bronchial gland secretion. It has also been proposed that these asthmatic air passageways are in a chronically contracted or reduced state in asthmatic patients and thus it is changes in the bronchial mucous membrane and secretions that trigger the symptoms of the acute asthmatic attack. Finally, the asthma attack may be propagated as a result of a reaction in the pulmonary blood vessels and a resultant decreased clearance of substances through either the pulmonary blood vessels or the draining lymphatics.

For treating asthma, curing or substantially improving the patient of the underlying bronchoconstriction, inflammation and mucous production can be desirable. Curing or substantially reducing the disease of the patient can result in a significant reduction or resolution of the signs of asthma. Some embodiments of the invention are directed towards reducing the forced expiratory volume (FEV1) of patients by about 5%, 10%, 15%, 20%, or more, reducing patients' rate of exacerbations, improving patients quality of life (e.g., by an improved integrated asthma quality of life questionnaire AQLQ score), increasing the percentage of symptom-free days (absence of cough, wheezing, breathlessness, sputum during day or night), reducing the number of puffs of rescue medication used, percentage of days rescue medication used, increasing morning peak expiratory flow (amPEF) and pre- and post-bronchodilator FEV1 and reducing the number of emergency department visits. Persistency of response can also be evaluated. Although the goal of some embodiments of the invention is to cure the patient of asthma, in some embodiments, systems and methods as disclosed herein can treat at least 70% of responders, at least 30% of whom are excellent or good responders, or in some cases where 50% are good or excellent responders and less than 30% who are non-responders. As the therapy is evaluated on more patients, more appropriate patient selection can allow for higher rates of responders.

Patient selection for the procedure can allow for highest response rates, particularly since severe asthma may not be a single disease as evidenced by the number of clinical presentations and outcomes. Asthma is increasingly being grouped into phenotypes which may evolve into endotypes—combinations of clinical characteristics and mechanistic pathways. For example, the Severe Asthma Research Program (SARP) identified five groups of adult asthma patients based on lung function, medication use, age at onset and frequency of exacerbations: three groups of mild, moderate and severe early-onset atopic asthma, a more severe late-onset obese group of primarily older women with moderate FEV1 reductions and frequent oral corticosteroid use, and a later-onset but long duration very severe, less atopic group, with less reversible airflow limitation. By including sputum eosinophil counts, 4 different groups of patients were generated: early onset atopic-asthma, an obese non-eosinophilic asthma, an early onset symptom predominant-asthma, and a later onset inflammation predominant asthma. In both of these grouping methodologies, severe asthmatics were distributed among several groups, supporting the heterogeneity of severe asthma. In one embodiment, the late-onset severe asthma group with high eosinophilic counts can be treated. A SARP study of asthmatic children found 4 clusters: later-onset with normal lung function, early-onset atopic with normal lung function, early-onset atopic with mild airflow limitation, and early-onset with advanced airflow limitation. As genetic and epigenetic diagnostic approaches to characterizing airway disease are developed, these may aid in the identification of patients that are best suited for a sympathetic neuromodulation approach for the treatment of asthma and other respiratory diseases.

In one embodiment, asthma is treated with a specific focus on asthma that is triggered by an allergic component. In one embodiment, patients are selected from a subset of asthmatic patients with severe resistant or severe persistent asthma. In one embodiment, patients are selected from a group of asthmatic patients with atopic asthma. In particular, some embodiments can be appropriate for patients who have severe asthma that are poor operative risks with marked limitations in cardiopulmonary reserve.

In one embodiment, the therapy may be delivered to adults above the age of 18 or adapted for treatment of the pediatric population. Care can be tailored based on patient demographics, duration of symptoms, previous and present treatments, number and type of other failed treatments, and/or other factors.

Sympathectomy was developed to help patients suffering from hyperhidrosis, excessive sweating, almost a century ago. Sympathectomy involves the division of adrenergic, cholinergic, and sensory fibers in the sympathetic trunk. Traditionally, sympathectomy is the total resection or ablation of the ganglia but the term is also used to describe the transection of the chain at the level of the rib. Occasionally, sympathectomy is also used to refer to cutting of the rami (white (also gray)) communicantes without division of the chain itself. Similar terms include sympathicotomy, which refers to transection of the sympathetic chain and sympathicolysis, which refers to destruction of the chain with a chemical agent. Sympathetic block typically refers to the placement of removable clips on the chain (thoracic blockade) or the administration of an anesthetic to the chain.

Sympathectomy was originally performed with a posterior approach that required a longitudinal incision from C7 to T4-T5 and resection of the ribs and the transverse process was required. A supraclavicular approach requiring close proximity to the phrenic, brachial plexus and stellate ganglion that resulted in a high rate of adjacent nerve damage. Endoscopic thoracic sympathectomy (ETS) was pioneered in the 1950s and more broadly adopted in the 1990s as a less invasive approach for treating hyperhidrosis, facial blushing, Raynaud's disease and reflex sympathetic dystrophy. In this anterior transthoracic procedure, a thoracic surgeon makes small incisions between the ribs and inserts an endoscope and a surgical instrument to access the sympathetic chain. The procedure offers advantages of superior visualization and lighting for more accurate delineation of anatomy, small incisions, can be performed bilaterally as an outpatient procedure, and does not require single-lung ventilation with a double-lumen endotracheal tube. The more common procedure involves single-lumen endotracheal intubation and a 5-mm trocar is inserted into the fourth or fifth interspace in the midaxillary line. The lungs are insufflated with carbon dioxide to compress lung apex away from the superior sulcus. A second 5-mm trocar is inserted at the base of the axillary hairline, through which a cautery device is used to transect the sympathetic chain over the anterior surface of the dorsal rib, sparing the ganglia themselves.

Sympathicotomy is now the most popular method to treat patients in which the inter-ganglion fibers are transected. The most recent procedure for sympathectomy is thorascopic video-assisted sympathectomy (VATS) for treating hyperhidrosis. In this procedure, two 2 mm incisions are made on each side of what and a small video camera and single dissecting instrument are passed into the chest. The incisions are so small that the procedure is called a "needle-scopic surgery." Like other methods, the sympathetic trunk is directly visualized and divided at the appropriate levels. Nearly all patients are discharged the same day and suffer only minor discomfort for a few days after the operation. Despite these minimally invasive treatment options and the safety and efficacy of the procedure, the procedure has not been widely adopted for the treatment of hyperhidrosis.

Other approaches that have not gained widespread adoption include single-port bilateral sympathectomy but this approach resulted in a higher rate of hemothorax requiring intercostal drainage.

Other approaches include radiofrequency sympathectomy, which has a largely remained the domain of hyperhidrosis.

Selective sympathectomy or ramicotomy has been developed in an attempt to decrease the incidence of compensatory hyperhidrosis (CH) in hyperhidrosis patients. This procedure preserves the sympathetic chain and divides only the rami communicantes, thereby minimizing the damage to the whole sympathetic system. The general consensus is that the rate of severe CS is lower but the technique results in a higher rate of recurrence than a conventional transection.

Long-term procedural success rates are on the order of 91 to 98%, the majority of patients requiring only once procedure. Recurrence rates of hyperhidrosis are on the order of X to 5 percent and incomplete response is typically attributed to an incomplete transection of the sympathetic chain.

Efficacy of sympathicolytic or chemical approaches to denervating the ganglia vary and have largely been applied to lumbar procedures.

Chemical sympathicolysis has also been described using phenol and alcohol (3 ml of 6.5-7% phenol and 3 ml alcohol) or phenol (7%) or alcohol alone (2.5%). In a chemical neurolysis study, n=2/23 patients had a recurrence of essential hyperhidrosis at a follow up between 8 and 18 months. Thus wider adoption of a chemical based-approach has been hampered by concerns about treatment longevity.

Efficacy of sympathicolysis varies. T2-T3 sympathicolysis with a thoracoscopic procedure resulted in 100% complete and permanent relief in treating palmar hyperhidrosis, 91% significant improvement in axillar hyperhidrosis at 1 year with 52% of patients showing a complete disappearance of hyperhidrosis.

Percutaneous chemical neurolysis has been performed in 23 patients with palmar hyperhidrosis using CT guidance to the gap of T3-T4 and then a large volume of injectate travels to the thoracic sympathetic nerve. Palmar hyperhidrosis efficacy was lower than observed with direct thorascopic sympathicolysis, curing 19/23 patients, requiring a second block with absolute alcohol in 4 patients, and in 2 patients there was recurrence at a follow-up between 8 and 18 months.

Chemical blocks are performed using anesthetics (1% lidocaine/30% iohexol, 2.5 ml 0.25% Marcaine with epinephrine for 1-10 days relief, median 4 days).

Some methods to achieve sympathectomy include:

Method of Royle. Open surgical procedure in which all rami are divided from the third thoracic ganglion to the inferior cervical ganglion and the trunk is severed just below the inferior cervical ganglion and third thoracic ganglion.

Method of Adson. Open surgical procedure in which all intervening rami from the second thoracic ganglion to just above the inferior cervical ganglion are divided and the trunk is severed above the inferior cervical ganglion and below the second thoracic ganglion.

Method of Leriche. Open surgical procedure in which the intercostal nerve is retracted upwards and the rami that enter the under surface of the nerve are transected. This approach is thought to be suitable only for mild cases.

Method of Levin. A minimally invasive approach in which, at a point 4 cm away from the spine, preferably in the third or fourth interspace (or T3-T6), a needle is introduced directly to the inferior margin of the rib at a 45 degree angle to a depth of about 2 cm. Precautions are taken to guard against perforation of the pleura the needle is pushed further towards the spine and 2.5 cc of absolute alcohol in injected in a series of small spurts. Occasionally the transverse process is bulky and obstructs the desired trajectory of the needle and then the needle is directed to travel immediately in front of and below the process. Four injections, once a week, are given followed by a month's rest, and then another series of four injections are administered should any trace of asthma persist. There is rarely any radical improvement until after the second or third injection. Case studies demonstrated complete disappearance of asthma in 100% patients (n=5) with some patients requiring only two injections while others required nine. Further work resulted in 72% (13/18 cases) with complete relief.

Modified Method of Levin. At a point about 3 cm from midline a solid cutting needle is introduced down to the lower border of the rib and is directed 50 degrees forwards, inwards, and downwards until the transverse process of the corresponding vertebra if felt. The upper margin of the rib is then followed by the fingertip to a point directly opposite the level of the process. A strong lumbar puncture needle is introduced on a slant from below so as to strike the upper margin of the rib immediately under the fingertip. The needle is then cautiously pushed upwards, inwards, and forwards closely hugging the upper margin of the rib for a distance of about 2.5-3 cm. Perforation of the pleura can be avoided provided the needle is closely applied to the upper boundary of the rib slightly on the posterior plane. The needle is then rotated to an angle of 90 degrees and the orifice of the needle is now directly behind the thoracic trunk. Assuming the pleura is intact, 1 cc of absolute alcohol is injected and the needle withdrawn. X-ray can be used to confirm the needle position. This procedure can be done for the third and second interspaces as well as the fourth but the maneuver is more challenging on account of the greater depth of the ribs. In case studies 100% of patients (n=3) were free of asthma and in further cases, 80% (⅘) obtained complete relief.

Percutaneous ablation is also largely the domain of lumbar sympathectomy. For thoracic approaches, percutaneous injection have relied on CT images for guidance based on anatomic landmarks. Direct visualization of the ganglia may not be possible using CT. The needle can be positioned at the tip at the upper joint of the costal head beside the T3 body and outside of the costal pleura. There is a lot of controversy about which level to denervate to ensure the greatest success with the least risk of compensatory hyperhidrosis. Most clinicians believe that the extent of compensatory sweating depends on the level or the extent of sympathectomy. Some physician performed electrocoagulation between T2 and T3 for palmar hyperhidrosis, T3 and T4 for axillary hyperhidrosis, and T2 and T4 for palmar and axillary hyperhidrosis.

In a 121 palmar hyperhidrosis patient study in which 61 patients underwent second rib (R2) transection and 60 patients underwent third rib (R3) transection, the failure rate was only 4.1% and there was only a slightly higher trend towards compensatory hyperhidrosis in the R2 group over the R3 group.

In a 141 patient study in which 68 patients underwent T3 and 73 patients underwent T4 sympathicotomy, all patients were effectively treated for their palmar hyperhidrosis. Improvement was more dramatic in the T3 group than the T4 group but the incidence of compensatory sweating and overly dry hands was lower in the T4 group than the T3 group. More patients were very satisfied in the T4 group than T3 but the 'partially' satisfied rate was comparable between the two groups.

Failure, or recurrence of hyperhidrosis, is largely attributed to incomplete interruption of the sympathetic chain. Nerve regeneration that occurs 2 to 5 years post-operation is thought to be a late result of incomplete destruction of the sympathetic chain or sympathetic ganglion. Hyperhidrosis recurrence occurs on the order of 0 to 7.6%. Similarly, reoperation rates are on the order of 0 to 3.2% and these procedures are typically successful.

If there is reoccurrence of sweating after treatment of IPPH, it is thought to occur within the first two years. Although there have been no large controlled studies to compare outcomes between surgical transection and resection, late recurrence of hyperhidrosis is thought to occur more frequently with a transection rather than a resection procedure.

Regeneration in thoracic or lumbar etc. can result in abnormal nerve sprouting after injury to the nerves. Sympathetic nerves may form aberrant connections with sensory nerves leading to pain.

Landmarks:

The ribs are an excellent landmark to guide surgeons on the level of the ganglia. The neck of the first rib is usually covered by a fat pad protecting the second ganglion. The second thoracic ganglion is consistently located in the second intercostal space. The third, fourth, and fifth ganglia are not consistently located in the corresponding interspaces and can be hard to visualize surgically.

Lumbar.

In the lumbar region, sympathetic block can be performed. The procedure is more straightforward because it does not involve the lungs. Typically an IV sedative, a local anesthetic is administered, contrast is injected, and a fluoroscope is used to identify painful areas to correct the location of the needle tip to assess location. To the inventor's knowledge, here are no needle based procedures for performing sympathectomy that are currently in use in either the thoracic or lumbar region.

Lumbar.

In the lumbar spinal cord, a temporary sympathetic block can be performed with a 19-gauge needle (12-18 cm long) delivering 15 ml of an anesthetic (Marcaine) to L1 or L4-L5. Insertion points are at the level of junction of $12^{th}$ rib and erector spinae muscles for L1 and the level of line drawn between posterior iliac crests for L4/L5.

Lumbar.

The retroperitoneal surgical technique is performed with an oblique incision from the lateral edge of the rectus towards the middle of the space between the ribs and the iliac crest ending at the anterior axillary line. The lumbar sympathetic chain is located medial to the psoas muscle overlying the transverse process of the lumbar spine. On the left side, it is adjacent and lateral to the aorta and on the right side it is beneath the edge of the inferior vena cava.

Alternate Celiac—

Celiac plexus block has conventionally been used to guide a celiac plexus block, also the CT-guided anterior approach and the endoscopic ultrasound-guided approach. New approach is the ultrasound-guided anterior approach to celiac plexus neurolysis with median plane single-needle entry to the preaortic area between the celiac trunk and the superior mesenteric artery.

Alternate—Paravertebral Block

Anesthetic is injected into the space where spinal nerves emerge from the intervertebral foramina. The result is an ipsilateral somatic and sympathetic nerve block of the respective dermatome. A single-side injection involving a larger volume (~15 cm3) at one or more paravertebral spaces or a multiple site smaller injection (3-4 cm3) volume at multiple levels, usually as many as 6 levels.

A handful of studies were published in the 1930s demonstrating the potential of dorsal sympathectomy for treating asthma.

In 1935, Levin published his work treating bronchial asthma by dorsal sympathectomy. From Levin's perspective, the sympathetic action is entirely reflex and "from a practical point of view, it matters little whether the sensory or motor branch of the reflex arc is severed; in neither case will exciting stimuli provoke a response (Levin 1935)." Levin goes on to provide this rationale that sympathectomy is a sure method by which to severe all sensory sympathetic stimuli and thus also disrupt or eliminate the motor half of the reflex arc. The procedure specifically denervates bronchial constrictor nerves derived from the second to the sixth dorsal rami.

Levin performed alcohol injection on 23 cases and obtained complete relief in 75% of patients with varying degrees of improvement in the remainder of the patients. Cessation of asthma was observed for between four months and over ten years in the patients have been followed. Resistant cases were chiefly those patients with emphysema and collapse of the lung. Perforation of the pleura occurred in 13% (3/23 cases) with no serious consequences. Levin recommends the rami be treated immediately below the point of junction with the intercostal nerves and the trunk divided above the level of the neck of the fourth rib.

Wilensky also concluded that more minimally invasive approaches were more desirable and resulted in more favorable results than more radical and invasive procedures such as posterior pulmonary plexus denervation (Wilensky 1940), which denervates the majority of the parasympathetic and sympathetic innervation to the lung. Wilensky performed the Levin procedure in 18 patients and 78% (14/18) had considerable improvement and, although all patients experience some degree of relief, 22% (4/18) did not have long-term improvement or the improvement was transient. Of the 14 patients, 6 were completely cured (43%), 4 were markedly improved with a great reduction in number and severity of attacks (29%), and 4 had slight relief with less frequent and milder attacks (29%). Some patients were cured for over four years.

Carr and Chandler performed an open surgical procedure to resect T3 and T4 ganglia bilaterally on 3 patients and T2 to T5 bilaterally on 2 patients. All patients demonstrated dramatic clinical improvements in their asthma symptoms and returned to work. Patients were followed up for as long as 10 years and improvement was sustained (Carr and Chandler 1948).

Abbott also performed single (right or left) and bilateral dorsal post-ganglionic sympathectomy on 14 patients with promising results: 29% cure (4/14), 64% responders with over 50% reduction in degree of asthma, and 35% no improvement (Abbott, Hopkins et al. 1950). Based on underlying co-morbidities, Abbott observed that patients that did not have major associated pulmonary suppuration or destruction had complete cure but those with destructive pulmonary suppuration such as emphysema did not respond as well. Results on a second cohort of patients receiving partial or complete pulmonary plexectomy and high right vagotomy were not improved over the dorsal sympathectomy cohort and were arguably worse (Abbott, Hopkins et al. 1950). Generally, dorsal sympathectomy does not result in any improvement in cough while high vagus resection can be of considerable value. However, dorsal sympathectomy in patients with severe bronchorrhea demonstrated substantial reductions in sputum production.

In addition to sympathetic denervation approaches, several parasympathetic denervation approaches have been developed including division of the right vagus at or below the level of the recurrent laryngeal nerve ((Abbott, Hopkins et al. 1950; Blades, Beattie et al. 1950)). These have then been combined with sympathetic approaches to yield extensive dual sympathetic/parasympathetic denervation: combining denervation of the pulmonary plexus (pulmonary plexectomy), dorsal sympathectomy, division of all branches of the vagus to the pulmonary hilum and lung below the recurrent laryngeal nerve, and stripping of the sheaths around the pulmonary artery and veins (Gay and Reinhoff 1934; Abbott, Hopkins et al. 1950; Blades, Beattie et al. 1950). In fact, some argue that complete sympathectomy is believed to be possible only by transecting the pulmonary plexus, denuding the main bronchi, and the great pulmonary arteries and veins (Dimitrov-Szokodi, Balogh et al. 1957). Gobell maintains that bilateral thoracic sympathectomy and vagal transection yield the best results in asthmatic patients with over 60% cured or improved (referenced in Feinberg, 1935).

Dimitrov-Szokodi demonstrated that by blocking the vagosympathetic pathway in the neck (resection of the branches of the vagus from the recurrent nerve to the pulmonary ligament) and the thoracic sympathetic chain paravertebrally (T2-T5 sympathetic ganglion removal via transection of the rami communicantes) that it is possible to halt a histamine-induced asthmatic attack in asthmatics (n=18). The group observed for the most part a reduction of mucous membrane inflammation and swelling, reduction of sputum production, reduction in eosinophilia. The group also observed a reduction in asthmatic signs, an indirect improvement in emphysema and a reduction in bronchospasm. On average, patients have an increase in vital capacity of about 18% and rise of 16% in average pulmonary ventilation rate. Finally, the heavy and frequent asthma attacks accompanying the condition had either stopped (10/18, very good) or were considerably reduced (7/18, good).

In summary, clinical data suggests that interruption of either the sympathetic or parasympathetic arms produces comparable results in the relief of asthma even though they are thought to have antagonistic motor effects, supporting the theory of a reflex arc. Interruption of the sympathetic or the vagus is sometimes curative, frequently beneficial and sometimes ineffective. Roughly 50 to 70% of patients are definitely improved while the 30 to 50%, after temporary improvement, are in no better condition than before the operation. The approximate 30-40% of patients who have been cured have been followed for 2 years or more.

Finally, patients whom fail a parasympathetic or sympathetic procedure that go on to have the other arm of the autonomic system denervated have the most disappointing results. This is likely because a neurogenic mechanism does not play a role in these patients and therefore they will not obtain relief from operation on any extrinsic neural pathways.

Newer studies. More recent studies evaluating pulmonary function after sympathectomy for the treatment of hyperhidrosis in patients with no lung disease have found no or only mild changes in pulmonary function and mild increases in airway resistance, small decreases in heart rate with preserved left ventricular function and ejection fractions, and also preserved exercise tolerance.

Gonzalez et al (2005) evaluated pulmonary function in 37 patients undergoing sympathectomy for primary hyperhidrosis. Patients with otherwise normal lung function demonstrated a 5.2% decrease in forced vital capacity (FVC), FEV1 and the forced expiratory flow (FEF) between 25 and 75% of vital capacity was decreased by 5.1% (Ponce Gonzalez, Serda et al. 2005). There were no differences in peak expiratory flow (PEF), however, and all patients remained asymptomatic. Three patients who were positive on methacholine challenge prior to surgery but 6 patients were positive after the procedure (not statistically significant). After 12 months, the forced vital capacity started to recover (+1.5%) but forced expiratory volume (FEV1) and FEF showed sustained reductions. The authors conclude that sympathectomy results in a mild impairment in bronchomotor tone with no clinical consequences.

Two patients in this series had asthma that were in stable condition and had a positive methacholine challenge test at baseline and after the procedure but the provocative methacholine concentration (PC20) was not higher. Furthermore, during follow-up, they experienced neither particular respiratory symptoms nor the need for rescue bronchodilators suggesting that their condition had not worsened (Ponce Gonzalez, Serda et al. 2005).

Ben-Dov reported no or mild effects on lung function after sympathectomy.

In a more recent study, Fredman and colleagues report worsening of asthma in some patients after thoracic sympathectomy. In their series of 626 patients, 14 of their patients experienced asthma before sympathectomy (Fredman, Zohar et al. 2000). After sympathectomy, 5 reported no change in the frequency or severity of their asthma, 1 described an improvement in their symptoms, and 8 reported a worsening of their asthma symptoms. In this subset of patients, 57% described an increase in the number and severity of asthma attacks. However, these adverse symptoms were not cited by the patients who regretted having undergone the procedure. Adar and colleagues reported non-specific mild respiratory complaints in 20% (18/93) patients that were followed up at around 18 months after the removal of T2/T3 ganglia for the treatment of plantar/palmar hyperhidrosis (Adar, Kurchin et al. 1977). In addition, in 2 patients there was a re-exacerbation of childhood bronchial asthma and in one patient there was reported cessation of attacks of asthma after the operation. This was a supraclavicular approach that also requires retraction of the phrenic nerve and so some of the side effects may be related to the invasiveness of this surgical approach.

There has been a resurgence of interest in recent years in the use of paravertebral blocks with anesthetics to temporarily alleviate pain after thoracic or thoracoabdominal surgery. These blocks are used for thoracic procedures including breast surgery, rib fractures, video-assisted thoracic surgery (VATS) and minimally invasive cardiac surgery. Depending on the extent of the surgery, paravertebral blocks can be a unilateral single needle-injection to a bilateral continuous catheter-delivered block. Unilateral thoracic paravertebral blocks (TPVB) can be performed to temporarily achieve anesthesia and analgesia when the afferent pain (somatic, sympathetic) input is predominantly from the unilateral chest, such as fractured ribs. Bilateral TPVB have also been used perioperatively during thoracic, video-assisted thoracoscopic surgery, appendectomy, cholecystectomy and breast surgeries to achieve postoperative analgesia. This can be achieved by delivering local anesthetic to the region to achieve ipsilateral somatic and sympathetic nerve blockade in multiple contiguous thoracic dermatomes above and below the site of injection. The technique is considered simple and easy to learn and safer and easier than a thoracic epidural. It is safe to perform in sedated and ventilated patients and does not require palpation of the ribs. There is a low incidence of complications.

An example of the different levels that the block can be performed depending on the target organ is provided below:

TABLE 1

Thoracic paravertebral levels to deliver therapy treat conditions affecting a given target tissue.

| Target Tissue | Continuous Paravertebral Block | Single Paravertebral Block |
|---|---|---|
| Breast | T1-T2 | T2-T6 |
| Esophagus/Stomach | T2-T3, bilateral | |
| Lungs/Thorax | T4-T5 (classic) or T5-T6 (intercostal) | |
| Liver | T6-T7, bilateral | |
| Abdomen | T8-T9, bilateral | |
| Pelvis (rectum, uterus, prostate) | T11-T12, bilateral | T10-L1 |

The purpose of these blocks is to temporarily block nerve conduction in the afferent fibers conveying pain signals as can be measured with the halt of somatosensory evoked potentials (SEPs).

In the paravertebral block approach, approximately 5 to 10 ml of anesthetic (1%) or analgesic (0.5%) is slowly injected. Motor blockade outside of the surgical dermatomes is minimal with an anesthetic. Failure rates associated with paravertebral blocks is published on the order of 6-10% and is thought to reflect the challenge in defining the paravertebral space. Compared to the epidural block, the paravertebral anesthetic block infrequently results in hypotension, does not carry the risk of postoperative nausea and vomiting, urinary retention, or pruritus. Also, it does not carry the risk of respiratory depression and the preservation of forced vital capacity after thoracotomy is improved (75% vs 55%).

Complications of these approaches include pleural puncture (around 1%), pneumothorax (0.5%), hematoma (2.4%), vascular puncture (3.8-5%), epidural or intrathecal spread. Pneumothorax is the most dreaded complication of the procedure in the ambulatory setting and is more likely to occur between T1 to T8 than T10 to L3. Epidural spread typically results in transient hypotension and bilateral lower limb weakness (~5%). Epidural spread can be avoided by taking a perpendicular approach to the skin as the spinous process is approach as opposed to a more lateral/medial angle and reducing the anesthetic administered to less than 15 ml. For example, by administering 5 ml of anesthetic in multiple levels, administering 5 ml of anesthetic followed by 10 ml of anesthetic at a later time, this complication can be avoided. Dural puncture and subsequent intrathecal needle placement and anesthetic injection is more problematic, particularly at T4 or higher, as patients most patients will require intubation or artificial ventilation until the effects of the injectate dissipate. These complications may be dramatically reduced with the use of ultrasound guidance and slowly delivering the anesthetic. One report found that 4 to 10% of patients have clinical significant parasympathetic discharge at needle placement resulting in hypotension, bradycardia and near syncope. To give perspective though, these complications are comparable to or less than the levels with other blocks such as epidural, intrapleural, or intercostal blocks.

These percutaneous approaches can be adapted to deliver agents or therapy to the sympathetic chain and rami to treat asthma and other pulmonary or cardiac conditions. More specifically, the direct percutaneous needle or catheter access to this space and can be used to deliver neuroablative agents or neuroablative therapy to the paravertebral space and specifically to the sympathetic afferents and/or efferents.

In one embodiment, the patient is placed in a seated position or alternately in a lateral position. Ideally, the treatment should be performed in an area with adequate monitoring and resuscitation equipment. The procedure can be performed with or without sedation. If sedation is needed, in one embodiment a combination of midazolam and fentanyl can be given to the patient and re-administered as necessary. The injection site is disinfected with chlorhexidine and anesthetized with 1% lidocaine delivered with a 25 gauge safety needle (3.75 cm). Typically, an 18- to 22-gauge Tuohy needle is employed to perform the procedure. A 25-gauge spinal needle may be used initially as a transverse process 'finder' needle.

In one method, the needle is inserted 3 to 4 cm lateral to midline aligned with the caudal end of the spinous process. The needle is advanced at a 90 degree angle to the skin in all planes to strike the transverse process or the head of the rib at a depth of about 2.5 to 3 cm. Following contact with the transverse process, the needle is walked off the lamina and advanced 1 to 2 cm in the angle of entry to the coronal plane either at the level above or below it. The angle is not to exceed 90 degrees to the coronal plane to avoid pneumothorax. The needle can be advanced with or without redirecting medially for 1 to 2 cm, as needed, or until the vertebral body is contacted.

Another approach involves inserting a needle 1 cm from midline at the level of the intervertebral foramen and advancing the needle in a perpendicular plane until it contacts the lamina. The needle is then walked off the lateral edge of the lamina and advanced 1 cm to deliver the anesthetic.

Yet another modification is inserting the needle perpendicular to the skin to contact the posterior transverse process. The needle is then withdrawn to the skin and redirected beyond the transverse process at a 15 to 60 degree angle to deliver the needle below the transverse process. A loss of resistance may be felt as the costotransverse ligament is pierced.

Yet another modification to the approach is to insert the needle 2.5 cm from midline at the level of the intervertebral foramen and walk it off the lamina and then advancing it 1.5 cm deeper at a 45 degree angle to the skin.

In yet another embodiment, the needle is advanced inplane between 2 transverse processes and positioned past the costotransverse intercostal ligament and posterior to the parietal pleura before 5 to 10 ml of anesthetic is delivered slowly. If the anesthetic is delivered in the right place, the pleura will be pushed anteriorly.

Approximately 5 to 10 ml of neuroablative agent are slowly injected after negative aspiration for blood. Also, a 'drop technique' may be employed, in which a drop of ropivacaine is placed on the top of the needle and the patient is asked to breathe deeply. If the ropivacaine drop follows the breathing pattern, the needle is through to be intrapleural/in the lung. If the ropivacaine drop is not affected by the breathing pattern and no blood is aspirated, the needle is connected to a tubing to allow for the slow injection of 5 ml of anesthetic with a 10 ml syringe. The injection should not offer a lot of resistance. If the block is continuous, a 22-gauge catheter can be introduces into the paravertebral space, typically 3 to 4 cm beyond the tip of the needle, and the needle withdrawn.

In this approach, multilevel paravertebral block or ablation can be achieved by introducing the needle or catheter at the thoracic third or fourth level and injecting approximately 10 ml of the agent.

In one embodiment, the delivery of 15 to 20 ml of a neuroablative agent to one level is as effective at achieving multi-level ablation as injecting 5 ml each in multiple adjacent injections. If a wide block is desired, however, it may be preferably to do multiple injections or 2 injections several dermatomes apart.

An intercostal approach takes advantage of the continuity between the intercostal and paravertebral spaces to deliver a neuroablative agent or therapy from an adjacent site. Using this technique, the segment to be treated is targeted via the corresponding intercostal space. This approach is more superficial and may be safer than the classic paravertebral access approach. This approach may have a lower risk of pneumothorax, hematoma, infection, neuraxial blockade, or vasovagal response. Thoracoscopic blocks using this approach are typically placed at level T5 or T6.

In one embodiment, a 5 cm, 18 G Tuohy (introducer) needle is inserted at a point 8 cm lateral to the midline and advanced into the intercostal space to make contact with the rib. When the contact is established, the needle is reoriented 45 degree angle rostral and 60 degrees medial to the sagittal plane to contact the lower third of the rib. The needle is then walked off the inferior border of the rib at the same orientation with the bevel oriented medially and advanced an additional 3 to 10 mm, more preferably 3 to 6 mm, under the rib to lie in the subcostal groove. After the slow injection of about 5 ml of anesthetic (ropivacaine, 0.5%), a 20 to 22 gauge catheter is advanced medially in the intercostal space through the needle toward the paravertebral space. In this approach, the needle orientation reduces the risk of pleural puncture. The catheter is advanced about 8 cm from the site of introduction of the needle and the introducer needle is removed. After the catheter is secured in place, an additional 10 ml of neuroablative agent is injected slowly after confirming negative aspiration of blood.

As with other approaches, one injection or one continuous delivery can provide multiple levels of paravertebral blockade. Injection of 10 ml of contrast or chemical agent through the intercostal catheter results in both extrapleural and paravertebral spread over multiple levels, typically 2 levels rostrally and 3 levels caudal to the catheter tip.

In the case of single injection, between 1 and 20 ml, more preferably 3 to 10 ml, more preferably 5 ml may be delivered to the paravertebral space. In the case of continuous delivery, an agent may be delivered at 7 to 10 ml/hour, more preferably 7 ml/hour, although bolus dosing of 3-5 ml may be employed as necessary to reach a particular adjacent dermatome.

In another embodiment, a single dose of anesthetic is delivered first prior to delivery of the neurolytic agent, to confirm appropriate placement of the chemical agent. Similarly, a single dose of anesthetic can be co-delivered with contrast agent.

In one embodiment, this approach is developed and the chemical agent is administered over a period of several days, most preferably several days, in order to achieve complete disruption of the sympathetic chain.

In another embodiment, contrast can be delivered to the site to confirm the spread of the injectate. A period of time, between 5 and 15 minutes, allows for the diffusion or clearance of the injectate from the site. At this point, 5 to 15 ml of neuroablative agent is delivered to the same region as the contrast.

Alternatively, contrast can be mixed with neuroablative agent and the spread of the agent can be confirmed intraprocedurally.

Injection of a neuroablative agent into this space will diffuse freely through the retropleural space, bathing the spinal nerves, the sympathetic trunk and its rami and the cardiac nerves which run anteriorly into the posterior mediastinum (T1 to T4).

While diffusion of a liquid or chemical agent through the rib and the posterior intercostal membrane is not possible, injected solution readily spreads around the internal aspect of the rib and through the internal intercostal muscle to gain access the subpleural space. From here, the injectate passes between the ribs and the pleura to the adjacent intercostal spaces by passing through the flimsy fibers of the internal intercostal muscle. Volumes of 3 ml or more will spread medially in the fascial planes to enter the paravertebral space and surround the sympathetic chain and have been used to achieve pain relief after cholecystectomy. Thus, in one embodiment 3 to 5 ml of a neuroablative agent injected at a point 7 cm from midline at approximately 3 mm beyond the lower edge of the rib. The injectate will travel within the intercostal space and may continue on to paravertebral space to surround the sympathetic chain. Depending on the volume and direction of the injectate, one injection or administration of therapy may be targeted to multiple adjacent intercostal and or paravertebral levels. An advantage of injecting at this lateral location is that the distance from the lower edge of the rib to the pleura is about 8 mm, leaving space for the needle. In another embodiment, more controlled destruction of the nerves can be desired. In this case, multiple bilateral levels can be injected with smaller volumes of neuroablative agent to achieve the same therapeutic effect.

In another approach, a posterior intercostal nerve block approach can be adapted to take advantage of the continuity between the intercostal and paravertebral spaces. In one embodiment, the neuroablative agent or therapy is injected or delivered, respectively, directly into one intercostal space to provide therapy to several adjacent dermatomes. Provided sufficient volume of an agent is delivered, the neuroablative agent may travel medially through the intercostal to the paravertebral space where it then spreads to longitudinally within the paravertebral gutter to multiple dermatomes. Care should be taken to avoid subpleural spread with this technique.

In another embodiment, a needle or catheter can be advanced into the extrapleural space between the pleural and the intercostal muscles and a pocket or potential space created full of neuroablative agent. The pocket can be a single level or extend over multiple rib levels.

In another embodiment, the catheter is directed into the subcostal groove and neuroablative agent is delivered entirely within one intercostal space. In yet another embodiment, the catheter is directed medially into the intercostal space itself, and neuroablative agent is delivered over three to 5 intercostal spaces.

In yet another embodiment, a catheter can be extended up the paravertebral gutter for two to four or five levels.

A modification of this technique is also described in which a patient is sits upright and the skin is pierced in the same transverse plane as the most caudal tip of the spinous process. A skin wheal is made at a distance of 3-4 cm lateral to the midline in the thoracic region. The surrounding paraspinal muscles are then infiltrated with local anesthetic as well. A 22 gauge 9 cm spinal needle is inserted through the wheel and the stylet removed. A 10-ml syringe containing 0.5% lidocaine is attached to the hub of the spinal needle and the needle is advanced to the vertebral lamina maintain a 45 degree angle to the coronal plane with medical direction. By starting at a 45 degree angle and gradually increasing it to no more than the perpendicular, the technique assures that at no time the needle is directed towards the pleura. In average sized patients this translates to a depth of 5 to 6 cm and somewhat less in women. Once the lamina is contacted by the syringe and aspirated for blood or cerebrospinal fluid, a small volume of anesthetic is delivered into the periosteum to provide further anesthesia for the block. Then a hemostat to be used as a depth marker is placed on the needle at a distance of 1 to 1.5 cm from the skin while the needle remains in contact with the lamina. Holding the hemostat in one hand and the syringe in the other, the spinal needle is withdrawn almost to the skin, redirected slightly laterally and readvanced in the same transverse plane with a greater angle to the coronal plane. This is continued until the needle is walked laterally off of the lamina and is able to be advanced to a depth at which the hemostat is in contact with the skin. Following negative aspiration of air, blood, or CSF, a 3 ml test does of lidocaine is injected. Three minutes later, the remainder of the dose of anesthetic can be slowly injected. Typically, a total of 4-5 ml are injected per spinal segment. Keeping the patients upright for 10 minutes can enhance the longitudinal spread. Depending on the volume of anesthetic used, block could be achieved anywhere from two to ten spinal segments. This method results in anesthetic deposited around the dural sleeve (peridural) as well as paravertebral space. As a result, sensory and sympathetic (and motor) block is achieved.

These blocks have also been performed using phenol neurolysis for cancer pain. Intrathecal injection is rarely observed (0.52%) as is transient hypertension (4.6%) and bilateral sensory blockade (1.3%), although there were no permanent sequelae.

Multi-level sensory blockade can be achieved up to 93%.

This approach is also used to treat reflex sympathetic dystrophy by some authors.

Approaches to confirm needle location include loss of resistance, pressure drop, neurostimulation, and ultrasound guidance are also disclosed.

Loss of resistance techniques can be used to confirm entry into the paravertebral space and are performed with an 18 gauge or lower Tuohy needle and a loss-of-resistance syringe filled with saline or air. The needle is simply advanced until the resistance is lost, indicating that the superior costotransverse ligament has been traversed.

The pressure transducer approach involves connecting a 18-gauge Tuohy needle to a pressure transducer via pressure tubing. When the needle enters the paravertebral space, the pressure drops but the needle should be advanced very carefully.

The neurostimulation technique involves using an insulated 18-gauge or 22-gauge Tuohy needle connected to a nerve stimulator delivering a current of 2.5 to 5.0 mA with a pulse duration of 0.1 milliseconds and a frequency of 2 Hz. When the needle is near the nerve bundle, a motor response is elicited as evidenced by the intercostal or abdominal muscles. The intensity of contraction is generally recognized to be related to the distance between the needle and the intercostal nerve. The ideal position of the needle is when the muscle response is maintained with a current less than 0.5 mA.

A low frequency ultrasound probe can be connected to an ultrasound machine (e.g. S-Nerve, Sonosite) parallel to the spinous process. The scan improves guidance during the 'classic' posterior paravertebral approach by providing identification of the transverse process, the costotransverse intercostalis ligament, the pleura, and the lung dynamically. Asking the patient to breath during this approach helps to facilitate the scanning. Similarly, ultrasound assists in the intercostal approach to the paravertebral space (10 to 15 MHz probe) by providing identification of the ribs and the pleura. As with the former approach, asking the patient to breath during imaging assists in visualizing lung movement. By rotating the probe over the long axis of the rib and tilting it, the external intercostal muscle and internal intercostal membrane can be identified, allowing placement of the needle between the internal intercostal membrane and the parietal pleura.

A variety of similar anesthetic block techniques can also be adapted for this purpose including: continuous intercostal nerve block, extrapleural intercostal nerve block, extrapleural paravertebral block, retropleural analgesia.

A multi-level (dermatome) paravertebral block can be achieved as followed. An 18-gauge Tuohy needle is inserted perpendicularly into the skin at the level of the T6-T7 interspace, 2.5 cm laterally to the tip of the spinous process, then further until the transverse process was reached. The needle is then slightly withdrawn and redirected rostrally at a 45 degree angle to the skin for up to 1.5 cm deeper than the depth of the bone contact. The catheter is then inserted through the needle 1 to 2 cm beyond its trip.

22-gauge Quincke spinal needles, 22-gauge blunt nerve block needles (Epimed Intl), 20 gauge radiofrequency blunt needles (Cosman Medical) can be utilized in some embodiments.

If a minimally invasive, endoscopic, or thoracoscopic procedure is desired, there are several approaches to transecting or ablating the nerves within the paravertebral foramen. In addition to cervicothoracic ganglionectomy at the desired levels and division of the rami communicantes, the following transection points can be done to reduce the likelihood of regeneration:

1) Transect lateral to the posterior root ganglion,
2) Transect the anterior and posterior root separately at a point just medial to the posterior root ganglion (extraspinal root section)
3) Transect the posterior root at a point just medial to the posterior root ganglion and then transect the anterior root more medially within the arachnoid
4) Transect the communicating rami through clipping or dividing.
5) Transection of the anterior root intraspinally.

If deemed necessary, a biocompatible suture or cuff or cylinder may be secured around the nerve stump to provide additional protection against nerve regeneration.

Access can be achieved with a 14/1000 guide wire through a commercially available 6-12 French steerable sheath.

The development of minimally invasive or percutaneous approaches to performing sympathectomy has been hampered by concerns about inadvertent damage to the intervertebral artery or veins. Hemothorax requiring pleural drainage occurs on the order of 2.5% in surgical thoracic sympathectomy procedures for the treatment of palmar hyperhidrosis. Accidental dissection of an intercostal vein can result in 300 to 600 ml blood loss during dissection of the sympathetic chain. Thoracoscopic procedures are careful to avoid dissection of the arteries and veins in the region, particularly on the right side as significant bleeding can result. Inadvertent damage and thus troublesome bleeding occurs more frequently when the vessels run anterior to the sympathetic chain.

Neural Circuits

Clinical research suggests that neural control of the heart and lung is abnormal and that neurogenic mechanisms may contribute to the pathogenesis and pathophysiology of acute and chronic cardiopulmonary disease. The maladaptive neural responses to disease are thought to originate from one or more of the: 1) parasympathetic afferent and/or efferent arm, 2) the sympathetic afferent and/or efferent arm, 3) 'intrinsic' peripheral neural circuits that lie within or just external to the lung or heart, 4) neural circuits between the lung and heart, 4) the central nervous system (CNS), and 5) the somatic nervous system.

Parasympathetic. There is general agreement that vagal efferent fibers primarily control airway smooth muscle tone (bronchoconstriction) and possibly mucus secretion. Vagal afferent fibers carry information on tracheobronchial pain and mediate the cough reflex. The vagal efferent fibers may become hypersensitized and trigger cholinergic reflex bronchoconstriction upon stimulation of sensory receptors in the airways by inflammatory mediators like histamine, bradykinin, and prostaglandin. Sympathetic arm control. The role of sympathetic efferent fibers and sympathetic sensory afferent fibers (or spinal cord-derived sensory fibers) in the initiation and persistence of asthma is poorly understood. Several studies and theories support for sympathectomy in the treatment of asthma since it may 1) disrupt the reflex spasm of the pulmonary veins allowing asthmogenic substances that have been trapped in the lung capillaries to be more effectively cleared from the lungs (Feinberg 1935) 2) resensitize the chronically constricted bronchial mucosa and pulmonary blood vessels to epinephrine and norepinephrine and other blood-born mediators, which exert a local effect in the lung by shrinking bronchial mucosal membranes and reducing secretions (Freeman, Smithwick et al. 1934; Balogh, Dimitrov-Szokodi et al. 1957) 3) overcome vagotonia, 4) neurolysis of the thoracic sympathetic ganglia and rami with absolute alcohol injections results in a cure or dramatic improvement in asthma in 75% of severe intractable asthma cases (Levin 1935). Excitatory non-adrenergic non-cholinergic neurons (eNANC). eNANC neurons may play a major role in neurogenic inflammation resulting in 1) increased afferent innervation in bronchi and vessels 2) increased sensitivity to substance P (SP) and neurokinin A (NKA) resulting in enhanced maximal contractile smooth muscle cell force in response to allergens, 2) hyperreactivity/hyperalgesia of airway sensory nerve endings, possibly due to epithelial shedding and exposure of these nerve terminals to mediators such as bradykinin; prostaglandins and cytokines; 3) Upregulation of sensory neuropeptide effects in asthmatic airways either through increased peptide production, increased NK1/NK2 receptor expression, or reduced peptide degradation. These neurons may travel with the parasympathetic and/or sympathetic system. Since asthmatic subjects have rapid and exaggerated bronchoconstrictor responses to a wide variety of stimuli, bronchial hyperreactivity may be triggered by a preponderance of excitatory (cholinergic and eNANC), a deficiency of inhibitory ($\alpha$-adrenergic receptors, reduced $\beta$-adrenergic receptors, iNANC) control, increased inflammation (mast cells) or due to a maladaption in the capacity for catecholamine clearance and or reuptake (norepinephrine reuptake transporter (NET)). A related hyperreactivity or hypersensitivity has been observed in the heart.

Some embodiments can modulate the activity of these hypersensitive feedback loops in order to restore function, possibly through the process of recalibrating or desensitizing the neural feedback or through deliberately the hypersensitizing an aberrant hyposensitive arm. Generally, then, therapy may be directed at modulating the extrinsic circuits from the heart and the lungs such as those within the sympathetic afferent—CNS—efferent feedback loop, the parasympathetic afferent—CNS—efferent feedback loop, or broadly from, for example, sympathetic afferents to the CNS to parasympathetic efferents or vice versa. In another embodiment, therapy may be directed at intrinsic circuits within the organs, such as between the anterior and posterior pulmonary plexuses or the intrinsic cardiac ganglionated plexuses or superficial and deep cardiac plexuses. In another embodiment, therapy may be directed towards extra-CNS feedback loops such the cardiopulmonary neural circuits, such as those fibers that run between the superficial and deep cardiac plexuses and the anterior and posterior pulmonary plexuses. In another embodiment, therapy may be directed towards aberrant extra-CNS feedback loops that form in response to ischemia or other damage to the nervous system. These aberrant connections may form between the autonomic and somatic nervous system or within the autonomic nervous system. In some embodiments, therapy is directed towards aberrant connections between the parasympathetic and sympathetic nervous system, the sympathetic nervous system and the afferent visceral/somatic nervous system.

Some embodiments relate to modulating the maladaptive neural responses that contribute to or are a result of lung or cardiac disease by disrupting the intrinsic and/or extrinsic neural reflex arcs of these organs. Interruption of these reflex arcs may result in a resetting or rebalancing of the autonomic nervous system and thus act as a physiologically adaptive response to the disease. The intrinsic reflex arc within the lung, mediating bronchospasm, containing the sympathetic, parasympathetic, somatic fibers and interneurons (e.g. intrapulmonary ganglion) may be targeted with the therapy, including but not limited to the posterior and/or anterior plexus. Alternatively, the extrinsic reflex arcs between the lungs and the heart, such as the cardiopulmonary reflex arc, may be targeted with the therapy. In another embodiment, the intracardiac ganglia are targeted to modulating the intrapulmonary ganglia, and vice versa. Alternatively, aberrant extra-CNS reflex arcs that form may be targeted, for example the aberrant connections that have been demonstrated between sympathetic efferent fibers and the dorsal root ganglia, or vice versa. In another embodiment, the parasympathetic-sympathetic reflex arc is disrupted in the region outside the CNS and outside of the organs, as the nerves exit the spinal cord or brain and course towards the organs. In some embodiments, the nerves lying in the paravertebral gutter and/or intervertebral foramen are modulated, including afferent and efferent nerves. In another embodiment, the afferent nerves carried in the vagus are modulated to disrupt the functional antagonism between the efferent sympathetic and parasympathetic nerves. In yet another embodiment, the afferent nerves carried in the sympathetic nerves are targeted and modulated to achieve the same effect. In some embodiments, the therapy is targeted at reducing the activity of the thoracic sympathetic afferent and/or efferent nerves. In one embodiment, the therapy is targeted to decrease the activity of the sympathetic afferent nerves innervating the heart and lung to disrupt the pro-inflammatory cascade that results in 'neurogenic inflammation' causing bronchoconstriction, vasodilation, inflammation, vascular hyperpermeability, cough, and mucous production in the lung, and angina, vasoconstriction, vasospasm, ischemia, atrial arrhythmias, ventricular arrhythmias, fibrillation, bradycardia or tachycardia, and myocardial infarction in the lung.

The sympathetic chain (or sympathetic trunk) is a bilateral paravertebral structure that runs posteriorly in the neck and posterior chest down to the level of the second lumbar vertebra. Along the length of the chain are sympathetic ganglia or cell bodies of the sympathetic post-ganglionic nerves (or paravertebral ganglia). Typically, the cervical sympathetic chain includes three ganglia, the superior cervical, the middle cervical, and the inferior cervical ganglia, although additional middle or intermediate ganglia have been observed. Continuous with the cervical ganglia are ten or eleven thoracic sympathetic ganglia. Frequently, the first thoracic ganglia is fused with the inferior cervical ganglia to form the stellate (cervicothoracic) ganglion which typically lies transversely and medially over the head of the first rib, at the level of C7, anterior to the transverse process of C7, superior to the neck of the first rib, and just below the subclavian artery. The chain courses through a potential space called the paravertebral gutter, discussed elsewhere.

The upper thoracic sympathetic chain is located behind the pleura and over the head and neck of the ribs, close to the articulation with the vertebra. The ganglia are typically located directly in front of the corresponding rib at the level of each thoracic nerve. The chain ascends vertically to supply each nerve root with an afferent and an efferent branch. White and grey rami communicans are the means by which the ganglia interact with the spinal nerves. The grey rami communicans are present in all segments and largely contain efferent postganglionic sympathetic fibers. The white rami communicans contain afferent and preganglionic fibers that run from T1 to L2 segments. The cervical connection to the spinal cord is thought to be through the white rami communicans of the upper thoracic nerves (Cunningham 1913). For example, the stellate ganglion receives a white communicating ramus from the first thoracic nerve and gives grey communicating rami to the eighth cervical nerve and the first thoracic nerve. The sympathetic chain and the white and grey rami communicans lie within the paravertebral gutter and thus therapies directed towards these targets can be delivered in the paravertebral gutter.

Preganglionic sympathetic nerves exit the spinal cord in the ventral root of the spinal nerve and pass into the corresponding sympathetic ganglion. These neurons may take several paths upon entering the ganglion: 1) synapsing with a post-ganglionic neuron within the same level of the sympathetic chain, 2) traveling up the sympathetic chain to synapse with a post-ganglionic neuron at a cervical or higher thoracic level, or 3) traveling down the sympathetic chain to synapse with a post-ganglionic neuron at a lower thoracic level. From there, the post-ganglionic neurons may travel to innervate the periphery by way of a) the gray communicating rami to the anterior/ventral, dorsal/posterior or other communicating rami, or b) passing up or down the sympathetic chain to exit the sympathetic chain before exiting to innervate the periphery (pre-ganglionic). The pre-ganglionic sympathetic efferent neurons release acetylcholine as their primary excitatory neurotransmitter onto the post-ganglionic sympathetic neurons.

Of relevance to sympathetic visceral targets, additional nerve fibers/rami containing efferent and afferent visceral sympathetic fibers course directly out from the sympathetic chain to the visceral structures. These nerve bundles can be barely visible threads or fine fiber bundles and often multiple nerve bundles can be observed exiting the sympathetic chain towards the viscera. At the level of the upper thoracic chain, these post-ganglionic fibers do not have distinct names, likely owing to their size and variability. In these cervical chain, these are referred to as the inferior, middle, and superior cardiac nerve (although these nerves also carry pulmonary fibers). In the lower thoracic chain, these fibers are called splanchnic nerves and contain a mixture of pre-ganglionic and post-ganglionic fibers traveling towards prevertebral ganglia and post-ganglionic fibers.

Of relevance to sympathetic cutaneous targets an estimated seven to nine rami emanate from each ganglia and many proceed posterolaterally to join the under surface of the intercostal nerve in the space immediately above (Levin 1935). These communicating branches may be myelinated or unmyelinated. The rami may also provide fibers to the visceral organs either directly or after they have joined the ventral ramus of the spinal nerve or intercostal nerve. Although the intercostal nerves are conventionally though to supply the thoracic wall, Levin believed that all of the dorsal sensory afferent sympathetic pulmonary fibers are contained in the communicating rami passing to the intercostal nerves, whether excitatory or inhibitory (Levin 1935). These fibers can also be targeted by delivering therapies to the paravertebral gutter.

Sensory (afferent) fibers enter through either the anterior/ventral (in largest numbers), dorsal/posterior or other communicating rami and then may a) bypass the sympathetic chain altogether, b) travel through the white ramus communicans, or c) travel through the gray ramus communicans through the chain to the white ramus communicans, on their way to the spinal cord through the dorsal root of the spinal nerve (cell bodies located in the dorsal root ganglion). Thus, these fibers are also present within the paravertebral gutter coursing through or adjacent to the sympathetic chain.

The peripheral branches from the upper thoracic trunk receive white rami from the upper thoracic sympathetic nerves. These vasomotor fibers innervate the thoracic organs such as the lungs and aorta. The peripheral branches from the lower thoracic trunk receive white rami from the lower thoracic nerves. These bundles are mainly distributed to structures below the diaphragm and comprise the viscero-inhibitory fibers for the stomach and intestines, motor fibers for part of the rectum, pilomotor fibers for the lower part of the body, vasomotor fibers for the abdominal aorta and its branches, and for the lower limbs, secretory, and sensory fibers for the abdominal viscera (Cunningham 1913).

Another observation is the presence of intermediate or collateral sympathetic ganglia near the sympathetic chain. This has been observed at all levels of the sympathetic chain although these ganglia appear to be more abundant in the lower thoracic and lumbar region. These accessory ganglia can be found adjacent to the sympathetic chain, along one of the rami communicantes, along the spinal nerve or a ramus of the spinal nerve, and even near the dorsal root ganglion. Intermediate ganglia have also been found along the cardiac or pulmonary nerves as the course to the organ, outside of the paravertebral gutter proper. These ganglia are thought to be a mechanism by which sympathetic efferent post-ganglionic fibers can be spared after sympathectomy in which surviving or adjacent pre-ganglionic nerves (with cell bodies in the CNS) sprout to reinnervate these intact ganglia. In one embodiment, the ability of nerves to track to these ganglia is prevented by the placement of a physical or other barrier in and around the paravertebral gutter to prevent sprouting neurons from reinnervating these intermediate/accessory ganglia.

FIG. 1 illustrates neural anatomy at a single thoracic level. Each spinal nerve separates into the dorsal (sensory) root 601 and the ventral (motor) root 602 to enter the spinal cord 520. The dorsal root 601 contains a spinal ganglia, the dorsal root ganglion 603, where the cell bodies of the sensory neurons are found. The roots lie in the intervertebral foramen and can be targeted indirectly by administration of therapy to the paravertebral gutter which spreads to the region of the intervertebral foramen. Alternatively, therapy can be injected directly into the intervertebral foramen to modulate the dorsal root ganglion 603, dorsal root 601, ventral root 602, or aberrant fibers that are coursing to these structures.

Figures 1A, 1B:
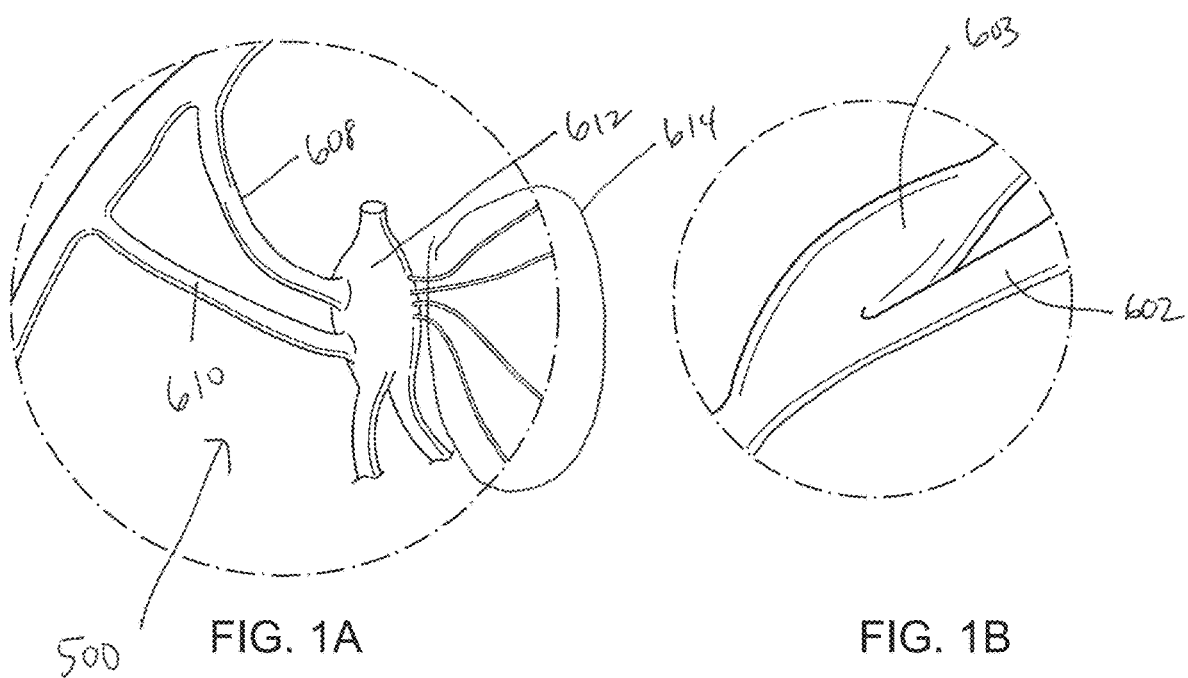
FIG. 1A is a close-up view of dotted circle 6A of FIG. 1 illustrating various structures within the paravertebral gutter.
FIG. 1B is a close-up view of dotted circle 6B of FIG. 1.

The spinal nerve splits to form the dorsal 604 and ventral 606 primary rami. The dorsal rami 604 supplies the back while the ventral primary rami 606 supplies the lateral and anterior walls of the trunk via the intercostal nerve to the lateral and anterior cutaneous nerves. As discussed above, the spinal nerves communicate with the sympathetic trunk with associated sympathetic ganglia 612 by way of the gray rami communicantes 608 and white rami communicantes 610 and thus carries both somatic and sympathetic fibers to the periphery. FIG. 1A is a close-up view of dotted circle 6A of FIG. 1 illustrating various structures within the paravertebral gutter 500 including the paravertebral sympathetic ganglia 612, gray ramus communicans 608, white ramus communicans 610, and visceral afferent and efferent fibers 614 (innervating, for example, the heart and lungs). The cutaneous branches of each spinal nerve (bilaterally) innervate one dermatome, or area of skin surface. In the case of the first and second spinal thoracic nerve (T1 and T2 dermatomes), the medial (ulnar) surface of the arm and forearm. From a sympathetic perspective, this is relevant the vascular tone, skin temperature, sweating in these dermatomes. FIG. 1B is a close-up view of dotted circle 6B of FIG. 1 illustrating the dorsal root ganglion 603 and ventral root 602.

Sympathetic innervation of the heart and lungs from the chain. The cardiac and pulmonary sympathetic innervation derives mainly from the upper thoracic sympathetic chain (T2 to T6 or, in some cases T8), with the majority of fibers originating in the first through fourth thoracic and traveling directly via post-ganglionic fibers to the heart and lungs or indirectly via preganglionic fibers that synapse on post-ganglionic nerves of the superior, middle, or inferior cervical ganglion. These post-ganglionic fibers form the superior, middle, and inferior 'cardiac' nerves that travel long the great blood vessels and form the superficial and deep thoracic aortic/cardiac plexus. Thus, pulmonary and cardiac contributions from the cervical sympathetic ganglion (and the stellate ganglion, in particular), are thought to be of thoracic origin although there is some thought that there are unique contributions from the cervical ganglia. In addition, fibers from the upper six thoracic ganglia (T1-T6) may travel back along the communicating rami to join the anterior roots of the thoracic spinal nerves and travel rostrally in the spinal column before existing to reach the third and fourth thoracic segments (T3-T4). From here, the pre-ganglionic fibers continue in the upper thoracic intercostal nerves and the thoracic sympathetic trunk to terminate in one of the two or three cervical ganglion.

The fibers from the thoracic sympathetic chain, generally T1 to T4, cross the azygous vein on the right side and the aorta on the left side to reach their cardiac and pulmonary targets. Some of the fibers pass from the back of the root of the lung to the pulmonary plexus.

The superior cardiac nerve arises from the superior cervical ganglion and or occasionally from the trunk between the superior and middle cervical ganglia. The right superior cardiac nerve passes either in front or behind the subclavian artery, and along the innominate artery to the back of the arch of the aorta where it joins the deep epicardial plexus. The right superior cardiac nerve also receives fibers from the external laryngeal nerve, vagus, and recurrent laryngeal nerve. The left superior cardiac nerve runs in front of the left common carotid artery and across the left side of the aortic arch to the superficial epicardial plexus.

The middle cardiac nerves arise from the middle cervical ganglia or from the trunk between the middle and inferior cervical ganglion. The right middle cardiac nerve descends behind the common carotid artery and runs in front or behind the subclavian artery at the root of the neck and then it descends on to the trachea, receiving a few filaments from the recurrent nerve and joins the right half of the deep epicardial plexus. This nerve also communicates with the right superior cardiac nerve and recurrent nerve. The left middle cardiac nerve enters the chest between the left carotid and the subclavian arteries and joins the deep epicardial plexus.

The inferior cardiac nerve arises from the inferior cervical ganglion and/or the first thoracic ganglion or stellate ganglion. Both right and left inferior cardiac nerves travel behind the subclavian artery and along the front of the trachea to join the deep epicardial plexus. Each of these nerves communicates freely behind the subclavian artery with the recurrent nerve and the respective middle cardiac nerve.

The post-ganglionic cervical fibers pass to the anterior pulmonary plexus (lungs) via these cardiac sympathetic branches, including through the superficial and deep cardiac plexi. These fibers may travel along the pulmonary artery or across the pulmonary ligament and travel ipsilateral and contralaterally.

The deep cardiac (or epicardial) plexus lies in front of the tracheal bifurcation and behind the aorta/aortic arch and rostral to the division of the pulmonary artery. This plexus contains cardiac sympathetic fibers from all of the right and left cervical sympathetic ganglia (with the exception of the left superior cervical ganglion/left superior cardiac nerve). The plexus also receives innervation from the superior and inferior cervical and thoracic branches of the right vagus nerve and superior cervical and thoracic branches of the left vagus nerve. These neurons may be pre- or post-ganglionic. The plexus goes on to form a left coronary (ventricle), right coronary (ventricle), ventral right atrial, ventral left atrial, left dorsal (atrium/ventricle), middle dorsal (left: atrium/ventricle), and dorsal right atrial subplexuses. Anatomists suggest that left subplexuses are typically from the left side of the deep cardiac plexus and the ventral and dorsal subplexuses are from the right preganglionic sympathetic and vagus as their branches course in the adventitia of the right pulmonary artery and superior vena cava.

The superficial cardiac (or epicardial) plexus lies in the concavity of the aortic arch and in front of the right pulmonary artery. The superficial plexus receives contributions from the left superior cervical ganglion and the lower superior cervical cardiac branch of the left vagus. The superficial plexus is closely connected with the deep cardiac plexus as well as the anterior and posterior pulmonary plexus. Fibers from the cardiac plexus also pass on to the pulmonary plexus and vice versa. The branches from the right half of the deep cardiac plexus pass in front or behind the pulmonary artery. Those that pass in front of the pulmonary artery send fibers to the anterior pulmonary plexus and then continue on to the anterior coronary plexus (right atrium and ventricle). The deep fibers that pass behind the pulmonary plexus distribute fibers to the right atrium and then on to the posterior coronary plexus. The branches from the left half of the deep cardiac plexus are connected with the superficial cardiac plexus and give filaments to the left atrium and to the anterior pulmonary plexus and then on to form the greater part of the posterior coronary plexus (left atrium and ventricle). Thus the cardiac and pulmonary plexuses are in continuity with one another.

Sympathovagal interconnectivity. The sympathetic fibers frequently anastomose with the vagal fibers. Cervical sympathetic fibers are also thought to be distributed to the vagi on both the ipsi- and contralateral sides. Sensory afferent fibers from the lung, whose ganglia are found primarily in the nodose ganglion run principally in the vagi but also to some extent in the sympathetic trunks. Similarly, some clinicians believe that bronchoconstrictor fibers from the right and left vagus are given off high in the neck and course down the ipsilateral or contralateral sympathetic trunk. From there they leave the trunk and join the posterior pulmonary plexus.

Sympatho-somatic interconnectivity. There are variable intrathoracic connections between the first, second, third, and fourth intercostal nerves and the brachial plexus which result in abnormal connections between the sympathetic chain and the brachial plexus. These connections are thought to contribute to failed sympathectomy.

Parasympathetic innervation to and in the lungs.

Vagal fibers run from the dorsal vagus nucleus in the vagal nerve trunk without interruption until they reach the lung hilum. The vagus extends branches to the lung from at or just above the level of the recurrent nerve to and along the pulmonary ligament. From the hilum, the vagal fibers divide into numerous small branches which mainly innervate the ipsilateral but also the contralateral lung. These branches form a part of the posterior pulmonary plexus on the right and left side and end in the ganglions situated along the posterior surface of the main or primary bronchi. From these ganglions the postganglionic fibers are distributed throughout the lung to the bronchial musculature.

Vagal fibers course along the pulmonary artery, superior pulmonary vein and pulmonary ligament. Vagal innervation is more extensive on the left side of the lung than the right. On the left side there are two relatively large fibers bundles which travel in and about the sheath of the pulmonary artery and two large branches to the left bronchus. In addition, on the left, four to eight major filaments are distributed between the pulmonary artery and bronchus. On the right side there are usually only two or three main branches and two to four finer filaments. Compared to the left side, a greater portion of the nerve trunks go to the main bronchus on the right side with relatively less going to the pulmonary artery. The nerve supply to the artery is less than that to the bronchus but is abundant. No large parasympathetic branches are seen going to the sheath of the veins.

Vagal fibers to the heart. The lung is innervated by efferent and afferent autonomic nerves supplied by the sympathetic and parasympathetic nervous system. Together, their fibers anastomose extensively with one another on the posterior surface of the hilum to form the posterior pulmonary plexus as well as on a smaller anterior pulmonary plexus. Vagal and sympathetic contributions are from both ipsilateral and contralateral origin. Both the sympathetic and parasympathetic are connected by a reflex arc via the respiratory center in the medulla.

These nerves regulate many aspects of airway function including airway smooth muscle tone, airway secretion, bronchial circulation, microvascular permeability, and the recruitment and activation of inflammatory cells. The innervation to the lung originates primarily from the larger posterior pulmonary plexus and secondarily the smaller anterior pulmonary plexus. These plexi are formed by both fibers from the sympathetic and vagal (parasympathetic) arms of the autonomic nervous system. There are as many sympathetic fibers entering the posterior pulmonary plexus as vagal fibers. The main bundles of the vagus are joined by numerous minute filaments deriving from the sympathetic chain and from other intrathoracic plexuses. These fibers are then redistributed in a succession of bronchial and submucous plexuses. Overall, myocardial tone, vascular tone, and/or airway smooth muscle tone are thought to be dependent on several factors, including parasympathetic, sympathetic, circulating factors such as epinephrine, NANC inhibitory and excitatory nerves as well as sympathetic innervation of the parasympathetic ganglia.

Airways. The parasympathetic nerves are the dominant neural pathway in the control of airway smooth muscle tone and airway secretion. The major neurotransmitter of cholinergic nerves is acetylcholine (ACH) which binds to muscarinic receptors. Stimulation of cholinergic nerves causes release of ACH resulting in bronchoconstriction, mucus secretion, and bronchial vasodilation. Cholinergic nerves also contain vasoactive intestinal peptide (VIP) and nitric oxide (NO) which are thought to act as co-transmitters with and functional antagonists to ACH. VIP receptors on these nerves (and NO through an unknown mechanism of action) bind to VIP and cause smooth muscle relaxation (see below).

Inhibitory nonadrenergic noncholinergic (iNANC) nerves may be the only neural bronchodilator pathway in human airways. These nerves release vasoactive intestinal peptide (VIP), nitric oxide (NO), peptide histidine methionine (PHM), and pituitary adenylate cyclase-activating peptide (PHM) and are frequently distributed close to parasympathetic nerves. Some of these neurotransmitters have also been co-localized with ACH in parasympathetic nerves. Research supports their role as a functional antagonist to cholinergic bronchoconstriction and propose that they act prejunctionally to inhibit ACH release. VIP receptors are also localized in pulmonary vascular smooth muscle, airway smooth muscle of large airways, airway epithelium, and submucosal glands. VIP is one of the most potent relaxants of smooth muscle and has also been demonstrated to stimulate mucus secretion, vasodilate pulmonary vessels, inhibit mediator release from mast cells, inhibit T lymphocyte proliferation, interleukin release from bronchial epithelial cells, and regulate isotype switching in B lymphocytes. Nitric oxide synthase (NOS)-containing nerves are found in tracheal and bronchial smooth muscle, around submucosal glands and around blood vessels where NO production may result in hyperemia, plasma exudation, mucus secretion, and skewing T lymphocytes towards a Th2 phenotype. Excitatory nonadrenergic noncholinergic (eNANC) nerves have also been identified in human airways and stimulation of these nerves in animals has been results in bronchoconstriction, mucous secretion, vascular hyperpermeability, cough, and vasodilation. This process is collectively called 'neurogenic inflammation' and has been demonstrated to be a result of the interaction between eNANC nerves and inflammatory cells. These neurons are a subpopulation of nonmyelinated sensory C fibers that release neuropeptide Y (NPY) and are the classic nociceptive neurons that transmit sensations of itch and pain associated with tissue injury. These neurons are stimulated by exogenous substances such as cigarette smoke, capsaicin or inhaled irritants and by endogenous substances like histamine, bradykinin and prostaglandin. Interestingly, these neurons also release neuropeptides in a 'neuroeffector' mechanism so their effects exert a local axon reflex. eNANC neurons release calcitonin gene-related peptide (CGRP), secretoneurin, the tachykinins (TK): substance P (SP) and neurokinin A (NKA) in addition to NPY. CGRP and NPY have potent vasodilatory effects and may also modulate immune cell function. CGRP, in particular, mediates long-lasting vasodilation through its direct action on receptors on vascular smooth muscle (less effect on smooth muscle or epithelial cells in human airways). CGRP has no effect on microvascular leak but may amplify SP-induced protein plasma extravasation and it may indirectly mediate bronchoconstriction. The TKs exert a wide variety of effects on smooth muscle cells, submucosal glands, epithelial cells, blood vessels, nerves, and immune system cells. NPY is thought to have no direct effect on airway smooth muscle but may cause bronchoconstriction indirectly via release of prostaglandins. SP induces venular vasodilation, increased vascular permeability, and immunoreactive nerves can be found in airway epithelium, around mucosal arterioles and submucosal glands, within bronchial smooth muscle and around local parasympathetic ganglia. SP and NKA receptors, NK1 and NK2, are primarily responsible for mediating the inflammatory effects of the TKs. The NK1 receptors are found on smooth muscle, pulmonary vessels, airway epithelium and submucosal glands where they mediate mucus secretion in peripheral airways and microvascular leak in postcapillary venules. They also play a role in clearing mucus, bacteria and inhaled particles by increasing ciliary beat frequency, releasing prostaglandins, and are involved in the migration and proliferations of bronchial epithelial cells. SP may be involved in the recruitment of neutrophils to airways and the activation and proliferation of fibroblasts. The NK2 receptors have not been fully characterized but have been demonstrated to mediate bronchoconstriction. Here, NKA is considerably more potent than SP and the effect is significantly greater in smaller bronchi than more proximal airways, suggesting that these peptides have a more important constrictor effect on more peripheral airways. Some evidence suggests that TKs may amplify cholinergic neurotransmission and modulate iNANC-mediated bronchodilation, contributing to exaggerated (van der Velden and Hulsmann 1999). TKs appear to mediate neutrophils (chemotaxis, aggregation, superoxide production, adherence), eosinophils (recruitment, degranulation), T lymphocytes (proliferation and cytokine production, chemotaxis), mast cells (histamine release), monocytes/macrophages (release of inflammatory cytokines), B lymphocytes (differentiation, immunoglobulin isotype switch), and dendritic cells (chemotaxis, antigen presentation).

Sympathetic efferent nerves are less abundant and are thought to play less of a role in the human airways relative to the parasympathetic nerves. They are primarily present in close association with submucosal glands and bronchial arteries although some researchers believe they have found non-myelinated efferent fibers within bronchiolar smooth muscle and alveolar ducts. The primary pre-ganglionic sympathetic (extrapulmonary) neurotransmitter is acetylcholine although nitric oxide, CGRP, VIP, substance P and encephalin have also been localized to pre-ganglionic nerve endings. Post-ganglionic sympathetic neurotransmitters are differentially released into the peripheral target tissue as a function of how they are stimulated. The main sympathetic neurotransmitters of sympathetic efferent post-ganglionic nerves are norepinephrine (noradrenaline) and the co-transmitter NPY which activate α- and β-adrenergic receptors. Other neurotransmitters and co-transmitters include ATP, NPY and enkephalins. Sympathetic innervation of human airway smooth muscle has not been observed although β2 adrenergic receptors are abundantly expressed on these cells and are presumed to be regulated in part by circulating epinephrine/norepinephrine released from non-pulmonary stores. However, adrenergic nerves may influence bronchomotor tone indirectly via prejunctional α- and β-adrenergic receptors. β-2 adrenergic receptors are abundantly expressed on human airway smooth muscle and epithelial and mast cells and activation of these receptors causes bronchodilation/bronchorelaxation. β1 receptors are found in human submucosal glands and alveolar walls. The α1 adrenergic receptor, mediating the contraction of smooth muscle, is relatively sparse. Prejunctional α2-adrenergic receptors may inhibit the release of norepinephrine and NPY from adrenergic nerves. Similarly, α2-adrenergic receptors may inhibit the release of tachykinin from sensory nerves. Cholinergic neurotransmission may also be inhibited via α2-adrenergic receptors.

Vascular innervation of the Lung.

From posterior pulmonary plexi, the pulmonary arteries receive a plexus of large parasympathetic and sympathetic nerve trunks coursing through the adventitial and periadventitial layer. Most of the fibers are found in the larger elastic arteries, fewer in the muscular arteries, and fibers are absent in vessels smaller than 30 µm. There is especially dense innervation of a population of arterioles arising at right angles from the pulmonary arteries which may play a role in the distribution of blood flow in the lungs. The majority of these fibers are myelinated but there are also smaller nonmyelinated fibers. Terminal twigs pass to the outer-third of the media where they travel to the smooth muscle cells of the media in the large elastic arteries. In the smallest muscular arterioles, these fibers remain external to the medial coat. Muscular arteries are supplied exclusively by fine fibers and there are relatively fewer fibers in the pulmonary veins. Axons with vesicle-rich segments are usually separated from muscle cells by the external elastic lamina and fibrocyte processes. Muscle cells, will extend pinocyte-rich vesicles across the EEL to these axons providing a nerve-muscle gap of 100 nm, and consistent with neurotransmission via transmitter diffusion from specialized regions of the axon.

Sympathetic nerves may be the primary neuronal pathway controlling the tracheobronchial blood vessels. Stimulating the sympathetic nerve fibers results in vasoconstriction of segments of the larger pulmonary vessels, but not those less than 0.6 mm in some cases. In some embodiments, sympathetic neuromodulation is effected herein without or without substantially ablating, denervating, or otherwise neuromodulating parasympathetic nerve fibers.

Cervical Ganglia. Innervation of portions of the face including the meninges, pupils, salivary glands, arteries, and sweat glands, arise from post-ganglionic cervical ganglion (including stellate ganglion) neurons ascending along the internal carotid body. Innervation of the posterior scalp and neck also originates post-ganglionic motor neurons from the superior cervical ganglion. Innervation of the brachial plexus originates from the middle and inferior cervical nerves and the chest and abdominal wall from the thoracic nerves.

Lower Thoracic, Lumbar, and Splanchnic Ganglia. Innervation of lower extremities originates from spinal cord segments T10 to L3 and are conveyed primarily through L1 to L4 ganglia. L1 and L2 ganglia are frequency fused and L2 and L3 ganglionectomy is usually sufficient to ameliorate symptoms of a variety of lower extremity conditions.

Indications for modulation of cervicothoracic sympathetic tone include diseases with persistent, adverse activation of sympathetic outflow to the heart and lungs including ongoing episodic sympathetic activation of cardiopulmonary, cardiac, pulmonary, arterial or venous target tissues, and defective neural reflexes, including sympathetic circulatory reflexes. While sympathetic overactivity of the kidneys and peripheral circulation mediates systemic adverse effects through vasoconstriction and increasing the work of the heart and by promoting sodium retention and ventricular overfilling, it is the sympathetic overactivity of the heart itself that is potentially the most damaging. For a time, this stimulation provides support to the failing myocardium but it leads to the development of ventricular arrhythmias, progressive left ventricular deterioration and mortality in a vicious positive feedback loop. Reduction of sympathetic tone in the thoracic cavity has a beta-blocking like effect, and to some extent, an alpha-blocking like effect, causing a reduction in heart rate, reducing myocardial oxygen demand, increasing diastolic perfusion time resulting in increased myocardial perfusion. Through an alpha-blocking like effect, reduction in sympathetic tone may have a vasodilatory effect or at least a protective effect against vasoconstriction. These combine to reduce angina symptoms and ischemia. Reducing afferent activity results in a reduction of activation of nociceptors which some researchers suggest have been sensitized, or converted from high-threshold to low-threshold nociceptors.

In some embodiments, treatment results in at least an amelioration of the symptoms associated with the pathological condition afflicting the patient, where amelioration is used in a broad sense to refer to at least a reduction in the magnitude of a parameter, e.g. symptom, associated with the pathological condition being treated. As such, treatment includes situations where the pathological condition, or at least symptoms associated therewith, are completely inhibited, e.g. prevented from happening, or stopped, e.g. terminated, such that the patient no longer suffers from the pathological condition, or at least the symptoms that characterize the pathological condition.

In some embodiments, systems and methods as disclosed herein are directed to modulating the sympathetic nervous system to the thorax targeting the cervical and upper thoracic sympathetic fibers, such, as for example, from the T1 to T5 paravertebral gutter, including one, two, or more of the following: T1, T2, T3, T4, and T5. Since the T1 ganglia is frequently fused with the cervical ganglia, the inferior cervical ganglion, procedures that block or ablate these ganglia are generally referred to as cervicothoracic sympathetic block or cervicothoracic sympathectomy, respectively. In some embodiments, treating cardiothoracic conditions through the delivery of neuromodulatory agents to the cervical ganglia may be desirable, however these are more likely to have off-target effects whether as a result of the procedure itself, the therapy spreading to non-target tissues and nerves, or undesirable side effects to the head and neck as result of modulating the cervical ganglia. In some embodiments, the treatment of cardiopulmonary conditions is achieved through the delivery of neuromodulatory agents to the thoracic sympathetic ganglia as well as the variable number of rami containing both afferent and efferent fibers that emanate from the chain, the roots, and the intercostal nerve. More specifically, the sympathetic chain together with the visceral rami or fibers traveling from the sympathetic chain directly or indirectly to the viscera are targeted. This can be achieved through the delivery of neuromodulatory agents into the paravertebral gutter.

Pulmonary.

In some embodiments, disclosed herein are systems and methods for decreasing the activity of the sympathetic arm of the autonomic nervous system to treat pulmonary diseases, including but not limited to asthma. The therapy may prevent, reduce the symptoms of, ameliorate, or cure asthma and comorbid diseases. The therapy may also be directed toward the prevention or treatment of other pulmonary diseases including but not limited to emphysema, pulmonary artery hypertension, chronic obstructive pulmonary disease, acute respiratory distress syndrome, pulmonary edema, pneumonia, pulmonary thromboembolism, chronic cough, acute or chronic bronchitis, cystic fibrosis, bronchiectasis, bronchopulmonary dysplasia, pulmonary fibrosis, interstitial lung disease, pulmonary edema, pleurisy, bronchiolitis, bronchial hyperresponsivity (BHR), acute respiratory distress syndrome (ARDS), and/or pain associated with lung and other tumors.

Asthma.

Disruption or denervation of the upper thoracic sympathetic chain can result in denervation of the sensory afferent and efferent fibers innervating the lungs, pulmonary arteries, bronchial arteries, and pleura. Based on preclinical and clinical research, sympathetic denervation may be helpful in 1) increasing pulmonary vascular dilation, reducing pulmonary vascular tone and thus reducing pulmonary pressures, improving oxygen transport and clearance of irritants from the lung; 2) reducing the local inflammatory response that occurs during an asthma attack, reducing eosinophil and neutrophil activation; 3) improved lymphatic clearance and a reduction in lung edema; 4) reduce mucus hypersecretion;

5) reduce local norepinephrine spillover in the lungs and the heart; and 6) possibly result in bronchodilation.

Pulmonary Artery Hypertension.

Given the beneficial effects observed preclinically and clinically in the treatment of pulmonary artery hypertension with local sympathetic (afferent, efferent) denervation of the nerve bundles coursing over and through the pulmonary arteries, pulmonary artery trunk and the nearby pulmonary and cardiac plexi, a more complete sympathetic denervation to the pulmonary arteries (and cardiopulmonary tissue generally) may be desired by delivering the therapy to the T1-T4/T5, or T2-T4 paravertebral gutter in some embodiments. This may be particularly desirable given the long distances that some of the extra-pulmonary artery nerves and plexi are from the vessel and thus the long distances that a chemo- or thermo-ablative therapy can travel to denervate these nerves. This also may be preferable in some cases over pulmonary artery regional denervation since these fibers are mixed sympathetic and parasympathetic nerves.

Alternatively, given the controlled nature afforded by the deposition of the therapy, the ability to fill a potential space and subsequent control the spread of the neuromodulatory agent, comprising, for example, a neuromodulatory agent in a hydrogel, it may be desirable to deliver the therapy directly outside the pulmonary artery and veins for the treatment of pulmonary artery hypertension, as opposed to the uncontrolled spread of a conventional neurolytic agent such as ethanol. The therapy may result in improvements in endpoints such as change (e.g., decrease) in BNP, change in 6 minute walk test (6 mwt), change in Doppler derived mean pulmonary artery pressure, blood pressure, pulmonary capillary wedge pressure, cardiac output, quality of life and mortality, and/or other parameters. These patients may also benefit from a dramatic reduction in the number of costly medications they are prescribed. This local approach has applications beyond the treatment of pulmonary artery hypertension since the pulmonary arteries and pulmonary trunk sit adjacent to the lower curvature of the aortic arch, where the cardiac (and pulmonary) plexi sit, largely adherent to the aorta. Thus delivery of a therapy here may have broader benefits in the treatment of cardiopulmonary conditions.

Angina and Refractory Angina.

Angina pain reduction by cervicothoracic sympathetic block or ablation is thought to be a result of the disruption of the pain signal relayed in the afferent visceral nerve fibers as well as reduced work of the heart through sympathetic efferent nerve disruption resulting in decreased norepinephrine release and binding to beta-adrenoreceptors. This beta-blocker-like effect can result in a reduction in cardiac contractility, reducing myocardial oxygen demand thereby reducing ischemia and thus ischemic-pain. A secondary vasodilatory effect following coronary blockade of alpha-adrenoreceptor mediated sympathetic vasoconstriction. The majority of these afferent and efferent fibers are relayed through the left stellate and left thoracic ganglia although there are bilateral projects to the left ventricle. Prolonged pain relief (weeks) after the administration of a short-acting local anesthetic to the stellate ganglion may potentially be explained through a down-regulation or resetting of the hypersensitive nociceptive pathway. The volume of anesthetic administered spreads unpredictably and in some portion of patients it travels down the paravertebral gutter to block variably to T2 or, in some cases, spreads down to T6, and may account for the variability in efficacy of the anesthetic blocks. The stellate anesthetic blocks need to be repeated every 2 to 6 weeks as the angina pain returns, at additional cost and increased safety risks from repeated procedures. If these blocks are repeated for over 6 to 9 months, anecdotal clinical evidence suggests that these blocks may become more long-lasting and in some cases permanent, perhaps due to the cumulative local toxicity of the anesthetic and/or chronic local inflammatory response from these injections. A more long-lasting and/or permanent therapy that is easily administered, specifically targetable, and more importantly, has an excellent safety profile, can be desirable in some embodiments, particularly one that involves a one-time outpatient procedure to treat the condition. The procedure could be performed with intravenous sedation and local anesthesia or with a local anesthetic alone.

Both stellate ganglion blocks and open surgical stellate or cervicothoracic sympathectomy has been demonstrated to relieve severe angina pectoris, and in many cases alleviating all angina pain. Angina patients typically have coronary artery disease (CAD), particularly as patients are living longer with the advent of coronary revascularization technologies. Stated another way, the therapy has the potential to treat patients with coronary artery disease, whether it be present in the coronary arteries sufficient to cause a >50% occlusion of these vessels, be present but be less than 50% occluded, or be absent in the coronary arteries and present in the smaller distal arterioles and capillaries feeding the heart. Thus, angina is one of the symptoms of coronary artery disease. In one embodiment, patients with chronic refractory angina (greater than 3 months of angina, reversible ischemia) the therapy is delivered to the T1 to T5 paravertebral gutter, such as the T2 to T4 paravertebral gutter to treat angina and patients' weekly angina attack frequency decreases, nitroglycerin consumption is reduced and maximum exercise capacity increased, and/or decrease in heart rate and blood pressure and reduction in ST-segment depression. The procedure may be performed, for example, endovascularly or transcutaneously. In another embodiment, patients that have undergone percutaneous coronary intervention (PCI) or coronary artery bypass grafting (CABG) but have achieved incomplete revascularization and/or have persistent or ongoing angina are treated in some aspects. In another embodiment, patients that have persistent or ongoing angina due to coronary artery disease but are unsuitable for PCI/CABG because of instability or procedural risk, number of vessels, procedural access etc. may be treated in some aspects. In yet another embodiment, the procedure can be performed as an adjunctive procedure to percutaneous coronary intervention (PCI) or coronary artery bypass (CABG) to relieve angina through, for example, the endovascular route with PCI and the transcutaneous or under direct visualization with CABG. Although this procedure can be performed for the treatment of angina, it can also be performed to reduce the risk of atrial and ventricular arrhythmias, reduce pre- and post-procedural vasospasm and potentially reduce the primary and secondary ischemic zone around an infarct. In some cases, the therapy is delivered to the patient prior to the start of surgery in order to have maximal clinical therapeutic benefit. In another embodiment, with the establishment of the safety of the procedure, the therapy can be delivered on an outpatient basis or elective basis to high-risk cardiac patients for temporary or permanent sympathectomy to treat both the underlying disease and/or their symptoms. In another embodiment, the therapy can be delivered to the approximately 30% of cardiovascular patients that cannot, for one reason or another, tolerate or be compliant to the therapeutic dose of their beta-blocker therapy.

Microvascular Disease. Of the patients with angina but no angiographic evidence of CAD, 50-65% of patients have coronary microvascular dysfunction (CMD) also known as microvascular coronary dysfunction (MCD). These patients are considered a higher risk subgroup of patients within Cardiac Syndrome X (CSX). Within women, 50-60% with angina have no obstructive CAD (>50% luminal diameter stenosis in >1 epicardial coronary artery), twice as often as men. These women have increased physician visits, increased hospital admission rates for angina, repeat invasive examinations and loss of quality of life and ability to work. MCD patients, frequently younger women, present with persistent worsening exertional chest pain, abnormal stress testing, the absence of obstructive coronary artery disease through coronary angiography and normal left ventricular function. In these patients, coronary reactivity testing (CRT) demonstrates a limited coronary flow reserve (CFR) to adenosine infusion and coronary blood flow reserve and coronary artery construction with acetylcholine, indicative of endothelial dysfunction. Adenosine stress cardiac magnetic resonance imaging demonstrates reduced perfusion during stress. Management of these patients can be challenging because they have ischemic-type ST-segment depression and noninvasive stress testing reveals perfusion/wall-motion abnormalities. These patients were thought to have a benign prognosis however data from the NHLBI-WISE study shows that up to 50% of these patients have MCD which is associated with a 2.5% annual adverse cardiac event rate including myocardial infarction, stroke, hospitalization for congestive heart failure, and sudden cardiac death. In this disease, the small arteries and arterioles downstream of the epicardial coronary arteries are the major sites of resistance to blood flow. Given that beta-blocker therapy is the first-line drug therapy for this indication and that sympathetic efferents also modulate coronary vascular and microvascular tone, these patients could benefit from a procedure to reduce sympathetic component of their disease, thereby treating both the symptoms (pain) and the underlying disease. In one embodiment, the aforementioned tests are used to stratify patients that are suitable for the procedure (Marinescu et al 2015). In particular, tyramine testing or adenosine testing for responsiveness are examples of tests that can be utilized. In one embodiment, the 10-30% of patients undergoing diagnostic angiography for diagnosis of CAD but have no evidence of the coronary artery disease despite ongoing ischemia-symptoms, such as angina, are treated with the therapy targeted to the T1-T4 paravertebral gutter unilaterally, such as, for example, on a first side of the paravertebral gutter, such as the left side. If symptoms are incomplete, a second side, such as the right side of the paravertebral gutter can be treated.

Atrial or ventricular arrhythmias. Development of cardiac sympathetic heterogeneity after myocardial infarction contributes to the lowering of threshold for ventricular arrhythmias and sudden cardiac death, particularly in the first 30 days after MI. This is hypothesized because of the close proximity of two zones of tissue: 1) sympathetically denervated tissue in the peri-infarct zone, in which the beta-adrenoreceptors on the myocardiocytes and other cells have become hypersensitized and 2) sympathetically hyperinnervated tissue, in which local ischemia and neuronal damage have triggered sympathetic nerve sprouting. Because these zones are close to one another, norepinephrine released from a hyperinnervated zone may exert its effects on the high density of beta-adrenoreceptors on the myocardial tissue, causing a change in the threshold for arrhythmias, and triggering an arrhythmia. In some embodiments, the arrhythmia to be treated can be, for example, atrial fibrillation, atrial flutter, paroxysmal supraventricular tachycardia, monomorphic or polymorphic ventricular tachycardia (VT), or ventricular fibrillation (VF). Patients may have sustained VT or nonsustained VT.

Ventricular arrhythmias. Patients may develop arrhythmias as a result of non-ischemic cardiomyopathy (NICM), ischemic cardiomyopathy, myocardial infarction, HCM, Sarcoid cardiomyopathy, ARVD, HOCM, and the like.

Some patients with implantable ICDs have recurrent ventricular tachycardia (VT). These patients may also undergo a catheter-based and/or epicardial VT ablation procedure and continue to suffer recurrent VT. These patients may in some cases be particularly suitable for the therapy described.

A reduction in ICD shocks, or the debilitating fear that some patients have that they might have an ICD shock, can be meaningful to these patients. As a result of the concern of having an ICD shock, many patients significantly limit their physical activities, causing a decline in their quality of life. These patients may become depressed. Providing these patients with an alternative to an ICD would be beneficial to these patients. Alternatively, providing patients and/or clinicians with a procedure that may improve the efficacy of the index procedure with limited additional safety risks, would be attractive.

Therefore the therapy can be beneficial treating patients: 1) prophylactically, at high risk for VT and SCD who have not yet had a recorded or observed event, 2) who, as a result of monitoring (Holter monitor, implanted (REVEAL LINQ), or as part of their pacemaker or other implant), have been diagnosed with VT, 3) with VT or other conditions in which an ICD would be recommended but the patient refuses or the healthcare system/patient cannot afford the cost of an ICD, 4) with an ICD but would like to reduce their concern that they will have an event resulting in ICD firing, even if it is appropriate, 5) with an ICD but suffer from inappropriate device firing, particularly since it is so painful 6) who have an ICD explanted and require some protection from sudden cardiac death, 7) that are high risk for an MI and would like to have the therapy performed prophylactically to reduce their chances of sudden cardiac death, 8) who have had an MI (acutely) and are at high risk for arrhythmias in the next 30-60 days, 9) who are undergoing PCI or CABG and would like some prevention from the post-operative arrhythmias, 10) refractory patients who have undergone VT ablation or who have VT or VF that is not ablatable and 11) patients undergoing hemodialysis who have a high rate of fatal arrhythmias and 12) patients with a CRT-D that are at high risk for arrhythmias and 13) with ventricular storm, particularly refractory or incessant ventricular storm, 14) with an ICD after surviving SCD, 15) suffering from syncope despite maximal beta-blockade and 16) that have had prior AF ablation, SVT ablation, VT ablation (SHD or idiopathic) that would otherwise be undergoing a first or second VT ablation procedure. In settings in which a precipitating cardiac event requires treatment, these procedures can be performed as a standalone or adjunctive procedure (adjunct to VT ablation, CABG, PCI, ICD implantation, AF ablation) and if the therapy is demonstrated to be safe, it can be used for secondary and primary prevention of arrhythmias. Alternatively, the therapy can be delivered on an elective basis during the course of ongoing drug treatment of a patients cardiac arrhythmias and other comorbidities, such as after or in conjunction with a diagnostic EP study. The procedures may be first performed as an anesthetic block to the target levels, for example, a stellate or cervicothoracic or thoracic paravertebral block, and then, pending the efficacy of the block or the challenges with repeated blocks, the block can be converted to a permanent solution, either during the same or a secondary procedure, to the delivery of a neurolytic in a hydrogel.

In some embodiments, a sympathetic neuromodulation procedure as described herein is performed in conjunction with ablation of an arrhythmic focus which may be performed with an endovascular or epicardial approach. Recently, clinical several trials have been initiated to study the effects of bilateral cervicothoracic sympathectomy for the prevention of ventricular tachyarrhythmias (PREVENT-VT, NCT01013714) or other sympathetic denervation approaches (RESET-VT, NCT01858194). Specifically, therapy delivered from T1 to T4 may have beneficial effects in freedom from ICD shocks, time to first event requiring ICD therapy or refractory/incessant VT, number of ICD shocks, occurrence of VT storm, occurrence of ICD storm, total VT burden, and survival free of ICD shock. Clinical data to date suggests that between 50-65% of patients have a complete clinical response following bilateral VT. Preclinical and clinical studies had demonstrated a reduction in VA occurrence, improved ventricular electrical stability, mean arterial pressure and infarct size (in acute MI applications). Treatment of VT or VF includes the delivery of the therapy to the stellate ganglion alone, T1 alone, or T1 to T4.

Atrial fibrillation. The autonomic nervous system can induce atrial tachyarrhythmias including atrial tachycardia and atrial fibrillation. Paroxysmal and persistent atrial fibrillation may be treated with a combination of the PVI isolation (or another existing catheter-based procedures that target and ablate the aberrant cardiomyocyte circuits) in combination with left and or right/sided paravertebral neuromodulation at the T1 to T4 levels. Alternatively, the neuromodulation gel may be delivered both into the paravertebral gutter and to the epicardial fat pads containing the ganglionated plexi (sympathetic, parasympathetic, interneurons).

Atrial fibrillation is one of the most widespread problems encountered after cardiac surgery, prolonging morbidity, mortality and duration of hospitalization. Atrial fibrillation and C-reactive protein levels have been demonstrated to peak at 2 days post-cardiac or non-cardiac surgery and then subside within a week. Furthermore, atrial fibrillation is associated with higher rates of stroke, CHF, and late AF in patients undergoing coronary artery bypass graft (CABG), aortic valve or mitral valve surgery. Postoperative AF (POAF) is maximal within two or three days after and remains high for a week after the procedure. In one embodiment, the sympathetic nervous system is partially or completely denervated in the region of the paravertebral gutter to block one of the triggers for the induction of atrial fibrillation.

Chronic heart failure. Disruption or denervation of the upper sympathetic afferent and efferent fibers results in denervation of the aortic arch baroreceptors and possibly the carotid baroreceptors and chemoreceptors, manifesting for example as a reduction in heart rate, heart rate variability and modulate ventilatory drive. Not to be limited by theory, sympathectomy may have a partial beta-blocker like effect, not only reducing the threshold for arrhythmias but triggering reverse remodeling in the heart. As a result, these changes may result in a positive improvement in chronic heart failure and a reduction in blood pressure. In a limited clinical study in which left lower $\frac{1}{3}^{rd}$ of the stellate ganglion and T3-T4 videothorascopic clipping, patients with systolic heart failure had improved left ventricular ejection fraction (LVEF). Patients with heart failure can be further broken down into their risk category based on their LVEF with patients with lower LVEF (<35%) being at highest risk for cardiac arrhythmias more than patients between 35-45% LVEF (intermediate risk) and patients >50% LVEF considered to have low risk of arrhythmias.

Myocardial infarction. Sympathetic nerves play a significant role in the initiation of acute myocardial ischemia as well as being subsequently further activated by ischemia, further aggravating the condition. Cardiac sympathetic denervation may in some cases result in reduced alpha-1 and alpha-2 adrenoreceptor mediated coronary vasoconstriction, the reduced alpha-1 mediated (epicardial) coronary artery spasm.

Other cardiac indications. Cardiac indications are typically treated by modulating the left sympathetic chain and then, as necessary to maximize efficacy, the right sympathetic chain although bilateral procedures are increasingly performed. Other cardiac indications for long-duration or permanent therapy directed towards the T1 to T4/5 paravertebral gutter and other anatomical targets include both ischemic and non-ischemic cardiac pain including Cardiac Syndrome X, Cardiac Syndrome Y (slow coronary flow), coronary artery spasm or Prinzmetal angina, aortic stenosis, left ventricular hypertrophy, mitral valve prolapse and other valvular diseases, abnormal cardiac nociception, and no reflow patients. In addition the therapy can be delivered to treat hypertension, including essential hypertension, secondary hypertension, and particularly neurogenic, obesity-related hypertension, benign hypertension, malignant hypertension, hypercatecholaminergic hypertension, as well as disorders of postural circulatory control causing syncope, acute or chronic heart failure, ischemic and non-ischemic cardiomyopathy, dilated cardiomyopathy, arrhythmogenic right ventricular cardiomyopathy, myocardial contractility disorder, acute coronary syndrome, compensated or decompensated or uncompensated heart failure, congestive heart failure, acute heart failure, early-stage heart failure, severe congestive heart failure with preserved ejection fraction (HFPEF), stress (takotsubo) cardiomyopathy, acute mental stress leading to angina, panic attacks accompanied by coronary artery spasm, mitral valve disease, aortic valve disease, psychogenic cardiovascular disease (heart disease attributable to stress or mental illness), ischemia and infarct size associated with myocardial infarction, patency or lack thereof of radial artery grafts after CABG, sudden death, stress-induced cardiomyopathy, coronary heart disease, heart disease and hypertension in patients with schizophrenia, panic disorders triggering cardiac arrhythmias, vascular disease unsuitable for vascular reconstructive surgery, improvement in blood flow after surgical grafting or other vascular surgery, reducing cardiac ischemia and secondary ischemia-reperfusion injury, syncope, cardiac arrest, ventricular storm, channelopathies and conditions with short- or long-ST segments elevation or QT prolongation/dispersion including catecholaminergic polymorphic ventricular tachycardia (CPVT) and Long QT syndrome. Not to be limited by theory, sympathetic denervation may also result in improved lymphatic flow from the lungs and the heart and thus provide symptomatic benefit in heart failure, hypertension (systemic, pulmonary, orthostatic), carotid sinus hypersensitivity, and pulmonary edema through improved drainage or clearance of fluid from the lungs and thoracic cavity. While the sympathetic nerve supply to the lungs and heart is largely derived from the thoracic sympathetic chain both directly and indirectly, many clinical researchers have shown that procedures targeted at the stellate ganglion alone (e.g. anesthetic block or surgical sympathectomy) may be sufficient to ameliorate symptoms of refractory angina or cardiac arrhythmias. For permanent procedures, however, these patients run the risk of Horner's syndrome. Furthermore, delivery of a neurolytic agent there is particularly dangerous since the typical volume injected there, between 10-20 ml, has been demonstrated to spread far from the site of injection.

Intrinsic cardiac. Atrial fibrillation may be suppressed by modulation of the sympathetic chain or the intrinsic cardiac autonomic nervous syndrome (ICANS) embedded within the epicardial fat pads and the ligament of Marshall (LOM). The four main ganglionated plexi (GPs) on the atrium are the anterior right GP or right atrial (RAGP) at the right superior pulmonary vein (PV)-atrial junction, the inferior right GP at the junction of the inferior vena cava and both atria, the superior left GP near the left superior PV-atrial junction and the left pulmonary artery and the interior left GP at the left inferior PV-atrial junction. Different locations to stimulate, target, and ablate are described in, for example, U.S. Pub. No. 2005/0261672 to Deem et al., and Scherlag et al. (2009) which is hereby incorporated by reference in its entirety.

Other targets. Local delivery to heart. In some cases, the targeting of the intrinsic cardiac nervous system is desired. The intrinsic system includes parasympathetic, sympathetic, and interneurons. Local delivery into the epicardial fat pads containing these nerves may be desirable. Alternatively transvascular delivery of the therapy through the coronary artery, great cardiac vein, or coronary sinus wall to the epicardial space may be performed to deliver therapy around the externally facing side of the vessel. Alternatively, a region of one of these vessels coursing across the epicardial surface of the heart may be used as a site to deliver the therapy to fill or partially fill the epicardial sac in order to achieve more widespread neuronal modulation or denervation. Similarly, adapting the devices used for intramyocardial delivery of cells to deliver the neurolytic hydrogel to the anterior wall of the left ventricle can in some embodiments be desirable, particularly since it is innervated by both the right and left cardiac sympathetic nerves. As with the paravertebral gutter, performing injections in and around the left side of the heart first and then performing them on the right side of the heart as necessary, may reduce the likelihood of arrhythmias or other adverse events from flooding the tissue with so much agent. In some embodiments, it is desirable to only denervate the left ventricle, and more specifically the anterior left ventricular wall.

Non Cardiac. Non-limiting examples of noncardiovascular indications for a long-duration or permanent therapy directed towards the lower cervical and thoracic paravertebral space include, for example, facial flushing, upper (palmar, axillary, craniofacial) or lower extremity hyperhidrosis, complex regional pain syndrome types I and II, neuropathic pain, pre- or post- or menopausal hot flashes, cancer-related hot flashes, sudden hearing loss, tinnitus, vascular insufficiency/occlusive vascular disorders, intraarterial embolization and vasospasm, Raynaud's, spasticity, motor dysphagia including dysphagia relating to the production of speech, cerebral vasospasm, sleep quality, obstructive sleep apnea, hypokinetic (Parkinson's) and hyperkinetic movement disorders (tremors, dystonia, chorea, tics, myoclonus, restless leg syndrome), lymphedema, neurogenic inflammation, hearing loss, cerebral ischemia, cerebral vasospasm, cerebral embolism, subarachnoid hemorrhage, metabolic syndrome, obesity, sleep disorders, polycystic ovarian syndrome, fertility hyperinsulinemia, hyperleptinemia, ulcers and acid reflux, idiopathic peripheral neuropathy, essential tremor, overactive bladder, testicular pain, knee osteoarthritis, cerebral palsy, lower and upper limb spasticity particularly after a stroke, panic disorders, parotid dysfunction, temporomandibular disorder, idiopathic facial pain, pain from shingles, intractable chest wall pain or oncologic thoracic pain, post-herpetic neuralgia, intractable itching, post-traumatic stress disorder (PTSD), memory dysfunction, poor lymphatic drainage and local edema of the upper extremity, as occurs after mastectomy other procedures involving surgery/radiation that disrupt the lymphatics, phantom limb pain, critical limb ischemia, amputation stump pain, pain following mastectomy, Bell's palsy, orofacial pain syndrome including neuropathic orofacial pain, vascular headache and sympathetically maintained headaches, neuropathic pain syndromes in cancer pain, sudden infant death syndrome, endometrial and/or peritoneal pain, anorexia nervosa, thoracic outlet syndrome, arthritis, post-traumatic sympathetic dystrophy, thromboangitis obliterans, diabetes and insulin resistance, particularly at early stages, collagen disease such as scleroderma, ischemic stroke and subarachnoid hemorrhage. Sympathetic denervation may also be beneficial in, for example, the treatment of inflammatory diseases or diseases with an inflammatory component such as acute inflammation, shock (hypovolemic, septic, neurogenic), sepsis, and acute respiratory distress syndrome by reducing neutrophil and natural killer cell counts and improving lymphatic flow, glaucoma, facial blushing of hyperhidrosis (T1 to T3, or T2 only), palmar hyperhidrosis (generally T2-T3), axillary hyperhidrosis (generally T2-T4), reflex sympathetic dystrophy or complex regional pain syndrome, dry eye or mouth disorders, ischemic or diabetic ulcers, limb ischemia or leg pain, vasospastic disorders, causalgia, peripheral arterial disease or occlusive arterial disease, burning pain accompanied by hyperpathia, hyperaesthesia, and hypercoagulative/prothrombotic states. In some embodiments, endpoints include, at least an amelioration of the symptoms associated with the pathological condition afflicting the host, where amelioration is used in a broad sense to refer to at least a reduction in the magnitude of a parameter, e.g. symptom, associated with the pathological condition being treated. In some embodiments, the endpoint can be reduction in a symptom such as anxiety and/or panic. In one embodiment, the treatment of hot flashes results in a reduction in mean hot flash scores and frequencies, such as measured by the Hot Flash Related Daily Interference Scale for example. Within these diseases, targeting of the stellate ganglion alone may be sufficient for treatment of CRPS (type I and II) of the upper extremities, chronic and acute vascular sufficiency, occlusive vascular disorders of the upper extremities, poor lymphatic drainage, edema of the upper extremity following breast surgery, post-herpetic neuralgia, sudden hearing loss, hyperhidrosis, Bell's palsy and orofacial pain, trigeminal neuralgia, vascular headache such as cluster and migraine headaches, phantom limb pain or amputation stump pain.

Hyperhidrosis. To date, the clinical focus of sympathetic chain disruption procedures has been the treatment of hyperhidrosis through the denervation of palmar and axillary sweat glands. The second thoracic ganglia (T2), and to a lesser extent the third thoracic ganglia (T3), innervate the eccrine sweat glands of the upper limbs. The fourth and fifth ganglia (T4, T5) innervate the eccrine sweat glands of the axilla. Of note, some groups have demonstrated that only a few T2/T3 fibers innervate the hands whereas fibers from T4 pass through T2 and T3 to innervate the hands and that T3/T4 fibers are the main source of innervation of the arm. Directing the therapy as described herein towards these levels can provide a more safe and permanent treatment of severe hyperhidrosis than a VATS-based procedure.

Long duration blocks for other applications. Long duration blocks, in which the therapy includes the delivery of a sustained or controlled release formulation of anesthetic in the hydrogel, can be administered to achieve a long-lasting block of the abdominal, thoracic, or lumbar levels. At the thoracic paravertebral gutter, the therapy can provide anesthesia for chest wall incisions, drain sites, and parietal pleura including the use of long-duration paravertebral blocks can be performed for breast surgery including axillary dissection, VATS surgery, minimally invasive cardiac surgery, and open thoracotomy. Not to be limited by theory, the use of thoracic paravertebral block can reduce cancer recurrence compared to other methods of anesthesia in patients undergoing mastectomy and therefore the therapy may be delivered to these patients. For abdominal surgery, the therapy can be administered bilaterally in some cases and can be performed prior to, in conjunction with, or after the procedure, as necessary. The therapy can be delivered to the lumbar plexus or the lumbar plexus-lower thoracic paravertebral gutter for anesthetic purposes prior to renal surgery, open and laparoscopic cholecystomy, appendectomy, inguinal hernia repair, and the like.

Chronic pain management. Long-duration or permanent therapy directed towards the paravertebral gutter (including cervical, thoracic, and lumbar) can be used for the treatment of chronic pain, particularly visceral pain. Given the recent discoveries that visceral and somatic hypersensitivity may be related to the activation of adrenergic receptors on sensory nerves (as well as transient receptor potential channels, opioid and cannabinoid) in addition to efferent nerves, the contributions of sympathetic nervous system to aberrant pain signals are increasingly appreciated. In some embodiments, therapy is delivered to the paravertebral gutter for the treatment of visceral, chronic or neurogenic pain including but not limited to fibromyalgia, complex regional pain syndrome, pain from mesothelioma, post-thoracotomy chronic pain, pancreatitis, gastrointestinal tract neuroinflammatory disorders such as irritable bowel syndrome (IBS), irritable bowel disease (IBD), ulcerative colitis, and Crohn's disease.

CNS. As a result of reduction in systemic sympathetic vascular tone and also possibly cerebrovascular tone and cerebrovascular vasospasm after ischemic or hemorrhagic injury, systems and methods as disclosed herein may be used to treat ischemic stroke and other neurological diseases where cerebral blood flow constrictions or ischemia are implicated such as migraine, headache and traumatic brain injury. In some embodiments, systems and methods may also be used to reduce the occurrence of ischemic stroke since cerebrovascular disease is often closely associated with cardiac disease. Similarly, modulation of the sympathetic nervous system can be used to modulate the release of anti-clotting agents, such as tissue plasminogen activator (TPA) into the blood.

Other organs. As with renal denervation, sympathetic chain denervation may have a similar beneficial impact on many other visceral organs. Ablation of the cervical, thoracic, cervicothoracic, and lower thoracic chain has been demonstrated to have direct or indirect (reduction in systemic norepinephrine, for example) benefits on non-target organs and pathophysiology. In particular, neuromodulation of the upper thoracic and cervical sympathetic chain modulates angiotensin II levels and thus the renin-angiotensin system (RAAS) and can be beneficial in the treatment of acute or chronic kidney disease and renal failure. Thus, the therapy can result in improvements in, for example, renal, adrenal, liver, pancreas, spleen, gastrointestinal, and biliary disorders.

Neuromodulation for neuronal survival and/or regeneration. For neuromodulation disorders such as postural syncope syndromes, attributable to disordered neural circuitry control, the therapy can be delivered to the paravertebral gutter, particularly the upper thoracic paravertebral gutter to increase the survival and/or neurotransmission in the sympathetic nerves. Many of these diseases are associated with neuronal cell death and reductions in norepinephrine in visceral organs. Neural degenerative diseases of the brain (e.g., Shy-Drager syndrome and Parkinson's disease) which impair the central control of reflex sympathetic outflow, and peripheral sympathetic nerve degeneration (pure autonomic failure) or accompanying long-standing diabetes, postural tachycardia syndrome (POTS) with an exaggerated reflex sympathetic nervous response to standing, as well as chronic fatigue, baroreceptor failure, fibromyalgia, diabetes and diabetic neuropathy, multiple system atrophy, PKU, seizures, epilepsy, dementia and neurocardiogenic (vasovagal) syncope may be targeted with a local delivery of neurostimulatory, neurosurvival, neuroprotective, or neuroregenerative agents in a controlled release formulation, preferably a gel.

Other targets. Non autonomic related. The control afforded by delivering neuromodulatory agents, for example, in a hydrogel permits the delivery of the therapy to other autonomic and non-autonomic (somatic) ganglia, plexi and nerves generally. The therapy in some embodiments permits the reduction in the local dose administered improving both efficacy, local and systemic safety.

Other targets. Local delivery for pain management. The therapy may also be delivered locally to nerves for the amelioration of symptoms related to peripheral neuropathies. A neurolytic agent delivered in a gel can be preferred in some embodiments since allows for reduction in the volume of agent delivered as 1) the drug can remain in contact with the nerve (ganglia, plexus, nerve fibers) at a neurolytic concentration for longer than an agent that washes over the nerve and spreads elsewhere. In one embodiment, the stellate ganglion block is performed with 1-3 ml of neurolytic/anesthetic agent in a gel as opposed to the 5-20 ml of anesthetic delivered today which is well documented to travel to many other off-target neural structures. Similarly, in one embodiment 5 to 10 ml of the therapy is delivered to the celiac plexus instead of the 10-30 ml of alcohol that is injected in the region today. This can significantly reduce the spread of a toxic agent through the retroperitoneum and potentially result in longer relief of symptoms. Other target tissues for the therapy include, but are not limited to the carotid sinus, the superior laryngeal nerve, the petrosal ganglia, the nodose ganglia, the glossopharyngeal afferents from the carotid body and carotid sinus, superior hypogastric plexus, ganglion impar, trigeminal ganglia, subarachnoid space, epidural space, carotid sinus nerves, celiac plexus, celiac ganglia, retroperitoneal nerves, neuroma, splanchnic nerves, splanchnic ganglia, aorticrenal ganglia and any ganglia or plexi lying in and around the aortic arch and descending aorta, pterygopalatine ganglion, and ciliary ganglion. Other targets include any of the locations that anesthetic blocks are placed currently such as the brachial plexus, retrobulbar, hypogastric plexus, nerves innervating the pectoral and serratus anterior, transversus abdominis, saphenous nerve, femoral nerve, blocks at elbow and arm, axillary block, infraclavicular block, suprascapular and axillary nerve block, supraclavicular block, interscalene block, and endoscopic or transabdominal blocks, or blocks for neuropathy. In particular, denervation of the nodose ganglia can be of particular interest since the ganglia play a key role in mediating cardiopulmonary and baroreceptor information and given the close proximity to other neural structures, delivery of a neurolytic agent in a gel can be desirable to control the spread of the neurolytic agent.

Identifying High Risk Refractory Angina/Ischemia Patients.

In some embodiments, high-risk patients can be qualified for receiving the therapy through coronary angiography, fractional flow reserve (FFR) assessment (with, for example intravenous or intracoronary adenosine) in which an FFR of 1.0 is normal or >0.94 or if the FFR is abnormal. Similarly, patients who are at high risk for arrhythmias are defined by HRS but are generally patients that have a previous myocardial infarction and should be considered for receiving the therapy.

In another embodiment, a patient that responds to an equivalent anesthetic block is considered a potential responder for the therapy and qualifies for receiving the therapy. The block may be a stellate ganglion block, an upper thoracic paravertebral block, a lower thoracic block, or a lumbar block. In one embodiment the block is performed, providing local anesthetic to the region and providing verification that the patient is likely going to be a responder to the therapy, and then the patient receives the neurolytic agent—hydrogel. In another embodiment, the patient receives a block and then comes back 2-6 weeks later when the block has worn off and/or the symptoms have returned.

Procedural Responders.

Assessing regional sympathetic nerve activity pre-, intra- and post-operatively allows identification of appropriate patients for the treatment, intraoperative confirmation of successful neuromodulation or neurolysis, and post-operative measures of short and long-term efficacy, respectively. In one embodiment, non-organ specific peripheral measurements of sympathetic modulation are monitored as a proxy for organ-denervation. In one embodiment, a pulse oximeter (a reflectance pulse oximeter) adapted for use on the palm. The difference between baseline laser Doppler blood flow and post-surgery blood flow, an over 200% increase in blood flow with an increase in palmar temperature of 1.44 degrees. In another embodiment, a pulse oximeter is used to monitor the perfusion index (PI) at baseline until the sympathectomy procedure and post-procedure. A successful sympathectomy is defined as a twofold increase in PI on the ipsilateral arm. The change in skin conductance occurs as early as 1 minute after transection of the chain.

In one embodiment, cardiac and pulmonary and/or cardiothoracic cavity nerves are assessed directly to assess the integrity of sympathetic nerve function to the organs. In one embodiment, a sympathetic nerve is stimulated with a current frequency of about 10 to 50 Hz and an amplitude of 0.1 to 20 mA to inhibit the action potential propagation of the nerve. Some stimulation parameters that can be used or adapted for use herein can be found, for example, in U.S. Pub. No. 2008/0147137 A1, which is incorporated for reference herein in its entirety. By stimulating at a high frequency, the afferent and efferent nerves may be blocked.

Another approach is to look at a modifications of conventional spectral HRV analysis permit calculations of low-frequency (LF) and high-frequency (HF) spectral power and their ratio (LF/HF) in the sympathetic modulation of patients with refractory angina. Cardiac sympathetic activity is measured indirectly by LF. However, increased skin temperature and decrease in skin resistance, particularly at the digits, as measured by increase in skin temperature measurements and thermography, increase in pulse amplitude (plethysmography), increased peak flow frequency in the radial and ulnar arteries, abolition of sympathogalanic response, and absence of sweating are considered indicators of sympathetic denervation.

For example, in a patient with refractory angina or evidence of cardiac ischemia, if a patient has normal coronary angiogram but an irregular FFR, the patient undergoes the sustained neuromodulatory block or neurolytic sympathectomy described herein. In one embodiment, FFR is performed during the procedure and there is an improvement in FFR pre- and post-the procedure as the coronary ischemia improves.

In another embodiment, in a patient undergoing catheterization for a procedure, a stimulating electrode is used to stimulate and detect signals and isolate the SNS. For example, these signals could be stimulated and subsequently recorded in the SA node or ganglionated plexus until they are recorded.

Pre- and Post-Procedural Approaches to Measuring Sympathetic Nerve Activity.

In another embodiment, patients undergo neuroimaging technology. Patients are placed in a GE Advance Scanner (GE) 6-18F-fluorodopamine was infused intravenously for 3 minutes and dynamic scanning data were obtained for thoracic radioactivity. By doing this pre- and post-procedure, successful cardiac sympathetic denervation is indicated by low concentrations of radioactivity in the interventricular septum and left ventricular free wall, at <5000 Bq/ml per MBq/kg and <4000 Bq/ml per MBq/kg. In another embodiment Iodine-123 metaiodobenzylguanidine scintigraphic (MIBG) assessment is performed, which reflects number of norepinephrine reuptake transporters in the tissue (heart, lung, or other organ) and is thought to be an indicator of sympathetic innervation. In some diseases this is likely to be the case, such as the demonstration through MIBG of the reinnervation of the heart after orthotropic cardiac transplant or in diseases with loss of cardiac sympathetic innervation, as in Parkinson's. MIBG studies highlight cardiac sympathetic nerve dysfunction irrespective of whether degeneration of the nerves results in lowered NE uptake or whether the sympathetic nerves are present but the NE uptake has been downregulated. Therefore, MIBG may be used not only to stratify patients at risk for various diseases (e.g. arrhythmias, cardiac arrest, stroke) but it can potentially be used to guide which patients should receive a treatment that modulates the activity of the dysfunctional sympathetic nerves.

Cardiac transplant recipients do not demonstrate 1-123 MIBG cardiac uptake when studied <6 months from transplantation. However, physiologic and biochemical studies suggest that sympathetic reinnervation of the heart can occur >1 year after transplantation.

Alternatively, regional sympathetic nerve activity can also be assessed by isotype dilution derived measurements of organ specific norepinephrine spillover into plasma and studies have demonstrated a dramatic and almost complete reduction in norepinephrine levels in the heart after orthotopic cardiac transplantation or the lung after lung transplantation. These results can be benchmarked against patients who received cardiac transplantation and contrasted with patients undergoing surgical sympathectomy on the left and or right and left sides.

Endovascular.

Recordings from post-ganglionic sympathetic efferent nerves, whether multi-unit or single-fiber recordings can be obtained from nerves innervating the lungs and heart via an electrophysiology diagnostic catheter placed in the placed in the pulmonary or bronchial arteries or veins, an intercostal vein or artery, the subclavian artery, the coronary arteries or coronary sinus, or the azygous/hemiazygous/accessory vein. In some embodiments, a catheter can be placed in the pulmonary artery or pulmonary artery trunk so that it can make direct measurements from sympathetic nerves innervating the heart and lungs, preferably from the extrinsic cardiac plexi.

Indirect assessments of cardiac sympathetic nerve activity may also be derived from paravertebral subcutaneous sympathetic efferents as there is a higher density of them there. In one embodiment, recording electrodes are inserted into the subcutaneous tissue on the patient's back on either side of the spine (dorsum) to measure sympathetic nerve activity. Experiments in dogs have demonstrated that these nerves fire in synchrony with cardiac nerves.

Tyramine Infusion Sensitivity.

Tyramine can be infused IV at a rate of 1 mg/min for 10 minutes into a supine patient with a hilt tilted at 15-30 degrees. Blood samples are drawn at baseline and 10 minutes during the infusion and assayed for catecholamine levels. Tyramine is a sympathomimetic amine and infusion will increase cardiac contractility (impaired inotropic response) in patients with intact cardiac sympathetic innervation but not patients with cardiac sympathetic denervation. Sympathetic nerves take up tyramine via the norepinephrine transporter which enters the axoplasm and then is taken up into vesicles via the vesicular monoamine transporter and in doing so, displaces norepinephrine into the axoplasm where it is deaminated to form dihydroxyphenylglycol. A portion of the norepinephrine is released into the extracellular fluid and binds to adrenoceptors on cardiac smooth muscles cells resulting in inotropic effects. Thus, attenuation of cardiac inotropic response to tyramine probably reflect decreased vesicular norepinephrine stores and is suggestive of a successful procedure.

Isoproterenol Infusion Sensitivity.

Patients with cardiac sympathetic denervation have exaggerated responses to isoproterenol, a beta-adrenoceptor agonist, possibly as a result of beta-adrenoreceptor upregulation/super sensitivity. On a separate day, isoproterenol was infused in 10 patients at four incremental doses of 3.5, 7, 14, and 35 ng/kg/min for 10 min each until the heart rate increased by 25 bpm from the baseline. Stroke volume, cardiac output, velocity index, acceleration index, pre-ejection period, left ventricular ejection time and electromechanical systole were measured noninvasively using the BioZ impedance cardiographic device, before and during the infusions. Total peripheral resistance and LVET index and PEP index, systolic time ratio and systolic time ratio index were calculated. A pattern of prolongation of PEP and shortening of LVET characterize myocardial infarction, angina pectoris, and heart failure. Thus patients who have undergone a successful procedure will have evidence of denervation supersensitivity within a week of their procedure, as evidenced by exaggerated cardiac responses to isoproterenol.

Non-limiting examples of tissues and vessels that can be targeted with systems and methods disclosed herein is listed below, as well as elsewhere herein.

Figure 2A:
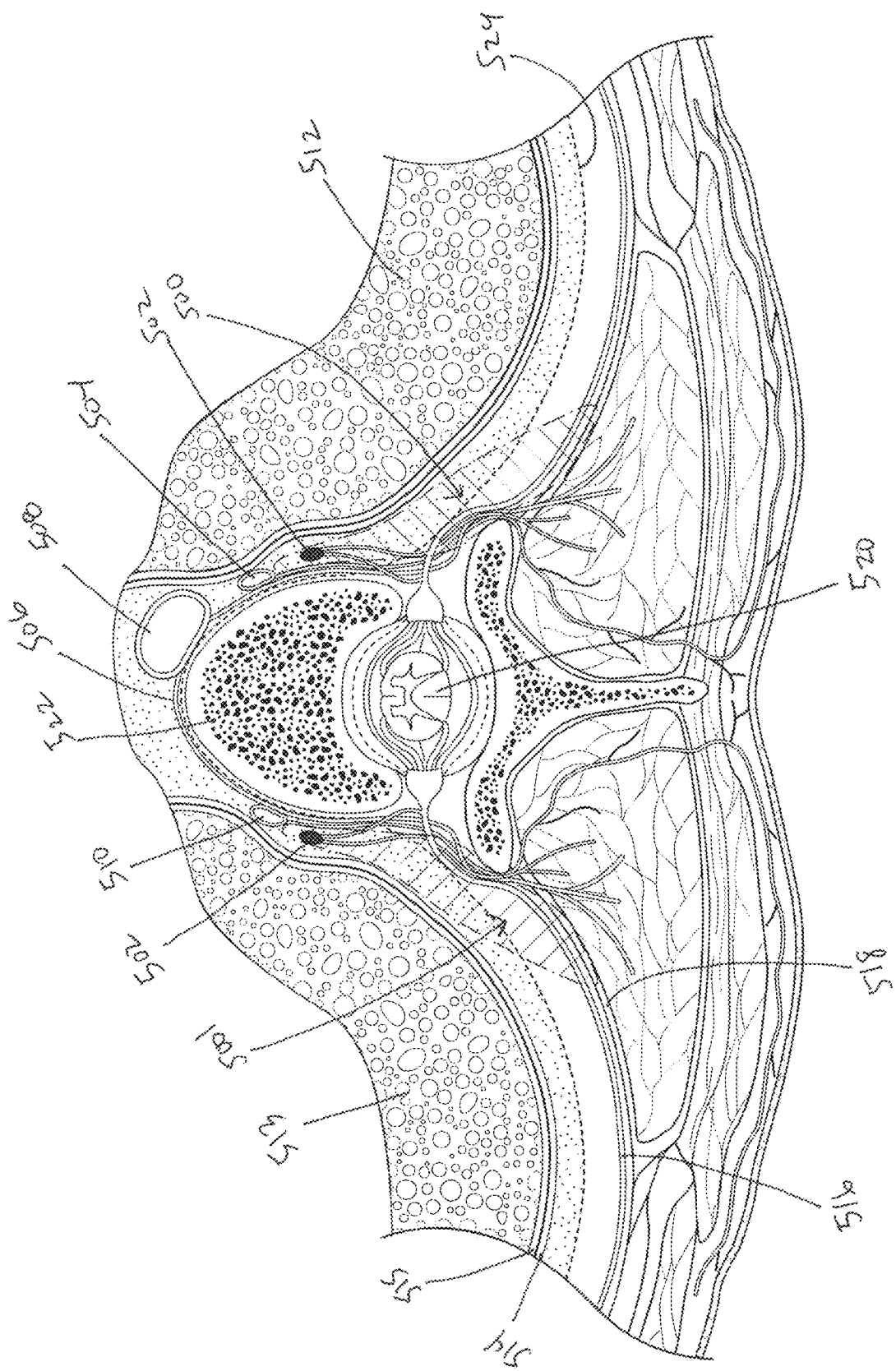
FIG. 2A is a horizontal section highlighting various anatomical features in the thoracic region.
Figure 2B:
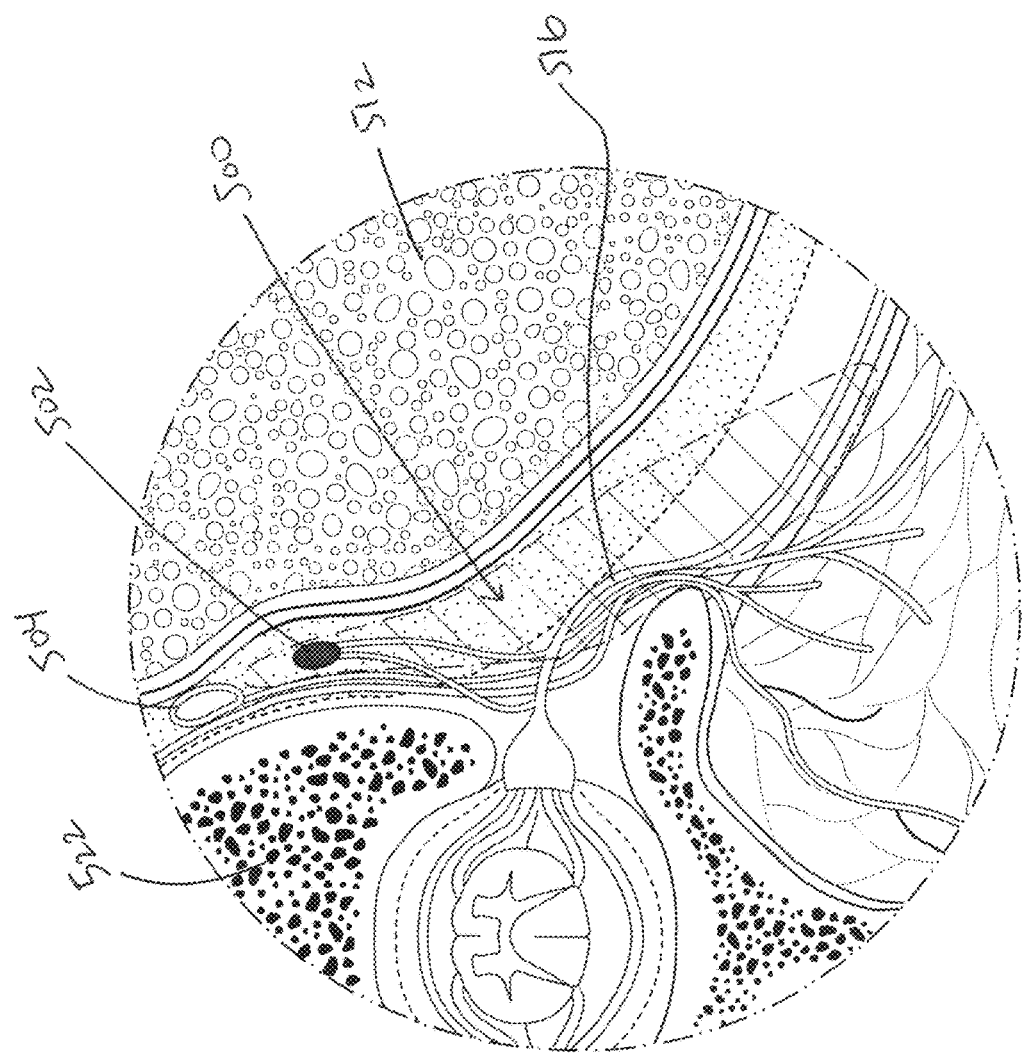
FIG. 2B is a close-up view of FIG. 2A illustrating selected structures illustrated in FIG. 2A in or in proximity to the paravertebral gutter.

Paravertebral space. The thoracic paravertebral space (TPVS) is a wedge-shaped (triangular) space that lies on either side of the thoracic vertebral column (vertebrae) at a given level that contains loose fatty tissue. FIG. 2A is a horizontal section highlighting various anatomical features in the thoracic region. Anteriorly or laterally the TPVS is bounded by endothoracic fascia 524 and parietal pleura 514, posteriorly it is bounded by the superior costotransverse ligament 518, and medially it is bounded by the posterolateral aspect of the vertebral body 522, the intervertebral disc and intervertebral foramen. Medially, the space is in communication with the epidural space via the intervertebral foramen. However, the continuity between the paravertebral and epidural space, particularly in older patients, is a subject of controversy. Laterally, the space communicates with the intercostal space, through which the intercostal artery 506, vein and nerve 516 (and accessory vessels) travel. The space is separated from the space above and below by the heads and necks of adjoining ribs. There is bilateral communication between the paravertebral spaces 500, 500' on either side of the vertebral column via the prevertebral and epidural space. The paravertebral gutter (shown cross-hatched: right 500', left 500) is the continuous channel that connects adjacent paravertebral spaces to one another on either side of the vertebral column via the prevertebral and epidural space. The paravertebral spaces extend from the first rib (stellate/T1 sympathetic ganglia) to the sacrum although it is divided into the thoracic paravertebral gutter space and the lumbar space, divided by the psoas muscle. The cervical stellate ganglia is contiguous with the paravertebral space as contrast injected there readily travels in the paravertebral gutter. Also illustrated herein is the descending aorta 508, azygous vein 504, accessory hemiazygous vein 510, sympathetic ganglia 502, right lung 513, left lung 512, spinal cord 520, and visceral pleura 515. FIG. 2B is a close-up view of FIG. 2A illustrating selected structures illustrated in FIG. 2A in or in proximity to the paravertebral gutter 500 (shown cross-hatched).

The TPVS space contains neural structures including the spinal (intercostal) nerve 516, the white and grey ramus communicans, the sympathetic chain 502, the dorsal/posterior and anterior/ventral ramus or divisions of the somatic nerves, the intercostal nerve and the rami communicantes as well as vessels including the intercostal artery and vein. The intercostal nerve 516 in this region includes the proximal part of the posterior division as well as the rami communicantes of the intercostal nerve 516. In this region, the sympathetic chain courses vertically over the heads of the ribs, just lateral to the radiate ligaments (Vallieres 2007). Also, the spinal nerves emerge from the intervertebral foramen and give off a dorsal and ventral ramus within the TPVS.

The paravertebral space can be further subdivided into an anterior (anterolateral extrapleural) space containing the sympathetic ganglia 502 and a posterior (posteromedial subendothoracic) compartment by the thin endothoracic fascia 524. In some embodiments, injections into the more anterior compartment can result in better longitudinal spread up and down the paravertebral gutter 500, 500' as well as more consistent anesthetic paravertebral blocks.

Intervertebral Foramen.

The intervertebral foramen protects the spinal ganglion and nerve roots, include the dorsal root ganglion as they exit the spinal cord. The foramen also protects the branches of the spinal arterial and venous systems.

Rami Communicantes.

Between one and nine or more anterior/dorsal rami come off of the thoracic sympathetic ganglia and/or chain within the paravertebral space and course directly to either the adjacent intercostal nerves or to the thoracic organs. The rami that travel directly to the lung and heart cross anteriorly or posteriorly over or across one of several great vessels in the thorax. 1) On the right side, rami from the cervical and thoracic sympathetic chain cross over the azygos vein and the arch of the azygos vein as it courses over the rostral aspect of the lung hilum. 2) On the left side, the cervical and upper thoracic rami cross over the accessory hemiazygos vein (or more caudally the lower thoracic cross over the hemiazygos vein) and may cross over the communicating vein that runs between the hemiazygos and azygos veins and along or around the intercostal veins. 3) On the left and right side, rami from the cervical and thoracic sympathetic chain cross posteriorly and/or anteriorly across the aorta and the arch of the aorta to the heart and lungs. For example, some of the rami from the upper thoracic and cervical sympathetic chain travel directly to the superficial and deep aortic plexus under the aortic arch and on the aorta. A portion of the right and left sided rami run along and/or around the intercostal arteries medially from the sympathetic chain back to origin of the intercostal arteries origin at the aorta and on to the heart and lungs. Some of the fibers also course rostrally and caudally around and along the aorta on to other plexuses, ganglia, and internal organs. 4) The rami may travel from coursing along one or more intercostal arteries to follow the bronchial arteries into the lungs. The posterior bronchial arteries, for example, travels across the posterior aspect of the bronchi. The afferent and efferent fibers may enter the lung around and along the bronchial vessels. In particularly, these bronchial vessels course through or alongside the posterior and anterior pulmonary plexus. 5) Lastly, they may cross the thoracic duct and the esophagus.

Intercostal Nerves.

Intercostal nerves are located bilaterally on the anterior rami of the upper eleven thoracic nerves. Each nerve gives a white branch to and receives a grey branch from a ganglion of the sympathetic trunk. The anterior nerve root enters the corresponding intercostal space as the intercostal nerve where it travels laterally to join the intercostal vessels in this space. At the angle of the ribs the intercostal nerves pass into the interval between the external and internal intercostal muscles. This neurovascular bundle runs forward between the muscles, to about the mid-axillary line. Then the intercostal nerve begins to pass obliquely through the internal intercostal muscle and emerges on the interior surface at the junction of the bone with the cartilage of the rib. From here, the nerve continues medially and is found between the internal intercostal muscle and the pleura in the case of the first two nerves and between the internal intercostal muscle and the transversus thoracis in the case of the third, fourth and fifth nerves. The intercostal nerve usually typically comprises three or four small bundles without any single enclosing fascial sheath. The nerve bundles cross the paravertebral space and make their way to posteriorly to the subcostal groove, the triangular space bounded by the rib, the posterior intercostal membrane and the internal intercostal muscle. This groove has an area of about 0.75 cm$^2$ and is largely filled with fat. Generally, the first two thoracic nerves supply the upper extremities and their thoracic branches supply the thoracic chest wall. The lower five thoracic nerves supply the chest wall and upper abdomen. The second to the sixth intercostal thoracic nerves and a small branch from the first thoracic intercostal nerve supply the chest wall.

Intercostal Artery.

In the uppermost two intercostal spaces, the intercostal arteries run dorsoventrally and are derived from the superior (supreme/highest) intercostal artery which is a division of the costocervical branch off of the subclavian artery. These arteries cross the left superior intercostal vein.

From the third (or fourth) thoracic level down (referred to as the lower nine levels), each vertebral level contains a pair of segmental arteries that arise from the posterior aspect of the descending aorta and are called the right and left (posterior) aortic intercostal arteries. Since the aorta lies on the left side of the vertebral column, the right aortic intercostal arteries are longer than the left and cross over the vertebrae behind the esophagus, thoracic duct and azygos vein. On the left side, the intercostal arteries are crossed by the hemiazygos vein. Both intercostal arteries run along the anterolateral surface of each side of the vertebral body and divide into a dorsal/posterior branch and ventral/anterior branch near the posterior aspect of the body, anterior to the neural foramen. Prior to the bifurcation, the arteries are crossed by the sympathetic trunk at the rib head. The vessels are covered by pleura. The dorsal branch travels posteriorly with the corresponding dorsal ramus of the spinal nerve and crosses below the transverse process, medial to the superior costotransverse ligaments. The ventral branch of the segmental artery becomes the (aortic) intercostal artery which runs laterally and inferiorly to the subcostal groove between the interior and exterior intercostal muscles near the posterior angle of the rib.

From the angles of the ribs onwards to a point midway between the vertebral column and the sternum, the aortic intercostal arteries lie under shelter of the notched lower margins of the ribs (subcostal groove) which bound the spaces superiorly. In this area, the intercostal vein is typically superior to the artery and both are superior to the accompanying nerve. However, there are significant inter-level variations and patient variability in the relative arrangement of the vessels with respect to the nerve.

The posterior intercostal arteries measure about 1.5 mm (range 1.0 and 2.2 mm) in the $2^{nd}$ intercostal space at their rib angle and are approximately 0.8 mm in outer diameter at the mid-axillary line. The diameter of the posterior intercostal artery increases down the thorax from 1.5 to 4.3 mm. The vascular bundle as a whole measures between 1.6 to 3.7 mm. There are collateral intercostal arteries which originate from the posterior intercostal artery at an angle of 45 to 60 degrees with it. The point of origin is between the vertebral body and the costal angle of the inferior border of the rib.

Intercostal Vein Anatomy.

The venous drainage of the vertebra and thoracic costovertebral area largely parallels the arterial blood supply. Right. On the right side, the first intercostal vein passes to the right brachiocephalic vein (right innominate vein). The second, third and fourth (posterior) intercostal veins drain into the right superior intercostal vein and then to the azygos vein which is located on the medial side of the fourth or fifth rib head. The fifth through the ninth intercostal veins drain directly into the azygos vein. Occasionally, the fourth intercostal vein drains together with the fifth through the ninth intercostal veins to the azygos instead of the right superior intercostal vein. The size of the superior intercostal vein increases as the vein nears the azygos vein. Of note, the right side the second through fourth intercostal veins widen appreciably as they drain to the superior intercostal vein at the rib head, as illustrated in a diagram of the third and fourth levels. Left. On the left side, the upper three or four intercostal veins unite and drain into the left superior intercostal vein, which drains into the left brachiocephalic vein at the lateral side of the rib head. Occasionally the first intercostal vein will drain directly into the left brachiocephalic vein. There may be a communicating branch from the left superior intercostal vein to the accessory hemiazygos system. The fifth through eighth intercostal veins drain into the accessory hemiazygos vein and then to the azygos vein. Anatomical variability results in the fourth intercostal vein occasionally draining into the accessory hemiazygos instead of the left superior intercostal vein. There may be a vessel communicating between the fourth and fifth intercostal veins thereby connecting the superior intercostal and accessory hemiazygos systems. On the left side, the intercostal vein size generally does not increase in size as the rip head and drains into the left superior intercostal vein.

The intercostal arteries and veins may pass anterior or posterior to the sympathetic trunk. Generally, the majority of intercostal veins pass posteriorly with the exception of the first intercostal vein. Similarly, the majority of aortic intercostal arteries pass posteriorly to the sympathetic trunk with the exception of the two intercostal arteries arising from the superior intercostal artery.

Intercostal veins vary tremendously in size, and are generally larger on the right than the left side of a patient. For example, in the third and fourth intercostal spaces, large veins are found in 36% and 68% of patients, respectively, on the right side. On the left side, only 2% and 5%, respectively, of the third and fourth intercostal veins are large. There is also variability in the size, presentation and location of anterior crossing intercostal veins, again, with these veins found on order of 15-30% of time on the right side but rarely on the left side.

Bronchial Arteries.

Bronchial arteries are systemic vessels bringing oxygenated blood from the descending aorta to the lung and bronchial tree.

Carrying less than 4% of the total cardiac output, bronchial arteries can be interrupted without causing any obvious dysfunction. These arteries appear to play a major role in the vital airway defenses, fluid balance, and metabolic function of the lung. In response to injury, these vessels can enlarge and may assist or take over the gas exchange function if the pulmonary function fails in any region of the lung. They decrease edema formation after ischemia and reperfusion and contribute to lung lymph flow.

More recently, the circulation, and the bronchial circulation specifically, is thought to play an important role in the pathogenesis of inflammatory airway disease. The bronchial circulation receives only about 1% of the cardiac output in health but serves an important role in maintaining airway and lung function. In disease, the bronchial circulation can increase in size to provide lung parenchymal perfusion when the pulmonary circulation is compromised. Bronchial blood flow is increased in patients with asthma (and not COPD) and is thought to be the result of a combination of angiogenesis and plasma leak.

The bronchial arteries originate orthotopically from the anterolateral aspect of the descending aorta between the level of T5 and T6. More rarely, they may also arise from the aortic arch or an aortic vessel collateral. There are rarely more than four ostia and the farthest apart averages 18 mm.

Right bronchial artery. Typically, one right bronchial artery arises from the first right aortic intercostal artery and courses to the lung (5 to 8.5 cm). Alternately, the right (superior) bronchial artery may arise from the thoracic aorta directly, from a common trunk to the right third (posterior) intercostal artery, the subclavian artery, the left superior bronchial artery or another right intercostal artery. During its course, the right bronchial artery typically lies with the intercostobronchial artery along the right anterolateral aspect of thoracic levels T3-T4 and then passes anteriorly on the right of the thoracic duct, crossing the esophagus from back to front and right to left before ending at the level of the main bronchus. The artery runs parallel to the arch of the azygos vein and the lymphatic vessels. The bronchial artery gives branches to the midportion of the esophagus, the trachea, the pericardium, the left atrium, and the mediastinal lymph nodes. The artery is especially close to the vagus nerve, which it crosses and with the branches of which it often intermingles. The bronchial artery branches to the visceral pleura and other mediastinal structures including the esophagus, hilar and peritracheobronchial lymph nodes, and the heart. The arteries are around 1.5 mm in diameter. The artery may be closely associated with the cardiopulmonary nerves arising from the right stellate ganglion and may serve as an extension of the sympathetic cardiopulmonary nerves to the heart and lungs.

Left bronchial artery. There may be one or two left bronchial arteries that have a shorter course to the lung than the right bronchial artery (2 to 4.5 cm). These arteries arise from anywhere over the right and left anterolateral aspect of the aorta. In up to 50% of cases, there may be a common trunk giving rise to the right and left bronchial artery but it is not typically the only blood supply the lung (only supply in 2.5 to 18.5% of cases). If there is a common trunk present, it runs only between 1 and 1.5 cm before the bronchial arteries branch.

Furthermore, numerous accessory bronchial arteries are common and appear to be of ectopic origin. Occasionally these vessels provide appreciable bronchial arterial flow. They arise from the aortic arch or the ipsilateral subclavian artery. On the right, where they are more common, they originate from the concavity of the aortic arch, the lower thoracic aorta and from the left subclavian artery or its branches.

Finally, there is especially dense innervation of a population of arterioles arising at right angles from the pulmonary arteries which may play a key role in the distribution of blood flow in the lungs.

Pulmonary arteries. Fibers also travel across pulmonary artery to the anterior pulmonary plexus (also pulmonary ligament).

Pleura.

The pleura lines the inner surface of the chest wall. The pleura is immediately adjacent to and covers the internal intercostal vessels, nerve, and ribs. Care should be taken not to significantly disrupt the pleura and thus cause a pneumothorax.

Target Nerve for Ablation within the Paravertebral Gutter or Intervertebral Foramen.

The target tissue may be, for example, any number of the following: the posterior/dorsal nerve root, the anterior/ventral nerve root, the dorsal root ganglion, the sympathetic cord or chain, the white ramus communicans, the grey ramus communicans, the sympathetic ganglion, dorsal root ganglion, the dorsal (primary) ramus/rami, the ventral (primary) ramus/rami, the intercostal nerve(s), the intrathoracic ramus between the first and second nerves or second and third nerves or rami that directly extend to the brachial plexus, other unnamed rami communicantes that originate from the sympathetic ganglion/chain and travel directly to the thoracic cavity, and unnamed rami communicantes that originate from the sympathetic ganglion/trunk and travel to the intercostal nerves. The afferent or efferent fibers may be part of a mixed fiber bundle, such as the white or gray ramus communicans.

Organ Targets.

In some embodiments, the therapy may target somatic motor, somatic sensory, sympathetic motor and/or sympathetic sensory fibers that innervate, for example, the following organs and tissues in the thoracic cavity: the trachea, right and left primary bronchi, right and left upper/middle/lower lobar bronchi and bronchial tree, right superior lobar bronchus/eparterial bronchus, hyparterial bronchus, esophagus, heart, thymus gland, the (parietal/visceral) pleura, pericardium, epicardium, diaphragm, thymus, transversus thoracis muscle, pectoralis minor/major, (superior/anterior/posterior) mediastinum, mediastinal fat pad, retrosternal fat pad, epicardial fat pads, lung root, lung hilum, lymph nodes including the tracheobronchial lymph nodes, bronchopulmonary lymph nodes, mediastinal lymph nodes (superior/central/posterior), diaphragmatic lymph nodes, left/right bronchomediastinal lymphatic trunk and posterior, left/right jugular lymphatic trunk, left, right subclavian lymphatic trunk, thoracic duct, the skin, the sweat glands, the diaphragm, and the peripheral vessels.

Indirect Nerve Targets.

As a result of modulation of the nerves in the paravertebral gutter, in some embodiments the therapy result in denervation of the following vessels, both the innervation of the sympathetic fibers to the vessels themselves, as well as denervation of the fibers coursing along or over these vessels to reach a distant target. These vessels include the ascending/descending aorta, aortic arch, superior vena cava, internal thoracic artery and vein, pericardiophrenic artery, intercostal artery and veins, musculophrenic artery and vein, superior phrenic artery and vein, right/left brachiocephalic vein, brachiocephalic artery, superior epigastric artery and vein, right/left common carotid artery, azygos vein, hemiazygos vein, accessory hemiazygos vein, communicating vein between azygos and hemiazygos veins, supreme intercostal artery and vein, costocervical trunk (artery), internal jugular, external jugular, right/left subclavian artery, right/left subclavian vein, left/right innominate vein, right/left pulmonary arteries and branches thereof, right and left (superior/inferior) pulmonary vein, pulmonary trunk, anterior/posterior bronchial artery, bronchial artery branches from the aorta to the trachea, esophageal artery and vein, inferior thyroid vein, internal/external and left internal jugular vein, thyrocervical trunk, celiac trunk, cephalic vein, superior/inferior mesenteric artery, hepatic artery or veins, portal vein, splenic artery or vein, thymic vein, anterior cardiac artery/vein, right/left coronary artery, circumflex branch of left coronary artery, anterior cardiac branch of right coronary artery, anterior interventricular branch of left coronary artery, posterior interventricular branch of right coronary artery, and other coronary artery branches, great cardiac vein/left coronary vein, middle/small cardiac veins, posterior vein of left ventricle, interventricular vein, and coronary sinus. Alternatively, the therapy may be delivered transvascularly to denervate the nerves around these vessels either on one or both sides of the vessel or circumferentially.

Similarly, modulating the nerves within the paravertebral gutter may directly or indirectly lead to denervation of the common carotid plexus, greater/lesser splanchnic nerve, inferior/superior cardiac nerve, ansa subclavia, nodose ganglion, superior cervical ganglion, middle cervical ganglion, inferior cervical ganglion or stellate ganglion or cervicothoracic ganglion, inferior cervical cardiac nerve, the recurrent laryngeal nerve, celiac ganglion, aorticorenal ganglion, superior mesenteric ganglion, the right/left vagus nerve (some sympathetic afferent/efferent fibers are speculated to join these bundles in humans), right/left phrenic nerve, esophageal plexus, posterior pulmonary plexus, anterior pulmonary plexus, deep cardiac plexus, superficial cardiac plexus, intercostal nerve, pericardial branches of the phrenic nerve, the epicardial branches of the atrioventricular bundle/node, sinoatrial node, and ganglia innervating the atria and ventricles. Alternatively, these ganglia and nerves may be targeted directly through a percutaneous, transcutaneous or endovascular route with the assistance of ultrasound, fluoroscopic, or CT guidance.

Direct/Indirect.

Neuromodulation can be achieved via direct or indirect application of energy or neuromodulatory agents to target neural matter, to adipose or fascial tissue that contains the neural matter or to vascular structures that support or intersect the target neural matter.

In another embodiment, the neuromodulatory agent is delivered to the sympathetic pre- or post-ganglionic nerve or parasympathetic fibers as they course through any number of the heart, trachea, bronchi, lungs, diaphragm, stomach, small and large intestines, colon, kidneys, ureters, bladder, liver, urethra, adrenal glands, omentum, gall bladder, ovaries, uterus, fallopian tubes, vagina, placenta, testes, epididymis, vas deferens, seminal vesicles, prostate, salivary glands, esophagus, spleen, thymus, pancreas, and endocrine glands (pituitary, pineal, thyroid, parathyroid, adrenal), cornea, iris, ciliary body, lens, retina, outer, middle or inner ear, olfactory epithelium, and the lymph nodes, vessels, and ducts.

In another embodiment, the neuromodulatory agent is delivered locally into the lungs by intrapulmonary injection, pleural injection, intercostal space injection, peri-tracheal injection, peri-brachial artery injection, peri-pulmonary artery/vein injection. Specifically, the target region is the lung hilum in some embodiments. This region, containing the pulmonary vasculature and the bronchi, and is bounded by the pleural sac, can be filled with the therapy by performing transarterial injections of the therapy from the right and left bronchial arteries in the region of the hilum. In another embodiment the neuromodulatory agent is delivered locally to the heart by intrapericardial, epicardial, epicardial fat pad, or intramyocardial injection. In another embodiment, the neuromodulatory formulation is delivered into the interstitial space surrounding the injured or ischemic myocardium. In another embodiment the neuromodulatory agent is delivered into the intrinsic pulmonary or cardiac plexi or the plexi between the two.

Targeting of Specific Arm.

The therapy may be directly towards a purely efferent or afferent nerves whether through spatial constraint of the delivery of the therapy to a specific region, such as the anterior/ventral nerve root or posterior/dorsal nerve root, respectively, or through the delivery of a neuromodulatory agent that has preferential affinity or stronger effect on one type of nerves over another, such as for sympathetic efferents over sympathetic visceral afferents. Alternatively, a mix of afferent and efferent fibers may be targeted as they run their course wrapping longitudinally along a blood vessel to the thoracic organs or simply crossing a blood vessel on their way to the thoracic organ. In some embodiments a specific neuron, soma, axon, or nerve fiber, nerve plexus/plexi or nerve bundle may be targeted. In addition, the methods and apparatus described herein may, for example, be used to modulate parasympathetic nerves and/or the central nervous system including the brain and spinal cord.

Terms for Neuromodulation and Energy Based Modalities.

Terms that describe modulation of the nervous system or neuromodulation refer to providing excitatory, inhibitory, blocking signals to the nerve increasing or decreasing the likelihood for an action potential, the modulation of the nerve to improve its survival or result in its cell death, the stimulation of a nerve to regenerate, the stimulation of a nerve to fire action potentials such as nerve stimulation, and/or result in the up- or down-regulation of proteins including neurotransmitters, receptors through viral or non-viral vectors delivering DNA, RNA, siRNA, microRNA (miRs), modified messenger RNA, or antibodies.

Neuromodulation approaches to block, temporarily block, or eliminate nerves include, for example, nerve blockade or blocking, neuroablation, chemoablation, radiofrequency ablation, neurolysis, chemolysis, chemical neuroablation, such as sympathicolysis. Alternatively, when a procedure to remove nerves is performed it may involve the following terms—icotomy, -ectomy etc. such as sympathectomy or sympathicotomy or ramisectomy. Neuromodulation can refer to chemical, mechanical, or electrical methods to modulate nerve conduction. Electrical methods include hyperpolarization block, cathodal, anodal, or collision block, as described for example in U.S. Pub. No. 2005/0228460 A1 to Levin et al., which is hereby incorporated by reference in its entirety. Overpacing or overstimulating a nerve (such as with a neurotransmitter, e.g. nicotine) may also induce a block by generating stimulating the nerve at a rate that exceeds its capacity to generate an action potential. In this manner, neurotransmitters stores are depleted and the nerve is temporarily unable to convey signals to other nerves and tissue.

The radiofrequency generator and catheter can have, in some embodiments a closed loop element to measure impedance, deliver electrical stimulation (e.g. 2 Hz current for motor and 50 Hz for sensory) to confirm the position of the electrode in the location of the paravertebral gutter as well as deliver ablative energy to arbitrarily or selectively interrupt the sympathetic chain. In one embodiment, sensory stimulation is carried out at 50 Hz until a tingling sensation in the select dermatome noticed using a 0.4 to 1 V stimulus. It may also be possible to perceive muscle contractions (anterior root) at a threshold 1.5 times below the sensory threshold. In addition, the system can perform thermal lesioning with a preferably bipolar electrode with a continuous and/or pulsed RF signal, and monitor the temperature at the tip of the device. In one embodiment, the RF energy is continuous, providing indiscriminate destruction of sympathetic afferents and efferents. Alternatively, the parameters of pulsed radiofrequency signal allow the targeted ablation of C-fibers. In one embodiment, a 100 mm cannula (Radionics SMK 22G, 5 mm active tip) is inserted and advanced to the paravertebral space. The stylet of the cannula is replaced with a flexible RF probe with either a monopolar electrode at the tip or bipolar electrodes spaced, for example, 1-10 mm apart which is advanced through the paravertebral space up to the desired thoracic level, for example from T4 up to T1, or up to the middle of the first rib. Alternatively, the catheter can be advanced rostrally one or two levels, the energy delivered, and then retracted and directed caudally where the catheter then delivers RF at one or two levels.

In one embodiment, contrast is injected (e.g. iohexol) to confirm the appropriate positioning of the cannula and confirm an extravascular location and absence of intrathecal or intrapleural spread followed by 2 ml of 2% lidocaine. The hydrogel formulation is then injected at the desired target levels. The hydrogel, such as the in situ crosslinked PEG-based hydrogel, has enough mechanical integrity to allow a catheter to move through them without collapsing. A flexible RF probe with a thermocouple electrode is advanced to the target region through the hydrogel. In this case, the hydrogel has created a potential space through which to deliver the RF energy with less concern for inadvertent perforation of the pleura. The RF probe may utilize a local cooling mechanism, such as a balloon, to prevent local destruction of the hydrogel where the highest temperatures are present (e.g. melting). Destruction of the ganglia and nerves within the paravertebral gutter occurs between 60° C.-up to 75° C. or more.

In another embodiment, saline (with or without contrast) is delivered through a catheter to fill the paravertebral gutter and to push the pleural membrane away from the sympathetic chain. The steerable RF catheter is advanced up or down the paravertebral gutter and energy delivered at appropriate intervals to destroy the sympathetic chain, sympathetic ganglia, and rami communicantes. In another embodiment, the advancing front of the RF catheter has a saline port that allows for a moving from of expansion of the pleura to create the potential space within the paravertebral gutter through which the catheter can advance safely. In another embodiment, the RF catheter has side ports that continuously deliver saline around the catheter tip and shaft to allow it to advance safely within the paravertebral gutter.

The probe may include continuous or overlapping probes (4 to 10 mm probe approximately 10 mm apart), both of which, with the appropriate spacing, can generate a contiguous lesion. Burns can then be performed in approximately 2-5 minutes with a cooling catheter. Radiofrequency is delivered at a frequency of 500 kHz and a power of 1-50 Watts for a defined period of time, for example 1-30 minutes, preferably 1 to 5 minutes. Several embodiments using low-dose radiofrequency ablation, such as those delivered to ablate target nerves within and alongside the adventitia of the renal arteries to treat hypertension, may be applicable. For example, ramped low power RF energy (5 to 8 watts) for a select period of time (2 minutes) may be desirable (as disclosed, for example, in U.S. Pub. No. 2011/0207758 A1 which is hereby incorporated by reference in its entirety). Various embodiments of methods, apparatuses, and systems for performing renal nerve ablation are described in greater detail in U.S. patent application Ser. No. 12/545,648, filed Aug. 21, 2009 and PCT/US09/69334, filed Dec. 22, 2009, both of which are incorporated herein by reference in their entireties. In one embodiment the energy is delivered circumferentially and in another embodiment the electrodes and the catheter can be biased to direct the energy in one direction, such as posteriorly.

Cryotherapy

In another embodiment, a cryoballoon or probe containing internally circulating liquid nitrogen can be similarly delivered within the paravertebral gutter as the RF system embodiments, except that the temperature between 0 to −200° C. (e.g. adaptation of CardioCryo technology).

Microwave energy delivered in the range of 0.9 to 2.4 GHz at a power of 1-100 Watts applied through monopole, dipole, half-dipole, or helical coil antenna.

Ultrasound.

The ultrasound transducer may range from 0.1 to 10 mm, more preferably 0.1 to 3 mm, more preferably less than 1 mm. At this range, frequencies from 2 MHz to 15 MHz may be employed, more preferably 5 to 10 MHz, more preferably 7 MHz. Using this range of frequencies, the transducer may be focused at a distance less than 25 mm, preferably less than 10 mm, more preferably less than 5 mm, more preferably 2-3 mm away. Overall transducer surface area may be 1 to 50 $mm^2$, more preferably 12 $mm^2$. Acoustic power may be around 1 Watt. The transducer may be a cylindrical transducer curved about its longer dimension, a cylindrical transducer curved about its shorter dimension, a concave transducer curved along the shorter dimension, or a flat transducer. An ultrasound transducer may also be employed that uses an inflatable membrane and solid diffraction lens. Multiple transducers with different focal lengths may be employed.

Minimally Invasive Optics.

In some embodiments optical fibers with a light source for illumination of the paravertebral gutter may be employed with these devices.

Catheter Based Transmural RF Delivery.

In one embodiment, a balloon flexibly and irregularly expands to conform to the vessel wall, such as a vein, particularly in regions where the vein is bifurcating and the ostia are irregularly shaped and sized. The balloon has cooling fluid in it to protect the vessel wall and an atraumatic tip on the balloon guide avoids damage to the vessel or trauma to the pleura.

Electromagnetic.

Paramagnetic nanoparticles or microparticles can be delivered to the region surrounding the sympathetic chain and then heated with an external electromagnet to ablate the nerves (ApexNano Therapeutics, Israel).

Insulated Tips.

A steerable cannula with a tapered tip can be placed at the target location. The cannula can have smooth tapered siliconized or non-siliconized insulation with tip exposures of 2, 4, 5, and 10 mm, or up to 20 mm. The tip may be straight, curved, and sharp, or blunt.

Nerve tissue may be decreased, partially or completely destroyed or removed, denervated deactivated, or down-regulated. Nerve tissue may undergo necrosis, apoptosis, atrophy, gene expression down or up regulation, protein expression down or up regulation, ablation. With some approaches, the entire nerve may be destroyed and in other approaches, specific regions of the nerves may be targeted such as the ganglia or soma, the axons, and/or the nerve terminals.

Intravascular Device Energy Modalities.

In some embodiments, the neuromodulation may be achieved from an intra- to extravascular approach via an endovascularly placed device in proximity to the target neural matter or through a percutaneous paravertebral approach. In some embodiments, the therapy can be delivered from an anterior approach directed towards the stellate ganglion and the top of the TPGS. Alternatively, an anterior approach similar to that of the approach to the stellate ganglion but with subsequent guidance-based navigation to the top of the paravertebral gutter, may be desired. In this manner, the therapy can be delivered from the top of R1 down to the desired target level directly. In some cases, the therapy is delivered from one injection site to multiple paravertebral levels, in contrast to other approaches that ablate only one level at a time, such as described, for example, in U.S. Pub. No. 2013/0296646 to Barbut et al., which is hereby incorporated by reference in its entirety.

Generally, the neural modulation may be achieved in some embodiments through electrical, thermal (heating or cooling; resistive or infrared), mechanical, or chemical energy. The energy delivery device can be located in or otherwise associated with the catheter and emits energy from the catheter. The energy delivery device may be located in a needle tip and energy is emitted from the needle in some cases. An energy delivery device such as, but not limited to, high voltage field pulses, direct current, monopolar radiofrequency (such as described, for example, in U.S. Pat. No. 8,175,711 to Demerais et al., incorporated by reference herein in its entirety), bipolar radiofrequency, pulsed radiofrequency, high-intensity focused ultrasound (HIFU)(continuous, pulsed) (such as described, for example, in U.S. Pat. No. 8,206,299 to Foley et al., incorporated by reference herein in its entirety), low-intensity focused ultrasound (LIFU), nonfocused ultrasound, other forms of ultrasound, microwave, laser, steam or hot water, cold radiation, cyrotherapy, optical, light, phototherapy, X-ray or radiation therapy (such as described, for example, in U.S. Pub. No. 2013/0035682 to Weil et al., which is hereby incorporated by reference in its entirety) magnetic, electromagnetic, plasma, reversible or irreversible electroporation, lithotripsy (extracorporeal, intracorporeal, extracorporeal shockwave therapy), vibrotactile, kinetic, potential, pressure, nuclear, elastic, and/or hydrodynamic energy (as outlined, for example, in U.S. Pub. No. 2013/0204068 to Gnanashanmugam et al., which is hereby incorporated by reference in its entirety). The mechanical device may perform, for example, cutting, sealing, ligation, or clipping.

These energy modalities can be delivered in conjunction with a blank gel or hydrogel if desired to improve the conduction or distribution of the electro-thermo- or mechanical signal. By way of example, delivering a gel to the target regions within the paravertebral gutter, for example, can allow for expansion of the paravertebral gutter space and subsequent delivery of a monopolar or bipolar RF catheter after insertion at one paravertebral level (e.g., endovascularly, transcutaneously) to the region without disruption of the pleura. The temperature at the target tissue should be 45° C. or more in some embodiments to cause irreversible damage to the neuron. Higher temperatures exceeding 90° C. may cause boiling of the tissue. The generally agreed upon target temperature for some embodiments is between 60 to 90° C. for about 90 seconds. By delivering an anesthetic in the gel, local pain relief can be achieved prior to the application of RF energy. Subsequently, the energy delivery can be achieved in a more uniform manner the sympathetic chain. In another embodiment, a 'blank' hydrogel is delivered and the properties of the hydrogel alone temporarily stun or block or permanently destroy the nerves within the paravertebral gutter. The hydrogel delivered may be acutely toxic to nerves, such as some of the Pluronic formulations, resulting in local cytotoxicity and nerve death. Alternatively, excipients, such as generally recognized as safe (GRAS) excipients may cause changes in ion fluxes in the neurons resulting in neuronal excitotoxic cell death is triggered. By way of example, the delivery of glutamate to the neurons may trigger local nerve degeneration. In another embodiment, the 'blank' hydrogel swells slightly as it equilibrates with the host tissue resulting in a compressive injury to the nerves within the paravertebral gutter, particularly since they are adherent to the vertebral body or rib. In another embodiment, a 'blank' gel (e.g., including galvanic alloy particles) undergoes an exothermic reaction and releases heat as it gels within the paravertebral gutter to destroy nerves. In another embodiment the gel is heated prior to its deposition in the paravertebral gutter, whether at the tip of the catheter delivery system or extracorporeally. In another embodiment it is a cryogel, and is injected in a cooled state, resulting in temporary or short-term block to the nerve fibers in the paravertebral gutter. In another embodiment, to overcome the challenges of advancing a catheter in the paravertebral gutter, an RF catheter has a port on the front or front sides of the catheter for delivering an advancing front of gel in front of the RF catheter to protect the pleura from inadvertent puncture. In this manner a catheter delivering mechanical or thermal energy can ablate multiple levels of nerves within the paravertebral gutter.

Drug Delivery Systems and Catheters to Deliver Those Gels.

Control the Spread.

Sympathetic chain neurolysis is performed on a very limited basis, typically in patients suffering from severe intractable pain in late stage cancer in which the benefits in pain reduction out way the risks. Paravertebral or stellate ganglion injections of alcohol or phenol are considered risky because of the adverse events that occur in some patients as a result of their unintended spread (as described, for example, in U.S. Pat. No. 8,211,017 to Foley et al., which is hereby incorporated by reference in its entirety). Along the sympathetic chain this can occur at 1) the cervical levels in which the neuromodulatory agent may spread to the recurrent laryngeal nerve, the vagus, or the brachial plexus (as is often observed with large volume anesthetic stellate ganglion blocks) resulting in adverse events and 2) paravertebral levels (thoracic, lumbar) in which the agent may spread to the intercostal nerves or through the intervertebral foramen to the epidural space causing temporary or permanent neuritis, neuralgia, and even rarely paraplegia. Therefore, formulations that can deliver a neurolytic agent into the paravertebral gutter while preventing the uncontrolled spread of the agent to off-target structures, particularly neural structures including the spinal cord, can be desirable. In one embodiment, the spread of the neurolytic is limited through the injection of the neurolytic in a biocompatible drug delivery system, preferably a gel. In this manner, the spread of the drug is determined initially to the location of the where the formulation is deposited and ultimately resides and subsequently the drug is reaches adjacent tissue through diffusion.

Single Level.

Furthermore, the uncontrolled spread of neurolytic agent has limited the use of a one-level injection therapy to reach multiple dermatomes or levels. As a result, many clinicians use more than one injection sites at multiple levels to achieve a continuous paravertebral block. By loading the neurolytic agent into a gel, the improved control of the spread of the neurolytic agent will also improve the longitudinal spread within the paravertebral gutter.

Local Delivery.

Another objective of delivery of neurolytic agents to the sympathetic chain or nervous system, generally, is to achieve a more consistent, complete and reliable denervation. Recent clinical studies have demonstrated that more complete denervation of the sympathetic fibers coursing around the renal artery is linked to improved and more consistent outcomes in the treatment of hypertension. By developing a more controlled delivery and more complete ablation, patients may elect the procedure if it has demonstrated to be safe, if the responder rate (efficacy) is high, and the efficacy is consistent. Denervation of the sympathetic chain is currently performed through a minimally invasive surgical procedure (VATS) on a limited basis for the treatment of complex regional pain syndrome or hyperhidrosis. Several papers have demonstrated that more complete denervation results in better efficacy in these patients. Sympathectomy (transection and removal of chain), for example, has superior efficacy and durability than sympathicotomy (in which the nerves are cut but the chain is not removed) or clipping of the chain. Percutaneous approaches have been limited to single-level RF ablation which is widely recognized to result in incomplete chain ablation due to the inability to precisely localize the sympathetic chain, resulting in only partial denervation.

There are only a handful of open-label limited patient studies exploring neurolytic ablation (alcohol, phenol) of the sympathetic chain, such as the stellate ganglia, for the treatment of other indications. In these cases, the desire to achieve effective denervation of the target tissue is achieved through the injection of large volumes of neurolytic agent in and around the target neural tissue. Presumably, the goal is to bathe the tissue in the neurolytic agent for as long as possible and to ensure complete coverage of the target tissue. Again, this high-volume high-spread solution comes at the expense of safety, thereby limiting the applications of neurolytic agents to medically refractory cases. Thus, a localized drug delivery system that delivers the neurolytic agent to the target neurons with minimal disruption to adjacent non-target neural structures can be desirable. In one embodiment, this can be achieved with a formulation in which the drug is delivered within a gel. In this embodiment the boundaries of the gel determine the deposition of the drug and the subsequent zone of diffusion of the drug out of the gel to the target tissue down the concentration gradient. In this embodiment, a smaller volume of neurolytic gel can be delivered to the patient than is delivered with an injection of a neurolytic alone.

Sustained Release.

In the case of the administration of a neurolytic agent, it is desirable that the agent be released from the drug delivery system in some embodiments from, for example, 12 hours to four weeks, 1 day to 1 week, or 1 day to 3 days. The drug delivery system, in some cases, affords higher loading levels of drug with reduced systemic toxicity than can be achieved with the drug alone. High local concentrations of the drug can be delivered in a sustained way such that although the drug is delivered above its therapeutic window, in the local cytotoxic range, the burst or spike in concentration that occurs after the delivery of the drug in a bolus can be reduced, and a more typical local sustained release profile can be achieved. A sustained release therapy for the treatment of cardiac arrhythmias, particularly ventricular arrhythmias though the denervation of, e.g., the T1-T4 sympathetic chain can be desirable.

Controlled Release.

In some embodiments, it can be desirable to deliver one, two, or more agents within its local therapeutic window for a longer period of time, such as with neuromodulatory agents. In one embodiment, these agents are delivered locally within their therapeutic window, in some cases without a burst phase in which the agents reach supraphysiologic/toxic levels. Again, with a higher drug loading level than can be achieved with a drug solution alone, sustained or controlled release of drug can be achieved, for example, for 1 day to 9 months, 1 week to 6 months, or 2 weeks to 4 months. In one embodiment, agents that can provide a 'chemical sympathectomy', such as reserpine, can be delivered locally to the cardiopulmonary sympathetic nerves to decrease the release of epinephrine and other neurotransmitters without destroying the sympathetic nerves themselves. Similarly, the durability of nerve block with sympathetic agents can be extended with a controlled release hydrogel. In one embodiment, the long duration treatment of angina can be desirable without denervating the nerves. In this manner, reserpine can be delivered through a controlled release drug delivery system for, e.g., the 3 month to 6 month or more treatment of refractory angina. Patients that undergo a temporary block, may escalate their treatment to a longer-duration temporary block and from there to the permanent neurolytic block if the other blocks are providing adequate relief.

Release Rate.

The release of the drug may be diffusion controlled, chemically or biodegradably controlled, solubility controlled (of the drug), solvent controlled (swelling, osmosis, rupture), or externally activated/modulated (e.g. magnetic system in which micromovement of magnetic beads within a hydrogel causes movement and thus drug release, low frequency ultrasound, electroporation), controlled by the extent of crosslinking and crystallinity, the size, thickness or volume of the drug delivery system, the porosity, and the solubility of the system (e.g. plasticizers or the additional of hydrophilic agents (e.g. glucose, mannitol)) that are rapidly dissolved and create a network or pathway for dissolution of the drug out of the system, or controlled by the degradation of the hydrogel scaffold. The release rate of the drug may also be controlled by the pH, ionic strength, temperature, magnetic field, ultrasound, or electrical stimulation. Preferably, the release of the agent is not controlled by the degradation of the polymer. The release rate may be monomodal, bimodal or polymodal. The release rate may include a burst phase and then a linear continuous sustained release phase. The solubility of the drug in the aqueous phase drives the rate of drug release with poorly water soluble drugs providing longer release than the higher solubility drugs.

Blank Hydrogel.

Another approach is to deliver a blank hydrogel to the site, defined as a hydrogel without any active pharmaceutical ingredient (API). The hydrogel may contain a neurotoxic solvent, such as ethanol, DMSO, propylene glycol, glycerine, glycerol, D-Limonene, methanol, ethanol, octanoic acid, 2-octanone, diethyl ether, benzyl alcohol or a preservative such as thimerosal or chlorbutanol. The hydrogel or crosslinking agents, the pH of the injectate, the pH of the formed hydrogel, the temperature liberated as a result of the gel crosslinking, or the change in the extracellular ion concentrations may cause local neurotoxicity in the absence of an API.

Expanding or Filling the Potential Space.

Given the variability in the position of the sympathetic chain within the gutter rostrocaudally, the variable number of rami and visceral fiber bundles coming off of the visceral chain, and the presence of intermediate ganglia outside of the sympathetic ganglia proper, it can be desirable to deliver an agent, such as a hydrogel, to fill the entire paravertebral space completely in order to denervate all or substantially all of the nerves crossing through the space including the fine hair-width fibers that are not visible to the naked eye. Delivering the solution in a suitably viscous formulation, such as a hydrogel, slurry, an injectable foam, a glue or an in situ forming injectable scaffold, including a hydrogel, slurry or other gel that can fill the majority of, or substantially the entire paravertebral gutter. Some examples of slurries that can be used with embodiments disclosed herein can be found, for example, in U.S. Pat. No. 7,057,019 to Pathak, which is hereby incorporated by reference in its entirety. In one embodiment, the therapy is a viscous solution or gel that can be injected with a minimally invasive technique to fill an anatomical space and adheres to the edges of the tissue. In filling the paravertebral gutter, a more complete acute denervation of the nerves in the paravertebral gutter as the agent is delivered in and around all structures within the gutter. This conformal filling of the paravertebral gutter can be performed with a radiopaque or echogenic polymer.

Preventing Reinnervation.

Approximately 5-10% of surgical sympathectomy patients have late recurrence of symptoms that is thought to be due to reinnervation. Specifically, they are attributed to incomplete resection or ablation of sympathetic pathways with 1) remaining residual sympathetic connections that may be strengthened by reinnervation 2) regeneration or surviving neurons and 3) the formation of alternate sympathetic pathways. More specifically, the efferent reinnervation is thought to be a result of preganglionic sprouting to and new postganglionic sympathetic nerve, possibly in the cervical sympathetic chain. Alternatively, reinnervation may be a result of afferent nerve sprouting to the cardiac tissue. One approach to preventing regeneration is to deliver a neuroinhibitory formulation to block regeneration through a lesion site. In one embodiment, the biodegradable or bioresorbable hydrogel maintains its integrity for the duration of attempted regeneration but is completely degraded or resorbed by the patient's body thereafter. More specifically, the bulk of the hydrogel degradation occurs after 2 to 6 months, more preferably 2 to 3 months. In this case, the lesion site is the region that was lesioned by the neurolytic agent, for example, after neurolysis of the paravertebral gutter between levels T1 to T4, the presence of a non-growth permissive hydrogel at the site prevents the formation of appropriate connections between remaining sympathetic fibers and thus prevents appropriate reinnervation of the target tissues. Similarly, without supporting glia in the matrix and the prevention of trophic factor diffusion through the gel the absence of trophic support will provide an additional barrier to axon outgrowth and subsequent reinnervation. Thus, while neurons initially extend axon growth cones, an adverse environment will result in dispersion of these nerve sprouts and ultimately aborted sprouting. At a clinical level, this may translate to fewer late therapy failures as a result of regeneration and or incomplete denervation resulting in faster reinnervation.

Porosity.

Controlling the pore size of the gel provides another mechanism to control the release of drugs, particularly low molecular weight drugs, as well as to prevent cellular infiltration or axonal regeneration within or across the hydrogel. In some embodiments, the gels can have a pore size of less than 50 µm, 20 µm, 10 µm, or even less. These gels can be non-porous or minimally porous for a period of time (e.g., 2-3 months) until the polymer beings to degrade. In some embodiments, the pores are too small for Schwann or immune cell ingrowth (e.g., less than 8 µm), and the density of pores is not such that a network is formed between the pores. In one embodiment, the use of low MW polymer chains between crosslinks reduces the chain flexibility, reduces mesh size/pore size, and convers an advantage to delay the release of drugs out of the gel. In one embodiment, small pores (<8 µm) assist with the echogenicity of the hydrogel but are smaller than infiltrative cells such as Schwann cells, other supporting cells, immune cells and axons. In still another embodiment, the pores are microporous (e.g., from about 100-500 Angstroms). Some examples of hydrogels with pores can be found, for example, in U.S. Pat. No. 8,399,443 to Seward, which is hereby incorporated by reference in its entirety.

The inability of cells to grow into the scaffold can be maintained in some cases for one to 6 months, such as one to two or three months, during which the damaged nerves are attempting to regenerate to targets on the other side of the gel. After this, the degradation of the polymer can result in cellular ingrowth.

In one embodiment, polymers with small pore or mesh sizes act as the rate-limiting factor in diffusion of drug out of the hydrogel. By controlling the pore size to less than 5 microns, or more preferably less than 1 micron, for example, a small molecule may diffuse out of the scaffold but cells such as axons, glia and inflammatory cells cannot enter the scaffold, inhibiting any functional reinnervation. Pore size can be varied with the degree of crosslinking and the molecular weight of the crosslinks of the gel.

In another embodiment, the pore size of the hydrogel can be controlled to prevent axon ingrowth with pores less than about 50 microns, 20 microns, or 10 microns. Alternatively, the scaffold pores are not interconnected within the matrix. Alternatively, the pores are not oriented in such a way to promote the extension of cells into the scaffold. For example, scaffolds without pores may not encourage axonal ingrowth.

Porous fibrous scaffolds, such as the self-assembling peptide hydrogel matrix, PuraMatrix, are less desirable in some cases since the polymerization results in a nanometer scale loose fibrous structure that is designed to encourage cell infiltration and growth within the scaffold. These scaffolds have been demonstrated to encourage attachment and outgrowth of neuronal cells, features that would not be suitable for providing a physical barrier to nerve regeneration. Some self-assembling peptide hydrogels are disclosed, for example in U.S. Pat. Nos. 8,465,752, 9,011,879, and 9,199,065 as well as U.S. Pub. No. 2011/0104061 and 2013/0287698, all of which are incorporated by reference in their entireties. However, in some embodiments, these hydrogels may not be suitable for this application given the high rate of cellular ingrowth.

Bioadhesive.

The hydrogel can be designed, in some cases, to covalently or noncovalently, ionically or nonionically, adhere to the adjacent tissue particularly that of the adjacent paravertebral gutter, including but not limited to the costotransverse ligaments, the parietal pleura, the vertebral body and/or rib(s), the endothoracic fascia. In one embodiment, it adheres directly to the nerves that it is surrounding through crosslinking with neural tissue. In one embodiment, cationic interactions improve the adhesion of a hydrogel to the tissue. Assuming good adhesion to this tissue, there will be very little, if any path for the regenerating neurons below and above the gel to travel. Systems that maintain a stable position and adhere to the site at which they were delivered for several months and do run the risk of migrating or compressing adjacent structures such as the lung or spinal cord can be desirable.

Neuroinhibitory Gels.

The goal of the majority of polymeric scaffolds in development is biocompatibility, the reduction of further neural damage, the prevention of scar tissue formation and encouragement of regrowth into and through the scaffold after an injury by either modifying the scaffold or changing the agent delivered. In some embodiments, the scaffolds are designed to do the opposite: to fill the cavity in order to prevent or inhibit regeneration of nerves across the lesion zone. After nerve damage, surviving axons for growth cones and sprout into the lesion site in an attempt to reinnervate their target, typically in search of growth-factor mediated guidance cues. This sprouting occurs for a finite period of time before the regenerative attempts are aborted. Alternatively, intact pre-ganglionic neurons may extend axons to innervate surviving post-ganglionic neurons or, in some cases, afferent neurons. In some embodiments, it can be desirable to inhibit the reinnervation of these neurons through the delivery of a gel alone or a gel loaded with neuro-inhibitory drugs, such as inhibitory peptides or extracellular matrix, to physically and/or chemically block the extension of neurites into and preferably around the gel.

In one embodiment, ingrowth into a hydrogel is inhibited by controlling the charge of the functional groups in the polymer. A neural or negatively charged polymer typically is non- or less permissive to axonal ingrowth while a positively charged hydrogel encourages ingrowth, promote tissue infiltration and axon regeneration.

In another embodiment, the hydrogel is designed that it provides a stable barrier to neurite outgrowth during the initial phase when axonal sprouting in response to injury is maximal. In this embodiment, the scaffold remains in place within the TPGS for 2 to 3 months.

In another embodiment, the hydrogel can encourage the formation of a growth inhibitory scar, forming a further communication barrier between the intact upper cervical chain and lower thoracic sympathetic chain.

In another embodiment, the hydrogels can be modified with peptides that are growth-inhibitory to neurons (as opposed to most modifications to improve ingrowth).

Location of the Ablation Along Nerve.

Ablation of the sympathetic ganglia and intermediate ganglia result in the destruction of the post-ganglionic sympathetic cell bodies innervating the target organ as opposed to distal ablation and subsequent rapid regeneration. Similarly, although the afferent and pre-ganglionic nerve cell bodies are not removed, their axons are destroyed close to their cell bodies in the dorsal root ganglion and sympathetic chain, respectively, resulting in less regenerative potential than if the axons were destroyed peripherally closer to their nerve terminal.

Pleural Sealant.

Although the rate of inadvertent pleural puncture or pneumothorax is low, the resulting adverse events, requirement for an indwelling catheter, and significantly extended length of stay in a hospital make this one of the top adverse events that clinicians worry about with paravertebral anesthetic blocks. In one embodiment, a hydrogel or therapy that can act as a tissue or pleural sealant to seal any inadvertent pleural puncture is desirable.

Echogenicity.

In one embodiment, the hydrogel is naturally echogenic, such that its injection and spread is visible under ultrasound guidance. In another embodiment, an agent or microbubbles or some either echogenic component is added to the hydrogel to improve its echogenicity. In some embodiments, the combination of the neuromodulatory agent and the hydrogel improves the echogenicity and/or allows the hydrogel to be visualized under color Doppler.

Flexibility.

In some embodiments, the gel can be flexible and compliant given its close approximation to the lungs and paraspinal muscles.

Swelling.

In some embodiments, the drug delivery systems undergo less than about 10%, 5%, or substantially no swelling at all when placed in situ for safety reasons.

A bioerodible drug delivery system that can control the spread of a low-molecular weight neuromodulatory drug over a period of days or months, that has the appropriate rheological and mechanical characteristics to permit the hydrogel spread within the gutter and reduce the off-target spread, provide a non-permissive substrate for neuronal outgrowth and a physical barrier to reinnervation, and/or functions as a tissue sealant can be desirable in some embodiments.

In Situ Forming Gels.

Of interest in some cases are in situ crosslinking synthetic polymers. In situ forming materials can be advantageous because they can be injected through a fine gauge needle as a liquid to the target zone and then form a solid scaffold in vivo that matches the contours of the potential space. In situ forming gels may transition from a solution to a gel as a result of pH, temperature, salt, light, biomolecules, solvent-exchange, UV-irradiation, ionic crosslinking, covalent crosslinking, electromagnetic field. Different types of crosslinking are described in U.S. Pub. No. 2014/0363382 A1 to Campbell et al., which is hereby incorporated by reference in its entirety.

Cross-Linked.

For cross-linked gels, in which two precursor solutions are typically mixed containing functional groups that react with each other to form a crosslinked gel, by varying the ratio of the precursor solutions, the concentration of an accelerator or crosslinking agent, the rate at which the two solutions form a solid hydrogel can be varied. Upon mixing the two precursors (low viscosity solutions approximating that of water), but before the formation of the solidified hydrogel, an 'intermediate' state of the gel in which the viscosity is between that of the precursor solution and the solidified hydrogel forms and can be injected into the TPGS and travel to the desired target level, up to 12 levels away, preferably 4-5 levels away, more preferably 2-3 levels or 4 to 15" inches away in some cases.

In another embodiment, one of the precursor solutions (A) is delivered first to fill the target levels followed by the second precursor solution (B) which crosslinks with precursor A from the distal to proximal target sites. In yet another embodiment, saline is delivered first to clear the TPGS and aid in the creation of the channel prior to administration of the first and second precursor solutions (A/B). In another embodiment, the precursor solution A is delivered first followed by the 50/50% mix of the two precursor solutions (A/B). In one embodiment, saline is only injected in a small bolus to confirm location of the needle tip or catheter in the right location but does not predilate this space.

Figure 3:
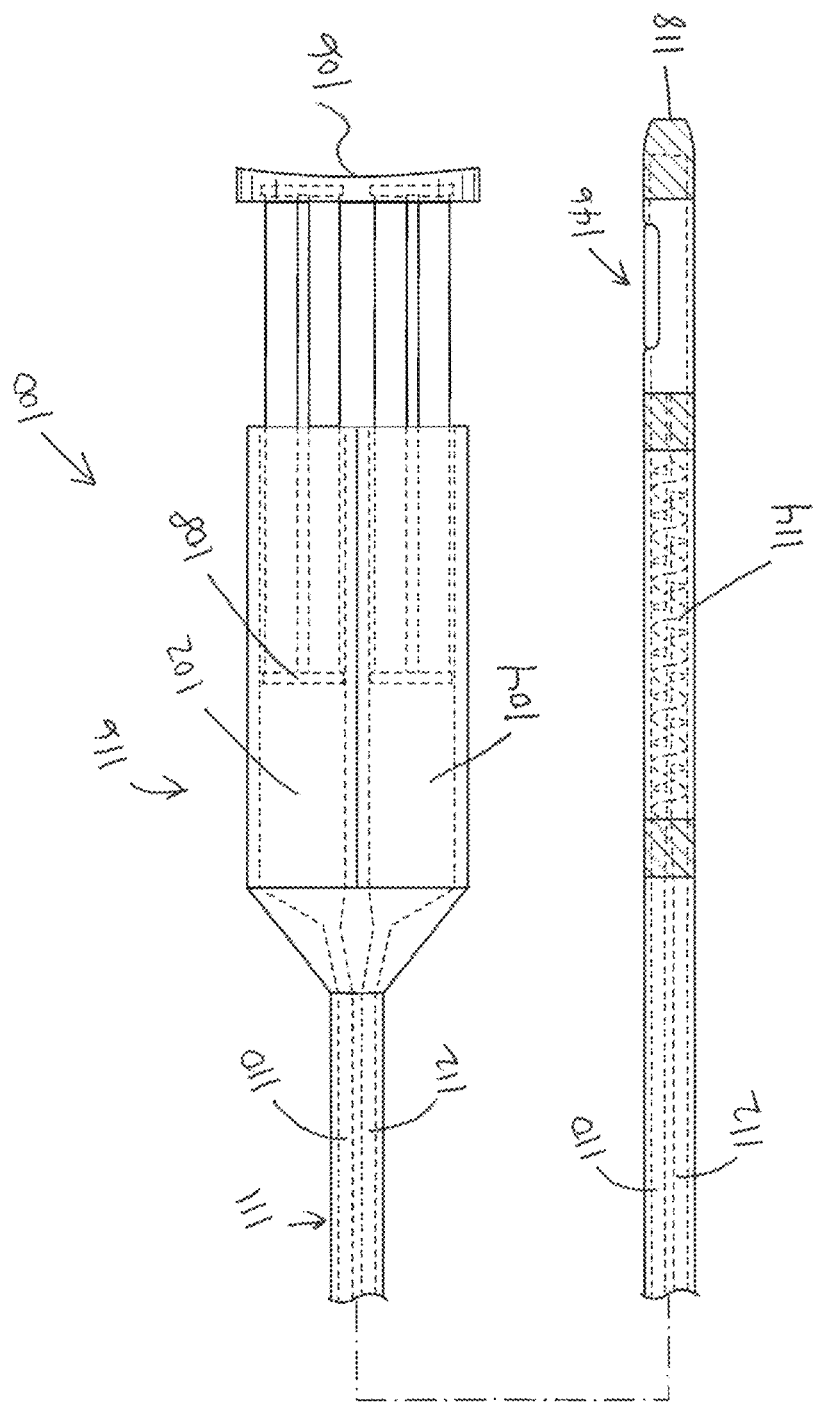
FIG. 3 illustrates an embodiment of a therapeutic agent delivery system including a catheter that can interface, e.g., removably interface with a syringe or other therapeutic agent housing.
Figure 4:
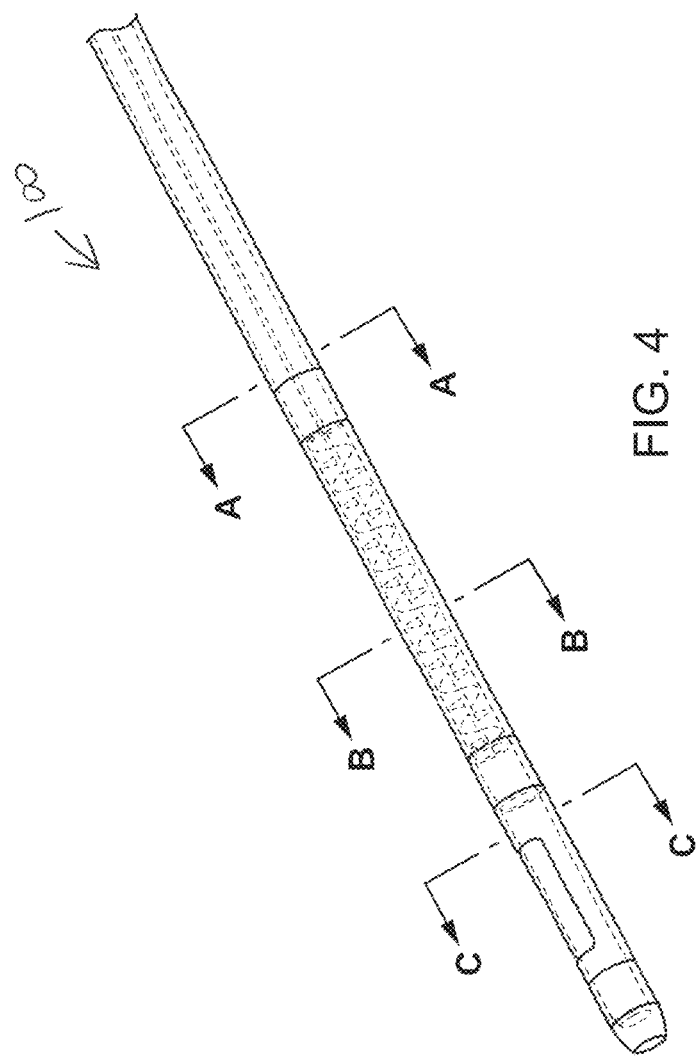
FIG. 4 illustrates a distal portion of the catheter.
Figure 4C:
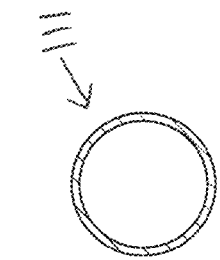
FIG. 4C is a cross-section through line C-C of FIG. 4.
Figure 4B:
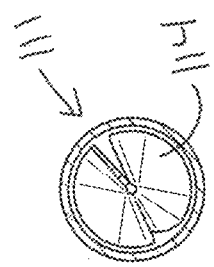
FIG. 4B is a cross-section through line B-B of FIG. 4.
Figure 4A:
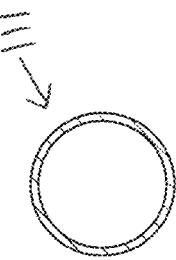
FIG. 4A is a cross-section through line A-A of FIG. 4.

FIG. 3 illustrates an embodiment of a therapeutic agent delivery system including a catheter 100 that can interface, e.g., removably interface with a syringe or other therapeutic agent housing 116 that can include a first chamber 102 configured to house a first precursor solution 102A and a second chamber 104 configured to house a second precursor solution 104B. The housing 116 can also include a control 106 such as a plunger at its proximal end. The distal end 108 of the plunger 106 when actuated can move the solutions 102A, 104B distally through an input port (e.g., a luer port) of the catheter 100 and downstream into discrete first and second lumens 110, 112 within an elongate shaft 111 of the catheter 100. The lumens 110, 112 can in turn merge into static mixer region 114 to create a mixed solution, which can be a cross-linked gel in some embodiments as described elsewhere herein. In other embodiments, the chambers 102, 104 can be directly proximate a single lumen which facilitates mixing within the lumen. The gel can be delivered to a target location via a distally or side-facing exit port 146 at the distal end 118 of the catheter 100. In some embodiments, a curved or bent needle (not shown) can be configured to extend radially outwardly from exit port 146 to assist with targeting depending on the desired clinical result. In some embodiments, the curved or bent needle can allow the catheter to be positioned endovascularly in a blood vessel proximate the target tissue (e.g., the paravertebral gutter), and the curved or bent needle can extend through the wall of the blood vessel into the paravertebral gutter for injection of the therapeutic agent(s). In some embodiments, the delivery catheter 100 can be delivered over a guidewire (not shown), and the delivery catheter 100 can have a proximal guidewire input port, a discrete guidewire lumen, and a guidewire exit port on the distal end, such as a distally-facing exit port. FIG. 4 illustrates a distal portion of the catheter 100. FIG. 4A is a cross-section through line A-A of FIG. 4 (illustrating the elongate shaft 111 and lumens 110, 112); FIG. 4B is a cross-section through line B-B of FIG. 4 (illustrating the elongate shaft 111 and mixer region 114); FIG. 4C is a cross-section through line C-C of FIG. 4.

FIG. 5 is a schematic illustration of a delivery catheter system including one or more therapeutic agent housings (e.g., syringes) removably connected to a catheter 200 configured to deliver a plurality of therapeutic agents into different anatomical locations, according to some embodiments of the invention. The catheter 200 can include a first input port that interfaces, e.g., removably with a first syringe or other therapeutic agent housing 116 that can include a plurality of chambers housing precursor solutions for, for example, a cross-linked gel as described in connection with FIG. 3 above. Actuation of a plunger 106 or other control on the proximal end of the first housing 116 will cause the plurality of precursor solutions to flow into first and second lumens 110, 112 within the first input port and through the elongate shaft 111 of the catheter 200, and distally the first and second lumens 110, 112 are in fluid communication with a distal static mixer region 114 as previously described. Distal to the mixer region 114 the mixed solution (e.g., a cross-linked gel) flows distally into a common lumen 122, and out a distally or side-facing first exit port 146. The system can also include a second therapeutic agent housing 117 that can include only a single chamber 150 as shown (or a plurality of chambers in other embodiments). In some embodiments, the chamber 150 can be configured to house a blank protective hydrogel or other therapeutic agent as described herein. Actuation of a plunger or other control 106 will move the therapeutic agent distally, such as through a second input port which can be a luer or other connector, and through a third lumen 129 extending distally through the elongate shaft 111 of the catheter 200, and distally past (but separated from and not merging into) the mixer region 114, and out a distal or side-facing second exit port 148 spaced apart, such as spaced radially apart from the first exit port 146. This advantageously allows for, in some embodiments, a first hydrogel (e.g., including a neurolytic agent) can be delivered in a first direction (e.g., caudally), while a second hydrogel (e.g., including a protective agent) can be delivered in a second direction different from (and in some embodiments opposite) the first direction (e.g., rostrally). In some embodiments, this can allow for sympathetic neuromodulation (e.g., denervation) of the thoracic sympathetic ganglia within the paravertebral gutter while protecting the inferior cervical sympathetic ganglia within the paravertebral gutter when the catheter is positioned proximate T1/R1. In some embodiments, a plurality of curved or bent needles (not shown) that can be jointly or independently actuated can be configured to extend radially outwardly from exit ports 146, 148 in different directions to assist with targeting depending on the desired clinical result.

In some embodiments, the delivery catheter 200 can be delivered over a guidewire (not shown), and the delivery catheter 200 can have a proximal guidewire input port, a discrete guidewire lumen, and a guidewire exit port on the distal end, such as a distally-facing exit port. FIG. 5A is a relatively more proximal cross-section of the elongate shaft 111 of the catheter 200 through line A-A of FIG. 5 (illustrating the elongate shaft 111 and first lumen 110, second lumen 112, and third lumen 129); FIG. 5B is a cross-section more distally, through line B-B of FIG. 5 (illustrating the elongate shaft 111, mixer region 114 where first lumen 110 and second lumen 112 have merged, and discrete third lumen 129); FIG. 5C is an even more distal cross-section through line C-C of FIG. 5 (showing elongate shaft 111 and two lumens therein: lumen 122 (after junction of the first lumen 110 and the second lumen 112) and third lumen 129.

Figure 6:
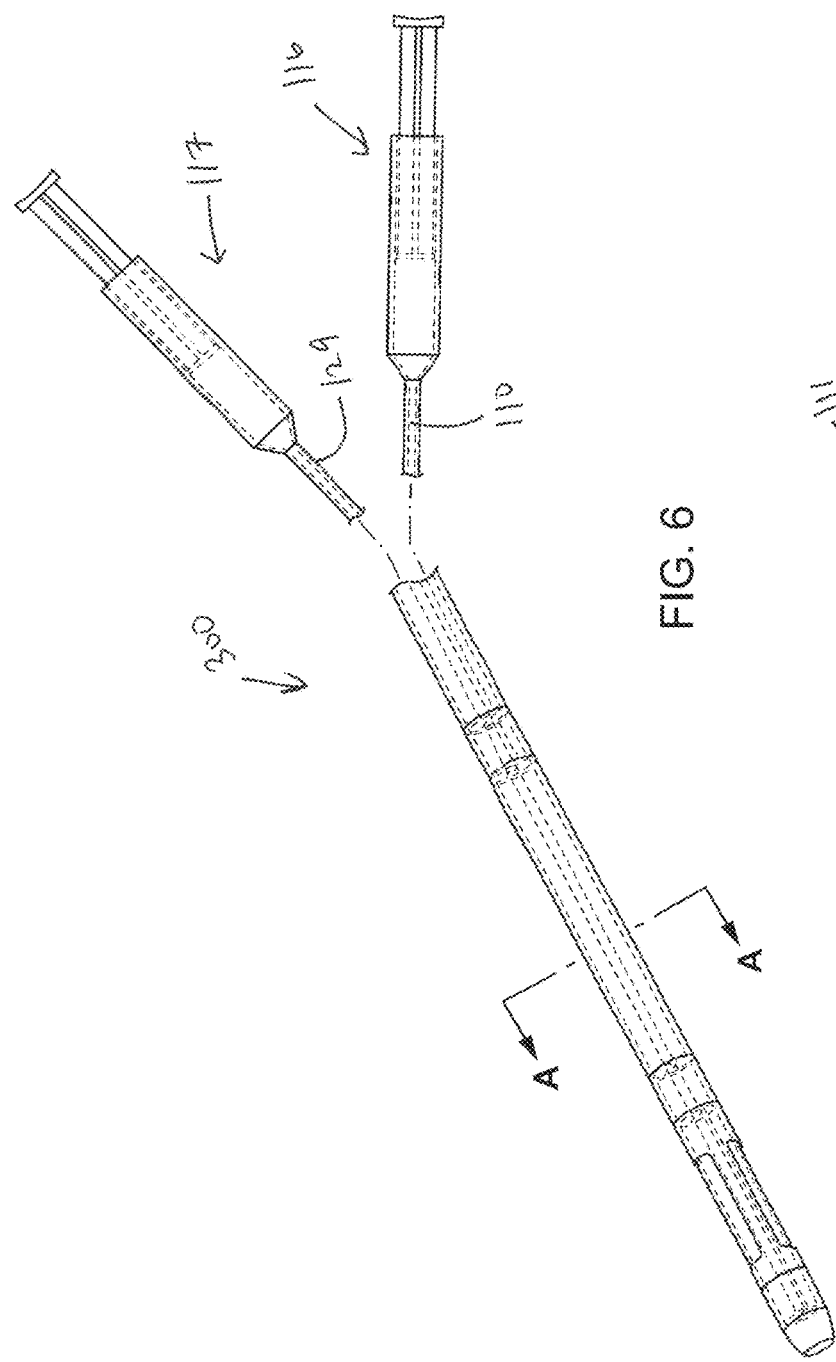
FIGS. 6-6A are schematic illustrations of a delivery catheter system similar to that illustrated in FIG. 5, except the first therapeutic agent housing has only a single chamber fluidly connectable via a first input port on the catheter to a first lumen.
Figure 6A:
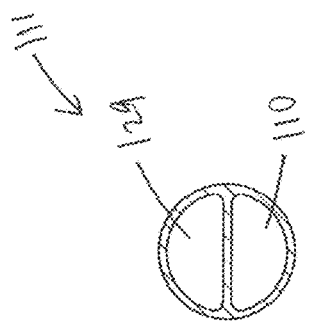

FIG. 6 is a schematic illustration of a delivery catheter system similar to that illustrated in FIG. 5, except the first therapeutic agent housing 116 has only a single chamber fluidly connectable via a first input port on the catheter 300 to a first lumen 110. The second therapeutic agent housing 117 also can have a single chamber fluidably connectable via a second input port on the catheter 300 to a second lumen 129. The first therapeutic agent housing 116 can house a "preformed" hydrogel (e.g., including a neurolytic agent) that does not necessarily require precursor solutions or mixing immediately prior to infusion. The second therapeutic agent housing can include a blank hydrogel or protective agent (e.g., hyaluronic acid) as previously described. FIG. 6A is a cross-sectional view through line A-A of FIG. 6.

Crosslinked PEG.

In one embodiment, a hydrogel such as one from the group of in situ polymerizing poly(ethylene glycol)-based hydrogels is selected for the delivery of drugs. Crosslinked PEG-based polymers are biocompatible, have controlled crosslinking, degradation, flexibility, and relatively high adhesion strength. In particular the use of multi-arm PEGs, such as 4-armed PEG that are functionalized to cross-link with one another can be of interest. Additional spacers can be added between the 4-armed PEGs to vary the mechanical and drug delivery properties (if desired) of the polymer. The molecular weights of the PEG arms, on average, may be between about 200 Da to 20 kDa, preferably between about 1 kDa and 8 kDa, more preferably between about 2 kDa and 5 KDa in some embodiments. The molecular weight of the PEG precursor can be, in some embodiments, between about 4 KDa and 100 kDa, more preferably between about 8 kDa and 10 kDa or 20 kDa and 35 kDa. Generally, about 4 to 30% w/w concentration of precursors are used to prepare gels in some embodiments.

The precursors may be a combination of an ester group on one PEG (precursor A) and a trilysine amine (precursor B). In some embodiments, the precursor A is a 20 kDa N-hydroxysuccinimide end capped PEG which is resuspended at the time of delivery in sodium phosphate buffer, the accelerator. The precursor B can be, in some cases, a trilysine acetate in a 0.075 M sodium borate decahydrate buffer (pH 10.2). A preservative may be added, for example butylated hydroxytoluene (BHT). In another embodiment, the PEG precursor is a higher molecular weight 31.5 kDa N-hydroxysuccinimide end capped PEG, with the same buffer and trilysine acetate buffer, which together form a gel in about 10 seconds. In this embodiment, the PEG precursor (lyophilized) is mixed with a diluent (e.g., the trilysine acetate buffer) in a dedicated syringe. The accelerator, the sodium phosphate buffer remains in a separate syringe.

These hydrogels remains in the paravertebral gutter for, e.g., between 2 to 3 months and then erode through hydrolysis, are resorbed, and fully cleared through renal filtration within, e.g., approximately 4 to 6 months. These in situ polymerizing hydrogels have been commercially developed as an absorbable perirectal spacer (SpaceOAR), and as a dural sealant (DuraSeal, Covidien). In addition to these technologies, other types of major hemostats, sealants and adhesives described by Mehdizadeh and Yang, Macromol. Biosci. (March 2013) are incorporated by reference in its entirety. By varying the ratio of the precursors, the in situ gelation time can be varied. Newer PEG hydrogel formulations have less swelling, which can be an advantageous characteristic in a formulation delivered adjacent to the spine.

In one embodiment, a 4 arm PEG amine (—NH2) and a 4 arm PEG NHS ester are mixed in the presence of HCl. The molecular weights and ratios of the two PEGs can be varied to control the properties of the polymer. In one embodiment, after the precursors are mixed, the sol to gel transition can be quick (2-13 seconds) or prolonged (1-2 minutes), to allow the gel time to migrate within the paravertebral gutter before removing the delivery system. In some embodiments, the liquid forms a gel in about 2 seconds, 10 seconds, 20 seconds, 120 seconds, or 240 seconds. In another embodiment, the crosslinked PEG hydrogels, described above, are injected without a neurolytic agent. In another embodiment, a neurolytic agent is loaded into the precursor A phase. In another embodiment, a neurolytic agent is loaded into the precursor B phase. In yet another embodiment, there is one neurolytic agent loaded in the precursor A phase and another drug loaded in the precursor B phase.

In another embodiment, hyaluronic acid is added to the precursor formulation to increase the viscosity of the solution in order that it can travel up and down the paravertebral space to the cover the target thoracic levels, and then gelling after that. For example, the PEG/HA mixture can be delivered between the T2 and T3 ribs (or between R2 and R3) and the agent flows out of the needle/catheter both rostrally and caudally. The ultrasound probe is advanced rostrally with the flow of the agent and when it reaches the lower border of the $1^{st}$ rib, the flow of material is halted. In another embodiment, when the materials reach the middle of the border of the $1^{st}$ rib, the flow of material is halted. In some cases, when the material reaches the superior or most rostral border of the first rib, the flow is halted and the caudal spread of the agent is noted prior to removal of the needle. In one embodiment, HA is crosslinked with bifunctionalized maleimide-PEG-maleimide polymer using enzymatic crosslinking and then crosslinked with a DA click chemistry reaction to have outstanding shape memory and anti-fatigue properties.

In yet another embodiment, the crosslinked PEGs can be mixed with low molecular weight PEG, such as PEGs with a molecular weight less than 3.35 kDa, including 200 Da, 400 Da, 1 kDa, or 2 kDa linear PEGs. These PEGs can assist in modulating the release of drugs from the polymer.

These crosslinked PEGs can be delivered through needles, such as for example 17 G or 18 G needles or with needles as high as 33 G, or about 27 G, giving them flexibility in terms of routes of administration (catheter-based or needle-based).

Other technologies that may be adapted for use with systems and methods as disclosed herein include the Focal Seal product, which forms in situ through photochemical/chemical polymerization of acrylate-capped PEG-PLL and poly(trimethylene carbonate), or CoSeal, is a covalently crosslinked PEG product comprised of two 4-arm PEGs with glutaryl-succinimidyl ester and thiol terminal groups.

PEG Generally.

PEG-based hydrogels are biocompatible, have controlled degradation, flexibility, and relatively high adhesion strength, particularly when crosslinked. Through careful selection of the molecular weight, the number of arms, and the reaction conditions, other in situ forming PEG hydrogels can be synthesized. The drug delivery systems may be comprised of functionalized linear PEG or multi-arm PEG derivatives (with reactive groups) such as those available from JenKem Technology or Nanocs. These functionalized systems may be crosslinked with one another through a covalent interaction. PEG may be functionalized with an amine group (or other acid reactive chemical group) that binds to a carboxylic group (or other amine reactive group). These include 3 arm PEG amine (—NH2), 4 arm PEG amine (—NH2), 4 arm PEG carboxyl (—COOH), 4 arm PEG SCM (4 arm PEG NHS ester), 4 arm PEG Succinimidyl glutaramide (—SGA) with a longer half-life than the —SCM) 4 arm PEG Nitrophenyl carbonate (—NPC) with a carbonate linker between the PEG and NHS ester in which the release of p-nitrophenol can be traced by UV spectroscopy, 4 arm PEG succinimidyl carbonate (—SC) with a carbonate linker and a longer half-life than —SCM, 4 arm PEG Maleimide (-MAL) which is selective for thiol groups and reacts at pH 5-6.5, 4 arm PEG Acrylate (-ACLT) for use in vinyl polymerization or co-polymerization, 4 arm PEG Thiol (—SH), 4 arm PEG Vinylsulfone (—VS) which binds to free thiol groups in aqueous buffer between 6.5 and 8.5 pH at room temperature, 4 arm PEG Succinimidyl Succinate (—SS) with a cleavable ester linker to make it a biodegradable hydrogel, 4 arm PEG Succinimidyl Glutarate (—SG) with a ester linker, 4 arm PEG Isocianate, 4 arm PEG Azide, 4 arm PEG norbornene. Similar reactive groups described above can be used with other multi-arm PEGs such as 6-arm and 8-arm PEGSs. The molecular weight of these polymers may vary from 1 KDa to 500 KDa. In a preferred embodiment, the polymer includes 4 arms although PEG-arms may increase to 16 arms. Similarly, any of the aforementioned polymers can be combined to form co-polymers, e.g. PEG-co-alginate, PEG-co-hyaluronic acid, etc. Alternatively, heterobifunctional PEGs, methoxy PEGs (-acrylate, -aldehyde, -amine, -biotin, -carbonate, -carboxyl, -hydrazide, -maleimide, —NHS, -oligopeptide, -phospholipid) can be used, and the like. In addition to these, Lipid-PEG derivates are also available.

Thermosensitive

In another embodiment, the gel may be an in situ thermosetting/thermosensitive gel, which requires a change in temperature to form a physical gel, typically at or below body temperature but it can be administered through a single lumen or channel without a need for mixing. The concentration of polymer can be such that it is in a low viscosity state at room temperature (for example, 23-25° C.) and a higher viscosity state at body temperature, or just below body temperature at 35° C.

Biodegradable PEG-based copolymers have been fabricated to degrade through hydrolytic, enzyme-catalyzed or mixed mechanisms. The majority of these ABA triblock, BAB and AB diblock copolymers are thermosensitive polymers that gel below body temperature, although some transition from in the opposite direction (gel at and above body temperature). These are not covalent bonds but the gel is formed through ionic or nonionic interactions, such as through chain alignment between their hydrophobic-hydrophobic regions. By controlling the molecular weight of these blocks, the gel transition temperature can occur between, e.g., 25-37° C., more preferably 30-35° C., more preferably 30-33° C. The % w/v of these gels is typically between 5 and 50% concentration, preferably between 5 and 40% concentration, more preferably between 10 and 20% concentration.

Examples of amphiphilic ABA/BAB triblock and AB diblock copolymers follow: The hydrophilic A segment in this case is the PEG or PEO and the hydrophobic B segment is most a PPs/polyester/POE/PHB or a PEO penetrating the inner cavity of cyclodextrins. PEG diblock and tri-block copolymers can be formed with polyesters including PEG-PLA, PEG-PGA, PEG-PCL, MPEG-PCL, PEG-PLGA, PEG-LA-PEG, PLGA-PEG-PLGA, PEG-PLGA-PEG, PEG-PCL-PEG, PEG-PGA-PEG, PCL-PEG-PCL or with trimethylene carbonate (PEG-TMC), PEG-chitosan, PEG-dextrose, PEG-gelatin, and other suitable combinations of polymers may be selected. In another embodiment poly (ethylene oxide-co-glycidol)-CHO is formed by mixing aqueous glycol chitosan and poly(EO-co-Gly)-CHO to form a cross-linked hydrogels in situ. Alternatively, an α-cyclodextrin/PEG-b-PCL-dodecanedioic acid-PCL-PEG hydrogel (MPEG-PCL-MPEG) showed promise for cardiac applications delivering cells and may be suitable for use in the paravertebral gutter. Alternatively, a four-arm PPO-PEO block copolymer (Tetonic) can be modified with acrylates for crosslinking and NHS-group added for reaction with tissue amines. PMID 20298770. Alternatively, the PEO-CMC hydrogel (Oxiplex, MediShield, Dynavisc, Aril, FziomMed) has many of the characteristics to make it an excellent polymer to deliver drugs to the paravertebral gutter. http://www.fziomed.com/core-science/. Still other polymers include, PEO-PHB-PEO hydrogels. PEG-PCL-PEG or PCL-PEG-PCL (PCEP) which transition from a solution at room temperature to a gel at body temperature are described. For example, in one embodiment, a PEG-PCL-PEG hydrogel (2K-2K-2K) forms a thermosensitive hydrogel that can be injected as a solution and forms a gel in situ. Neuroprotective drugs can be safety mixed into the hydrogel solution prior to injection in situ. Also, pH-block copolymer hydrogels may be well suited for this application and may include diblock copolymers such as PEG-PCL, PEG-PLA or triblock copolymers such as PEG-PLGA-PEG.

Pre-Formed PEG Hydrogels.

In another embodiment, PEG can be crosslinked ex vivo, dehydrated and then crushed.

These particles can then be resuspended in an aqueous buffer with or without drug and stored in a preloaded syringe for injection. The advantage for this type of delivery system is the ability to provide clinician with the drug delivery system ready for use. One example of this technology is the TraceIT hydrogel (Augmentix), which is an injectable hydrogel that is visible under ultrasound, CT, and MR that can be injected with a 25 G needle and remains in place for approximately three months and gradually degrades through hydrolysis and is bioresorbed over 7 months. The iodinated PEG confers the visibility under CT and MR. In one embodiment, a PEG (non-iodinated) slurry is injected into the paravertebral gutter with a wt % of between 2.5% and 20%. The neuromodulatory agents described may be incorporated into the hydrogel. Drugs with low solubility may be incorporated as crystals, particulates, or in a suspension. Higher water solubility drugs, incorporated in a hydrogel, typically only release for hours to days. If they are additionally incorporated into microspheres, liposomes, or nanoparticles, their release rate can be delayed and they can provide more sustained release. Further examples can be found, for example, in U.S. Pub. No. 2014/0363382 to Campbell et al., which is hereby incorporated by reference in its entirety.

Hyaluronic Acid.

The hyaluronic acid (HA) can be formulated with a range of viscosities and modulus of elasticities. Since it is shear-thinning or thixotropic, it can easily be injected through higher gauge needles and after it is injected the gel returns to its intramolecular and intramolecular ionic links are restored. As the shear force is increased, such as during injection, the hydrogel becomes thinner (shear-thinning) allowing the delivery of some hydrogels through a standard syringe needle or catheter such as a 27 G or 29 G thin walled needle or a 30 G needle, as necessary.

By varying the molecular weight of HA, the degree of crosslinking and the concentration of reactive HA precursors, hydrogels of varying pore size and viscosity and degradation rate can be produced. HA is negatively charged and so it can absorb a lot of water and expand forming a loose hydrated network. The HA may be in the form of randomly crosslinked HA chains and neuromodulatory agents can be encapsulated in the network without any covalent linkage. HA can be reacted with an excess of glycidyl methacrylate (GMA) to form crosslinked HAHA can be crosslinked with bisepoxide, divinyl sulfone derivatives under alkaline conditions, glutaraldehyde, biscarbodiimide and hydrazides under acidic conditions.

HA-based hydrogel particles (HGPs) also known as microgels or nanogels can be synthesized from water in oil emulsion crosslinking to form aqueous droplets of HA. These microscopic gels provide a convenient method to deliver drugs in the aqueous phase inside these gels.

Considerable work has gone into developing HA-based gels to solve the various needs of dermal fillers based on if tissue plumping or filling versus small wrinkle filling are needed. As a result, these gels have a wide variety of viscosity after injection. The complex viscosity (n*) relates to how the hydrogel flows from the needle and then later how much it spreads. Generally, Restylane SubQ>Perlane>Restylane, in that order, are more viscous hyaluronic acid fillers than Juvederm, Voluma>Juvederm Ultra Plus>Juvederm Ultra which have low viscosity. In these embodiments, it is preferably to have a hyaluronic acid based delivery system with a higher viscosity filler so that the agent will remain in place.

The following hyaluronic acid/hyaluronan based products include, for example, Perlane, Juvederm (Ultra, Ultra XC, Volume XC), Restylane and Hyalform, and collagen-based products such as Evolence. Perlane is more viscous than Restylane containing particles between 750 and 1000 microns, similarly Juvederm's line contains hyaluronic acids with different viscosities/thicknesses.

Another advantage to hyaluronic acid based products beyond their extensive clinical evaluation is that it is possible to dissolve excess filler with hyaluronidase. In one embodiment, the glycosidic bonds of hyaluronic acid can be cleaved with Vitrase (ovine hyaluronic acid, 200 USP/ml) which can be injected by itself or with saline into the site containing the hyaluronic acid to assist in the diffusion of fluid and clearance of the hyaluronic acid. For example, in one embodiment 20 mg/ml of crosslinked hyaluronic acid (cross-linked with BDDE) is suspended in PBS at neutral pH. Lidocaine (0.3%) can also be incorporated the gels to reduce the pain associated with injection Hyaluronidase is also delivered locally to increase nerve permeability and is sometimes used in conjunction with 10% hypertonic saline as a neurolytic agent and to break up adhesions in the spine (1500 U/10 ml). Conventional hyaluronic acid hydrogel crosslinking can be employed, as disclosed, for example, in U.S. Pat. No. 4,582,865 to Balazs et al., which is hereby incorporated by reference in its entirety.

Ethanol Based Systems.

With hydrophobic drugs and hydrogel monomers or hydrogels are soluble in ethanol, a high drug-loaded hydrogel can be created. Since ethanol can act as either a solvent for the polymer as well as a neurolytic agent and the alcohol is rapidly absorbed once placed in the body, novel hydrogels using alcohol may be possible. In one embodiment the neurolytic agent is coadministered with the hydrogel in an aqueous/ethanol solution. The ethanol, between, for example, 10 and 50 wt %, more preferably 30%, can be incorporated in a HA- or PEG-based hydrogel. With regard to the in situ forming crosslinked hydrogels, the ethanol can either be incorporated in the precursor solution prior to mixing the agents and formation of the gel. This may be reflected in the kit in which the alcohol is an additional vial.

In another embodiment, the active agent is added to the polymer solution where it is either dissolved (soluble) or dispersed (insoluble—suspension/dispersion) in the polymer solution. After the solution is injected into the target site, the solvent (ethanol) diffuses away from the polymer-drug mixture while water diffuses in, causing the polymer to turn into a solid drug delivery implant. The drug is subsequently released by diffusion or dissolution. In one embodiment the drug is dissolved in ethanol and the monomers PEG methyl ether (MPEG)—PLA, acrylol chloride macromonomer, itraconic acid, and MPEG methacrylate to form poly (LA-IA-MEG). In one embodiment, ethanol is added to the aqueous phase of the polymer and modifies the gelation time. Addition of ethanol, for example 25% ethanol, improves the mechanical properties of the gel.

Poloxamers.

The Pluronic class of polymers are nonionic triblock copolymers of poly(ethylene oxide)-poly(propylene oxide)-poly(ethylene oxide) (PEO—PPO-PEO) that are thermoreversible polymers that are thought to form as micelles aggregate together above the critical micellular concentration (CMC) to form a gel. Poloxamers form hydrogels as homopolymers or as uncomplexed multi-block copolymers. Poloxamer properties can further be controlled through crosslinking to improve the release of drug and modify the sol-gel transition behavior and critical gelation temperature and concentration. Poloxamers, such as P407, can be injected into the potential space and used to protect tissues encapsulated in the semi-solid gel from thermal damage such as RF, ultrasound, and radiation. Poloxamers form at between 10 and 60% wt/volume, more preferably between 20 and 50%, more preferably 25-35% wt/vol. The P407 is thermoreversible (15.4% in water) and transitions to a semi-solid at body temperature. Pluronic F-127 is a nonionic surfactant polyol (MW 12.5 KDa) with 7% PPO that at low concentrations forms micelles and at high concentrations packs to form high modulus gels. HPMC can be added to Poloxamers to prolong the gelation time. In another example, a polaxamer-heparin hydrogel if formed from poloxamer (PEG-propylene glycol-PEG). In another example, 20% ethanol is added to the Poloxamer solution without affecting the concentration for gelation. At 30% ethanol and 35 wt % F-127 can form at 20 degrees Celsius. As another example, two Pluronic block copolymers can be mixed to vary the properties of the gel. In one embodiment, Pluronic F127 can be loaded with the neurolytic agent and then F-127 can be mixed with F-68 to assist in reducing the gelation temperature.

Other Polymers.

The aforementioned not limiting, there is an unmet need for an injectable gel, that includes a glue, slurry, scaffold, or hydrogel- or a more simple emulsion or other viscous solution formulation that can deliver a neuromodulatory agent or combination of neuromodulatory agents. In some embodiments, the therapy can include neuromodulatory agent(s) delivered in a gel. In some embodiments the neuromodulatory agent is co-delivered with an anesthetic and/or contrast agent. In some embodiments, the anesthetic, if delivered, is administered immediately prior to the injection of the therapy.

Formulations include gels, and more particularly hydrogels that can form either through physical crosslinking (ionic interactions, hydrogen bonding, hydrophobic-hydrophobic interactions) or chemical crosslinking (Schiff base crosslinking, Diels-Alder crosslinking, Michael addition, CuAAC, SPAAC, Thiol-ene, Oxime, and Radical polymerization. The polymerization of hydrogels can be induced by physical mixing, temperature, pH, UV light exposure, and/or ionic concentration. Polymeric gels may be homopolymers, copolymers, or multi-polymer interpenetrating polymeric hydrogels. The gels may be nonionic (neutral), anionic, cationic, amphoteric electrolytes (ampholytic, acid and base groups), or zwitterionic (anionic and cationic groups in each structural repeating unit).

Echogenicity

In some embodiments, the gel can be sufficiently echogenic to allow the clinician administering the therapy to confirm its appropriate delivery within the paravertebral space as well as to track its subsequent spread up and down the paravertebral gutter. In some embodiments, the gel has low to no internal pores, decreasing the rate water permeation through the gel, decreasing the rate of drug release, and preventing the ingrowth of neuronal and non-neuronal cells.

After the gel has formed at the site or has been delivered to the site, the gel may provide for sustained or controlled release of the agent. This can provide more effective means to deliver therapeutic or neurotoxic concentrations locally to the target tissue. In the case of a neurolytic agent, this can allow more complete denervation of the nerves that are in direct contact with the gel whether through 1) encapsulated or surrounded with the gel, 2) partially surrounded by the gel on one side and another anatomical structure on another side (blood vessel, bone, organ, adipose, fascia, extracellular matrix, lymph node etc.), or indirectly via drug diffusion across extravascular tissues or adipose tissues. By completely filling the potential space, the thread-like rami communicantes that are not visible to the naked eye are also destroyed. This can be advantageous since if they are not transected or cauterized during a surgical sympathectomy or RF percutaneous sympathectomy procedure, they provide a surviving pathway or, alternatively, a pathway for appropriate regeneration or reinnervation of fibers later.

Blank Gel.

In another embodiment, blank (non-drug loaded hydrogel) can be injected to off-target neural structures to act as a buffer to prevent drug spread to neural or other tissue that needs to be protected from the effect of the neuromodulatory agent. Subsequently, a drug-loaded hydrogel can be delivered to the desired levels for ablation. The blank hydrogel can be injected up against with the other neuromodulatory-gel. In the case of short-acting agents, the blank gel only needs to protect adjacent neural tissue as long as the neurolytic agent is released and so the gel in some cases preferably degrades faster in the tissue than the neurolytic-loaded hydrogel. In a further embodiment, the blank and neurolytic-loaded.

Polymers.

The drug delivery system may be comprised of a nondegradable polymer such as silicone, cellulose or ethylene vinyl acetate copolymer (EVAc), polystyrene, acrylamide, or cyanoacrylate glues. However, in some embodiments, the drug delivery system is comprised of biodegradable or bioerodible polymers. The drug delivery systems may be comprised of natural polymers including, but not limited to glycosaminoglycans and polysaccharides including but not limited to collagen, alginate, chitosan, pullulan, hyaluronic acid, hyaluronan, gelatin, carboxymethylcellulose (CMC) silk fibroin, dermatan sulfate, chitin, and chondroitin sulfate and derivatives thereof. Synthetic biodegradable polymers such as polylactic acid (D-, L-, D/L, PLA), polyglycolic acid (PGA), polylactic-co-glycolic acid (PLGA), polyaminoacids, polyorthoesters (POE), polycaprolactone (PCL), polyphosphoesters (PPE), poly(urethanes), polyanhydrides, polyimide, propylene glycol, poly(ethylene oxide), olyethylene glycol (PEG), poly(2-hydroxyethyl methacrylate) (PHEMA), and poly N-(2-hydroxypropyl)-methacrylamide (PHPMA), poly(methylmethacrylate) (PMMA) (Artecoll or Artefill—microspheres in a collagen gel), polyacrylamide (Aquamid) poly(ester urethane), cyclodextrin, poly(alkene oxide), poly (hydroxyalkanoate), poly(R-3-hydroxybutyrate) (PHB) and co-hetero-polymers thereof. Other components include glycerol, poly(glycerol-co-sebacic acid), and poly(ethylene oxide) (PEO) These polymers can be further modified to create hydrogels with cholesterol methacrylate or 2-ethoxyethyl methacrylate (EOEMA). The polymers can include linear backbones or star or branched polymers with molecular weights ranging from 1 kDa to 500 kDa, more preferably 2 kDa to 300 kDa. Some examples include but are not limited to poly(epsilon-caprolactone-co-ethyl ethylene phosphate, a copolymer of caprolactone and ethyl ethylene phosphate (PCLEEP), polilactofate-PLA (PPE-PLA) copolymer (Paclimer Microspheres), polyanhydride-co-imide, poly(TMA-Tyr-:SA:CPP 20:50:30) polymer (Chiba et al), poly(vinyl alcohol) based cryogels. For these purposes, polyscaccharides, N-isopropylacrylamide (NIPAAm) copolymers (thermosensi), poloxamer and its copolymers, pEO-P(D,L)LGA copolymers and liposome based systems. In one embodiment, copolymerization of NIPAAm, acrylic acid and hydroxymethacrylate and TMC (HE-MAPTMC) may be suitable for injection.

Additional biodegradable polymers, solvents, aqueous carriers, are described in, for example, U.S. Pat. No. 6,545,067 to Buchner et al. and U.S. Pub. No. 2014/0363498 to Sawhney et al., both of which are incorporated by reference in their entireties).

Natural Gels Based Gels:

Chitosan-β-glycerophosphate/hydroxyl-ethyl cellulose (chitosan/β-GP/HEC) hydrogels, chitosan-polylysine hydrogels, alginate hydrogels, and collagen hydrogels can also be utilized in some embodiments, as can rapid gelling hydrogels composed of mixtures of chitosan-thiol modified and polylysine-maleimide give gelation times of between, e.g., about 15 and 215 seconds. These hydrogels have excellent hemostatic properties. In another embodiment gelatin methacrylate can be utilized.

Fibrin-Based Gels.

Chondroitin sulfate proteoglycan gel (CSPGs), such as Aggregan, Neurocan, Brevican, Versican, and NG2 exert inhibitor influences on axon growth as can urinary bladder matrix (UBM). Fibrin and fibrinogen, whether mammalian or non-mammalian, may be used as an injectable gel but may be less desirable because of its ability to support neurite extension. Matrigel and other fibrin gels in some cases do not stay around for long enough to prevent regeneration. However, fibrin may be conjugated with PEG to improve its characteristics. In one embodiment, the drug is delivered in a crosslinked fibrin matrix, sealant glue or slurry, such as the FDA approved Tisseel. By varying the concentration of thrombin used to induce polymerization, the solution to gel transition can be controlled.

Other commercial formulations that may be suitable include collagen based gels such as Evolence (with Glymatrix technology), calcium hydroxyapatite microspheres (CaHA, Radiesse), and pro-fibrotic PLLA microspheres (Sculptra), and/or the fibrin matrix or glue (Tisseel) made of fibrin and thrombin.

Biodegradable alginate or collagen, or agarose-chitosan hydrogels. In one example a chitosan hydrogel is prepared by mixing chitosan (2% w/v) with dibasic sodium phosphate (DSP) to for a gel that at body temperature. In one embodiment, the BST-Gel platform (Biosyntech, Canada) is utilized, that includes chitosan neutralized with beta-glycerophosphate (GP) which forms a gel at room temperature.

Pullulan.

In another embodiment hydrogels made from pullulan, a natural polysaccharide, that have excellent oxygen barrier properties, highly transparent, and is non-hydroscopic, may be used. Acutely, the polymer may result in pH changes in situ that may be toxic to neurons. In one embodiment pullulan is modified to form pullulan methacrylate (PulMA) to hydrogels to deliver drugs.

Thermochemical Ablation.

The use of liquid alkali may be a safe and effective method to ablate nerves. Permeable oil-packed alkali metal sodium-potassium (Na—K), in which the oil controls the rate of heat release during the Na—K reaction with water in living tissue. Alternatively, the delivery of a single electrophilic reagent, such as acetyl chloride (AcCl, 4 mol/L) or acetic anhydride (Ac(2)O) can be delivered in vivo to cause a significant pH change or temperature increase of around 300° C. (PMID 23311380). Two component systems containing HCl or acetic acid in either $NH_4OH$ or NaOH also have potential. Similarly, the exothermic reaction caused by the initiators and the hydrogel polymerization in situ can liberate heat and cause nerve degeneration.

Delivery of Cells for Applications where Neuroregeneration, Neuronal Survival, or Neuroprotection are Desired.

In another embodiment, pluripotent cells can be delivered in the hydrogels to differentiate into neurons, glia, or other supporting cells within the sympathetic chain. These transplanted cells can provide for the release of growth factors, cytokines and anti-inhibitory molecules to promote regrowth, to target the sympathetic afferent and efferent nerves. In one embodiment, these cells secrete nerve growth factor (NGF).

Retrograde.

In some embodiments, the drugs can be delivered to the ganglia after injection into the pericardial sac or into the heart. In these embodiments, the drug can be delivered transcutaneously into the pericardial sac or other target heart location. The drugs are taken up at the nerve synapse and are retrogradely transported back to the sympathetic efferent ganglia located in the sympathetic chain or the afferent visceral nerves located in the dorsal root ganglion. In another embodiment, drugs are delivered locally within the pericardial sac to target the interneurons located in the ganglionated plexi located around the heart.

Anterograde.

In other embodiments, it can be desirable to deliver the drug from the sympathetic chain to the afferent and efferent nerve terminals/synapses in the heart. In this manner, drugs that will be taken up at the soma or dendrites and delivered after anterograde transport to the heart and/or lungs.

Circumferential.

One of the challenges with injecting neurolytic agent around a vessel is achieving circumferential delivery of the drug. In one embodiment, a pre-configured fiber is injected transvascularly out of a curved needle and the polymer self-forms a coil-like shape around the vessel that provides sustained release of a neurolytic agent circumferentially around the vessel. The noodle may have a curved shape within the lumen of the needle or it may assume a curved shape as it exits the lumen of the needle and comes in contact with water.

Mechanism of Drug Release.

In applications requiring the sustained release of a neurolytic agent for days to weeks but the prolonged presence of a drug delivery system such as a hydrogel to prevent nerve regeneration, the release of the drug is in some embodiments not controlled by the degradation of the polymer. Sustained release gels may additionally incorporate complexes, microspheres, nanospheres, nanocrystals, micelles, liposomes, nanoliposomes, or nanocomplexes, as known in the art. Alternatively, a viscous formulation such as a suspension, emulsion or a slurry can be delivered to the tissue, such as a slurry of hydrogel particles, in which the release rate is primarily controlled by the environment into which it is injected. Drug diffusion through gels can also be controlled by the polymer concentration, the degree of swelling (hydration factor).

Microspheres.

In order to provide more controlled release and reduce the burst, the drugs may be loaded into microspheres. These microspheres can be delivered in a slurry or incorporated into a hydrogel. In one embodiment, the microspheres are incorporated into an in situ forming hydrogel. In another embodiment they are incorporated into a lyophilized phase of the in situ polymerizing hydrogel in which they will only get resuspended when they are ready for use. The microspheres may release the neuromodulatory agent with or without neuromodulatory agent also loaded in the hydrogel phase. Alternatively, the microspheres may release one agent and the aqueous phase of the hydrogel may release a different agent. In this embodiment, the release rates of the drug from the microsphere and gel phase may differ. Typically the release of drug from the microspheres will be slower than that from the hydrogel. In some embodiments, the microspheres are biodegradable so that they are eventually cleared from the site of injection.

Microspheres can be formed by single or double-emulsion. In one embodiment, a poly(ethylene glycol) based microsphere system if formed with a water-in-water emulsion process. A single (W/O) or double W/O/W emulsion process can be used to prepare the drug. By adjusting the number of sites of hydrolysis, emulsion conditions and varying the PEG molecular weight the degradation and erosion can be controlled. In one embodiment, PEG-diacrylate (PEGDA) chains are reacted with dithiol molecules to form hydrolytically labile ester linkages proximal to thioether bonds, PEG-dithiol (PEG-DTT). A water-in-water emulsion process is then used to synthesize the PEG microspheres. Alternatively, the PEG-DTT polymer solution can be dispersed in a 40 kDa dextran-rich aqueous phase and the acrylate groups in the droplets can be crosslinked with UV light to form microspheres. The microspheres are removed from the emulsion by dilution of the dextran-rich phase and centrifugation.

Nanoparticles

If intracellular delivery of these agents is desired, the neuromodulatory agent can be encapsulated within nanoparticles which are more readily endocytosed into the cells.

Alternatively, the gold nanoparticles can be conjugated directly to the neuromodulatory agents as these readily accumulate within neurons.

Nanocrystals.

For example, a drug may be formulated in nanocrystals and dispersed in a drug delivery system. The crystals can be sieved to achieve a particular range of particle size in order to better control the release of drug. Alternatively, the drug may be micronized to reduce the size of the drug particles.

In some embodiments, the drug release occurs through diffusion of the drug from the drug delivery system. In one embodiment, the drug crystals are loaded into the hydrogel, and the release of the drug occurs as the hydrogel absorbs water after implantation causing solubilization of the hydrophobic drug crystal and subsequent sustained diffusion into the surrounding tissues, thus the polymer hydrogel itself is imparting Coprecipitates.

Instead of microspheres, the poorly water soluble drugs may be complexed with one or more pharmacological carriers. In one embodiment an inert water-soluble carbohydrate is selected to form a coprecipitate with a neuromodulatory agent in order to better control the release profile of the drug. For example, the drug can be coprecipitated with fructose, polydextrose or xylose at a ratio of drug:carrier of between 1:5 to 1:20.

Embedded drug delivery systems to facilitate controlled release of drugs from the hydrogels include The drug is loaded into microspheres in a hydrogel that provide the rate-limiting release of the drug. The polymers may degrade by bulk or surface erosion over a period of days to weeks to months, as needed for a given application. For example, in one embodiment, a thermoresponsive Poloxamer gel is combined with pH sensitive chitosan nanocomplexes containing the active agent.

Polymer Conjugation.

The polymer may be conjugated to the drug with an enzymatic or hydrolytic linkage. In one embodiment, the linkage is a hydrolytic linkage off of the backbone of is the polymer and upon delivery into an aqueous environment, hydrolysis causes release of the drug.

Lipophilic for Depots.

Highly lipophilic agents may be particularly desirable agents to deliver to nerves and are efficient in forming depots in the fascia and adipose tissue through which these nerves run.

Differential Sensitivity.

In another embodiment, a chemical agent is delivered that is preferentially more sensitive to one type of neural fiber than another. For example, sympathetic efferent fibers are recognized to be more sensitive to anesthetic than sensory afferent fibers. In another embodiment, the soma themselves are targeted such as the sympathetic ganglia or the dorsal root ganglia.

A further embodiment includes adding proteolytically degradable sites in the PEG system, enabling both proteolytic and hydrolytic or mixed-mode degradation.

Free Base.

Alternatively, the drug can be converted to its free base, where applicable, and injected or delivered as a viscous paste directly or incorporated within a drug delivery system.

Drug Loading Levels.

The drug loading level can be in some embodiments about 1% to 80%, about 5 to 50%, or about 5 to 20% in some cases Volumes of Agent or Formulation Administered.

Although the physician will have the discretion to deliver the appropriate volume of therapy to the paravertebral gutter, the following table provides a guide to volumes injected according to some embodiments. More typically volumes from about 1 ml to 30 ml are delivered in and around various neural targets. In the paravertebral gutter, volumes between about 1 ml and 20 ml are delivered to treat the target vessels or organs, more typically between about 2.5 and 10 ml, or 1 and 5 ml.

Specific Dermatomes.

In some embodiments, the agent would be delivered to the T2 to T5 dermatomes, or the T2 to T4 dermatome. In some instances patients will respond better if the T1 to T5 levels are treated or only the T1 to T3 dermatome. Similarly, some patients with a fused inferior cervical and T1 ganglion, the stellate ganglion may benefit from therapy being delivered to this level as well.

TABLE 2

Spread of chemical agent

| Volume | Distance | Spread | Failure |
| --- | --- | --- | --- |
| 2-5 ml | Single level | None or minimal | — |
| 5-8 ml | Three level | None or minimal | — |
| 10 ml | 3.5 ± 1.5 dermatome segments | 70% paravertebral, 10% cloud distribution, 7% intercostal | 6% |
| 15 to 20 ml | Avg. 5 levels somatic (range 1-9), Avg. 8 levels sympathetic (range 6 to 10) dermatomes | Unilateral (occasionally bilateral), paravertebral, intercostal, epidural | 6-10% |

Gel Set Times.

In situ crosslinkable agents can be formed in which both reagents, typically with at least one of them a polymer, are modified with a functional group to allow crosslinking. By varying the concentration of the agents, the degree of substitution of the active/functional groups, and the molar ratio of the two crosslinking agents, the gelation can be modulated. In gels that have a sol-gel transition, this can occur from between 1 second to 5 minutes, in some cases between 1 to 3 minutes. This may refer to the time after initiation (e.g. temperature change, pH change, crosslinker mixing) until the formulation is no longer injectable or flowable, even if it hasn't yet reached it maximal strength characteristics.

Minimal or Non-Swelling.

In some embodiments, the formulation should not result in a clinically significant change in size, such that upon delivery there is less than 50%, preferably less than 30% or more preferably less than 10% swelling. The swelling may be cationic or anionic or, in the case of cross-linked hydrogels it may be a function of cross-link density.

Durability of Effect.

Agents may be delivered that cause short-term denervation followed by axonal sprouting and regeneration. Agents may be delivered that result in long-term permanent denervation either by destroying fibers that are not capable of regeneration, by destroying a long enough region of the axon or axon bundle that the fibers cannot regenerate or lack the appropriate trophic factor support to guide the fiber regeneration back to the original source, or by destroying the soma themselves. Agents may be delivered that provide for an inhibitory environment to prevent axon regeneration.

Other Target Tissues.

In another embodiment, the injectable formulation can be delivered locally until it covers the desired target neural tissue even in an unbounded space, such as the case with the celiac plexus or other perivascular plexi, in and around the aorta and aortic arch, in and around the azygous, hemiazygous, accessory hemiazygous vein, or from the bronchial arteries to the region containing the plexi in and around the lung hilum. In yet other embodiments, the viscous solution or hydrogel can be injected perivascularly to obtain substantially 100% circumferential delivery of the neuromodulatory agent.

Degradation or Erosion and/or Resorption.

The degradation, erosion, absorption or clearance of these drug delivery systems can be in some embodiments between one week and one year, preferably one week and 6 months, more preferably between one and three weeks in the blank hydrogel embodiments, and between one week and 9 months in the neurolytic-hydrogel group, preferably between 2 to 6 months. If the system undergoes enzymatic or hydrolytic degradation, this begins after the nerves have become chronically degraded, e.g., between two or three months. The scaffold or hydrogel can be designed to fully resorb within the body after the period for axon sprouting and attempts at reinnervation/regeneration is over. Typically this will be on the order of 2 weeks to 1 year, more preferably 2 weeks to 6 months, more preferably two to four months. The hydrogel may be biodegradable or bioerodible and can be ultimately cleared from the site.

Timing of the Delivery of the Formulation.

In one embodiment, the therapy is delivered in as a one-time inpatient or outpatient procedure. However, repeat procedures may be necessary if there is some reoccurrence of symptoms. In the preferred embodiment the hydrogels degrade within two to three months after injection and the re-establishment of connections is prevented. Thereafter the hydrogel may be gone should an additional procedure be required.

Frequency of Administration.

Current chemical neurolysis approaches may not be as long lasting as energy-based approaches such as radio- or cryofrequency for achieving nerve degeneration. As a result, chemical denervation approaches such as phenol or alcohol may in some embodiments require a second or third application/procedure in order to maximize effectiveness. Effectiveness may be maximized by either extending the lesion, treating more fibers, or preventing regeneration. In one paper 19/23 patients required one injection of alcohol in the lumbar chain only and the remaining 4 required a second block.

In another embodiment, the neurolytic agent is administered first and then one or two weeks later, the biodegradable hydrogel is inserted.

Example 1

Sustained release. HA was conjugated to 4-arm PEG-amine (10 kDa) with 1-ethyl-3-(3-dimethlaminopropyl)-carbodiimide hydrochloride as a cross linker at a 100:1 ratio. Reserpine crystals were then incorporated into the HA/PEG hydrogel at a loading level of 150 µg in 10 ml hydrogel. When injected into the subcutaneous space, the reserpine was released at 15% within the first 1 hour, 50% within 6 hours, 80% at 18 hours and 100% at 24 hours.

Example 2

In another embodiment, NHS-ester activated chondroitin sulfate is crosslinked with 6-arm PEG amine. After an initial burst of 15% of the drug loading, the reserpine is mixed in to release approximately 20-50 µg per day from the hydrogel for 3 to 4 weeks.

Example 3

In one embodiment, NGF is delivered from an in situ forming thermosensitive hydrogel, such as PEG-PCL-PEG or heparin-poloxamer (HP) gel such as those used for delivering NGF to the spinal cord to treat spinal cord injury in rats (PMID 26472614). Additional hydrophilic and hydrophobic polymeric additives, such as PVA, PEG or PCL can be added to vary gel concentration or drug release. In another embodiment, NGF is released from a crosslinked 20 kDa 4-arm PEG homopolymer. The larger size of the molecular delivered permits the sustained release of NGF without any additional additives.

Example 4

In another embodiment, NGF is delivered in a diblock copolypeptide hydrogel (DCH) to serve as a depot for drug release at a drug delivery rate in steady state at about 20 ng/ml.

Example 5

In one embodiment solutions of covalently crosslinked multi-armed PEG hydrogel particles of about 70 m in diameter are formulated in a PEG (20 kDa) water solution to improve the injectability of the slurry.

Example 6

Valproate-loaded chitosan nanoparticles were prepared. The chitosan solution (0.3% (w/v) in 5.54% sodium acetate, pH 5.5) was added dropwise to the continuously stirring mixture of tripolyphosphate (TPP, 2.5% w/v) and sodium valproate (25 mg/ml). The slightly negatively charged chitosan nanoparticles form through ionotropic gelation with particle sizes less than 100 nm a loading level of up to 50% and drug release for about a week. The nanoparticles are loaded in a PEG-PLGA-PEG triblock (33 wt % solution, MW 3300) hydrogel, resulting in valproate drug release for a week and persistence of the hydrogel in vivo for over a month.

Example 7

A Poly(N-isopropylacrylamide) (pNIPAm) based thermo-sensitive microgel was loaded with desipramine (50 mg/ml) hydrochloride, a cationic drug, which binds to the polymer via the carboxyl groups. The resultant thermoresponsive polymer microgels range in size from 500 to 800 m in water. Drug was released from the hydrogel for between 1 and 3 days.

Nanocrystals.

In one embodiment, an in situ thermo-sensitive hydrogel loaded with nanocrystals (NCs) of a hydrophobic drug such as reserpine at a drug loading of up to 5 mg/ml, more preferably 3 mg/ml. In another embodiment, the gel is loaded with paclitaxel at up to 3 mg/ml. PMID 24512789. In another embodiment, a PTX-NCs-Gel system with Pluronic F-127 uses PTX-NCs and Taxol as controls.

Drugs

Overall concept of drug delivery. In some embodiments, chemical agents may be delivered to or near the neural target tissue in order to affect pulmonary function. Chemical ablation may be desirable over thermal ablation approaches in some cases because it may reduce or eliminates pain and unpleasant sensations during the procedure. The agents may be delivered by a percutaneous, transcutaneous, or endovascular approach or even through an endoscopic or thoracoscopic approach. The agents may result in chemoablation or chemolysis or chemical sympathicolysis in some cases. The delivery of the therapeutic composition or agent can be controllable with respect to the number of levels above and below the injection site and the neural targets within the paravertebral space. The agent delivered can in some embodiments travel both medially to the paravertebral space and rostrally/caudally through the subpleural space to cover three or four dermatomes.

Generally, chemical agents that exert a specific neuromodulatory effect on neurons can be desired depending on the desired clinical result. Most of the agents developed to impair or destroy the sympathetic nervous system are targeted at post-ganglionic neurons. However, some approaches to the destruction of the pre-ganglionic neurons or transmission between pre and post ganglionic neurons can also be utilized. Classes of drugs include but are not limited to ionotropic, chronotropic, metabotropic drugs that suppress neurotransmission, anti-depressants, anti-psychotics, NMDA antagonists, opioid analgesics, anti-depressants, alpha-1 or beta2-adrenergic antagonists or alpha-2 agonists, calcium-channel blockers (CCBs), anesthetics, neurotoxins, neuroablative agents, depolarizing agents, non-depolarizing agents, hyperpolarizing agents, sympathicomimetics, sympatholytics, sympathetic antagonist, sympathotoxins, immunosympathectomy agents, auto-immune sympathectomy agents, anti-neuronal immunotoxin agents, antihypertensive agents, TRPV1 antagonists or agonists, tricyclic anti-depressants, low and high affinity Na+ blockers, imidazoline receptor agonist, ganglionic blocking agents, neurotransmitters, parasympathicomimetics, corticosteroids, and anti-neoplastic drugs. These agents may be delivered alone or in combination to exert a neuromodulatory effect directly or indirectly. These agents may result in a temporary block, a long-term-block, a temporary degenerative response without cell recovery, or a permanent degenerative effect. These methods may result in reversible or irreversible effects. These agents may also have an anti-inflammatory or neuroprotective effect. In some embodiments, it can be preferable to co-deliver anesthetic with or without epinephrine or norepinephrine in the neuromodulatory solution in the paravertebral space to reduce complications.

Objectives/Unmet Need with Drugs.

Cardiac disease, and in particular heart failure, is characterized by increased sympathetic release of norepinephrine (norE), depleted cardiac stores of NE, accompanied with a defect of norE uptake in the cardiac sympathetic nerve terminals. The defect in the uptake is in part due to a reduction in noreE transporter density in the sympathetic nerve endings and may be a major contributor to the elevated myocardial interstitial norE. Increased interstitial norepinephrine reduces myocardial adrenoreceptor density, increases myocyte apoptosis, and lowers the threshold for cardiac arrhythmias. In addition, these acute surges or norE are thought to increase the propensity for myocardial infarction in patients with coronary artery disease as the resultant blood pressure surge and vasoconstriction trigger a fissure in a coronary artery plaque, providing a thrombogenic focus together with increased Given the high levels of norepinephrine release that occur when the sympathetic ganglia are surgically transected, thermally ablated, or denervated with an excitatory neuromodulatory agent or agents that temporarily increase the levels of norepinephrine at the synaptic cleft, the development of neuromodulatory agents that directly or indirectly block or reduce the release of norepinephrine acutely, subacutely, or chronically are desirable for certain indications, particularly cardiac indications. The therapy, including a neuromodulatory agent and a carrier, can be delivered to the paravertebral gutter, containing the sympathetic chain, intermediate ganglia, rami communicantes and intercostal vessels. The carrier can be, for example, a hydrogel or other viscous formulation that can be used to deliver the neuromodulatory agent. The therapy may also be delivered to intermediate/accessory ganglia lying along the nerve roots or rami communicantes or along the nerves as they course to the visceral organs and vessels. Alternatively, the therapy may be delivered specifically to the region in between or surrounding the dorsal root and the dorsal root ganglion (DRG), particularly if sympathetic fibers have been identified innervating the DRG. In particular, the selection of neuromodulatory or neurolytic agents that directly or indirectly reduce the release of norepinephrine from sympathetic nerves followed by or in concert with triggering neuronal cell death such as through necrosis, autophagy or apoptosis, "dark" compacted death or a combination of these, can be desired.

In one embodiment, it can be desirable to deliver a neurolytic agent that can be taken up locally at the sympathetic ganglia (pre- or para-vertebral, may be mixed with parasympathetic fibers) and then directly or indirectly prevent or limit the release of norepinephrine at the nerve presynaptic terminal. As local intracellular or extracellular levels of the neurolytic agent rise, the drug initially modulates the nerve activity within its therapeutic range to exert a beneficial effect on reduction in norepinephrine spillover; as the drug concentration continues to rise to toxic levels it triggers pre- and/or post-ganglionic efferent neuronal cell death. At high concentrations, neurotoxicity to afferent and pre-ganglionic neurons that course through or in the paravertebral gutter is also possible. In one embodiment, the specificity of the neuromodulatory drug for the post-ganglionic nerves results in only the sympathetic efferent fibers being targeted. In yet another embodiment, the neuromodulatory drug targets only the sympathetic afferent fibers. In another embodiment, the drug targets only the pre-ganglionic fibers, reducing the extent of denervation supersensitivity. In another embodiment, such as for applications for the treatment of angina or ventricular arrhythmia, both the afferent and efferent sympathetic fibers are targeted. In another embodiment, such as for applications for arrhythmias (atrial, ventricular), it may be desirable to denervate only the pre-ganglionic sympathetic fibers, the post-ganglionic sympathetic fibers, or both fiber types. In yet other embodiments, it may be desirable to denervate the parasympathetic, sympathetic, and/or interneuron fibers in the cardiac intrinsic ganglia and plexi or subsets of neurons thereof. In another embodiment, it may be desirable to modulate only a subset or subsets of the fibers, by a different classification, such as by size and presence or absence of myelin. Similarly, it may be desirable to modulate C fibers (nonmyelinated, pain, nonlocalizing ache), temperature, touch, postganglionic autonomic), B fibers (preganglionic autonomic), or A-delta (Pain, fast-localizing, temperature, firm touch), A-gamma (muscle spindle stretch), A-beta (light touch and pressure), and A-alpha (somatic motor and proprioception) fibers differentially.

Reducing norepinephrine release can be achieved, for example, by blocking or inhibiting the action potential of the post-ganglionic neuron, blocking the release of acetylcholine from the pre-ganglionic sympathetic neuron, blocking the acetylcholine receptors on the post-ganglionic neuron, blocking the action of acetylcholine-induced depolarization, blocking the synthesis of norepinephrine (norE), blocking the transport of norE, blocking vesicular norE release and vesicle cycling, competing with or replacing norE transport into vesicles, depletion of neurosecretory vesicle content, modulating the calcium currents. This can result in a reduction on local norepinephrine levels at the tissue level and may translate to a reduction in norepinephrine spillover from the organ.

Alternatively, the neuromodulatory agent may be delivered to the neurons within the therapeutic window and provide a sustained block of norepinephrine release or neuronal activity, resulting in a long-lasting but reversible chemical sympathectomy without denervation of the nerve. In one embodiment this can be achieved by sustained release of a presynaptic alpha-2 receptor agonists such as dexmedetomidine or the non-selective alpha blocker phentolamine. In another embodiment, this can be achieved with the sustained release of reserpine, a VMAT-2 receptor antagonist, a catecholamine depleting agent. In another embodiment this can be achieved with pentolinium, a nonexcitatory ganglionic blocking agent. In other embodiments, the co-transmitters neuropeptide Y or histamine may also be reduced. In another embodiment, a local anesthetic, such as bupivacaine, results in local anesthetic effects. At higher concentrations, these agents result in neurolysis of the sympathetic visceral efferent (and also afferent) nerves innervating the thorax. Generally, because these agents are functioning through a non-excitotoxic mechanism of cell death, longer duration exposure may necessary to achieve neuronal degeneration.

In yet another embodiment, neuromodulatory agents can be delivered at the nerve terminals or synapses in the periphery at the target tissue, such as the lung or the heart. In some embodiments, the greatest proportion of cell receptors for the drugs are found at the nerve terminal or synapses. In other embodiments, the drug can cross the cytoplasmic membrane or is taken up through endocytosis or receptor-mediated endocytosis and transported retrogradely to the cell body, in this case the sympathetic ganglia to trigger apoptosis or neuronal cell death. The following drugs may be used as neuromodulatory agents, or, at higher concentrations, they may act as neurolytic or neurotoxic agents.

Action Potential Blockers.

Drugs that block the depolarization and effectively prevent the nerve from reaching a threshold to trigger an action potential or drugs that are hyperpolarizing or prolong the hyperpolarization of the neuronal cell membrane may be effective at preventing or reducing the release of norepinephrine at the synapse. These drugs may result in an inhibitory postsynaptic potential or IPSP.

Ion Channel Modulation.

Drugs that block calcium channels such as dihydropyridine (DHP)-type blockers (e.g. nifedipine, felodipine, nicardipine, nimodipine, and amlodipine), and non-hydropyridine blockers (phenylalkylamines (e.g., verapamil), benzothiazepines (e.g., diltiazem), nonselective agents (e.g., mibefradil, bepridil, flunarizine, fluspirilene, and fendiline). In particular, the neuronal N-type blockers omega-conotoxin GVIA (0.9 microM) which blocks NE and histamine release from sympathetic neurons but does not alter neuronal NE uptake or storage, or ziconotide, or T-type blockers such as amiloride (500 microM) which modulate dorsal root ganglion activity, L-type blockers like ethanol, verapamil, or combination L- and T-type antagonists such as lomerizine, P-, Q- and N-type blockers such as omega-grammotoxin SIA or omega-agatoxin IVA may be employed. Ranolazine, which blocks the late inward sodium current, may be beneficial if delivered locally to the sympathetic ganglia since it blocks the neuronal sodium channel and may have a role in relatively reducing sympathetic activity relative to parasympathetic. Drugs that activate potassium channels hyperpolarize and stabilize the cell membranes, reducing calcium entry, preventing vasoconstriction may be employed. These include, for example, diazoxide, minoxidil, nicorandil and pinacidil. Na+/H+ exchange inhibitors such as benzamil, cariporide, sabiporide, amiloride or the more specific derivatives, dimethylamiloride or ethylisopropylamiloride, reduce neuronal cell excitability, and markedly attenuate norE overflow which may be desired. Drugs that block sodium channels may be selected including 1,-8-cineole. Hyperpolarization-activated cyclic nucleotide-gated channels (HCN) inhibitors, such as ivabradine, lamotrigine, gabapentin, propofol, and lidocaine may be employed. The anticonvulsant valproic acid has been demonstrated to hyperpolarize sympathetic ganglia and trigger neurotoxicity at higher concentrations.

Sigma Receptor (σ1Rs) Agonists.

Sigma receptor agonists may rapidly inhibit or block all calcium channel subtypes found on the cell body of the sympathetic neurons (N-, L-P/Q- and R-type calcium channels) at the sympathetic ganglia or intrinsic ganglia (e.g. intracardiac), accelerate calcium channel inactivation rate, and shifted the activation toward more negative potentials. Sigma-1 receptor agonists include haloperidol, ibogaine, (+)-pentazocine, and 1,3-Di-O-tolylguanidin (DTG) as well as berberine, citalopram, dextromethorphan, dehydroepiandrosterone (DHEA) and pregnenolone, fluoxetine, igmesine, ketamine, methamphetamine, methoxetamine, noscapine, phencyclidine, novocaine, prilocaine and other opioids buprenorphine, tramadol. Buprenorphine has been reported to be used in Ganglionic Local Opioid Analgesia (GLOA) blocks at the stellate ganglion for the treatment of upper body chronic pain syndromes. Antagonists to these receptors have also been demonstrated to exert anti-nociceptive actions both centrally and peripherally by modulating pain hypersensitivity. Amiodarone is a class III antiarrhythmic agent that has beta blocker-like and calcium channel blocker-like actions, increasing the refractory period via sodium- and potassium-channel effects, and has demonstrated neurotoxicity. The first generation antipsychotics chlorpromazine and pimozide or second generation less-cytotoxic antipsychotics olanzapine and risperidone, for example, are cytocidal. As with other cytotoxic agents, their cytotoxic potential is usually after the receptors have been saturated and may be related to cholesterol-related mechanisms and changes in lipid metabolism.

Anesthetics also block voltage-gated sodium (or calcium) channels and thus block nerve activity sympathetic efferent and afferent nerves and may be employed from the amnio-amides, amino-esters, or other group. These drugs have demonstrated cytotoxicity in visceral sensory neurons (sympathetic) and sympathetic efferent (pre- and post-) ganglionic neurons at higher concentrations which can be used to achieve a permanent nerve block. Anesthetics (aminoesters, aminoamides) include N-butyl tetracaine (37 mM, 1.11% tetracaine-HCl) and other tetracaines, bupivacaine, ropivacaine, ketamine, lidocaine, procaine, iontocaine, chloroprocaine, EMLA, prilocaine, benzocaine, mepivacaine, neosaxitoxin, tetrodotoxin, saxitoxin, prenylamine, Marcaine, lignocaine, levobupivacaine, benzocaine, menthol, and the like. In one embodiment, the procedure is performed under ether anesthesia because these can, in some cases, result in faster depletion of norepinephrine content than pentobarbitone anesthesia after surgical sympathectomy.

In one embodiment, the local concentration and duration of anesthetic exposure can be controlled to permit differential blockade and or differential neurotoxicity. For example, the type B fibers (e.g. sympathetic efferent) may be blocked followed by the type C fibers (e.g. sympathetic or somatic afferent). Many anesthetics have multiple inhibitory effects such as lidocaine, which is also a nicotinic acetylcholine receptor blocker. At higher concentrations necrotic and apopotic (lidocaine, amitriptyline) cell death may be triggered by other mechanisms. In one embodiment, 2% lidocaine is delivered locally. In another embodiment, 5% bupivacaine is delivered locally. In another embodiment, prilocaine is administered to inhibit nerve firing immediately and may also inhibit the NET transporter.

Drugs that induce, potentiate, or increase the persistence of hyperpolarization via the 5-HT1 receptor such as 5-hydroxytryptamine, 8-OH-DPAT and 5-Carboxamidotryptamine (5-CT), haloperidol or ketanserin may be employed. This mechanism may also result in a reduction in acetylcholine from pre-synaptic pre-ganglionic sympathetic efferent neurons. Other agents that reduce the synaptic transmission in sympathetic ganglia include lysergic acid diethylamide, methysergide, and chymotrypsin. Other agents that may be of interest are drugs than enhance the uptake of norepinephrine into the nerve.

Vesicular monoamine transport (VMAT) inhibitors, and VMAT-2 inhibitors in particular, are another class of compounds that may be used to modulate or chemodenervate. VMAT 2 inhibitors include reserpine (RES, also blocks VMAT-1), bietaserpine, ketanserin, tetrabenazine (TBZ), phenylethylamine, MDMA (Ecstacy), N-methyl-4-phenylpyridinium (MPP+), non-hydroly sable GTP-analogue guanylyllimidiodiphsphate GMP—P(NH)P and VMAT-1 inhibitor fenfluramine. These drugs belong to the class of indole alkaloids and also include ajmaline, mediodespidine, desperidine, syrosingopine and rescinnamine. In particular, reserpine depletes the granular uptake and storage of catecholamines through near irreversible binding to VMAT-2, such as norepinephrine, and 5-hydroxytryptamine (5-HT) and does not excite sympathetic efferent post-ganglionic neurons, leading to a chemical sympathectomy. Reserpine may be delivered locally at doses of, for example, about 0.1 to about 10 mg, about 0.5 to about 5 mg, about 1 to about 2 mg per injection at a concentration of between about 0.1 to about 1 mg/ml, such as 0.02 to 0.5 mg/ml, or 0.03 to 0.25 mg/ml.

Nondepolarizing Ganglionic Blockers.

Nicotinic receptor blockers competitively block the action of acetylcholine on nicotinic receptors or block the ion channel that is gated by the nicotinic receptor. In one embodiment, nicotinic receptor blockers can be delivered locally to the sympathetic nervous system, such as the ganglia themselves, and block efferent neurotransmission irrespective of the neurotransmitter released at the nerve endings (e.g. norepinephrine, acetylcholine, histamine, NPY). Ganglionic blockers include chlorisondamine, tetraethylammonium (TEA), methyldopa, neostigmine, pempidine hydrogen tartrate, hexamethonium, decamethonium, mecamylamine, methyllcaconitine trimethaphan camsylate, trimetaphan camphor sulfonate, rocuronium, ibogaine, 18-methoxycoronaridine, dextromethorphan and pentolinium tartrate, and other polyalkylpiperidines and their derivatives. Other agents include monoxidine, amantadine, erysodine, tubocurarine chloride, varenicline, atracurium besylate, dehydronorketamine, ketamine, alpha-conotoxin, alpha-bungarotoxin and their pharmaceutically acceptable salts and optical isomers, and high-concentrations of bilirubin. In one embodiment, hexamethonium was injected locally. Alpha7-nicotinic acetylcholine receptor (a7-nAChRs) antagonists may be particularly suitable for the application such tetrodotoxin, nitro-L-arginine, and guanethidine.

Agonists of muscarinic acetylcholine receptors, also found on sympathetic nerves, are responsible for inhibitory post-synaptic potentials (IPSPs) and slow excitatory (EPSPs) under certain conditions such as atropine or scopolamine or other drugs that are inhibitory such as γ-aminobutyric acid GABA or GABA agonists (e.g. GABAB agonists), or baclofen. Alternatively, some antagonists of muscarinic receptors may also be selected to reduce nerve transmission, such as pirenzepine. Aromatic amino acid hydroxylase inhibitors, that inhibit tyrosine hydroxlase activity including halogenated phenylalanines, 3-alkly methyltyrosines, 3-substituted alpha-methyltyrosines, and 3-alkyl-methyltyrosines or antibodies to tyrosine hydroxylase, or antihypertensive drugs that modulate TH activity, such as anti-DBH, hydralazine, may be employed. Drugs that degrade catecholamines or drugs that inhibit the biosynthesis of norepinephrine as anti-dopamine beta-hydroxylase (anti-DBH) or DBH inhibitors such as nepicastat, or hydralazine may be employed. MAO enzymes' primary role is the metabolism of exogenous amines, control of neurotransmitter levels and intracellular amine stores and in the catabolism of neurotransmitters in the periphery. MAO-A preferentially oxidizes serotonin and norepinephrine, whereas MAO-B oxidizes phenylethylamine (PEA), with dopamine and tyramine being substrates for both isoenzymes.

There are several other classes of drugs of interest that modulate norepinephrine release. Several agents that modulate norepinephrine release indirectly include 1) Autoinhibitory Alpha-2 adrenoreceptor agonists, mimicking the action of norepinephrine, are located primarily on the presynaptic postganglionic nerve ending and inhibit the further release of norepinephrine from the neuron and may reduce the neuronal supersensitivity. These agents include dexmedetomidine, oxymetazoline, rilmenidine, moxonidine, agmatine and clonidine and non-selective phenoxybenzamines. The latter agents also act on the imidazoline (1) receptors. Non-selective alpha blockers, acting on alpha-2 receptors include phentolinamine, an irreversible phenoxybenzamine. 2) Nucleoside transport inhibitors. For example, draflazine, which increases adenosine concentrations in the synaptic cleft which in turn inhibit norepinephrine release through stimulation of pre-synaptic receptors, 3) Autoinhibitory H3 histamine receptor agonists such as (R)-alpha-methylhistamine, which inhibit the co-release of norepinephrine and histamine. 4) Serotonin (5-HT) acting on an autoinhibitory receptor, has also been demonstrated to inhibit norepinephrine release, 5) Presynaptic imidazoline receptor agonists which inhibit the release of norepinephrine including antazoline, cirazoline, idazoxan, 6) Guanidines such a guanidine chloride and derivatives, aganodine, arginine, and saxitoxin have been demonstrated to inhibit norepinephrine release from sympathetic nerves, 7) non-depolarizing neuromuscular blocking drugs that also modulate sympathetic efferent and afferent nerves including Cistracurium besilate (Nimbex), one of the isomers of atracurium, 8) hormones such as estrogen (beta-estradiol) which reduce NGF protein and TH protein content and reduced sympathetic neuron survival, and 9) sustained release of tyrosine hydroxylase inhibitor metirosine (alpha-methyl-p-tyrosine or AMPT) that has been demonstrated to reduce the release of norepinephrine and epinephrine, 10) In addition, angiotensin type II receptor blockers such as losartan may inhibit sympathetic nerve activity 12) In another embodiment, blockers of the p75 receptors and tropomyosin-related receptor tyrosine kinases (Trk), such as TrkA, reduce adrenergic output and neuronal survival. Blocking the activation of TrkA by NGF prevents the potentiation of an excitatory noradrenergic transmission at the neuron-myocyte synapse. Similarly, stimulating the p75 neurotrophic receptor promotes inhibitory acetylcholine release. 13) Adenosine and adenosine agonists, activates K+ and Cl-conductances, limits synaptically evoked depolarization and Ca2+ influx, directly protecting neurons against Ca2+ mediated overload but at high concentration cause apoptotic cell death.

Drugs that improve the reuptake of norepinephrine from the synaptic cleft directly or indirectly include perindopril, candesartan, and valsartan, or through modulation of dynamin-mediated endocytosis and vesicle cycling. Another approach is to reduce the activity of the pre-ganglionic neurons. Alfuzosin, (10-40 mM) the alpha-1 receptor antagonist, reduces sympathetic pre-ganglionic sympathetic nerve activity and thus reduces the post-ganglionic nerve firing and norepinephrine spillover. In yet another embodiment, p75 neurotrophin receptor (p75NTR) agonists, such as through proNGF, NGF, LIF, IL-6, IL-1, TNF-alpha, BDNF or proBDNF may denervate the sympathetic ganglia and block sympathetic sprouting to the DRG.

In another embodiment, it is desirable to prevent the activation of visceral afferent nociceptive C fibers that either travel with the sympathetic or parasympathetic nervous system, so as to block or reduce the transmission of pain. Since many of these fibers travel with the sympathetic nervous system through the sympathetic chain, therapies designed to modulate this class of neurons alone or in combination with sympathetic efferent fibers is desirable. NGF is a survival factor for both developing afferent and sympathetic efferent nerves, and has recently been demonstrated to play an important role in the generation and perpetuation of neuropathic, inflammatory and ischemic pain and hyperalgesia across the afferent (somatic/visceral) and sympathetic efferent neurotransmission. In one embodiment, an agent that blocks or antagonizes NGF or blocks its binding to TrkA is administered. Drugs that reduce the survival and/or axonal outgrowth after injury, such as through sequestration or reduction in nerve growth factor (NGF) levels, may be desirable. These include neurotrophic Tyrosine kinase receptor A (TrkA or NTRK1) antagonists that sequester NGF via the TrkA domain 5, antibodies to TrkA or NGF, such as local anesthetics.

In another embodiment, a patient may be prescribed reserpine and/or one, two, or more therapeutic agents as disclosed for example herein orally, intravenously, subcutaneously, intramuscularly, transdermally, or through another route of administration for one to three days prior to the procedure in order to lower their systemic norepinephrine levels prior to the procedure. In another embodiment, the patient continues to take reserpine or other therapeutic agent(s) for a specified time such as 30 to 60 days after the procedure.

In another embodiment, delivery of leukemia inhibitory factor (LIF), interleukin-6 (IL-6) or ciliary neurotrophic factor (CNTF) will trigger in a switch from adrenergic nerves to a cholinergic phenotype, reducing the release of norepinephrine. In another embodiment, inhibitors of LIF, IL-6 and CNTF may be delivered to reduce the sympathetic nerve sprouting to form connections with the dorsal root ganglion. In another embodiment, blocking the sodium Navv1.6 channel reduces pain, sensory neuron excitability and sympathetic sprouting. In another embodiment, beta-3 adrenoreceptors antagonists are delivered to the region containing the DRG to modulate the sympathetic post-ganglionic activity.

In indications in which acute and subacute control over local or systemic neurotransmitter levels is not necessary or desirable, alternative neuromodulatory agents can be employed to modulate the nervous system, particularly the sympathetic nervous system. Drugs that hyperpolarize cells to temporarily cause hyperexcitability through the increased dumping of neurotransmitter only to later cause the nerve to degenerate are of particular interest. These include tricyclic anti-depressants and other anti-depressants, and other non-specific agents such as those that temporarily increase the levels of neurotransmitter in the synaptic cleft before blocking and reducing neurotransmitter levels. These agents can be used in combination with anesthetics to reduce or eliminate the norepinephrine release. Secondarily, agents that result in excitotoxic cell death, in which neurons are damaged or killed by excessive stimulation are described.

Alcohol and phenol (carbolic acid, monohydroxybenzene) are both commonly used neurolytic agents. Alcohol causes an immediate progressive burning paresthesia that lasts several hours but a wide range of ethanol concentrations are effective at destroying nerves through extraction of cholesterol and phospholipids and subsequent sclerosis. Concentrations above 50% are well established to result in neurolysis, such as about 75%, 80%, 99% or 100%. One-hundred percent ethanol has been demonstrated to completely destroy the cell bodies and axons of sympathetic, sensory and motor neurons but come with a higher risk of adjacent neuritis. Phenol has mild anesthetic properties and causes a focal hemorrhagic necrosis and dissolves axons and Schwann cells inside the basal lamina, resulting in damage to the entire endoneurium. Regeneration in the periphery may begin in 2 weeks in preclinical studies. The drug can be injected at, for example, between 3 and 10%, more typically between 6.7% to 7% in oil or glycerol, such as Phenol-Aqua (7%) or phenol-glycerol (5%). Higher concentrations have been applied, such as about or at least about 10%, 25%, 50%, and 75%, such as between about 10-50% phenol in ethanol is desirable in some cases. Both produce severe burning pain immediately upon injection which may last about a minute. Glycerol is an anhydrous less toxic alcohol with weaker penetration, less extensive neuronal damage and faster regeneration than alcohol and phenol. Iohexol (30%) may also be employed. Alternatively, sodium tetradecyl sulfate (STS), an anionic surfactant and sclerosant drug with detergent properties may be selected.

By incorporating these readily available neurotoxic agents into a formulation that will slow or control their spread, adverse events and complications arising from their use can be limited. In one embodiment, ethanol is incorporated in the gel as a solvent for the neuromodulatory agent that is delivered. In another embodiment, there is no neuromodulatory active agent and ethanol alone provides the neurolytic effect but its spread is controlled by its containment within a formulation. In one embodiment, after delivery, the rapid tissue absorption of ethanol into the surrounding hydrophobic neurons and adipocytes causes the liquid formulation to gel.

Norepinephrine reuptake inhibitors (NRIs) and less specific norepinephrine serotonin reuptake inhibitors (SNRIs) (and selective serotonin/5-hydroxytryptamine reuptake inhibitors (SSRIs) and dopamine reuptake inhibitors) block the reuptake of norepinephrine at the synaptic cleft thereby increasing and sustaining the action of norepinephrine at the nerve terminal in the heart and other tissues. Norepinephrine uptake transporters (NET) includes Uptake 1, present in the neurons and lung pulmonary endothelial cells and uptake 2 transporter, present in the myocardium. Reuptake inhibitors include guanethidine, 1-methyl-4-phenyl-pyridinium ion ($MPP^+$) and Oxidopamine or 6-hydroxydopamine (6-OHDA), alpha-methyldopa, bretylium tosylate, guanacline, bethanidine and debrisoquine, desipramine, nisoxetine, ritanserin, setoperone, volinanserin, duloxetine, citalopram, fluvoxamine, zimeldine, sibutramine, Levomilnacipran, debrisoquine, lobeline and amezinium. Dopamine reuptake inhibitors include GBR-12909 and amfonelic acid. Many of these agents also function as MAO inhibitors to prevent norepinephrine deamination and some as a VMAT agonist. Although not a reuptake inhibitor, alkaloid cocaine interferes with Uptake-1. Guanethidine (1-2 mg/ml) is particularly interesting in some embodiments because it can both increase the norepinephrine in the synaptic cleft (transient sympathomimetic) initially through NET1 activity but also acting as a monoamine depleting agent, and blocks adrenergic transmission. High or sustained doses lead to neuronal cell death in both efferent and afferent nerves, such as capsaicin-sensitive primary sensory nerves. Preferably, these agents are delivered to nerve terminal or peripheral synapse of the post-ganglionic sympathetic nerve in the heart, lung, or tissue innervated by post-ganglionic sympathetic efferent nerves. At high concentrations, these agents result in immunotoxic NK- and mononuclear-cell mediated death as can be seen by degeneration of sympathetic ganglia in the sympathetic chain.

Anti-Depressants.

In another embodiment, the neuromodulatory agent is an anti-depressant such as bupropion, doxepin, desipramine, clomipramine, imipramine, nortriptyline, amitriptyline, protriptyline, trimipramine, tianeptine, fluoxetine, fluvoxamine, paroxetine, sertraline, phenelzine, tranylcypromine, amoxapine, maprotiline, trazodone, venlafaxine, mirtazapine, their pharmaceutically active salts and/or their optical isomers. In a very preferred embodiment, the anti-depressant is either bupropion or a pharmaceutically acceptable salt thereof, or nortriptyline or a pharmaceutically acceptable salt thereof. Bupropion, desipramine and imipramine are also ganglionic blocking agents (nicotinic) and at higher doses is toxic to afferent and efferent nerves.

Microtubule disrupting agents or cytoskeletal drugs that interact with actin or tubulin may also be used to denervate neurons such as phalloidin, cytochalaisin D, Latrunculin, colchicine (1 and 10 microM), demecolcine, jasplakinolide, nocodazole, paclitaxel (taxol), and vinblastine. Other potential approaches include inhibition of phophoinositide 3-kinase (PI3K), serine-threonine protein kinase B (Akt), extracellular signal-regulated kinase (ERK) pathway, the P38 mitogen activated protein kinase pathway (MAPK).

Cholesterol oxides (PMID 9566506) cause rapid cell sympathetic ganglia cell death in vitro at concentration of 4 ug/ml (10 uM) within 36 hours. The most potent of these 25-OH-cholesterol has demonstrated neurotoxicity across a range of cell types.

MAO-A and COMPT inhibitors, including tyramine, clorgyline, paragyline and 3,5-dinitrocatechol, Ro 41-1049, selegiline, tranylcypromine may result in excitatory chemical sympathectomy if delivered in high enough levels.

Immunosympathectomy can be achieved with Anti-Nerve growth Factor (anti-NGF, Tanezumab, Fulranumab), auto-immune sympathectomy with Anti-Dopamine Beta Hydroxylase (DHIT), DBH or Anti-acetylcholinesterase (Anti-AChE, immunotoxin sympathectomy with OX7-SAP, 192-SAP IgG, DBH-SAP or DHIT. Toxins such as botulinum toxin (BOTOX, DYSPORT type A through G, such as described, for example, in U.S. Pat. No. 6,743,424 to Donovan, which is hereby incorporated by reference in its entirety), tetrodotoxin, neosaxitoxin, may also be effective.

Efferent Nerve Degeneration.

Botox can be advantageous in some embodiments for delivery to the sympathetic chain because it preferentially targets the pre-ganglionic sympathetic efferent nerves by blocking the release of acetylcholine. Blocking the sympathetic pre-ganglionic stimulation of post-ganglionic nerves has been demonstrated to dramatically reduce norepinephrine release from the post-ganglionic nerves. Botox injections typically last between 3 to 6 months, providing a sustained reduction in efferent nerve activity during this time. Furthermore, denervation of pre-ganglionic fibers, while leaving the post-ganglionic fibers intact results in reduced denervation supersensitivity (upregulation of beta-adrenergic receptors in the heart). As with all drugs, 'off-target' effects on post-ganglionic and afferent nerves are likely, although the agent will likely have a less powerful effect on these nerves.

Afferent Nerve Degeneration.

High concentrations of capsaicin result in a stimulatory denervation of afferent nerves with small diameter soma (dark B-type)>intermediate diameter soma (light-A type) >type C fibers>thinly myelinated Aδ fibers and therefore may be used to provide short-term degeneration of sensory somatic or visceral fibers. Alternatively, resiniferatoxin (RTX) underway for trials for intrathecal administration for intractable pain, may also be suitable for applications in the paravertebral gutter as it is a highly selective agonist of the TRPV1 receptor and can selectively ablate afferent neurons. Some anesthetics have relatively selectivity for C fibers and can potentially be administered at a concentration that ablates afferent fibers but only blocks other fibers types. In some embodiments, the delivery of excitotoxins such as kainic acid (0.5 nmol/ul), kainate/kanamycin, or N-methyl-D-aspartic acid (NMDA, 6.8 nmol/ul) and NMDA subtypes, okadaic acid, GM1 ganglioside, quisqualate or a-amino-3-hydroxy-4-isoxazoleproprionic acid (0.54 nmol/ul) can be applied that have been demonstrated preclinically to target only afferent, not efferent fibers. These agents result in considerable loss of cell bodies but spare axons and appear to be selective for the denervation of vagal afferent neurons but only stimulatory to the afferent dorsal root fibers.

Drugs—Gene Therapy.

Alternatively, a gene therapy based approach to silencing nerves can be used to effectively halt neural activity of a pathway. For example, DNA, RNA, RNAi, and/or siRNA can be delivered to send a neuron into a pro-apoptotic pathway, to deliver a light-sensitive protein so that light can halt neurotransmission in a cell, such as described in U.S. Pub. No. 2013/0225664 to Horsager et al., which is hereby incorporated by reference in its entirety. Neurotrophic factors (e.g. GDNF, BDNF, or NGF) or neurotrophic factor receptors (e.g. TrkA or p75 low affinity NGF receptors) can be knocked out or deleted. Alternately, the phenotype of neurons can be altered such as from noradrenergic to cholinergic or neurotransmitter synthesis can be up or down regulated through changes in transcription and translation factors. Examples of proteins whose expression can be directly or indirectly up- or down-regulated include leukemia inhibitor factor, phenylethanolamine-N-methyl transferase (PNMT), tyrosine hydroxylase (TH) or Df3H.

Modulating supersensitivity may be desirable specifically pre- or post-junctional supersensitivity, in which the responsiveness of cells is characterized by a leftward shift of concentration-response curves for agonists.

Suicide Axoplasmic Transport (Retrograde).

In yet another embodiment, a neuromodulatory agent can be delivered at the distal nerve terminals and retrogradely transported to the ganglia to modulate the nerve. In this manner, nerves innervating a target tissue or organ can be selectively denervated, such as, for example, with Adriamycin or Epirubicin. In one embodiment, 0.05 to 1 mg of Adriamycin (doxorubicin) can be delivered to the heart, lung, and great vessels of the thorax to selectively destroy non-motor afferent and efferent sympathetic and vagal fibers, providing an avenue to deliver the cytotoxic drugs to nerves away from the intrathecal space. These tissues include the pericardial sac, the epicardial fat pads, the nerves traveling along or across the coronary arteries, coronary veins, coronary sinus, the nerves traveling around the pulmonary arteries/veins, the pulmonary artery trunk, the aorta, the bronchial arteries/veins or lung root/hilum. These agents may be delivered through a transvascular or percutaneous or other minimally invasive approach. If performed carefully, high local concentrations of Adriamycin can be delivered to the sympathetic chain with careful avoidance of the intrathecal space, to achieve post-ganglionic sympathectomy. This cell death can also be achieved with other retrogradely transported agents such as *Ricinus communis* agglutinins and highly toxic lectins for example. Alternatively, neurotoxic or neurolytic drugs can be conjugated to retrogradely transported peptides or proteins, such as wheat germ agglutinin (WGA), dextran, horse radish peroxidase (HRP) for rapid axonal transport to the perikaryon from a nerve terminal or crushed/transected nerve. In another embodiment, the retrograde transport can be used to deliver drugs that support neuronal survival and/or regeneration. In another embodiment, viruses than are known to be transported retrogradely and transsynpatically can be used to deliver neuroprotective agents from the periphery directly to the target cells in the central nervous system, such as the hypothalamus. In one embodiment, the retrograde transsynaptic tracer pseudorabies virus (PRV) coated nanoparticle loaded with NGF can be delivered to the paravertebral gutter for delivery both locally and to central nervous system. For example, agents can be delivered into the paravertebral gutter that are then taken up by pre-ganglionic neurons and transported transynaptically to the locus coeruleus for the treatment of Parkinson's disease. These agents may also provide for improved local survival of neurons within the sympathetic chain, as these patient's also suffer from loss of cardiopulmonary sympathetic nerves.

Double Crush or Synergistic.

In some embodiments, nerves may receive a "double crush" in which two, three, or more therapeutic agents or factors, in series or in parallel, lead to effective neuroablation through, in part, a synergistic effect. The first factor may be the presence of an existing precondition such as neuropathy or diabetes prior to receiving the second 'crush', the neurolytic agent. In another embodiment, the first crush may be a systemically administered agent, (whether delivered, for example, orally, intravenously, intraarterially, intraperitoneally or as an inhaled agent) that lowers the threshold for neurotoxicity before a local agent is delivered to ablate the nerves in the region. In one embodiment, reserpine is administered systemically, and then a neurolytic agent, such as lidocaine, is administered locally, as described, for example, in U.S. Pat. No. 4,029,793 to Adams et al. or U.S. Pat. No. 7,928,141 to Li, both of which are incorporated by reference in their entireties. In another embodiment, an anesthetic agent is delivered first to block the nerves and reduce the pain, and then subsequently a neurolytic agent is delivered that acts synergistically with the anesthetic agent to locally denervate the neurons. In another embodiment, a local agent is delivered and coupled with a mechanical or thermal signal to cause more complete neuronal cell death, such as a neurolytic agent combined with high-frequency ultrasound or radiofrequency ablation. In another embodiment, the synergistic effect may allow for a reduction in the dose or concentration of one or both agents, thereby reducing systemic toxicity.

In another embodiment, other drugs with known neuromodulatory effects, many with transient or acute excitotoxic effects, include, for example, glutamate, glutamine, polyglutamine, isoniazid, crotoxin, taipoxin, phenylephrine, tryptamine or 5-hydroxytryptamine, chlorpromazine, clozapine, doxorubicin (TRPV1), NMDA, MPTP, chlorpromazine and other phenothiazines, ampicillin, N-(2-Chloroethyl)-N-ethyl-2-bromobenzylamine (DSP-4), lanthanides, yohimbine, nicotine and lobeline and amphetamine (mixed agonist-antagonists), nicitinamide and nicotinic acid and derivatives, lectins, trimethyltin (TMT), NSAIDs such as indomethacin, nitrosoureas such as streptozotocin, streptomycin, gentamycin, bleomycin, 6-hydroxydopamine (100 mg/kg sc), kainite, quinolinic acid, phenytoin, bupropion, thalidomide, quinolinate, fluoroquinolone antibiotics such as moxifloxacin, levofloxacin, and ciprofloxacin, varatum alkaloids such as proveratrine or veratridine, *vinca* alkaloids such as vincristine, bortezomib (glove and stocking peripheral neuropathy), rotenone (pesticide), yessotoxin (increase in cytosolic calcium), brevetoxin (L-glut and L-asparate), the fluoroquinolones including ciprofloxacin, gatifloxacin, gemifloxacin, and levofloxacin; myelin fludarabine, methotrexate, vinblastine sulfate (0.4 mg/kg sc), vincristine, cisplatin, oxaliplatin, ormaplatin, gentamycin, gemcitabine, sorafenib, angiotensin II agonists, saralasin, bleomycin, taxol/paclitaxel, L-arginine, phenytoin, caspace, caffeine, captopril, paclitaxel which induce ceramide synthesis include chemotherapeutic agents, gamma interferon, matrix metalloproteinases, and anandamide. Corticosteroids such as prednisone, methylprednisolone, triamcinolone diacetate, triamcinolone acetonide, or betamethasone can also be utilized. Drugs which block GABA-ergic transmission of sympathetic ganglia such as bicuculline and metrazol, VMAT-2 agonist methylphenidate, amphetamine, the powerful toxic lectin ricin, ergotoxine or ergotamine or ergotoxine derivatives (ergocristine, ergocornine, ergocryptine, methysergide) paralyze the sympathetic nervous system or cabergoline, pergoline or lisuride, gambierol, pyrethroids, ivabradine, mibefradil, nicorandil, trimetazidine quinapril, losartan, droperidol, tramadol, labetalol, spiperone, picrotoxin, butyl aminobenzoate, HA H3 receptor antagonist thioperamide, opipramol, pentazocine, lacidipine, 3-hydroxy-3-methylglutaryl coenzyme A (HMG-CoA) reductase inhibitors including mevastatin and lovastatin; rimcazole, panamesine, rimcazole, metaphit, tizanidine, apraclonidine, oxaprotiline, and spermine are some examples. Alternatively, sustained release of fast anterograde transport blockers has been implicated in acrylamide and gamma-diketone-mediated, and 2,5-hexanedione (2,5-HD) nerve degeneration.

Other non-pharmacologic chemical agents include salicylic acid (10% in ethanol), menthol, isotonic dextrose, hypotonic saline (e.g., half-normal saline or less, or dextrose in water), hypertonic saline (10%, 1.7M, 100 mg/ml) severe pain) or hyperbaric solution (5-8% glucose) which may be effective against C-fibers. Yet other agents include liquid nitrogen and hydrogen peroxide, octanoic acid, methanol, D-limonene, kainic acid, domoic acid, diethyl ether, and L-2-chloropropionic acid.

Similarly, many of these agents may initially increase neurotransmitter levels at the synaptic cleft but rapidly halt neurotransmission resulting in catecholamine depletion at lower doses and then cause degeneration at higher doses possibly through an immune related mechanism or cause an initial upregulation in neurotransmission followed by neurodegeneration. Further examples of therapeutic agents that can be utilized with systems and methods as disclosed herein can be found, for example, in U.S. Pat. No. 6,932,971 to Bachmann and U.S. Pub. No. 2006/0280797 to Shoichet et al., U.S. Pub. No. 2015/0132409, 2015/0202220, U.S. Pat. Nos. 8,975,233, 9,056,184 to Stein et al., U.S. Pub. No. 2013/0252932 and U.S. Pat. No. 9,011,879 to Seward, all of which are incorporated by reference herein in their entireties.

In some embodiments, it can be desirable to protect a first population of nerves adjacent or in proximity to another second population of nerves that are receiving a neuromodulatory therapy or undergoing some other treatment. In one embodiment, the soma, ganglia, plexi, that require neuroprotection can be surrounded with a neuroprotective biocompatible 'blank' gel in which the neuroprotection is provided by the compliance of the gel with the tissue and the mechanical barrier of drug diffusion through the gel or formulation. In this manner, neurolytic or neurotoxic agents can be delivered alone or in combination with a gel the adjacent tissue while protecting other critical structures or tissues. The hydrogel may also protect other vital structures from chemical, thermal, or mechanical damage. Another embodiment involves the delivery of a neuroprotective agent or agent that antagonizes or attenuates the effects of the neurolytic agent within the gel. Like combinations with a neurolytic agent, delivering a gel with a neuroprotective agent that is retained in the gel and has limited spread to the regions in which the neurolytic agent is delivered can be desirable. For example, a neuroprotective agent can be applied to the nerves that it is desired to spare directly or in a sustained release formulation, such as a hydrogel. This procedure can be performed percutaneously or endovascularly prior to the injection of a neurolytic agent either alone or in a hydrogel. This may be performed through the same delivery effector such as a needle, such as through a double lumen with two exit ports facing opposite each other or another angled orientation with respect to the sidewall of the catheter. In some embodiments, delivery of the hydrogels may be performed through the same lumen but the gels are injected serially with the blank or neuroprotective-gel delivered first followed by administration of the neurolytic gel or vice versa. In one embodiment, the delivery of the neuroprotective agent/gel can be delivered in one location through a needle or lumen and then the needle or lumen can be rotated and oriented 180° (such as rostral followed by caudal) to deliver the neurolytic agent/gel to a second location to the nerves it is desired to ablate. For example, it may be desirable in some embodiments to ablate or neuromodulate only the T1 sympathetic ganglia and below. Because 80% of the time the T1 ganglia is fused completely or partially with the inferior cervical ganglion, it may be desirable to deliver a neuroprotectant gel or blank gel at the $1^{st}$ rib to the inferior cervical ganglia through an ultrasound- or CT- or other image-guided approach. This guidance, for example, may be done utilizing one of the anterior approaches to access the stellate ganglion, as performed with stellate ganglion block. After this, either through the same lumen or through a catheter extended within or over the existing lumen, a neurolytic gel may be administered to the lower half or third of the stellate ganglion, the T1 sympathetic ganglion. In doing so, avoidance of Horner's syndrome may be possible. Specifically, the lumen can be directed upward toward the inferior cervical ganglion at the upper margin of the $1^{st}$ rib to deliver a blank hydrogel. The lumen can then be rotated caudally to deliver a neurolytic-hydrogel to T1 to T4, as desired. Alternatively, injections of neuroprotectant gel or 'blank' gel can be made into the relevant intercostal spaces to prevent the intercostal nerves against intercostal neuritis, or into the dorsal or ventral roots, or into the intervertebral space or the intrathecal space to prevent spread to the roots or spinal cord, respectively.

In other embodiments to permit neuroprotection, one group of neurons can be protected via the distal delivery of agents at their axons or nerve terminals, away from the cell bodies in the sympathetic ganglia. The neuroprotective agent delivered there may block or reduce the activity of the specific population of nerves that it is desired to protect. In this embodiment, the neuroprotective agent and/or gel may be delivered distally to the targeted neuroablation zone along the axons or nerve terminals to have neuroprotective effects on the soma and axons directly within the neuroablation zone. In one embodiment, the agent is an anesthetic and protects the neuron from excitotoxic cell death. Alternatively, the agent may act as a specific antagonist to the mechanism of the neurolytic agent that is delivered. The neuroprotective agent may, for example, exert an effect for 24-48 hours, the same duration of the activity of the neurolytic agent at the injection site. Specifically, in the case of the undesirable effect of neuroablation of the inferior cervical ganglion causing temporary or permanent ptosis component of Horner's syndrome, the neuroprotective agent can be topically applied or injected into the eyelid to reach the retractor muscle of the upper eyelid, the levator palpebrae superioris muscle. In another embodiment, it is desirable not to denervate a given organ when performing a chemical sympathectomy. In order to achieve this, injections of the neuroprotective agent are made into the organ capsule (such as the pericardial sac, pleura, or peritoneum, for example, or into the vasculature suppling the organ or extravascularly to the nerve bundles coursing into the organ. This neuroprotection can also be provided to populations of neurons undergoing mechanical axotomy, such as in VATS procedures.

Neuroprotective/Neurocounteractive Drugs.

Neuroprotective drugs can be delivered alone locally or distally or delivered in a gel or formulation to control their spread and direct the agents to the tissue that requires protection. For example, an anesthetic can be delivered to the nerve terminals to prevent neurotoxicity that is induced by excitotoxicity, NGF or CNTF can delivered to prevent neurotoxicity from vincristine and Taxol. Other agents include potassium channel blockers including amiodarone, clofilium and semtilide to counter-act, for example, potassium channel agonists. Similarly, the calcium channel antagonist flunarizine, cinnarizine, diphenylpiperazines protects against neuronal cell death in preclinical models of axon transection or crush. Dexamethasone or alpha-lipoic acid can be delivered to attenuate the neurotoxiity of bupivacaine and lidocaine and reduce provide protection to sympathetic neurons from immune-cell mediated necrosis and apoptosis such as with agents like guanethidine. MAO inhibitors have been demonstrated to counteract the chemical sympathectomy caused by reserpine. Alternatively, a high-K+ environment (greater than or equal to 33 mM), the actions of a VMAT, such as tetrabenazine (TBZ) can be blocked with a catecholamine uptake also helps to prevent sympathetic cell death. Minocycline and deferoxamine mesilate, amifostine, glutathione, diethyldithiocarbamate, Org 2766, curcumin, or vitamin E can prevent against cisplatin toxicity. Others drugs with recognized neuroprotective effects include the L-type Ca2+ channel blocker, nimodipine (2 microM) has been demonstrated to be neuroprotective in both DRG and CNS, as well as nifedipine and nilvadipine, metformin, dexamethasone, estrogen (neuroprotective or neurocytotoxic), bupropion, or the MAO-B inhibitor deprenyl, or the adenosine A2A antagonist MSX-3, or topiramate (TPM) and lacosamide which stabilize hyperexcitable membranes, calcineurin inhibitors (CNI) include cyclosporin, tacrolimus, and sirolimus. As such, in some embodiments, a first agonist therapeutic agent can be delivered to a first location, and a second antagonist therapeutic agent to the first therapeutic agent can be delivered to a second location.

Neuron Survival or Neuron Regenerative Drugs.

In still other embodiments, neuromodulatory drugs that provide a neuroprotective or neuron survival cues to the sympathetic afferent and efferent nerves are delivered directly or in a gel-based platform to provide sustained releases of pro-survival, pro-regenerative, pro-differentiation cues. For example, controlled delivery of nicotine to the sympathetic chain, increases NGF production and thus the survival encourage the survival of afferent and efferent sympathetic nerves for the treatment of neurogenic orthostatic hypotension (NOH), cardiopulmonary denervation associated with Parkinson's disease (PD), cardiopulmonary denervation associated with diabetes and pure autonomic failure (PAF). Agents may also indirectly have a beneficial effect on nerves in the CNS, such as the locus coeruleus in Parkinson's disease. Alternatively, the local sustained delivery of L-dihydroxyphenylserine (L-DOPS) can be delivered to the cardiac sympathetic nerves to generate norepinephrine since these nerves are firing at the appropriate rate.

Dosing

If chemodenervation is desired, the degree of neurotoxicity may be related to the concentration or dose administered. Generally, the toxicity increases with a longer duration of exposure above the therapeutic range. For example, the highest concentration of anesthetic used in local nerve blocks is around 2% in some cases. For a neurolytic application, the local concentration of lidocaine, lignocaine, or mepivacaine delivered may be about or at least about 5%, or bupivacaine may be about or at least about 1-2%.

Percutaneous Devices

Unmet need: In addition to the complications associated with the uncontrolled spread of agents like ethanol, the paravertebral block (PVB, anesthetic) injections themselves may be associated with an unpredictable clinical spreading pattern that can vary from time to time within a given patient. This results in a failure to achieve paravertebral anesthetic block in up to 10% of patients.

A reliable, safe approach to disrupt or block multiple contiguous levels of the paravertebral gutter can be desirable to prevent the need for guidance and repeat insertion of needle or catheter at each sympathetic chain level. In the case of percutaneous approaches, this would significantly reduce the pain and anxiety associated with the procedure and potentially procedural complications. The procedure could be achieved with a flowable therapeutic composition, such as a hydrogel in some embodiments. In some embodiments, the paravertebral gutter can be accessed endovascularly, such as via a wall of the azygous vein in some embodiments, as opposed to transcutaneous paravertebral blocks.

Therefore, in addition to the appropriate selection of neuromodulatory agent and injectable formulation, the use of an appropriate device delivery system to administer the therapy in a safe and efficacious manner can be highly advantageous in some embodiments. In some embodiments, injection of the therapy, including but not limited to a) a neuromodulatory agent or agents alone, b) neuromodulatory agents delivered in a formulation such as a hydrogel, c) excipients (such as those from the GRAS list) delivered in a formulation such as a hydrogel, d) solvents delivered in a formulation such as a hydrogel, or e) a hydrogel alone without an active agent, is delivered into the paravertebral gutter or space. The paravertebral gutter can be accessed from multiple minimally invasive approaches including both the anterior (T1) and paravertebral approach transcutaneously and an arterial or venous approach endovascularly, and it can be preferred in some cases to deliver the agent into or toward the anterior region of the paravertebral gutter to permit longitudinal spread of the agent. Alternatively, the paravertebral gutter can be directly visualized as part of a VATS or surgical procedure and the therapy delivered through the pleura into the paravertebral gutter directly or injected into and around the site after the sympathectomy. The therapy can be delivered unilaterally or bilaterally during a procedure, such as for example on the left side first, and then the right side as needed to achieve maximal therapeutic benefit or vice versa, or only the left side or the right side. Alternatively the procedures can be performed in a staged fashion. In one embodiment, patients receive a stellate ganglion block or paravertebral block with anesthetic prior to the delivery of the neurolytic-hydrogel to confirm that they are responders and to identify any challenges with the patient anatomy.

In some embodiments, the injectate is delivered and the travel is limited to within the paravertebral gutter or space. The thoracic paravertebral gutter space (TPGS) is defined between T1 and T12. A stellate ganglion block, lumbar paravertebral block, and lumbar plexus blocks (psoas compartment block) can also be considered types of paravertebral block. The cervical and thoracic paravertebral space are continuous with one another. The thoracic paravertebral and lumbar retroperitoneal paravertebral space may be in continuity via subendothoracic fascial communication, although in most cases the origin of the psoas muscle seals off the thoracic paravertebral space below T12, rendering the two paravertebral regions succinct (Karmakar et al 2011). For descriptive purposes, each segment of the space is limited superiorly and inferiorly by the heads of the corresponding ribs.

TPGS.

The thoracic paravertebral space or paravertebral gutter is a wedge-shaped potential space that can be created by fluid distention when a needle is placed next to the vertebral column or anterior to the transverse process but posterior to the parietal pleura. The paravertebral space contains the intercostal nerves as they emerge from the vertebral foramen, the dorsal rami, the rami communicantes, the intercostal vessels, the sympathetic chain, intermediate ganglia (if present), and loose connective and adipose tissue. The nerves are unsheathed for the most part, allowing for rapid uptake of neuromodulatory agents. The space is bounded posteriorly by the superior costotransverse ligament and laterally by the posterior intercostal membrane, anteriorly by the parietal pleura, medially by the postero-lateral aspect of the vertebra, the intervertebral disc, and the intervertebral foramen, superiorly by the occiput, inferiorly by the alair of the sacrum. Anteriorly, there is no place for the material to advance unless the pleura is breached. Lastly, the TPGS can be further subdivided into the anterior and posterior segments by the thin fibroelastic endothoracic fascia. The sympathetic chain lies in the more anterior region of the paravertebral space. In some embodiments, the paravertebral gutter is filled with the neuromodulatory formulation and the agent spreads within the gutter to reach the target levels. Direct injection into the sympathetic chain and associated ganglia is avoided in some embodiments as this may limit the spread of the agent to the sympathetic chain itself and not the finer surrounding structures such as the rami communicantes and intermediate ganglia, if present.

Challenges

However, laterally, the agent can spread into the intercostal space and medially it can travel through the intervertebral foramen/transforaminally to the epidural space. This is particularly true of ethanol injections, which rapidly and distantly spread from the site of injection. Finally, the prevertebral fascial lies anterior to the vertebral bodies and can provide a route to administer a formulation bilaterally. In the cervical region, injectate can travel from the inferior cervical/stellate ganglion to the brachial plexus, vagus nerve, recurrent laryngeal, phrenic nerve and inadvertent injections into the vertebral artery and inferior thyroid artery have been reported. In the thoracic region, injection to intercostal nerves resulting in intercostal neuritis, or rarely, injection into the epidural space has been reported.

Blind.

Figure 7A:
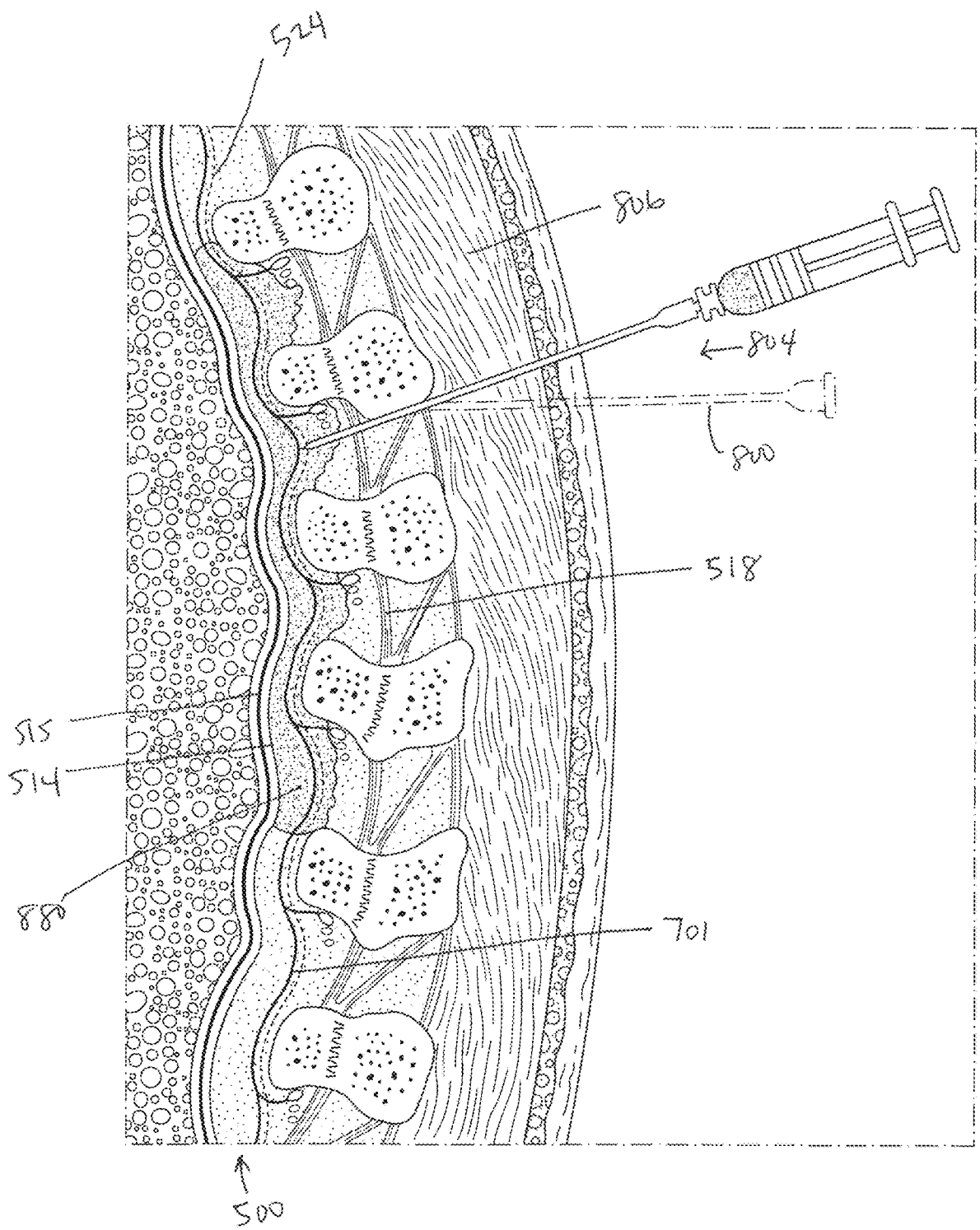
FIGS. 7A and 7B illustrate embodiments in which a gel can be flowed into the paravertebral space.

The objectives of some embodiments of the procedure are to 1) deliver the therapy longitudinally within the paravertebral gutter consistently and successfully and 2) to avoid injection of the formulation into critical adjacent structures such as vessels, organs such as the lung and associated pleura, and lymphatics. This can be achieved with a blind approach in some patients (or other imaging guidance in other embodiments as described elsewhere herein). The transcutaneous or percutaneous approach to the paravertebral gutter is based on the injections of anesthetics performed today to achieve paravertebral block (PVB). The paravertebral space is approximately 2.7 cm (range 1.7 to 4.31 cm) from the skin surface and with a slightly oblique approach this distance become 4.4 cm (range 3.5 cm to 6 cm). As illustrated in some embodiments of the method as shown in FIG. 7A, these injections can be performed blindly or under imaging guidance by advancing a 18-gauge Tuohy needle (800, shown in phantom) 2 to 5 cm lateral to the midline perpendicular to the skin. The needle 800 passes lateral to the spinous process and penetrates the superior costotransverse ligament 518 by a loss-of-resistance technique. Alternately, a needle is advanced to contact the transverse process upon which it is angled superiorly or inferiorly and advanced 1 to 1.5 cm until loss of resistance to saline is appreciated. A click may be felt as the superior costotransverse ligament 518 is penetrated. There is occasionally a gap between the lateral and medial portion of the superior costotransverse ligament 518 that prevents the use of a loss of resistance technique to confirm that the needle tip is in the right location. The needle 800 is then slightly withdrawn and redirected cephalad at a 45 degree angle to the skin for up to 1 to 1.5 cm deeper than the depth of the bone contact. The catheter 804 is then inserted through the needle 800, 1 to 2 cm beyond its tip, and a therapeutic agent, such as a hydrogel for example can flow into path 880 across multiple levels within the paravertebral gutter 500. Also illustrated are thoracic ribs at the T1-T6 levels (R1, R2, R3, R4, R5, R6).

Figure 7B:
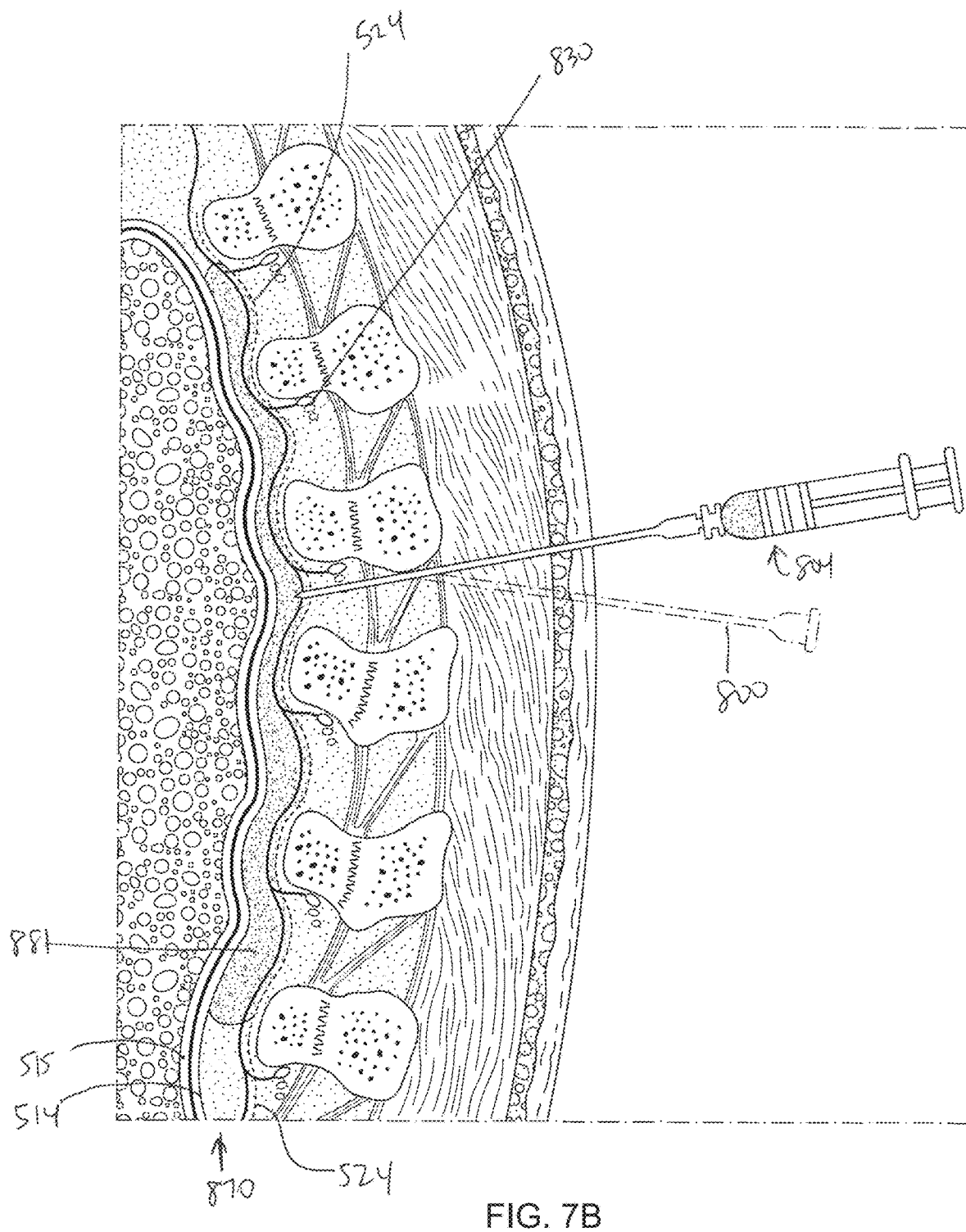

In some embodiments, the therapy is injected into the potential space of the paravertebral gutter and more preferably in some embodiments the anterior paravertebral gutter 870 (and makes flow path 881) as illustrated in FIG. 7B in order to achieve optimal rostro-caudal spread while minimizing adjacent spread into the intercostal space. This may be achieved through a single injection anteriorly past the endothoracic fascia 524 to achieve multi-level paravertebral therapy to the thoracic paravertebral space or through a series of single-level injections to cover the multiple target levels. Also illustrated is the dorsal/ventral root 830.

There is +/−1 level variability in some cases on where the stellate ganglion resides, and it is a long fused ganglion so most often it is from C7 to T1/R1 but may sometimes be found extending between R1 and R2. It can be desirable to target the middle and/or lower stellate ganglion in some embodiments. As such, in some embodiments possible target locations for injection where the actual stellate ganglion location is unknown includes, for example: the bottom of R1; the middle of R1; and the top of Rib 1 (using the rib as a landmark). On the caudal end, the first 4 sympathetic ganglia (T1-T4) can be covered in some embodiments. Most of the ganglia sit in between the ribs, so in some cases the agent has to flow down to the top of the 5th rib to cover those levels. In some embodiments, T5 is covered as well to obtain more complete denervation so the gel can travel caudally going to the next rib (R6).

Figure 8:
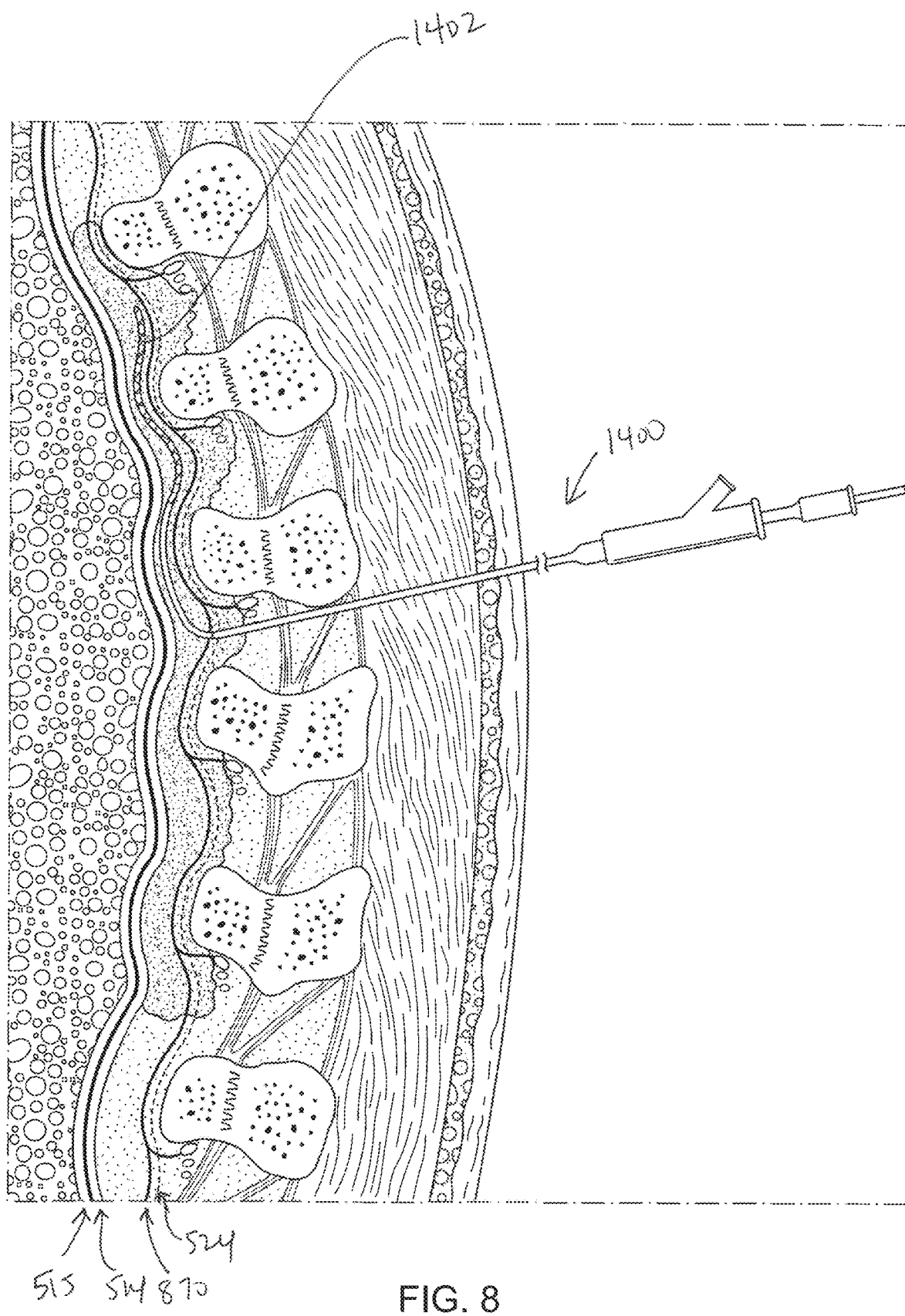
FIG. 8 illustrates an embodiment of a system and method for sympathetic neuromodulation similar to that described in FIGS. 8A and 8B above, and also including an energy delivery effector.

FIG. 8 illustrates an embodiment of a system and method for sympathetic neuromodulation similar to that described in FIGS. 7A and 7B above, and also including an energy delivery effector 1402, such as one, two, or more RF electrodes for multi-segment RF ablation within a desired anatomical target location, such as the paravertebral gutter for example. One, two, or more hydrogels can be delivered as described herein unidirectionally or bidirectionally. A flexible RF catheter 1400 can be delivered through an introducer needle (e.g., Tuohy needle). The gel 870 in combination with the energy delivery effector 1402 can aid in thermal spread, prevent pleural puncture, and assist in guiding the catheter with rigidity in some embodiments. The RF catheter 1400 can be activated to ablate one, two, or more segments, and the catheter 1400 can then be rotated and deployed in a different direction, e.g., one, two or more segments caudally. In other embodiments, multiple segments can be ablated one at a time, from rostrally to caudally or vice versa.

Levels Targeted.

Figure 9A:
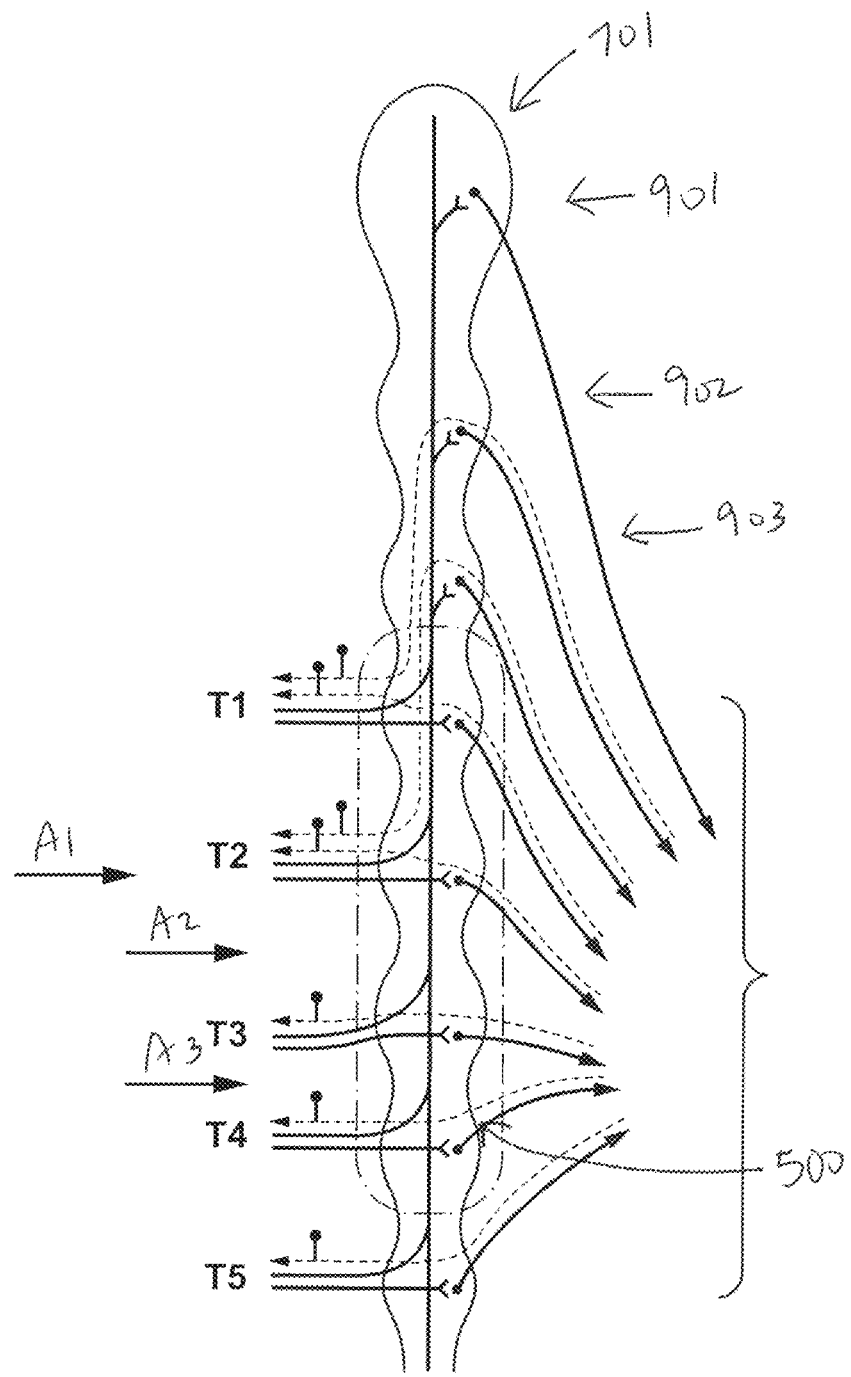
FIGS. 9A and 9B illustrate embodiments of target injection sites into the paravertebral space, focusing on the neural anatomy.
Figure 9B:
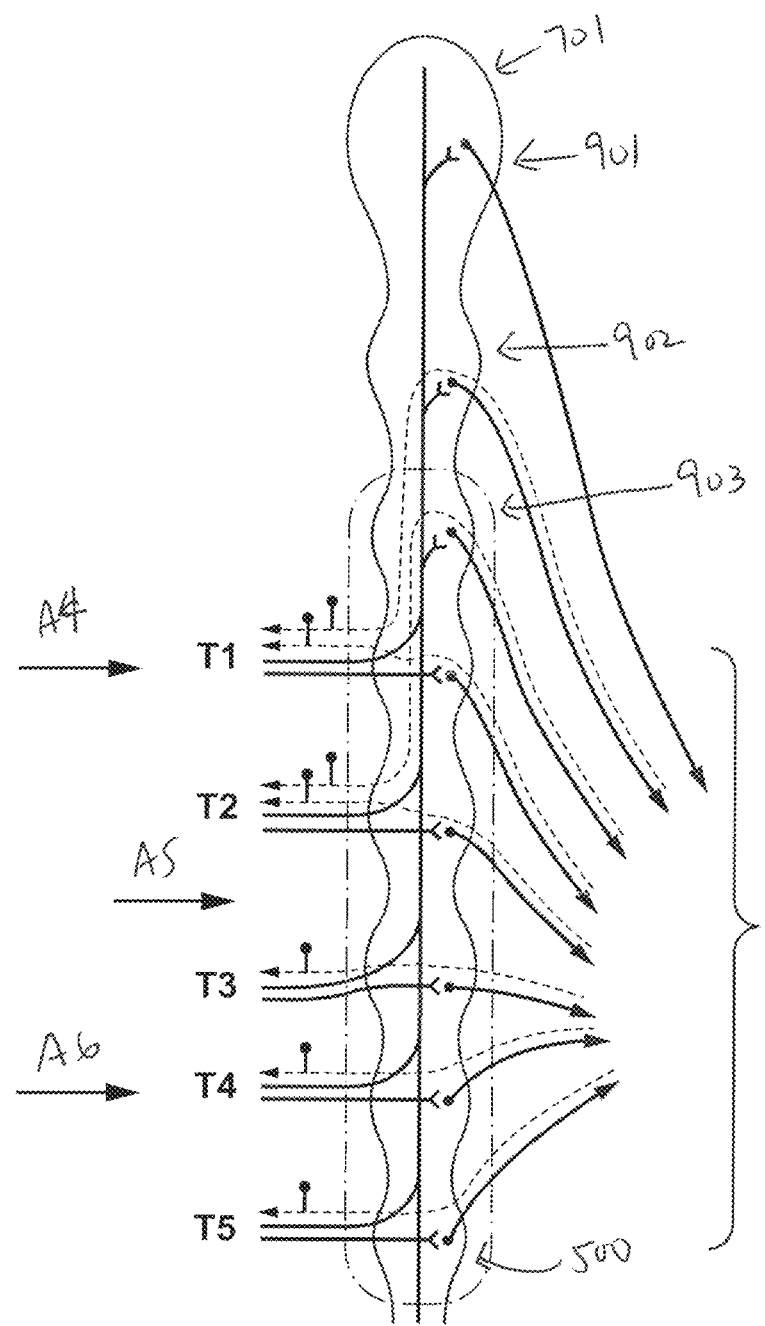

In another embodiment, the needle or catheter delivers agent to multiple dermatomes or cervicothoracic levels. This can be achieved in a contiguous (stellate/T1 to T5, or T2 to T4) or non-contiguous fashion (e.g., injections at T1, T2, T3, T4 and T5 or injections at every other level at T1 and T3 and T5). In one embodiment, the needle is advanced at T2 or T3 levels to deliver the therapy rostrocaudally from T1 to T4/5, in which the delivery of the therapy is discontinued upon the agent reaching T1/R1 (the first rib). In another embodiment, the needle is inserted at T4 and the agent is directed rostrally until it reaches T1 to deliver therapy to T1 to T4. In another embodiment, the needle is inserted at T1 and the agent is directed caudally until it reaches T4 or T5. Generally, the sympathetic ganglia are located in between the ribs while the chain itself (the region between the ganglia) runs over the ribs, although this is not always the case. The first rib (R1) can be used as a guide for injection to T1 or the lower half of the stellate ganglion. Specifically, the upper border, middle, or lower border of R1 can be used as a visual marker of the transition between the T1 and inferior cervical portion of the stellate ganglion. Using the rib as a marker, the therapy can be delivered within the paravertebral gutter to these anatomical targets. In yet another embodiment, two injections are performed at T2 and T4 with 5 to 10 ml of therapy to fill the paravertebral gutter from T1 to T4. If coverage of the entire thoracic paravertebral space desired then preferably three injections of 5-10 ml of the formulation at T3/4, T6/7, and T8/9 can be performed in some embodiments. FIGS. 9A and 9B illustrate schematic examples of neural anatomy and non-limiting treatment locations. In some embodiments, the superior 901, middle 902, and inferior cervical ganglion 903 of the sympathetic chain are spared. This target region of the T1 to T4 (or T5 in FIG. 9B) paravertebral gutter is shown schematically in the region circumscribed by dashed line 500. Various non-limiting examples of injection site(s) are shown by arrows. FIG. 9B schematically illustrates more extensive treatment depending on the desired clinical result by flowing a therapeutic agent, e.g., a neurolytic hydrogel from the inferior stellate ganglion 903 to T5. Various non-limiting examples of injection sites are shown by arrows A4, A5, A6.

Cervical.

The upper, middle, and inferior cervical ganglion may also be targeted with injections of the therapy. The stellate ganglion alone or in combination with other levels is of particular interest in some diseases. For targeting the stellate, the therapy can be delivered in and beyond the paravertebral gutter from a location between R1 and R2 upwards beyond the upper border of R1. Alternatively, by utilizing the various anterior approaches to delivering therapy to the stellate ganglion using the C6 or C7 transverse process as a guide (as is routinely used for performing stellate ganglion blocks (anesthetic) (Abdi et al 2004), the therapy can be delivered to the stellate ganglion alone or the stellate ganglion and down through the paravertebral gutter to other target levels. The transverse process of C6 is identified through palpation of the anterior part of the neck, about 3 cm lateral to midline. The palpating finger maintains transdermal contact with the process while controlling the left carotid artery. With the patient reclining at 20-30° and a standard long beveled 21 G needle 1.5" needle, the needle is advanced to the bone. If desired, a 2 m length of fine-bore connector or manometer tubing permits separation of the needle for the syringe barrel, permitting finer control over the injection. The tubing is prefilled with the injectate to avoid dead space or injection of air. Following negative aspiration to confirm that the needle is not in the vasculature, 10-15 ml of bupivacaine is injected with repeat check aspirations at 3-4 ml. Patient is maintained in the semi-recumbent position for 15 minutes. This approach may be targeted for the treatment of, for example, tinnitus, post-traumatic stress disorder (PTSD), and hot flashes. In one embodiment, PTSD is treated with the delivery of therapy to only the right stellate ganglion.

Lumbar.

If therapy is desired in the lumbar psoas compartment, the therapy can be delivered in the fascial plane within the posterior aspect of the psoas major muscle to the femoral nerve, lateral femoral cutaneous nerve, and the obturator nerve. The transverse process is the primary guidance landmark since one third of the muscle originates from the anterior aspect of the transverse process and two-thirds originates from the anterolateral aspect of the vertebral body. One ml of solution may provide L2, L3, and L4 coverage and higher volumes may result in postsympathectomy neuralgia that beings a couple weeks after the procedure and may last for weeks to years.

Unilateral Vs Bilateral.

In one embodiment, the needle or catheter delivers drug to the target neural tissue unilaterally to target the ipsilateral neural tissue. In another embodiment, the needle or catheter delivers drugs to the target tissue unilaterally in order to deliver the therapy to bilateral neural targets. For example, in one scenario, the agent is delivered on the right side of the body and spreads prevertebrally across to the contralateral paravertebral space to target the sympathetic chain bilaterally at that level. In yet another embodiment, a procedure in which a needle or catheter is directed to two succinct bilateral locations to treat bilateral neural targets is desired.

In one embodiment, a Philips iU22 ultrasound system (Philips Healthcare) with a high-frequency 3D 4D volume linear array transducer (VL13, 13 to 5 MHz) is used. For a paramedian sagittal scan, the ultrasound transducer is positioned over the sagittal scan line at the mid-thoracic level with the orientation marker directed cephalad. For the transverse scan, the ultrasound transducer is rotated 90 degrees to position the orientation marker laterally to obtain images between C7 to T5. On transverse section, the transverse process creates an acoustic shadow anteriorly obscuring the thoracic paravertebral space but the transverse process and pleura are readily visualized. If the injection is performed between 2 adjacent transverse processes away from the acoustic shadow, reflections from the superior costotransverse ligament, the paravertebral space, the parietal pleura, and the lung tissue may be identified. The color Doppler signal of the intercostal artery can also be identified close to the inferior border of the transverse process. In a multi-planar 3-D view, the thoracic paravertebral region is easier to identify in the transverse plane. As needed, measurements of the depth of the transverse process, superior costotransverse ligament, and pleura are taken and an angle correction for needle insertion depth can be estimated.

In another embodiment, a 180 Plus US Machine (Sonosite) with a 10-5 MHz 38 mm broadband linear array transducer (depth between 5 to 7 cm) set in 'General' imaging mode was used for preliminary ultrasound pinpointing followed by needle insertion. As needed, short-axis scanning can be performed with the transducer placed medially and then moved 4 to 5 cm laterally to pinpoint the respective paravertebral areas and vertebral and intervertebral level. The probe can also be rotated to scan the area longitudinally (long-axis). In the short axis view, a 17-G Tuohy needle (Epi Mini Set 17G Polymedic, Tenema) is inserted out of plane immediately down and medial to the ultrasound probe. The Tuohy needle is advanced point by point in increments, aiming at the paravertebral space after feeling the click of the tip of the needle through the superior costotransverse ligament anterior to the muscle. After each advance, 0.2 ml of normal saline can be injected allow for sonographic visualization of the needle tip. Confirmation that the needle is in the paravertebral space can be performed by injecting 1 or 2 ml of saline and sonographically observing the dilation of the paravertebral space. Once the space is identified, the needle is disconnected from the normal saline syringe/barrel and after a negative blood and air aspiration test, the formulation is delivered. As required, the air aspiration test may also serve to remove the saline from the needle lumen in preparation for delivery of the therapy. In an alternative embodiment, a soft-tipped 19-G polyethylene catheter can be inserted 2-3 cm beyond the tip of the needle, the needle removed, and the therapy delivered from the catheter. In yet another embodiment, a slightly oblique ultrasound scan is performed using a curved array transducer to provide visualization of the transverse process, pleura and costotransverse ligament. After an inline approach with an 16 G-18 G Tuohy needle approximately 2 to 3 cm lateral from midline, 10 ml of normal saline is injected to confirm the position of the needle tip by distension of the space under ultrasound prior to delivering the therapy through the same lumen. Color Doppler imaging may be used to help determine the location of the injectate. Under ultrasound guidance, a lateral subcostal approach at the angle of the rib is taken and ultrasound is used to identify the rib, the space between the inner and internal intercostal muscles, and the pleura. Injectate will travel from this location back to the paravertebral gutter where it can ascend or descend several dermatomes.

In one embodiment, the hydrogel is injected beyond the costotransverse ligament. In yet another embodiment, it is injected 1 cm from the pleura.

Lumbar.

Ultrasound guidance can similarly be used to access the lumbar plexus using either the transverse or longitudinal axes. In some embodiments, the ultrasound transducer is placed 4 to 5 cm lateral to the lumbar spinous process at a depth of 11-12 cm, frequency of 4 to 8 MHz to. The transverse process of L3-L4 is identified, and the transducer is directed medially to assume a transverse oblique orientation. The psoas muscle, just deep to the transverse process, can be visualized through the acoustic window between the two adjacent transverse processes. The articular process of the facet joint, the deeper inferior vena cava on the right or aorta on the left, and the intervertebral foramen can be visualized with this approach. The needle is guided to the posterior part of the psoas muscle where the roots of the lumbar plexus are located. Other techniques are detailed, for example, on the web page http://www.nysora.com/techniques/neuraxial-and-perineuraxial-techniques/landmark-based/3282-lumbar-plexus-block.html.

Stellate.

There are several approaches to the stellate ganglion as described, for example, elsewhere herein.

Ultrasound.

In some embodiments, the injections are performed under real-time ultrasound, MRI-, CT- or fluoroscopic guidance with lower rates of complications. In the preferred embodiment, the paravertebral space is accessed under ultrasound guidance. The transcutaneous procedure may be performed through either a transverse or oblique paramedian (OPM) or sagittal approach with either in-plane or out-of-plane needle entry (Krediet et al 2015). High resolution ultrasonography using a high frequency linear array probe (5 to 10 MHz or 8-15 MHz) can improve the efficacy and safety of the procedure. If the thoracic levels targeted are very high because of the trapezius and rhomboid muscles or low because of the erector spinae muscles, a different probe may be selected. The patient can either be placed in a seated, lateral decubitus or prone position. Prior to the procedure, the spinous processes and injection sites can be drawn on the patient. Similarly, the rostral and caudal extent that the therapy will be delivered can be explored with ultrasound prior to the procedure by moving the probe longitudinally. A 17 or 18 gauge Tuohy needle can be desirable for visualization and stability as well as the ability to inject the gel.

Tracking Spread.

In the aforementioned approaches, the rostrocaudal spread of the therapy can be tracked with ultrasound. In one embodiment, the rostral spread of therapy can be followed with the ultrasound probe longitudinally (long-axis). The therapy can be preferably echogenic such that its travel can be tracked. In another embodiment, the ultrasound probe is moved to the furthest edge of the target level. In the treatment of the upper thoracic sympathetic procedures, the ultrasound probe can be placed at T1, the stellate ganglion, or T2, to visualize the most rostral spread of the therapy and discontinue the delivery of the therapy to the paravertebral space. Alternatively, if the therapy is delivered to the paravertebral space from the stellate ganglion/T1, the ultrasound probe can be placed at T4 or T5 to visualize the most caudal spread and then discontinue the injection of the therapy once the target has been reached.

Blank Hydrogel.

In one embodiment, the top boundary of the first rib is first injected with blank hydrogel, approximately 2 to 5 ml, to surround the inferior cervical ganglion or upper half of the inferior cervical ganglion and provide a physical barrier to the spread of neuromodulatory agent or neuromodulatory-agent loaded hydrogel, to the inferior cervical ganglion and the numerous other structures in the lower cervical region. This may be performed as a separate procedure or it may be performed contiguous with the administration of the neuromodulatory agent-loaded hydrogel. In one embodiment, the device that delivers the therapy has a valve at the distal end of the barrel, proximal to the needle that permits blank hydrogel to be delivered first followed by neurolytic agent-loaded hydrogel second. In another embodiment, the Tuohy needle is divided into two channels inside the needle with two non-contacting circular side ports on either side of the needle. In this embodiment, one exit port may be through the needle bevel and the other a side port on the opposite of the needle from the bevel. Alternatively, the needle may now permit exit of the therapy from the bevel, but from two ports on either side of the needle, each connected with the internal channels, to permit flow of blank hydrogel rostrally and neurolytic-agent loaded hydrogel caudally either serially (blank first) or together. Alternatively, an atraumatic blunt catheter can be advanced approximately 1 cm from the Tuohy needle to deliver the therapy from a side port or a two-channel catheter can be advanced approximately 1 cm from the Tuohy needle to deliver a blank hydrogel in one direction and the neurolytic agent-loaded hydrogel in the opposite direction. Alternatively, a catheter can be inserted to the paravertebral space over the trip of the needle and advanced by 1 cm before the needle is removed. In still other embodiments, a balloon or curtain or other device can be expanded from a delivery port on the needle to prevent backflow of gel to non-target levels. Alternatively, a catheter with a soft atraumatic tip that has a steering handle and locking mechanism can be advanced to preferentially deliver the therapy rostrally or caudally by preferentially directing the tip of the device rostrally or caudally. The aforementioned devices may contain another port to allow for delivery of additional anesthesia as necessary without having to move the device.

Protection from Pleural Puncture.

The Tuohy needle bevel can be shortened as desired to render the tip less traumatic. In some embodiments, the gel is delivered directly from the Tuohy needle. In other embodiments the gel is delivered from a catheter that is extended between 1 and 2 cm from the tip of the Tuohy needle. This provides a mechanism to direct the flow of the therapy rostrally or caudally through the use of an atraumatic steerable tip. Preferably the tip is visible under ultrasound, particularly as it is advanced away from the acoustic shadow.

Ports for Delivering Therapy.

Thermosensitive, shear-thinning, or other hydrogels can be injected through a single lumen or port, or multiple lumens. Cross-linked hydrogels, which typically contain two or more components, can be mixed in various settings including 1) out of the patient (pre-mixing), prior to delivery, 2) within the delivery device but still outside of the patient, 3) within the delivery device, within the patient, and 4) at the distal tip of the delivery device, inside the patient. In the case of the mixing being required near the tip of the catheter, a multi lumen catheter with a transition zone that permits turbulent flow might allow for more flexibility to mix the agent more proximally to where it is injected in some embodiments. The transition time from a solution to a gel can be controlled by relative mixing the agents and their relative proportions. In one embodiment, the extent of the caudal spread is determined by what levels the gel travels to relative to the T1 ganglia and the $1^{st}$ rib. In another embodiment, the agent spreads down from the R1 rib/thoracic ganglia to the R4 or R5 (rib) level. In another embodiment a balloon is inflated of a compliant sheet of material is deployed to prevent spread in the opposite direction from the needle tip.

Identifying the Correct Anatomical Location.

The desired spread of the neuromodulatory agent can in some embodiments be in a longitudinal spreading pattern instead of intercostal (IC), cloud-like (CL) spread or a combination thereof. In one embodiment, the spreading pattern of the neuromodulatory agent or neuromodulatory agent/gel can be better controlled by placing the needle with the guidance of a nerve stimulator, in the more ventral part of the thoracic paravertebral space, anterior to the endothoracic fascia, to achieve multi-segmental longitudinal spread. This helps to prevent non-target spread and also reduces the volume of neuromodulatory agent that needs to be delivered to achieve spread to the target levels of the sympathetic chain. The thin endothoracic fascia is the deep investing fascia of the thorax and attaches to the ribs and medially to the mid-point of the vertebral body, dividing the paravertebral space into an anterior and posterior compartment. Clinical studies have demonstrated that, using a dorsal paravertebral approach, the needle initially enters the dorsal part of the TPGS which results in muscle contractions at 2.5 mA and then, as the needle position is advanced to the ventral portion of the TPGS in close proximity to the nerve, an appropriate muscle response of 0.5 mA is observed.

In one embodiment, a single puncture is performed at the desired level (between T2 and T8) region using a nerve stimulator guided technique. At the T3 location, the costotransverse ligament is punctured using a 21 gauge unipolar insulated needle with a conductive atraumatic short beveled tip (10 cm long, Stimuplex, B. Braun) and a nerve stimulator (initial stimulating current at 2.5 mA, 1 Hz, 9V) is advanced until an appropriate intercostal (upper thoracic) or abdominal muscle (lower thoracic) response is visualized. The needle is then further advanced anteriorly until the appropriate muscle response can be achieved with stimulation at a current less than 0.5 mA or less (1 Hz, 9 V) and the injection is performed at this location. In this embodiment, the needle tip is close to but not in the sympathetic chain. Approximately one to 15 ml of the neuromodulatory formulation, such as one to 10 ml of neuromodulatory are delivered and can spread approximately one to 6 levels longitudinally, or more preferably one to 4 or 5 levels.

Methods related to the use of robotics for both the diagnostic and therapeutic, or combined modalities, are also described. Robotic systems can be used to deliver the therapy stereotactically to the paravertebral gutter and then integrated diagnostic electrodes can be used to monitor the neural response to therapy whether through a percutaneous or endovascular approach. These robotic systems may provide advanced needle/catheter control including force sensing, temperature sensing, rotation, advancing and withdrawal, and tip curve control, balloon expansion. For example, the Stereotaxis system (Niobe Magnetic Navigation System) which has been used to treat hypertension via renal denervation might also be useful for this application. The system can include an irrigated magnetic catheter and an advanced electroanatomic mapping system allowing for advanced mapping and navigation allowing for less contrast and radiation. Alternatively, a robotically controlled steerable catheter like the one developed by Hansen Medical (Magellan or Sensei Robotic control systems) could be used to facilitate accurate navigation and delivery of the different ablative modalities (RF, Cryotherapy, neuromodulatory agents, etc.) to the paravertebral gutter. In another embodiment, a percutaneous needle arm with a subcutaneous electrode placed and held in the paraspinal musculature to record the sympathetic activities prior to, during, and after therapy without concern for procedural needle or catheter inadvertently moving during the procedure due to operator error, such as with the Intuitive Da Vinci. In another embodiment entry into the appropriate location within the paravertebral gutter can be conveyed with a signal on the handpiece, such as a green In another embodiment, integrated ultrasound guidance system provides feedback on the needle tip location (e.g. shown in red superimposed on ultrasound image) as well as the trajectory of the needled tip (dotted green line, a projection of path going forward). In some embodiments, the robotic arm can include a needle attachment for a posterior approach to the spine allowing the use of more sensitive and quantitative force-sensing at the catheter tip or tool tip and or direct visualization with miniature cameras to assure that vessels are not damaged In another embodiment, a subcutaneous electrode placed in the paraspinal musculature records the sympathetic activities prior to, during, and after therapy. In another embodiment entry into the appropriate location within the paravertebral gutter can be conveyed with a signal on the handpiece, such as a green In another embodiment, the ultrasound guidance system provides feedback on the needle tip location (e.g. shown in red superimposed on ultrasound image) as well as the trajectory of the needled tip (dotted green line, a projection of path going forward). In another embodiment, this procedure can be performed with an robotic arm, such as the Intuitive Da Vinci with a needle attachment for a posterior approach to the spine allowing the use of more sensitive and quantitative force-sensing at the catheter tip or tool tip and or direct visualization with miniature cameras to assure that vessels are not damaged Monitoring Sympathetic Tone During and after the Procedure.

Classical methods to determine the effectiveness of sympathetic block are to measure changes in skin temperature, heart rate, and/or heart rate variability. Microneurography may also be used to measure changes in peripheral sympathetic nerve activity, for example in muscle. At the stellate level, the most common sign of the effectiveness of the block is Horner's syndrome (unilateral miosis, ptosis, and anhidrosis), however, since the fibers to the head and neck to not supply the thorax, the presence of Horner's syndrome is not indicative of cardiopulmonary block or denervation. As a result, there is a need for more specific methods to monitor cardiac or pulmonary sympathetic tone to determine the efficacy of a neuromodulatory therapy intraprocedurally. Moreover, the ability to deliver the neuromodulatory therapy at one level within the paravertebral gutter and be able to confirm successful delivery of the therapy to another level of the paravertebral gutter through the modulation of sympathetic nerve activity at another level can be desirable. In another embodiment, fusion imaging, with real-time 3-dimensional visualization and navigation tools can be utilized to guide the procedure. By using the spinous processes to register the ultrasound images with a 3-D reconstruction of 2-D CT or MRI images, structures that could otherwise not be seen with ultrasound are revealed.

Subcutaneous monitoring can provide a convenient and minimally invasive approach to monitoring sympathetic ganglia nerve firing. In one embodiment, such as when a transcutaneous approach to delivering the therapy will be undertaken, electrodes are placed subcutaneously to monitor the subcutaneous sympathetic nerve activity at the level (dermatome) that is directly innervated by the sympathetic nerves to which the therapy is administered. Alternately, the subcutaneous nerves arising from an adjacent or more distal level from where the therapy is administered, can be monitored. Specifically, two pairs of bipolar electrodes are placed at an interelectrode distance of 4 cm in the subcutaneous tissue superficial to the third intercostal space. Ipsilateral subcutaneous sympathetic nerve activity in the upper thorax arises from the dorsal cutaneous branch which supplies fibers to the ramus cutaneous lateralis and a deeper branch to the paraspinal muscles. In particular, Robinson et al (2015) have demonstrated in dogs that the paraspinal subcutaneous sympathetic nerve firing patterns correlate well with the activity of the cardiac visceral sympathetic nerve firing patterns. With the appropriate signal filtration and processing, as described in Robinson et al (2015), recordings of subcutaneous sympathetic nerve activity (SCNA) (that correlate with cardiac (stellate) sympathetic nerve activity (SGNA)) are made.

In some embodiments, the spontaneous sympathetic nerve activity can be recorded subcutaneously at baseline prior to the delivery of the therapy, during the therapy and after the therapy. In one further embodiment, successful paravertebral spread of the hydrogel up to the T1 (stellate ganglia) after the injection of material into the paravertebral gutter between the third and fourth ribs can be confirmed by monitoring the subcutaneous sympathetic nerves in the dermatome supplied by the stellate/T1 ganglion. In other embodiments, it can be recorded continuously, as described in 2006/0004413, which is hereby incorporated herein by reference in its entirety. If the spontaneous activity is not enough, the patient can receive an IV injection of a neurostimulatory agent, such as adenosine or apamin for example. Successful neurolytic ablation of the stellate ganglion would then eliminate or reduce the activity triggered by the administration of the neurostimulatory agent.

Alternatively, an electrode catheter or electrode needle (Stimuplex Ultra, Braun) can be placed in the paravertebral gutter and the sympathetic ganglion can be stimulated and or locally during the procedure. In one embodiment, the catheter or needle delivering the therapy can stimulate and or record the sympathetic nerve activity. Alternatively, the sympathetic nerve activity of a distal ganglion can be recorded with an electrode placed percutaneously in the paravertebral gutter, such an electrode placed at the lower border of the $1^{st}$ rib to measure the T1 (stellate) ganglion activity. This provides additional confirmation beyond ultrasound that the appropriate spread of the neuromodulatory agent in a hydrogel has occurred from the level from which it was injected to reach the distal and furthest target that the therapy is targeted, in this example, T1. In yet another embodiment, cervical sympathetic activity can be monitored through a subcutaneous and or direct paravertebral approach to confirm the absence of a change in sympathetic activity in non-target cervical level or lower thoracic levels, for example.

As with transcutaneous approaches to monitoring procedural efficacy, endovascular monitoring approaches are also desired. When the therapy will be administered through an endovascular, particularly intravenous approach, a variety of diagnostic and stimulatory electrophysiology catheters can be employed at various locations within the vasculature to assess the effectiveness of the therapy and the appropriate spread of the agent to the desired targets within the paravertebral gutter. In one embodiment, an endovascular catheter with a stimulating electrode is placed substantially adjacent to the sympathetic chain, such as in an intercostal artery or vein, the azygous vein (or hemiazygous/accessory hemiazygous), the subclavian artery, or the costocervical trunk. The electrodes in this embodiment can in some cases be preferably located on the same catheter that is delivering the therapy transvascularly to the paravertebral gutter. The diagnostic electrodes can be used to locate the sympathetic chain, such as where the vessel crosses the sympathetic chain (e.g. superior intercostal vein) or where the vessel is in close proximity to the sympathetic chain (subclavian artery, one of the azygous or intercostal veins). After determining the chain location or the direction of the chain, the catheter can deliver the therapy to the paravertebral gutter in and around the sympathetic chain. In this manner, the sympathetic chain allows identification of the paravertebral gutter. Alternatively, the diagnostic electrodes can be used to record the spontaneous firing of the sympathetic chain discretely or continuously during the procedure to confirm the effectiveness of the therapy at that level. Other embodiments permit diagnostic catheter monitoring of adjacent levels to confirm the spread of the therapy rostrally or caudally. In one embodiment, the therapy is delivered from the superior intercostal artery into the paravertebral gutter and a diagnostic catheter is placed in the $4^{th}$ intercostal vein to record the activity of the sympathetic ganglia/chain there.

Alternatively or in addition to the above, diagnostic EP catheters can be placed endovascularly to monitor the activity of the post-ganglionic sympathetic fibers as they course to the heart and lungs and great vessels. For example, diagnostic electrophysiology catheters can be placed in the coronary sinus, the high right atrium, the subclavian artery or the right ventricular apex, to monitor cardiac sympathetic nerve activity. Diagnostic catheters can be placed in the pulmonary arteries, pulmonary trunk and bifurcation, lower curvature of the aortic arch, or the aorta to measure cardiopulmonary sympathetic activity. Diagnostic catheters can be placed in the bronchial and pulmonary vessels as they enter the lung hilum to monitor pulmonary sympathetic activity. In these endovascular embodiments, the parasympathetic and somatic nerve activity may also be monitored, particularly since the vagus and the fibers coming off of the vagus often travel with the sympathetic nerves. In one example, left cardiac sympathetic nerve firing can be recorded in the left subclavian artery by locating the electrodes substantially adjacent to the ansae subclaviae (AS). By rotating, advancing, or withdrawing the catheter in the subclavian artery the AS site can be identified by measuring a change in arterial pressure increase, as described in Zarse et al 2005. Once located, the catheter can be stabilized in this location to provide ongoing measurement of sympathetic nerve activity and or to provide local transvascular stimulation of these nerves, as needed.

In order to assess the cardiopulmonary response to the therapy, hemodynamic measurements using a Swan-Ganz catheter to record pulmonary artery pressure and determine cardiac output, heart rate, total peripheral resistance, sinus rate and sinus cycle length, and rates of LV systolic pressure increase can be made. Electrophysiologic measurements including RR, PR, QRS-QT, QTc intervals can be measured as well as local conduction velocity, as detailed in (Zarse et al 2005). These measurements can made at baseline, pre-procedurally, and post-procedurally to assess changes in cardiopulmonary sympathetic nerve activity. In this manner, the successful delivery of the therapy to the paravertebral gutter can be assessed.

Guidewires with electromechanical sensing tips may be suitable devices for monitoring the activity of the cardiopulmonary sympathetic nerves at the aforementioned locations and assessing the success of the procedure as described in U.S. Pub. Nos. 2016/0029960 and 2015/0224326, which are hereby incorporated herein by reference in their entireties.

Another approach, particularly for the development of devices to treat cardiac arrhythmias, the therapy can be performed in conjunction with a diagnostic EP study, as known in the art. During the these studies, electrodes are placed in the high right atrium near the sinus node, the area of the His bundle, the coronary sinus that lies in the posterior atrioventricular groove and near the left atrium and ventricle and in the right ventricle. Carotid sinus massage and pharmacologic administration of sympathetic and parasympathetic agonists and antagonists (infusions of atropine, isoproterenol, epinephrine, beta blockers) can be used to monitor changes in autonomic balance between the sympathetic and parasympathetic systems before, during, and after the procedure. Also, programmed electrical stimulation, targeted at the sinus node, AV node, His-Purkinje system and ventricular myocardium can also be used to assess autonomic function. These procedures may also be used to guide the additional administration of the therapy to adjacent levels. In one embodiment, cardiac sympathetic innervation is not significantly reduced after delivery of the therapy to, for example, to the paravertebral gutter from the bottom of the first rib to the bottom of the $5^{th}$ rib. In this embodiment, assuming successful procedural placement of the neuromodulatory hydrogel, additional neuromodulatory hydrogel may additionally be delivered to the upper half of the stellate ganglion, specifically the inferior cervical ganglion, such as through an anterior percutaneous image-guided procedure targeting C6/C7.

Repeat Procedures.

As necessary, the agent or therapy may be delivered on successive treatment days. In one embodiment, an anesthetic is delivered to a target site(s) to confirm safety and/or efficacy and the non-reversible therapy is then delivered on the same day or within 30-days of the trial anesthetic procedure. In another embodiment, the therapy is delivered at regular intervals in order to maximize efficacy. For example, the therapy can be delivered at 0, 30, and 60 days at the same levels or adjacent levels.

Combination Therapy.

The therapy may be delivered in combination with acute or chronic drug therapy, any other therapeutic denervation therapy such as renal denervation, adrenal denervation, pulmonary trunk or bifurcation denervation, pulmonary artery denervation, carotid body denervation, baroreceptor denervation, and tracheal or bronchial denervation, coronary artery bypass graft, atrial or ventricular arrhythmia ablation, or procedures to produce complimentary or synergistic effects in the treatment of chronic diseases, particularly since there are many comorbidities associated with these diseases.

Direct needle injection into the sympathetic chain/ganglia. Direct injection into nerves is often avoided in some embodiments because of concerns of damage to the nerves. However, in some embodiments, targeted delivery of a neuroablative agent within the sympathetic chain and ganglia itself is possible. In one embodiment, a needle enters the sympathetic chain either directly or indirectly and a volume, e.g., 5 ml of the therapy mixed with contrast agent is injected into the chain itself. The agent may travel within the sympathetic chain and the epineural sheath itself rostral and caudal to the injection site. There are examples of diffusion of 15 and 30 ml of dye within the tibial nerve between approximately 14 and 17 cm, respectively.

Endovascular Approaches.

With any of these approaches, in some embodiments the goal of administering therapy is to disrupt the internal and/or external reflex arcs within the lung, heart and the surrounding vessels to achieve a beneficial therapeutic effect. This can be achieved by disrupting nerve fibers that innervate an anatomical target, such as the lung directly or that innervate targets that also indirectly modulate cardiopulmonary function such as the nerves that afferent/efferent nerves that innervate the carotid sinus and baroreceptors or carotid body, aortic arch baroreceptors, pulmonary trunk and pulmonary artery baroreceptors, pulmonary and bronchial artery innervation.

Unilateral vs Bilateral. The therapy can be delivered either from an endovascular approach or a percutaneous approach aimed at gaining access to the region containing the targeted neural structures. In one embodiment the therapy is delivered unilaterally to either the right or left paravertebral gutter. In another embodiment, the therapy is delivered bilaterally, to both the right and left paravertebral gutter. In another embodiment the therapy is delivered to the anterior or posterior rami unilaterally or bilaterally. In these instances, one, two, or more spinal levels or dermatomes are treated. In some embodiments, the target region for neuromodulation is the nerves contained within and crossing through the thoracic paravertebral space (TPVS) on their way directly or indirectly to the heart, lungs, aorta, esophagus or other organs or vessels.

The targeted neural structures may be coursing through a potential space (TPGS) or coursing over or along a vessel. The sympathetic chain, for instance, travels largely parallel to the azygous/hemiazygous veins until it reaches upper four levels of the sympathetic chain. On the right side, the second, third and fourth posterior intercostal veins gather medially to form the superior intercostal vein which connects to the azygous vein on the right side. On the left side, these veins connect to the hemiazygous or accessory hemiazygous vein. For the most part, the sympathetic chain crosses anteriorly to these vessels.

Anatomic Landmarks on Fluoroscopy.

Figure 10A:
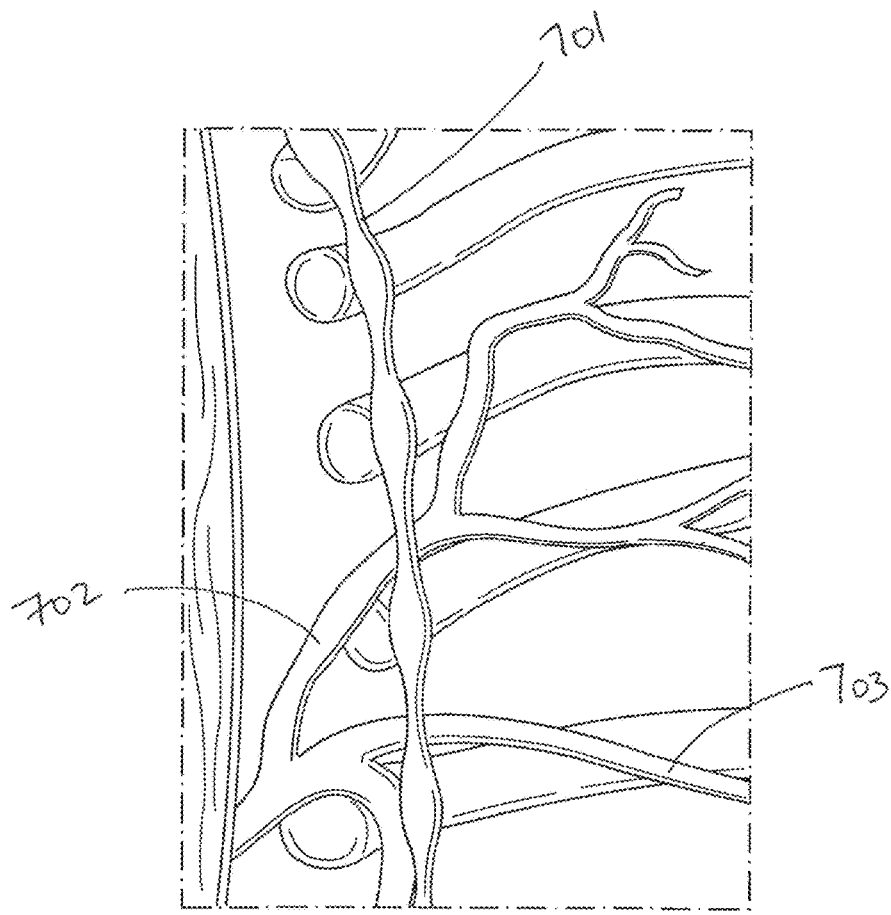
FIG. 10A illustrates one embodiment of possible selected upper thoracic anatomy.
Figure 10B:
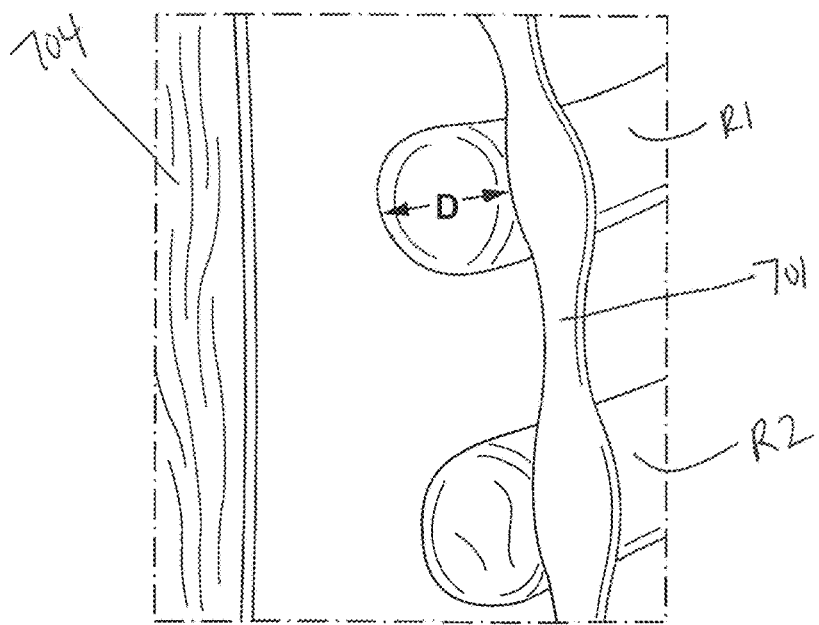
FIG. 10B illustrates some embodiments of distances from the medial margin of rib head to the medial margin of sympathetic chain.

The head of the ribs can be used as a guide for the location of the sympathetic chain and thus the paravertebral gutter under fluoroscopy. FIG. 10A illustrates one embodiment of possible selected upper thoracic anatomy, including thoracic ribs R1, R2, R3, R4, R5, and the sympathetic chain 701 coursing anterior to the ribs. Also illustrated is the superior intercostal vein 702 which can course under the sympathetic chain 701 and other intercostal veins, e.g., 703. For example, T1, T2, and T3 are approximately 4, 6, and 6.4 mm from the medial margin of the rib head. Using this as a guide, the delivery of the therapy into the paravertebral gutter can be straightforward. However, given the variability in the vein sizes at the upper thoracic levels as well as between the right and the left side, as well as the variability in the first 4 levels of the sympathetic chain 701, the device design can in some embodiments be versatile and flexible for different sized vessels and can permit the delivery if the vein 702 is running parallel to or across the paravertebral gutter. There is a unique relationship that exists between the ribs R and the sympathetic chain 701, as illustrated in FIG. 10B. In some embodiments, the location of the sympathetic chain 701 can be utilized as a marker for the paravertebral gutter, because: (1) The ribs R are in a known location under fluoro; (2) the sympathetic chain 701 very predictably travels in parallel to the spine effectively orthogonally to the ribs R; (3) the sympathetic chain 701 is by definition in the paravertebral gutter; and (4) if the distance of the sympathetic chain 701 from the gutter is known, one can likely successfully inject within the paravertebral gutter. The tables below include some embodiments of distances from the medial margin of rib head to the medial margin of sympathetic chain shown as distance D in FIG. 10B (mean±SD).

TABLE 3

Distance from medial margin of rib head to the medial margin of sympathetic chain (mean ± SD) (Lee et al 2011)

| Level of vertebrae | Right side | Left side |
|---|---|---|
| T1 | 4.1 ± 0.8 | 4.4 ± 1.1 |
| T2 | 6.1 ± 1.3 | 5.7 ± 1.1 |
| T3 | 6.6 ± 1.1 | 6.1 ± 1.1 |
| Width of sympathetic chain ± | | |
| T1 | 5.7 ± 1.6 | 6.6 ± 1.7 |
| T2 | 4.1 ± 1.0 | 4.2 ± 0.7 |
| T3 | 3.0 ± 1.2 | 3.4 ± 0.7 |

In this way, one can be freed from trying to understand the particulars of the venous anatomy relative to the chain or the gutter and can focus on the relationship between the rib and the catheter. This can be effective, for example, as a particular solution for R2, R3, and R4 and further rostral. It may or may not be as effective for R1, as the vessel may be running parallel to chain).

Some embodiments can include the following steps: (1) insert the catheter at (R2, R3, R4) intercostal or superior intercostal vein; (2) the fiducials are located at a fixed distance relative to one another, and one is directly aligned with where the needle exits. For example, one fiducial is at tip and the other fiducial is at the level where the needle is injected and then another fiducial on the catheter (back towards handle) is 7.5 mm.

In some embodiments, a fiducial can be in a shape such that it is clear which way it is facing. When, for example, an L shaped fiducial is in the correct location, it can be read under fluoro, when it is in the incorrect location it looks like an upside down L. Other shapes can be used. This can assure that the needle is pointing ventrally.

Bone. Either transcutaneous or endovascular. In one embodiment, a safety device can be designed so that the therapy cannot be injected unless it is in contact with bone. In this way, the catheter tip, or the blunt needle tip are advanced and there is a mechanical probe on the tip that makes contact with the bone. When the probe tip is appropriately pushed, an internal valve inside the lumen of the catheter/needle is pushed such that the lumen lines up with the opening on the side of the catheter. In one embodiment, the opening is directed rostrally, in another embodiment it is directed caudally. In yet another embodiment, it is directed laterally. In another embodiment, communication from two channels is lined up with two openings on either side of the catheter when the probe is appropriately pushed. In one embodiment, the mechanism of actuation is spring-loaded, in another embodiment it is a button that requires less force to actuate. In another embodiment, the sensor is an impedance sensor, detecting a difference in impedance between the bone and non-bone. In another embodiment, the sensor delivers an electrical signal and measures the threshold for stimulation before this is translated into a mechanical opening. By offsetting the opening off of the tip of the catheter, delivery of the therapy is assured within the paravertebral gutter. When the probe tip is not engaged or activated, the valve or opening to deliver the agent is closed (safety valve) and it acts as a safety mechanism to prevent injection of neurolytic agent in the wrong location. In one embodiment, the device itself has a closed loop system to stimulate and record the electrical or electromyographic signals (nerve, muscle, respectively), first to confirm the correct location and then, during and after the procedure to confirm that the therapy was delivered.

Endovascular. In one embodiment, the intercostal vein or superior (supreme) intercostal vein are pushed up against the inferior edge of the rib and the agent injected here in and around the rib head.

Transcutaneous/Percutaenous. In one embodiment, the catheter or needle makes contact with the vertebral body and agent is injected from here into the paravertebral gutter.

In some embodiments, the paravertebral space can be accessed on the venous side through an endovascular access approach via a suitable vein such as the femoral vein, a subclavian vein, or internal jugular vein on the right or left side. Therapy can be delivered, for example, from a proximal location within the internal jugular, the supreme/superior intercostal vein, the azygos vein, intercostal vein(s), azygous arch, the venous communication between the hemiazygous and azygos veins, the hemiazygous vein, the accessory hemiazygous vein, or the vena cava. The paravertebral space can be accessed on the arterial side through an endovascular access approach via a suitable artery such as the femoral artery, subclavian artery, brachial artery or radial artery. The therapy can then be delivered from the aorta, the aortic arch, the pulmonary arteries, the bronchial arteries, the subclavian artery, the costocervical trunk and/or the intercostal arteries. The following description describes some embodiments of different access routes in more detail. Vascular access may be preferred in some embodiments over paravertebral access as it may provide a more straightforward and safe method to deliver the therapy into the anterior paravertebral gutter.

Venous Access.

Right Side.

From a femoral vein, a catheter can be inserted up the inferior vena cava to the superior vena cava from where it can travel across the arch of the azygos vein to access the right thoracic paravertebral space.

On the right side, the second, third, and fourth intercostal veins drain into the azygos vein located on the medial side of the fourth or fifth rib head. A large intercostal vein is present in approximately 40% at the third and 70% at the fourth intercostal space (Haam) but the majority of the veins at the third intercostal space are medium or small. The majority of these veins take a posterior pathway relative to the sympathetic chain but between 15-28% take a more anterior course. These intercostal veins course through the paravertebral gutter; either the sympathetic chain or the distance from the azygous vein or bony landmarks (vertebral body, rib head) can be used as landmarks to determine the site of administration of therapy to assure delivery into the paravertebral space.

At T4/T5 and below, the azygous vein runs more or less parallel to the sympathetic chain. At these mid- to lower-thoracic levels, the therapy can then be delivered directly from the azygous vein itself towards the paravertebral space containing the sympathetic chain and rami. Although the azygous vein is just outside of the paravertebral gutter, by utilizing the ease of movement of the vessel within the fascia surrounding the vein, the catheter can assume a biased configuration against the left/lateral wall of the azygous vein to approximate the paravertebral space. The catheter can then advance a needle at a 0 to 90 degree angle into the space, more preferably a 30 or 45 degree angle to deliver the therapy into the paravertebral space. In one embodiment, the needle is inserted posteriorly, posteriolaterally, or laterally to avoid inadvertent pleural puncture. The two key structures to avoid are the pleura and the intervertebral foramen. If the injections are lateral, the likelihood of delivering agent into the intervertebral foramen is low. Fiducials can be placed on the catheter and the handle to make sure that the orientation of the needle and catheter is correct. Furthermore, by utilizing a needle with a curved trajectory, it is possible to 'catch' the thin wall of the vein and advance a needle across it. Alternatively, an expandable highly compliant conformable balloon can be expanded within the space causing a balloon to unfurl and deliver a needle through the vascular wall such as the Mercator Bullfrog catheter as described in U.S. Pat. No. 8,708,995, which is hereby incorporated by reference in its entirety. Alternatively, devices developed for injecting cells into cardiac tissue can be adapted for delivery of the therapy to the paravertebral gutter, including the Transvascular TransAccess Delivery System, Stiletto, Myostar, and Myocath devices, C-Cath devices. In one embodiment, the catheter can be advanced and pressed against the bone of the rib or the vertebral body, so the therapy can be injected safely without concern for the pleura. Contrast agent can be administered to ensure correct delivery into the anterior paravertebral space as well as the appropriate rostrocaudal spread. In addition, because a relative large volume is being injected through a needle (e.g. 5-10 ml) as opposed to 0.1-1 cc of fluid, the device may need to be secure so that the needle does not inadvertently slip back into the vasculature and inject gel into the bloodstream and/or tear the vein. In some embodiments, the systems and methods can include an indicia of needle trajectory on or operably connected to the delivery device, such as described for example in U.S. Pat. No. 6,746,464 to Makower, hereby incorporated by reference in its entirety.

Alternatively, the catheter can be advanced and inserted from the azygous vein into the superior intercostal vein. (In some instances, the supreme intercostal vein is accessed off of the right brachiocephalic vein (right innominate vein) or subclavian in which case a subclavian vein access approach may be selected.) At this right R1 level, the sympathetic trunk is immediately adjacent to the supreme intercostal vein to the first rib, as verified under fluoroscopy. The catheter can be configured to bias medially along the rib to deliver the agent into the paravertebral gutter and the needle can be advanced in the posteromedial direction to deliver the agent safely into the anterior paravertebral gutter. In this approach the curved needle enters and then directs the flow of drug caudally, delivering the therapy from T1 down to T4 or T5. Thus the therapy is delivered from the supreme intercostal vein will flow to multiple paravertebral levels. Typically a volume of 5 to 10 ml of agent will be delivered. In some instances, lateral deflection of the supreme intercostal vein will be required to access the paravertebral gutter. This can be accomplished via a steerable catheter and/or guidewire in some embodiments.

In another embodiment, multiple overlapping injections are made with smaller volumes of agent to the paravertebral space. In this approach, a smaller volume is delivered at the $1^{st}$ rib (between 2 to 5 ml) from the supreme intercostal artery and then the catheter is advanced until it is adjacent to the $2^{nd}$, $3^{rd}$, and $4^{th}$ rib (R2, R3, R4) either off of the supreme intercostal artery or from second through the third (or fourth) intercostal veins. If additional levels need to be treated, the catheter can then be returned to the azygous and advanced directly to each of the fourth, fifth, and/or sixth intercostal veins. (The fourth intercostal vein may come off either the superior intercostal vein or the azygos vein in some cases) In one embodiment, therapy is delivered at each of the desired intercostal levels on each side, using the ribs as a visual guide. The use of a contrast-loaded gel can guide the physician how far apart to make the injections and what volume to deliver.

In yet another embodiment, the catheter can be directed within the venous system to deliver therapy from one location to multiple adjacent levels: in which the location is the 1) the azygos vein, preferably at the level of the third or fourth rib, 2) the second intercostal vein, 3) the third intercostal vein, 4) the fourth intercostal vein, or the 5) fifth intercostal vein and an injectable neuromodulation agent can be delivered to reach multiple contiguous thoracic levels through the continuity provided by the paravertebral space. The agent or therapy can then be delivered rostrocaudally, rostrally, or caudally to multiple levels to ablate the nerves in the paravertebral gutter. In some embodiments, the agent can travel around the vertebra to reach the both paravertebral spaces. If therapy is delivered from the azygous vein directly, it can be preferable in some embodiments to deliver therapy between the branches of the intercostal arteries towards the sympathetic chain. If the therapy is delivered from the intercostal vessels, in some embodiments the therapy is injected as the catheter is biased toward the intercostal vessel branch, and a needle extended from the tip of the catheter into and through the venous wall. In some embodiments, the needle is a curved needle so that it can 'catch' the venous tissue on its trajectory.

In another embodiment the device includes a catheter with a steerable and/or curvable needle that can be advanced directly out of the tip of the catheter to catch the rostral venous wall as the intercostal vein arches off of the parent vessel. The needle punctures the vessel at the rostral side of the vein so that neither the sympathetic chain or the pleura are punctured. The needle can have a preset curve (e.g., made of nitinol or another shape memory material) or can be deflectable through an angular range (e.g., via one or more pullwires connected proximally to a control that can be actuated by an operator).

The therapy can also be directed towards the fibers that and run across on either side of the azygous vein on their way to the pulmonary hilum. In this manner, fibers traveling from the cervical and thoracic chain that travel across or around the azygos vein on the right side can be targeted. In some cases, the azygous curves over and grooves the right lung before entering the superior vena cava just before it enters the heart and is known as the azygous lobe of the lung or the azygous arch. In one embodiment, therapy is directed from the curve of the azygous towards the nerves that cross the azygous or that are in proximity to the azygous that directly innervate the lung, such as the anterior and/or posterior pulmonary plexi or nerves that innervate the heart, such as the superficial and deep cardiac plexus. Unlike other therapies directed at denervation, circumferential ablation of these vessels may not be necessary because the fibers to the heart and lung are crossing over the vessel as opposed to coursing along it. In some embodiments, two linear ablation RF lines are made on either side of the azygous to achieve sympathetic denervation of the heart and lung.

Left side. For left sided therapy, in some embodiments, the catheter is introduced into the femoral vein and advanced up the inferior vena cava to the right and left ascending lumbar veins and on to the right azygos vein and the left hemiazygos vein, respectively. The left hemiazygos vein typically communicates directly with the accessory hemiazygos vein and so catheter access can be gained directly into the accessory hemiazygos system. In the absence of continuity, the accessory hemiazygous may be accessed directly off of the azygous vein. Therapy can be delivered from the accessory hemiazygos vein or hemiazygos vein directly to the targeted paravertebral space(s), particularly in the mid- to lower-thoracic levels, as described above. For the lower thoracic levels, the catheter can be advanced into the left-sided intercostal veins and therapy delivered to the paravertebral space from there. The intercostal vessels on the left side are considerably smaller than the left above T5. For example, at the third and fourth intercostal space, over 80 percent of intercostal veins are smaller vessels with only 10-15% medium and 2-5% large. The majority of these vessels, including the superior intercostal vein, take a posterior path relative the sympathetic chain. Various embodiments for delivering the therapy to the left side are described above. Similarly, as fibers cross the accessory hemiazygous on their way to the plexi of the heart and lungs in a similar fashion to the azygous, these regions may be treated with linear RF burns.

Figure 11C:
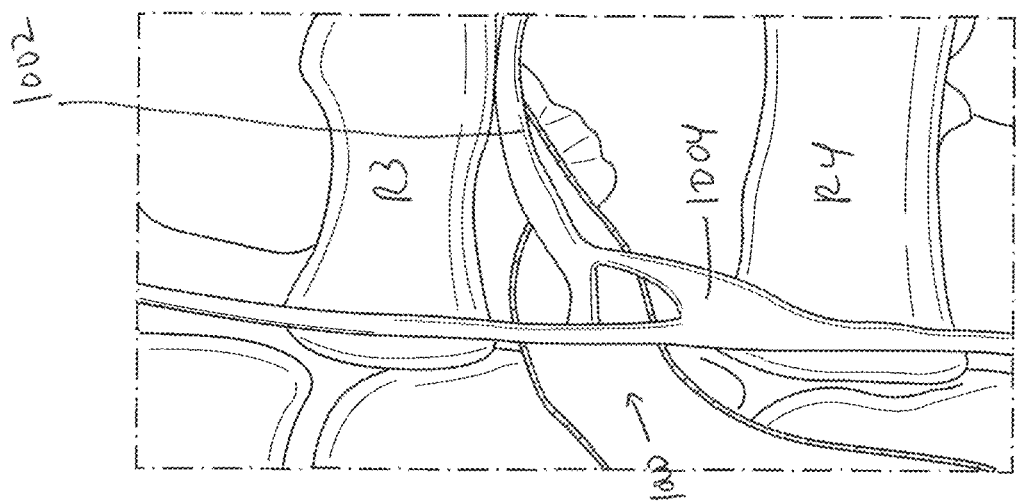
FIGS. 11A-11C illustrate different anatomical variants in anatomy of the intercostal veins.
Figure 11B:
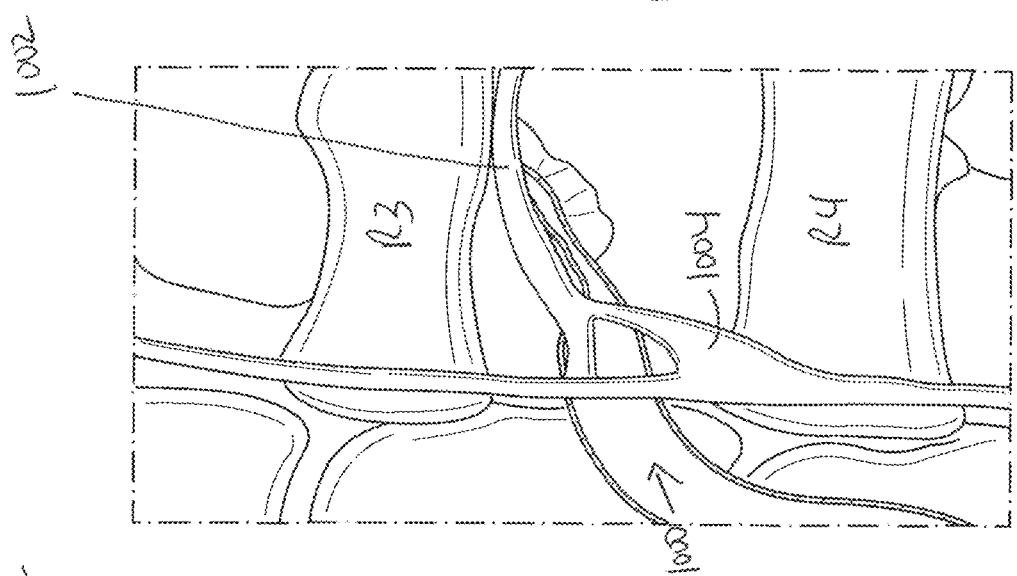
Figure 11A:
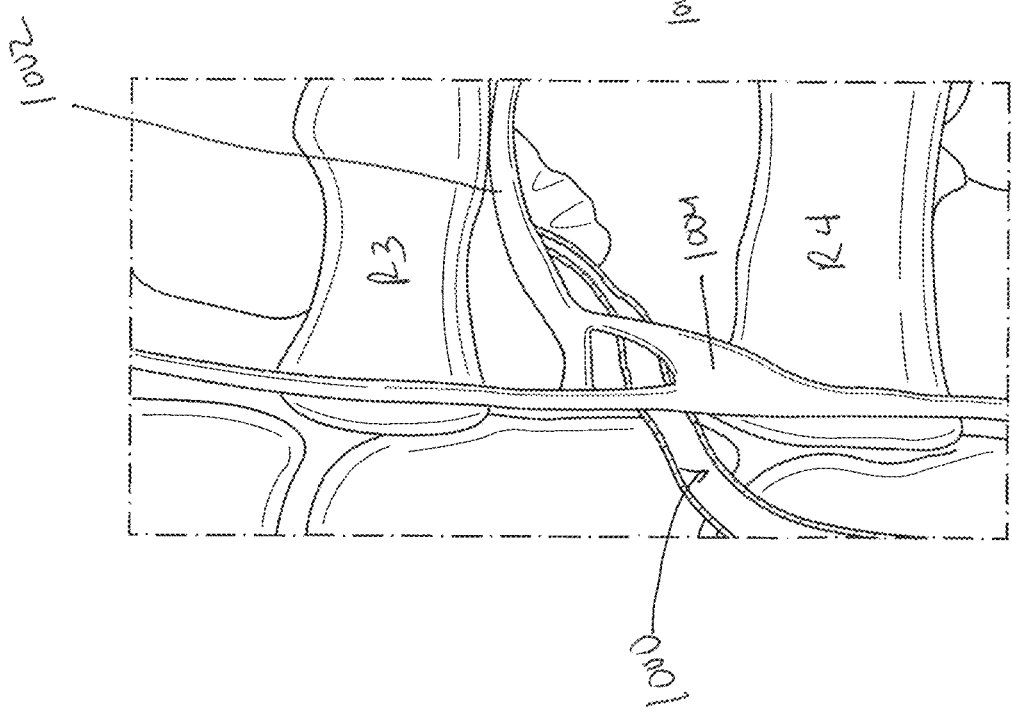
Figure 12C:
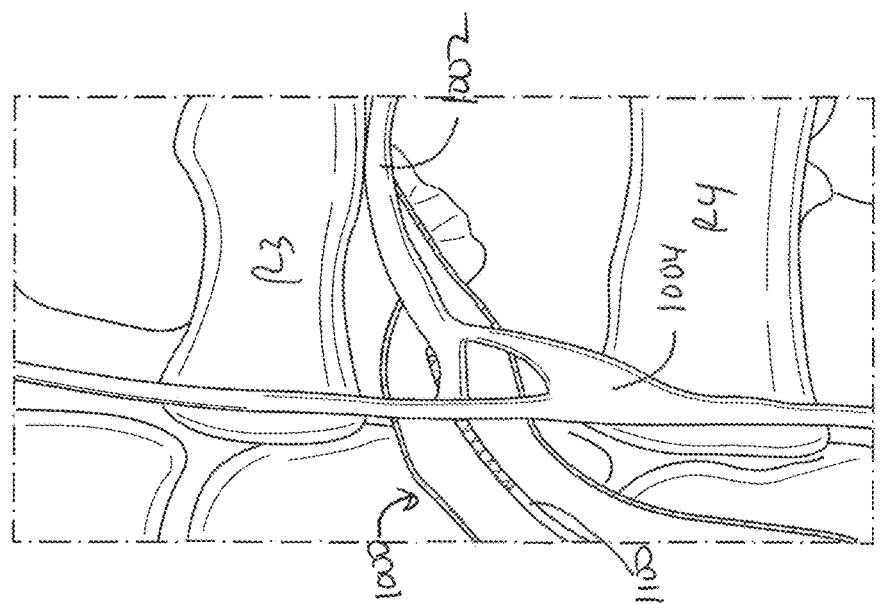
FIGS. 12A-12C illustrate the respective anatomy of FIGS. 11A-11C, with a catheter being deployed into the superior intercostal vein.
Figure 12B:
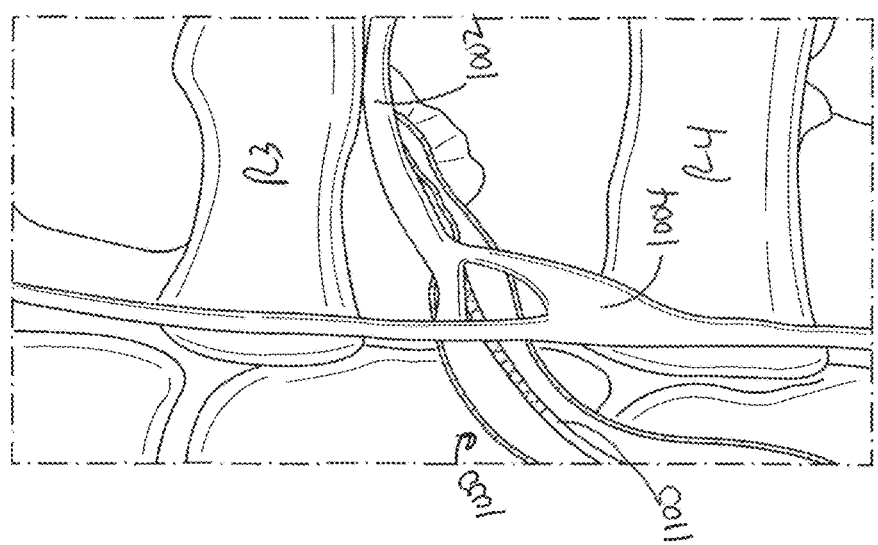
Figure 12A:
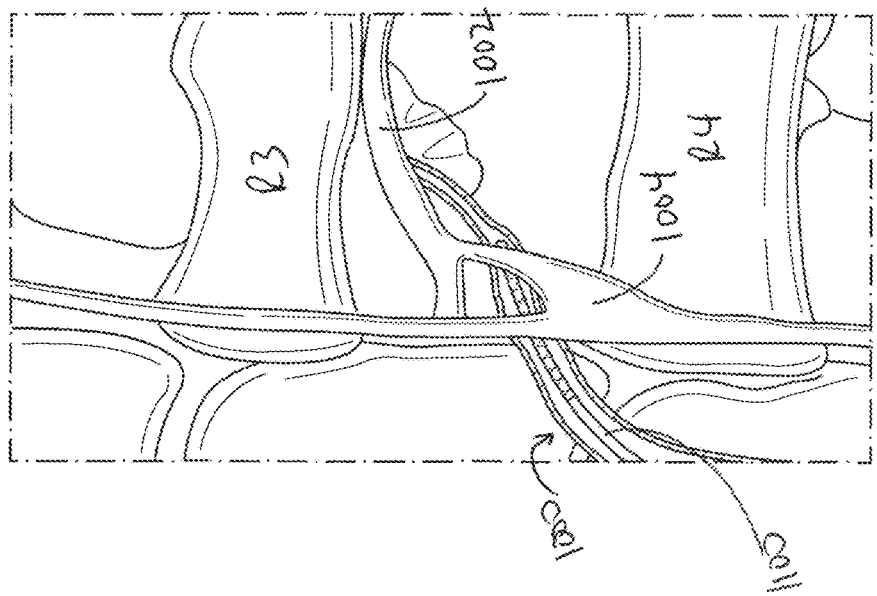
Figure 13C:
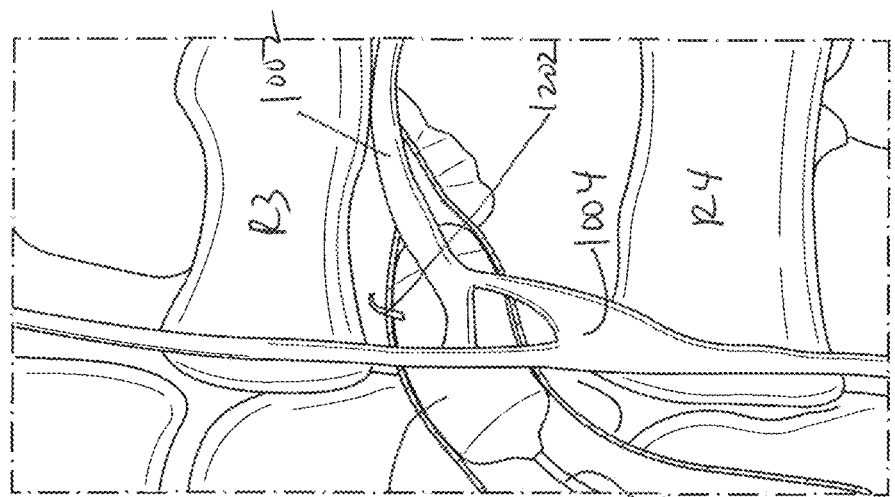
FIGS. 13A-13C illustrate the respective anatomy of FIGS. 11A-11C, illustrating expansion of an expandable member positioned at the distal end of the catheter against the wall of the vessel.
Figure 13B:
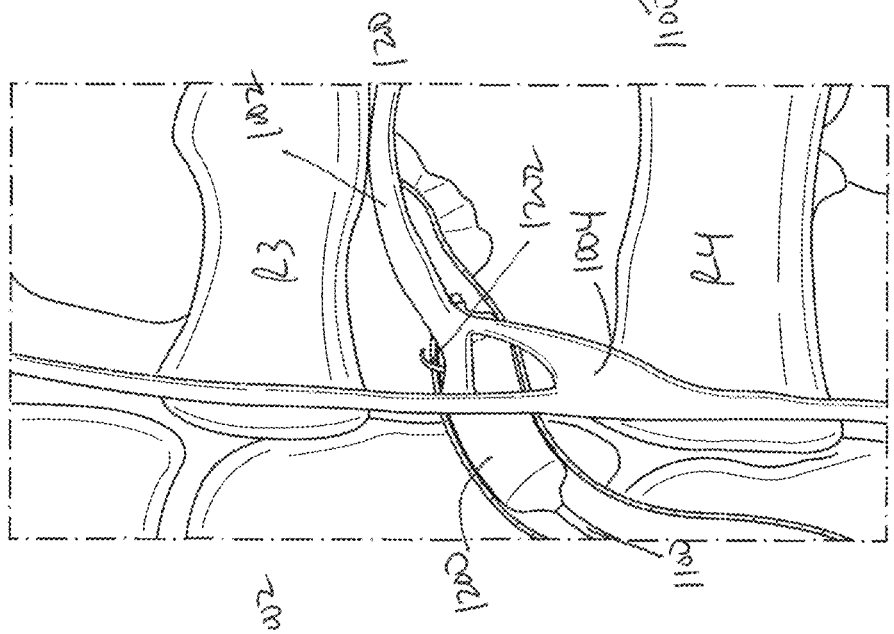
Figure 13A:
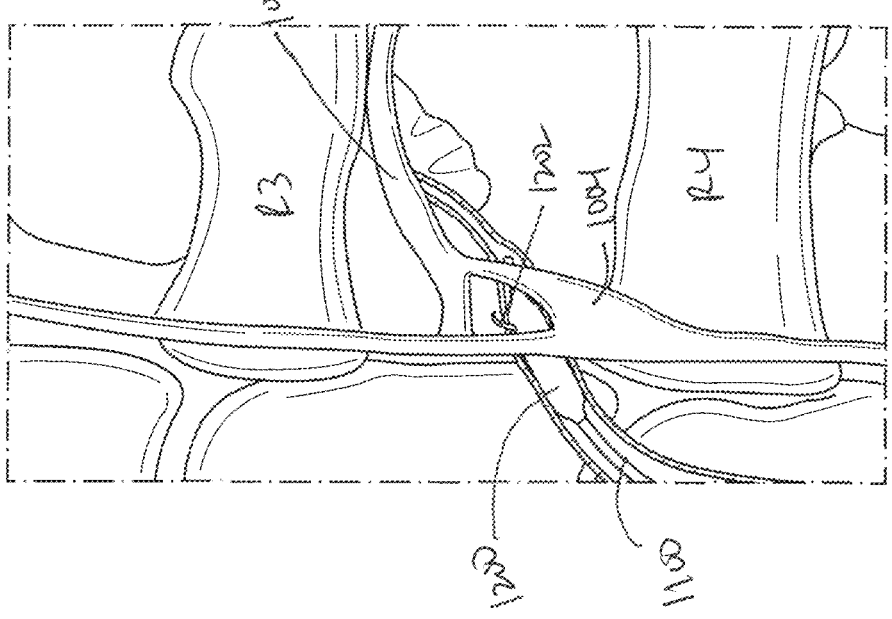
Figure 14C:
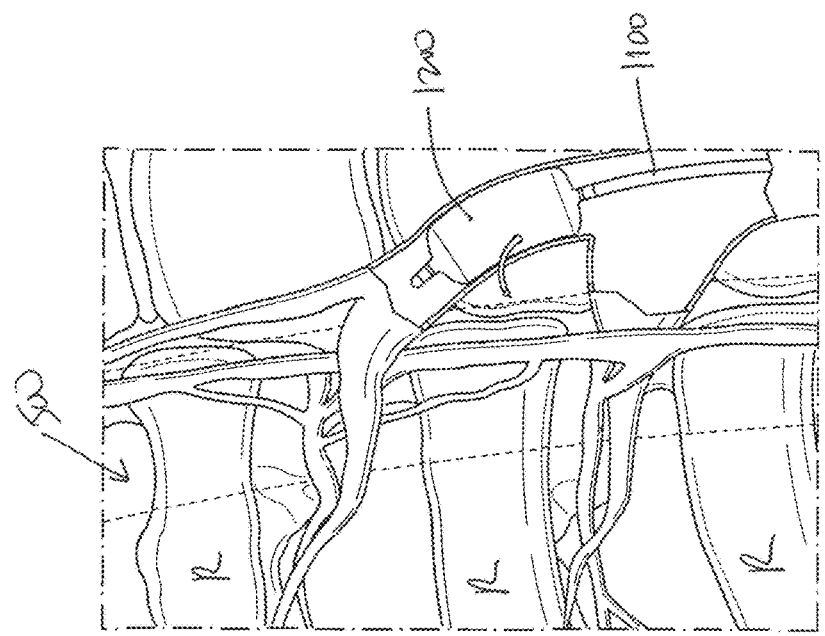
FIG. 14C illustrates the curved needle sheathed by or otherwise associated with the expandable member coming into contact with and extending radially outwardly through the wall of the vessel.
Figure 14B:
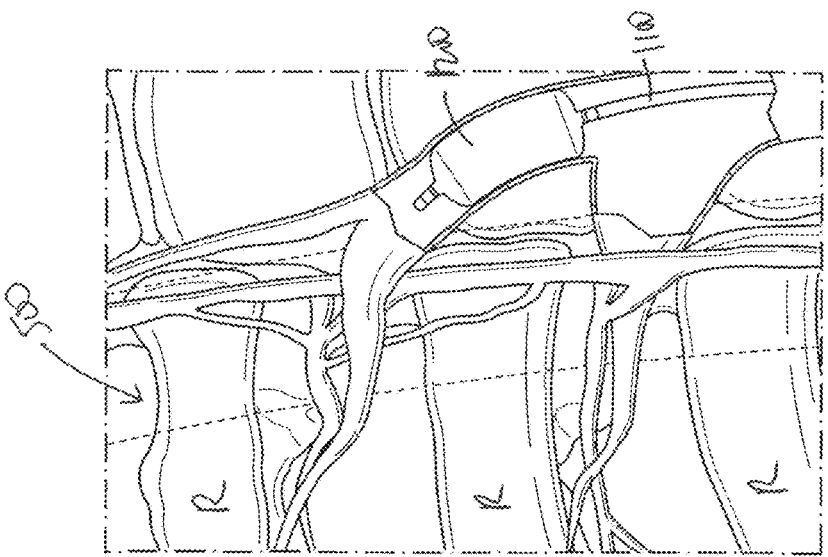
FIG. 14B illustrates schematically the expandable member being expanded.
Figure 14A:
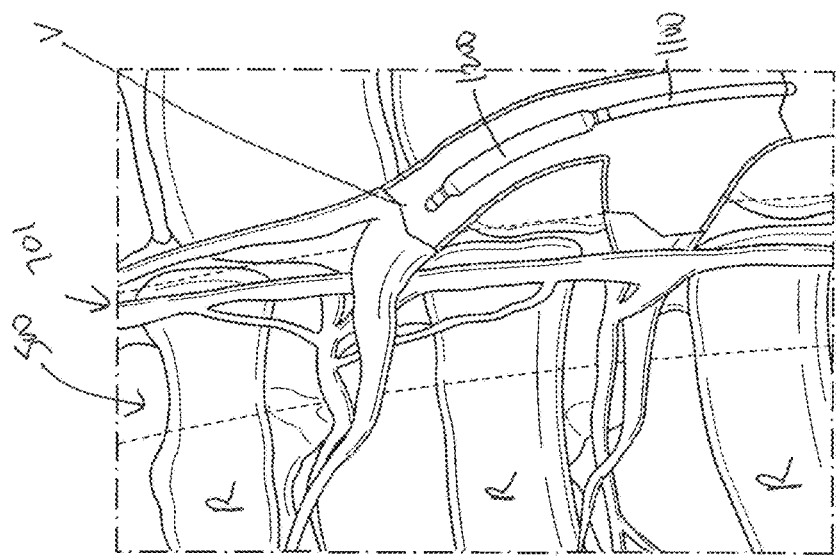
FIG. 14A illustrates schematically a different view of a catheter with an expandable member at its distal tip within a vessel.

FIGS. 10A-10C illustrate different anatomical variants in anatomy of the intercostal veins, e.g., the superior intercostal vein 1000 with respect to the left third intercostal ganglion 1004 and nerve 1006. Also shown are the left third rib R3 and left fourth rib R4. FIG. 11A illustrates a relatively small superior intercostal vein 1000 that courses generally inferior to the left third intercostal nerve 1002; FIG. 11B illustrates a medium-sized superior intercostal vein 1000 that courses generally inferior to or at the level of the left third intercostal nerve 1002; and FIG. 11C illustrates a relatively large superior intercostal vein 1000 that courses at some points superior to the left third intercostal nerve 1002. FIGS. 12A-12C illustrate the respective anatomy of FIGS. 11A-11C, with a catheter 110 being deployed into the superior intercostal vein 1000. FIGS. 13A-13C illustrate the respective anatomy of FIGS. 11A-11C, illustrating expansion of an expandable member 1200 (e.g., an inflatable balloon) positioned at the distal end of the catheter 1100 against the wall of the vessel 1000. A curvable needle 1202 sheathed by, or otherwise operably associated with the expandable member 1200 can deploy a needle across the wall of the vessel 1000, and the therapeutic agents can be delivered into the desired anatomical location (e.g., the paravertebral gutter) as described elsewhere herein. The expandable member can then be contracted (e.g., by deflation of the balloon) and the catheter 1000 removed from the body. FIG. 14A illustrates schematically a different view of a catheter 1100 with an expandable member 1200 at its distal tip within a vessel V, such as an intercostal vein for example. Also shown is the sympathetic trunk 701 and the paravertebral gutter (500, within dotted lines). FIG. 14B illustrates schematically the expandable member 1200 being expanded (e.g., balloon inflation). FIG. 14C illustrates the curved needle 1202 sheathed by or otherwise associated with the expandable member coming into contact with and extending radially outwardly through the wall of the vessel V, and the therapeutic agents can be delivered into the paravertebral gutter 500. The catheter 1000 can then be removed as previously described.

Bilateral. If bilateral therapy is desired, the catheter can then be retracted back to the superior vena cava and advanced up to the left brachiocephalic vein and then directed caudally in the superior intercostal vein. From here, therapy can be delivered to the second through the fourth intercostal veins. Occasionally there is a connection between the fourth and fifth intercostal veins, in which case therapy can also optionally be delivered from this route to the fifth intercostal vein. Alternatively, if there is communication between the hemiazygos and the azygos veins, a catheter can be directed from the azygos system, across the communicating vein between the hemiazygos and azygos veins, up the accessory hemiazygos vein and into the intercostal vein system. If therapy to the fifth intercostal vein is also desired, the catheter can then be returned to the azygos vein and advanced across the accessory hemiazygos vein to reach the fifth and sixth intercostal veins. In approximately 15% of individuals, the accessory hemiazygos vein is incompletely formed and in these situations the azygos is located closer or on the midline. In these patients, the catheter can be advanced directly from the azygos vein to the intercostal vein. As with the right side, therapy can be delivered from each of the second to the sixth, such as the second to the fifth, or the second to the fourth intercostal veins to reach the sympathetic chain and surrounding nerves at those respective levels.

In the same manner that the delivery to multiple contiguous paravertebral spaces is achieved on the right side, therapy can be delivered from one of the 1) superior intercostal vein, 2) the accessory hemiazygos vein, preferably between the intercostal veins 3) the superior intercostal vein 4) the second intercostal vein 5) the third intercostal vein, 6) the fourth intercostal vein, 7) the fifth intercostal vein or 8) the T-junction that forms between the communicating vein that forms between the communicating vein (from azygos), the accessory hemiazygos vein and the hemiazygos vein.

The catheter can be advanced along the intercostal veins to the region between the accessory hemiazygos vein (or hemiazygos vein, as appropriate) to at or adjacent to where the sympathetic chain crosses the intercostal vein.

If venous access to these locations is desired from the right internal jugular vein, the catheter can then be advanced through the right brachiocephalic vein to the superior vena cava and then the azygos vein to access the right side as described above. Access to the left side is from the right internal jugular vein to the right brachiocephalic vein to the left brachiocephalic vein down to the superior intercostal vein as described above. Occasionally, the supreme/superior intercostal veins on the right and left side drain into the azygos vein directly.

If venous access to the right or left sides is desired from percutaneous puncture to the right subclavian vein, access is gained to the right brachiocephalic vein (right innominate) and then continues to the appropriate location as described above. Similarly, if venous access is desired from percutaneous puncture to the left subclavian vein, access is gained to the left brachiocephalic vein (left innominate) and then continues to the right or left side as described above. Occasionally, the azygos vein opens into the right brachiocephalic or even the right subclavian directly instead of the superior vena cava. Alternatively, the pulmonary veins have been found opening into the azygos vein. In these cases, the access route may have to be adjusted accordingly. Percutaneous access can also be made through a radial vein or other veins of the upper thorax.

In another embodiment, catheter access to the bronchial veins is desired. These veins can be accessed directly from the azygos vein on the right side or the left superior intercostal vein or accessory hemiazygos vein on the left side.

Arterial Access.

As with the venous access, in some embodiments the goal of an endovascular approach is to access the sympathetic chain and adjacent afferent/efferent nerves that innervate the lung at the second through sixth, most preferably second through fifth, and ideally the second through fourth levels.

The approach to accessing the second thoracic level differs from the third levels down and is described here. From a right or left femoral artery, a catheter can be advanced up the descending aorta across the aortic arch, through the brachiocephalic trunk (artery) to the right subclavian artery, to the costocervical trunk, if present, and down the superior (supreme/highest) intercostal artery. This artery provides blood to the stellate and/or T1 ganglia. Alternatively other direct unnamed branches from the subclavian, branches from the inferior thyroid artery and ascending cervical arteries also supply blood to the stellate ganglion) The right second posterior intercostal artery provides direct access the second thoracic level on the right side. On the left side, the catheter can then be maneuvered up the descending aorta, across the aortic arch and up through the left subclavian artery to the costocervical trunk and down the superior (supreme/highest) intercostal artery to the left second posterior intercostal artery. For the remaining thoracic levels three through six, the posterior intercostal arteries can be accessed directly from the descending aorta on the right and left side. Therapy can be delivered from an intravascular location in the intercostal vessel immediately adjacent to the sympathetic chain or from the region between the sympathetic chain and the attachment of the intercostal artery to the aorta. Ablating along this vessel allows for therapy delivery to the afferent and efferent rami that run along to vessel to the heart and lungs. Given that this is an arterial system, the Mercator Bullfrog catheter as described in U.S. Pat. No. 8,708,995 to Seward et al., which is hereby incorporated by reference in its entirety, can be adapted for doing delivery into this space.

Arterial access can also be gained directly from an access point in the right or left radial artery and a catheter advanced from the radial to the brachial artery to the subclavian artery. Additional advancement from the subclavian artery is described above to the second (posterior) intercostal artery as well as the third through sixth intercostal arteries above. In one embodiment, the right and left thoracic sympathetic chain are accessed through the right and left sided arterial access points, respectively. In another embodiment, the brachial artery is accessed instead of the radial artery.

As with the endovascular venous access approach, multi-level therapy may be achieved to the neural structures within the paravertebral gutter through a catheter positioned at one arterial access point, including but not limited to one of the following: 1) the second posterior intercostal artery, 2) the third posterior intercostal artery, 3) the fourth posterior intercostal artery, or the 4) fifth posterior intercostal artery. An agent or therapy may travel from one intercostal level to treat multiple adjacent thoracic intercostal levels through the continuity provided in the paravertebral space. The agent or therapy can then be delivered rostrocaudally, rostrally, or caudally to multiple levels to treat the nerves in the paravertebral gutter. Alternatively, therapy may be delivered directly from the aorta to the paravertebral gutter.

In another embodiment, the catheter is advanced from the descending aorta to the left bronchial arteries (superior, inferior) directly from where therapy is delivered to the lung hilum on the right and left sides. On the right side, the right bronchial artery can be approached from the thoracic aorta directly or from a common trunk to the right third (posterior) intercostal artery to the right bronchial artery. The right bronchial artery may also originate from the left superior bronchial artery or another right intercostal artery. An agent or therapy may be delivered directly from the bronchial artery to the region surrounding the bronchial artery. In one embodiment, therapy is delivered from the posterior bronchial artery that runs with/along to the posterior pulmonary plexus. In this manner, the nerves in posterior pulmonary plexus may be targeted.

In another embodiment, the catheter is advanced into the aortic arch and therapy is delivered to the lower curvature of the arch, from where therapy is delivered. This lower curvature is a lower pressure system than the upper curvature and thus has less arteriosclerotic plaque. The lower curvature also is adjacent to the superficial cardiac plexus and the baro- and chemo-receptors that regulate the cardiopulmonary system. The lower curvature also allows delivery directly to the nerves entering on the trachea and right and left primary bronchus.

In another embodiment, the catheter is advanced down the descending aorta and therapy is delivered circumferentially around the aorta to address fibers that are running posteriorly, laterally and anteriorly around the great vessel.

In one embodiment, the venous system is accessed to deliver therapy to the right side and then the arterial system is accessed to deliver therapy to the left side or vice versa.

In another embodiment, therapy is directed towards the renal artery first followed by treatment of the sympathetic chain and/or associated rami. In yet other embodiments, therapy is directed towards the carotid body, carotid sinus, the parasympathetic system or more specifically the vagus, prior to or concurrent with treatment in some embodiments.

Direct Intercostal Access to Intercostal Artery or Vein.

As an alternate to above traditional vascular access points, an ultrasound probe can be used to guide and introduce a needle and catheter directly into the intercostal vessels from a more lateral position relative to the spine. Again, a target level is identified, using the rib/spinous process as a guide, and the access is on the underside of the target rib. The catheter is advanced along the intercostal artery or vein until it is adjacent to the sympathetic chain, or, approximately 1-2" from the connection with the azygous/accessory hemiazygous/hemiazygous. An EP catheter can be used to ID the sympathetic chain. At this location, an agent or therapy can be delivered in or around the sympathetic chain or in/around the paravertebral space. Alternatively, the catheter can be advanced more medially through the intercostal artery or vein to modulate the nerves innervating the bronchial arteries.

Intraprocedural Monitoring of Sympathetic Activity.

During the procedure, using a standard procedural approach with femoral access, coronary sinus recordings with a fixed curve decapolar catheter/quadriplar catheter can be made to monitor the cardiac sympathetic nerve activity.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "accessing the paravertebral gutter" includes "instructing the accessing of the paravertebral gutter." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. Furthermore, various theories and possible mechanisms of actions are discussed herein but are not intended to be limiting.

What is claimed is:

1. A method of modulating nerves of a cardiac plexus of a patient, comprising:
    inserting a catheter percutaneously into a first blood vessel;
    advancing the catheter into a second blood vessel;
    penetrating a wall of the second blood vessel with a portion of the catheter, thereby accessing the cardiac plexus; and
    modulating nerves within the cardiac plexus by delivering a gel comprising a therapeutic agent to contact at least a portion of the cardiac plexus.

2. The method of claim 1, wherein the modulating comprises delivering the gel, wherein the gel is a hydrogel comprising a therapeutic agent to modulate nerves in the cardiac plexus.

3. The method of claim 2, wherein the hydrogel comprises an in situ crosslinking hydrogel or an injectable hydrogel slurry.

4. The method of claim 1, wherein the modulating comprises reducing the signs or symptoms of cardiac arrhythmias.

5. The method of claim 1, wherein the cardiac arrhythmias comprise atrial fibrillation.

6. The method of claim 1, wherein the modulating comprises reducing the signs or symptoms of one or more of congestive heart failure, cardiogenic pain, and coronary artery disease.

7. The method of claim 1, wherein the gel comprises polyethylene glycol.

* * * * *